United States Patent
Bernardon

(10) Patent No.: US 6,689,922 B1
(45) Date of Patent: Feb. 10, 2004

(54) VITAMIN D ANALOGUES

(75) Inventor: Jean-Michel Bernardon, Le Rouret (FR)

(73) Assignee: Galderma Research & Development S.N.C., Valbonne (FR)

(*) Notice: Subject to any disclaimer, the term of this patent is extended or adjusted under 35 U.S.C. 154(b) by 0 days.

(21) Appl. No.: 09/830,973

(22) PCT Filed: Oct. 28, 1999

(86) PCT No.: PCT/FR99/02637

§ 371 (c)(1), (2), (4) Date: Jul. 26, 2001

(87) PCT Pub. No.: WO00/26167

PCT Pub. Date: May 11, 2000

(30) Foreign Application Priority Data

Nov. 2, 1998 (FR) .......................................... 98 13747

(51) Int. Cl.[7] .............................................. C07C 33/38
(52) U.S. Cl. ..................... 568/807; 514/649; 514/712; 514/713; 514/720; 514/728; 514/733; 514/736; 514/738; 560/73; 564/373; 568/47; 568/631; 568/644; 568/645; 568/646; 568/744; 568/807; 568/811
(58) Field of Search .................................. 568/646, 645, 568/644, 47, 811, 631, 744, 807; 560/73; 564/373; 514/649, 712, 713, 720, 728, 733, 736, 738

(56) References Cited

U.S. PATENT DOCUMENTS

| | | | |
|---|---|---|---|
| 4,567,184 A | * | 1/1986 | Musser |
| 4,778,931 A | * | 10/1988 | Musser |
| 5,877,342 A | | 3/1999 | Bernardon et al. |
| 6,214,878 B1 | | 4/2001 | Bernardon et al. |

FOREIGN PATENT DOCUMENTS

| | | |
|---|---|---|
| EP | 0776881 A | 6/1977 |
| EP | 0850909 A | 7/1998 |

* cited by examiner

Primary Examiner—Michael L. Shippen
(74) Attorney, Agent, or Firm—Burns, Doane, Swecker & Mathis, L.L.P.

(57) ABSTRACT

The invention concerns novel bi-aromatic compounds having the formula:

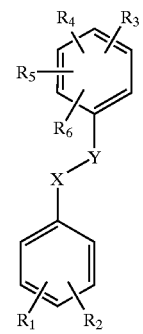

Figure 1:
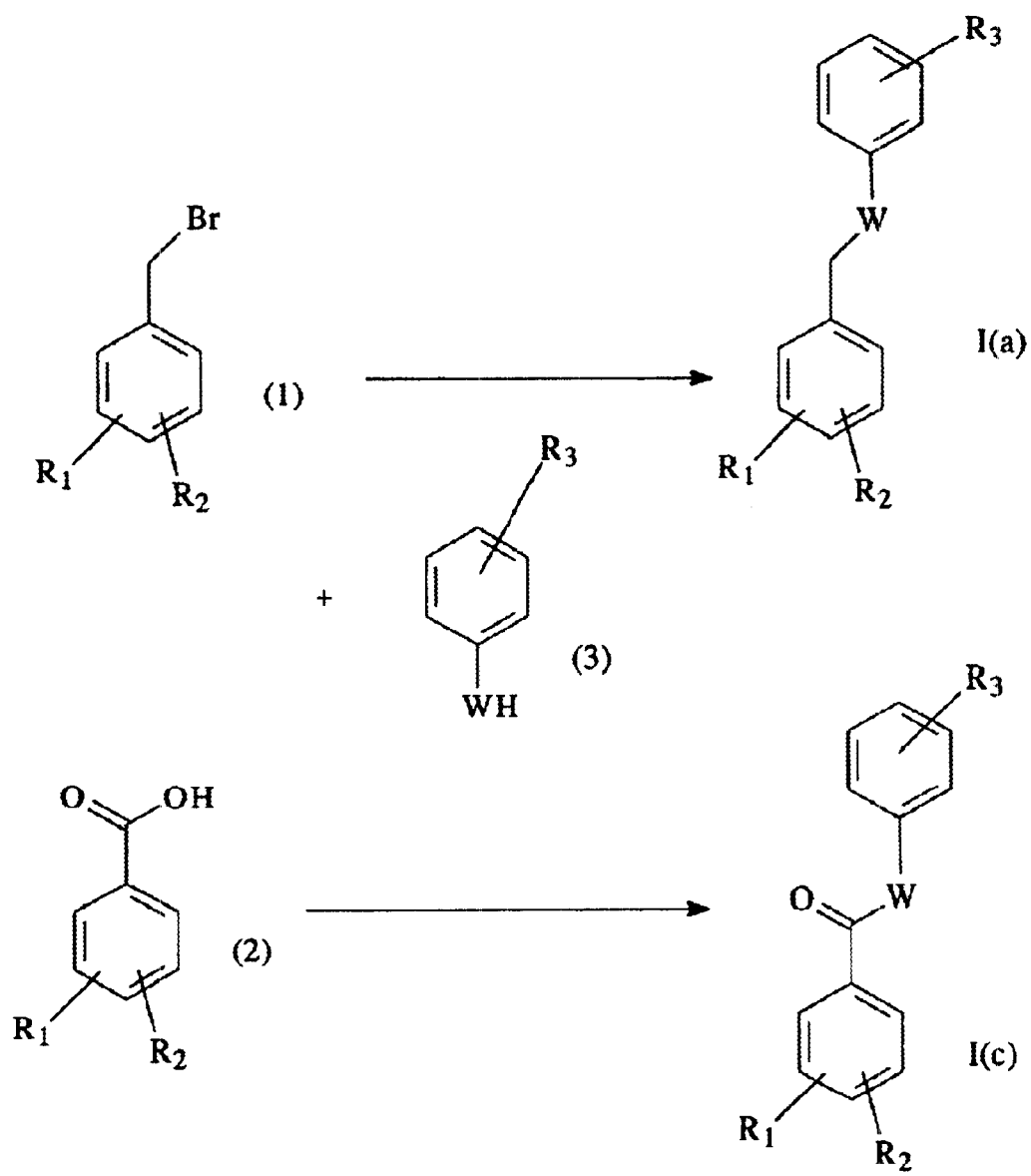
Figure 2:
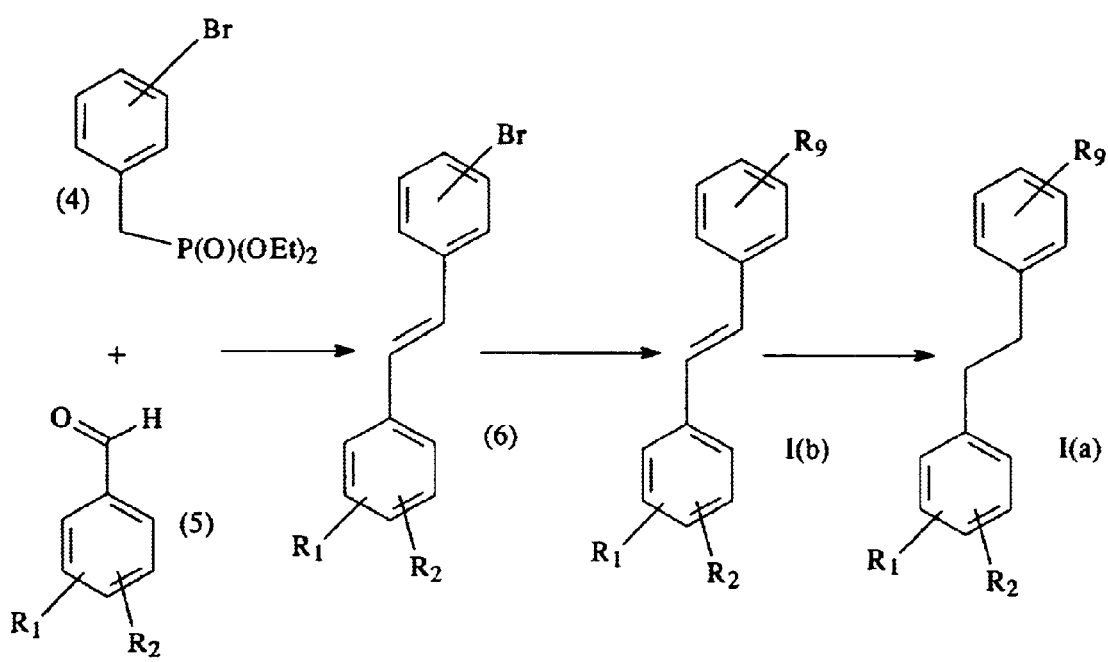
Figure 3:
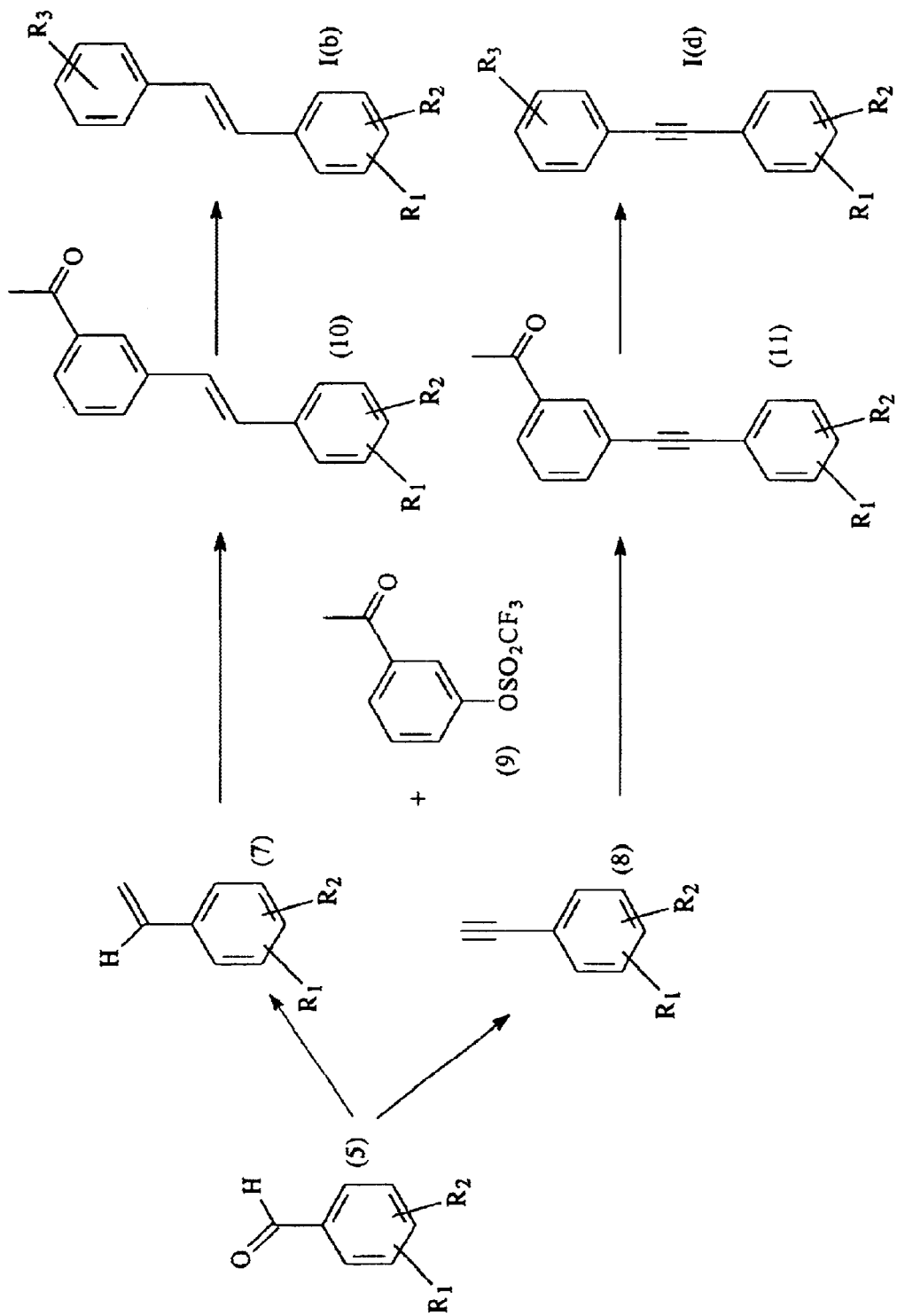

which are analogs of vitamin D, the process of preparing them, as well as their use in pharmaceutical compositions in human or veterinary medicine, particularly in dermatology, cancer treatment, treatment of auto-immune diseases, and in organ or tissue transplants. Cosmetic compositions and methods of use are also included.

82 Claims, 6 Drawing Sheets

VITAMIN D ANALOGUES

The invention relates, as new and useful industrial products, to biaromatic compounds which are analogues of vitamin D. It also relates to the process for their preparation and their use in pharmaceutical compositions intended for use in human or veterinary medicine, or alternatively in cosmetic compositions.

The compounds according to the invention have a marked activity in the fields of cell differentiation and proliferation and find applications more particularly in the topical and systemic treatment of dermatological conditions (and the like) linked to a keratinization disorder, of conditions with an inflammatory and/or immunoallergic components and of hyperproliferation of tissues of ectodermal origin (skin, epithelium and the like), whether benign or malignant. These compounds may, in addition, be used to combat skin ageing, whether photoinduced or chronologic, and to treat cicatrization disorders.

It is also possible to use the compounds according to the invention in cosmetic compositions for body and hair hygiene.

Vitamin D is an essential vitamin for the prevention and treatment of defects in the mineralization of cartilage (rickets), and of bone (osteomalacia), and even of certain forms of osteoporosis in the elderly subject. However, it is now accepted that these functions extend well beyond the regulation of bone metabolism and of calcium homeostasis. Among these, there may be mentioned its actions on cell proliferation and differentiation and the control of the immune defences. Their discovery has opened the way for new therapeutic approaches in dermatology, cancerology as well as in the field of autoimmune diseases and that of organ and tissue transplants.

An effective therapeutic application has for long been hampered by the toxicity of this vitamin (hypercalcaemia which is sometimes fatal). Currently, structural analogues of vitamin D are synthesized, some of which conserve only the differentiating properties and have no action on calcium metabolism.

One of the aims of the present invention is to provide new compounds which are structural analogues of vitamin D, which show a selective activity on cell proliferation and differentiation without exhibiting a hypercalcaemic character.

Another aim of the present invention is to provide new compounds which are analogues of vitamin D, which are easier to synthesize and therefore more economical compared to what was previously known.

Thus, the present invention relates to compounds which may be represented by the following general formula (I):

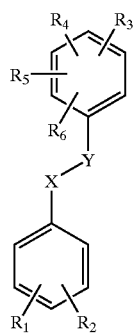

in which:

$R_1$ represents a hydrogen atom, a methyl radical or a radical —$(CH_2)_n$—$OR_7$, $R_2$ represents a radical —$(CH_2)_n$—$OR_8$, n, $R_7$ and $R_8$ having the meanings given below, X—Y represents a bond chosen from the bonds of the following formulae (a) to (d) which may be read from the left to the right or conversely:

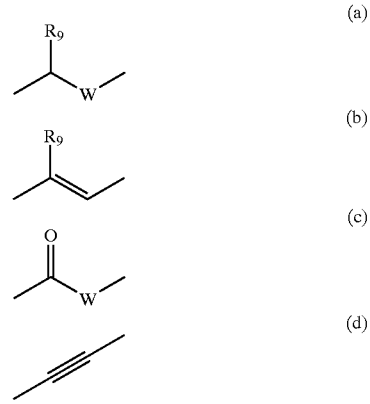

$R_9$ and W having the meanings given below, $R_3$ represents the chain in vitamin $D_2$ or in vitamin $D_3$,

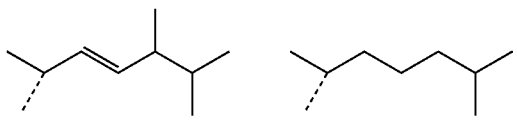

the dotted lines represent the bond linking the chain to the benzene ring represented in Figure. (I), or $R_3$ represents a chain having from 4 to 8 carbon atoms which is substituted with one or more hydroxyl groups, it being possible for the hydroxyl groups to be protected in the form of acetoxy, methoxy or ethoxy, trimethylsilyloxy, tert-butyldimethylsilyloxy, tetrahydropyranyloxy and optionally in addition:

which is substituted with one or more lower alkyl groups or cycloalkyl groups and/or which is substituted with one or more halogen atoms and/or which is substituted with one or more $CF_3$ groups and/or in which one or more carbon atoms of the chain are replaced by one or more oxygen, sulphur or nitrogen atoms, it being possible for the nitrogen atoms to be optionally substituted with lower alkyl radicals and/or in which one or more single bonds of the chain are replaced by one or more double and/or triple bonds, $R_3$ being positioned on the benzene ring at the para or meta position with respect to the X—Y bond, $R_4$, $R_5$ and $R_6$, which are identical or different, represent a hydrogen atom, a lower alkyl radical, a halogen atom, a radical —$OR_{10}$, a polyether radical, $R_{10}$ having the meaning given below, n being 0, 1 or 2, $R_7$ and $R_8$, which are identical or different, represent a hydrogen atom, an acetyl radical, a trimethylsilyl radical, a tert-butyldimethylsilyl radical, a tetrahydropyranyl radical, $R_9$ represents a hydrogen atom or a lower alkyl radical, W represents an oxygen atom, a sulphur atom, a radical —$CH_2$— or a radical —NH— which may be optionally substituted with a lower alkyl radical, $R_{10}$ represents a hydrogen atom or a lower alkyl radical.

The invention also relates to the optical and geometric isomers of the said compounds of formula (I) as well as their salts in the case where X—Y represent a bond of formula (a) and W represents a radical —NH— optionally substituted with a lower alkyl radical.

When the compounds according to the invention are provided in the form of salts, by addition of an acid, these are pharmaceutically or cosmetically acceptable salts obtained by addition of an inorganic or organic acid, in particular hydrochloric, sulphuric, acetic, fumaric, hemisuccinic, maleic and mandelic acid.

According to the present invention, lower alkyl radical is understood to mean a linear or branched radical having from 1 to 6 carbon atoms, and preferably the methyl, ethyl, isopropyl, tert-butyl and hexyl radicals.

Cycloalkyl radical is understood to mean a cyclic or polycyclic alkane radical containing from 3 to 10 carbon atoms. Preferably, the cycloalkyl radical is chosen from an adamantyl radical or a 1-methylcyclohexyl radical.

Halogen atom is understood to mean preferably a fluorine, chlorine and bromine atom.

Polyether radical is understood to mean a radical having from 2 to 5 carbon atoms which is interrupted by at least two oxygen atoms such as the methoxymethoxy, methoxyethoxy and methoxyethoxymethoxy radicals.

Among the compounds of formula (I) which fall within the scope of the present invention, the following may be mentioned in particular:

3-Hydroxymethyl-5-{2-[3-(5-hydroxy-5-methylhexyl) phenyl]vinyl}phenol,

3-Hydroxymethyl-5-{2-[3-(6-hydroxy-6-methylheptyl) phenyl]vinyl}phenol,

3-[3-(5-Hydroxy-1,5-dimethylhexyl)phenoxymethyl]-5-hydroxymethylphenol,

6-[3-(3,4-Bis-hydroxymethylbenzyloxy)phenyl]-2-methylhepta-3,5-dien-2-ol,

6-[3-(3,4-Bis-hydroxymethylbenzyloxy)phenyl]-2-methylhexan-2-ol,

6-[3-(3,4-Bis-hydroxymethylphenoxymethyl)phenyl]-2-methylheptan-2-ol,

7-[3-(3,4-Bis-hydroxymethylphenoxymethyl)phenyl]-3-ethyloctan-3-ol,

5-{2-[4-(5-Hydroxy-5-methylhexyl)phenyl] vinyl}benzene-1,3-diol,

5-{2-[4-(5-Hydroxy-5-methylhexyl)phenyl] ethyl}benzene-1,3-diol,

5-{2-[4-(6-Hydroxy-6-methylheptyl)phenyl] vinyl}benzene-1,3-diol,

5-{2-[3-(6-Hydroxy-6-methylheptyl)phenyl] vinyl}benzene-1,3-diol,

5-{2-[4-(6-Hydroxy-6-methylheptyl)phenyl] ethyl}benzene-1,3-diol,

5-{2-[3-(6-Hydroxy-6-methylheptyl)phenyl] ethyl}benzene-1,3-diol,

2-Hydroxymethyl-4-{2-[3-(5-hydroxy-5-methylhexyl) phenyl]vinyl}phenol,

2-Hydroxymethyl-4-{2-[4-(5-hydroxy-5-methylhexyl) phenyl]vinyl}phenol,

2-Hydroxymethyl-4-{2-[3-(6-hydroxy-6-methylheptyl) phenyl]vinyl}phenol,

2-Hydroxymethyl-4-{2-[4-(6-hydroxy-6-methylheptyl) phenyl]vinyl}phenol,

2-Hydroxymethyl-4-{2-[3-(5-hydroxy-5-methylheptyl) phenyl]ethyl}phenol,

2-Hydroxymethyl-4-{2-[4-(5-hydroxy-5-methylhexyl) phenyl]ethyl}phenol,

2-Hydroxymethyl-4-{2-[3-(6-hydroxy-6-methylheptyl) phenyl]ethyl}phenol,

2-Hydroxymethyl-4-{2-[4-(6-hydroxy-6-methylheptyl) phenyl]ethyl}phenol,

2-Hydroxymethyl-5-{2-[4-(5-hydroxy-5-methylhexyl) phenyl]vinyl}phenol,

6-[3-(3,4-Bis-hydroxymethylbenzyloxy)phenyl]-2-methylheptan-2-ol,

4-[3-(5-Hydroxy-1,5-dimethylhexyl)phenoxymethyl]-2-hydroxymethylphenol,

6-{3-[2-(3,4-Bis-hydroxymethylphenyl)vinyl]phenyl}-2-methylhexan-2-ol,

7-{4-[2-(3,4-Bis-hydroxymethylphenyl)vinyl]phenyl}-2-methylheptan-2-ol,

6-{4-[2-(3,4-Bis-hydroxymethylphenyl)vinyl]phenyl}-2-methylhexan-2-ol,

5-{2-[3-(6-Hydroxy-6-methylheptyl)phenyl]-1-methylvinyl}benzene-1,3-diol,

5-{2-[3-(5-Hydroxy-5-methylhexyl)phenyl] vinyl}benzene-1,3-diol,

5-[3-(6-Hydroxy-6-methylheptyl)phenoxymethyl] benzene-1,3-diol,

5-{2-[3-(7-Hydroxy-7-methyloct-1-enyl)phenyl]vinyl}-benzene-1,3-diol,

5-{2-[3-(7-Hydroxy-7-methyloctyl)phenyl] vinyl}benzene-1,3-diol,

4-{2-[3-(6-Hydroxy-6-methylheptyl)phenyl] vinyl}benzene-1,2-diol,

3-{2-[3-(6-Hydroxy-6-methylheptyl)phenyl] vinyl}phenol,

6-{3-[2-(3,5-Bis-hydroxymethylphenyl)vinyl]phenyl}-2-methylhexan-2-ol,

3-{2-[3-(7-Hydroxy-7-methyloctyl)phenyl]vinyl}phenol,

7-{3-[2-(3,5-Bis-hydroxymethylphenyl)vinyl]phenyl}-2-methylheptan-2-ol,

7-{3-[2-(3,4-Bis-hydroxymethylphenyl)vinyl]phenyl}-2-methylheptan-2-ol, 7-{3-[2-(4-Hydroxymethylphenyl) vinyl]phenyl}-2-methylheptan-2-ol, 4-{2-[3-(7-Hydroxy-7-methyloct-1-enyl)phenyl] vinyl}benzene-1,2-diol, 7-[3-(3,4-Bis-hydroxymethylphenylethynyl)phenyl]-2-methylheptan-2-ol, 5-{2-[3-(6-Hydroxy-6-methylhept-1-enyl)phenyl] vinyl}benzene-1,3-diol, 5-{2-[3-(7-Ethyl-7-hydroxynon-1-enyl)phenyl] vinyl}benzene-1,3-diol, 5-{2-[3-(7-Hydroxy-1-methoxy-1,7-dimethyloctyl) phenyl]vinyl}benzene-1,3-diol, 5-{2-[3-(6-Hydroxy-1-methoxy-1,6-dimethylheptyl) phenyl]vinyl}benzene-1,3-diol, 5-{2-[3-(5-Hydroxypentyl)phenyl]vinyl}benzene-1,3-diol, 5-{2-[3-(5-Hydroxy-6-methylheptyl)phenyl] vinyl}benzene-1,3-diol, 5-{2-[3-(6-Hydroxy-7-methyloctyl)phenyl] vinyl}benzene-1,3-diol, 5-{2-[3-(5-Hydroxy-6-methylhept-1-enyl)phenyl]vinyl}-benzene-1,3-diol, 5-{2-[3-(6-Hydroxy-7-methyloct-1-enyl)phenyl]vinyl}-benzene-1,3-diol, 5-{2-[3-(1,6-Dihydroxy-1,6-dimethylheptyl)phenyl]-vinyl}benzene-1,3-diol,
5-{2-[3-(6-Hydroxy-1,6-dimethylhept-1-enyl)phenyl]-vinyl}benzene-1,3-diol,
6-{[3-(3,4-Bis-hydroxymethylbenzyloxy)phenyl]-methylamino}-2-methylhexan-2-ol,
5-{[3-(3,4-Bis-hydroxymethylbenzyloxy)phenyl]-methylamino}-2-methylpentan-2-ol,
6-{[3-(3,4-Bis-hydroxymethylbenzyloxy)phenyl]-methylamino}-3-ethylhexan-3-ol,
7-{[3-(3,4-Bis-hydroxymethylbenzyloxy)phenyl]-methylamino}-3-ethylheptan-3-ol,
5-{[3-(3,4-Bis-hydroxymethylbenzyloxy)phenyl]-ethylamino}-2-methylpentan-2-ol,
6-{[3-(3,4-Bis-hydroxymethylbenzyloxy)phenyl]-benzylamino}-3-ethylhexan-3-ol,
7-{3-[2-(3,4-Bis-hydroxymethylphenyl)ethyl]phenyl}-3-ethylocta-4,6-dien-3-ol,
6-{3-[2-(3,4-Bis-hydroxymethylphenyl)ethyl]phenyl}-2-methylhepta-3,5-dien-2-ol,
7-{3-[2-(3,4-Bis-hydroxymethylphenyl)vinyl]phenyl}-3-ethylocta-4,6-dien-3-ol,
6-{3-[2-(3,4-Bis-hydroxymethylphenyl)vinyl]phenyl}-2-methylhepta-3,5-dien-2-ol,
7-[3-(3,4-Bis-hydroxymethylphenylethynyl)phenyl]-3-ethylocta-4,6-dien-3-ol,
7-[3-(3,4-Bis-hydroxymethylbenzyloxy)phenyl]-3-ethyl-3-octanol,
(4E,6E)-7-[3-(3,4-Bis-hydroxymethylbenzyloxy)phenyl]-3-ethylocta-4,6-dien-3-ol,
(4E,6Z)-7-[3-(3,4-Bis-hydroxymethylbenzyloxy)pheny]-3-ethylocta-4,6-dien-3-ol,
7-[4-(3,4-Bis-hydroxymethylbenzyloxy)phenyl]-3-ethyl-3-octanol,
(4E,6E)-7-[3-(3,4-Bis-hydroxymethylbenzyloxy)phenyl]-3-ethylnona-4,6-dien-3-ol,
(4E,6Z)-7-[3-(3,4-Bis-hydroxymethylbenzyloxy)phenyl]-3-ethylnona-4,6-dien-3-ol,
(E)-6-[3-(3,4-Bis-hydroxymethylbenzyloxy)phenyl]-2-methylhept-3-en-2-ol,
(E)-7-[3-(3,4-Bis-hydroxymethylbenzyloxy)phenyl]-3-ethyloct-4-en-3-ol,
(E)-7-[3-(3,4-Bis-hydroxymethylbenzyloxy)phenyl]-3-ethyloct-6-en-3-ol,
(Z)-7-[3-(3,4-Bis-hydroxymethylbenzyloxy)phenyl]-3-ethyloct-6-en-3-ol,
(E)-8-[3-(3,4-Bis-hydroxymethylbenzyloxy)phenyl]-2-methylnon-7-en-2-ol,
(Z)-8-[3-(3,4-Bis-hydroxymethylbenzyloxy)phenyl]-2-methylnon-7-en-2-ol,
(E)-9-[3-(3,4-Bis-hydroxymethylbenzyloxy)phenyl]-3-ethyldec-8-en-3-ol,
(Z)-9-[3-(3,4-Bis-hydroxymethylbenzyloxy)phenyl]-3-ethyldec-8-en-3-ol,
8-[3-(3,4-Bis-hydroxymethylbenzyloxy)phenyl]-2-methyl-2-nonanol,
9-[3-(3,4-Bis-hydroxymethylbenzyloxy)phenyl]-3-ethyldecan-3-ol,
(E)-7-[3-(3,4-Bis-hydroxymethylbenzyloxy)phenyl]-3-ethyloct-6-en-4-yn-3-ol,
(3E,5E)-7-[3-(3,4-Bis-hydroxymethylbenzyloxy)phenyl]-2,7-dimethylocta-3,5-dien-2-ol,
(4E,6E)-7-[3-(3,4-Bis-hydroxymethylphenoxymethyl)phenyl]-3-ethyl-octa-4,6-dien-3-ol,
(3E,5E)-6-[3-(3,4-Bis-hydroxymethylphenoxymethyl)phenyl]-2-methyl-hepta-3,5-dien-2-ol,
(Z)-7-[3-(3,4-Bis-hydroxymethylbenzyloxy)phenyl]-3-ethylnon-6-en-3-ol,
(Z)-6-[3-(3,4-Bis-hydroxymethylbenzyloxy)phenyl]-2-methyloct-5-en-2-ol,
(Z)-7-[3-(3,4-Bis-hydroxymethylbenzyloxy)phenyl]-3-ethyldec-6-en-3-ol,
(Z)-6-[3-(3,4-Bis-hydroxymethylbenzyloxy)phenyl]-2-methylnon-5-en-2-ol,
(Z)-8-[3-(3,4-Bis-hydroxymethylbenzyloxy)phenyl]-3-ethylnon-7-en-3-ol,
(E)-8-[3-(3,4-Bis-hydroxymethylbenzyloxy)phenyl]-3-ethyl-non-7-en-3-ol,
8-[3-(3,4-Bis-hydroxymethylbenzyloxy)phenyl]-3-ethylnonan-3-ol,
7-[5-(3,4-Bis-hydroxymethylbenzyloxy)-2-methoxyphenyl]-3-ethylnona-4,6-dien-3-ol,
7-[5-(3,4-Bis-hydroxymethylbenzyloxy)-2-methylphenyl]-3-ethylnona-4,6-dien-3-ol,
7-[3-(3,4-Bis-hydroxymethylbenzyloxy)-5-methoxyphenyl]-3-ethylnona-4,6-dien-3-ol,
7-[3-(3,4-Bis-hydroxymethylbenzyloxy)-2-methoxyphenyl]-3-ethylnona-4,6-dien-3-ol,
7-[3-(3,4-Bis-hydroxymethylbenzyloxy)-4-methylphenyl]-3-ethylnona-4,6-dien-3-ol,
1-[3-(3,4)-Bis-hydroxymethylbenzyloxy)phenyl]ethanone O-(2-hydroxy-2-methylpropyl)oxime,
1-{1-[3-(3,4-Bis-hydroxymethylbenzyloxy)phenyl]-propoxy}-3-ethylpentan-3-ol,
(E)-7-[3-(3,4-Bis-hydroxymethylphenoxymethyl)phenyl]-3-ethylnon-6-en-3-ol,
(E)-7-[3-(3,4-Bis-hydroxymethylbenzylsulfanyl)phenyl]-3-ethyloct-6-en-3-ol,
(E)-7-{3-[(3,4-Bis-hydroxymethylbenzyl)methylamino]-phenyl}-3-ethyloct-6-en-3-ol,
(E)-6-[3-(3,4-Bis-hydroxymethylbenzyloxy)phenyl]-3-ethyl-6-methylhept-4-en-3-ol,
7-[3-(3,4-Bis-hydroxymethylbenzyloxy)phenyl]-3-ethyl-7-methyloctan-3-ol,
7-[3-(3,4-Bis-hydroxymethylbenzyloxy)phenyl]-3,7-diethylnonan-3-ol,
(E)-6-[3-(3,4-Bis-hydroxymethylbenzyloxy)phenyl]-1,1,1-trifluoro-2-trifluoromethyl-oct-5-en-2-ol,
2-{4-[3-(3,4-Bis-hydroxymethylbenzyloxy)phenyl]hexyl}-1,1,1,3,3,3-hexafluoropropan-2-ol,
(E)-7-[3-(3,4-Bis-hydroxymethylbenzyloxy)phenyl]-3-ethyl-4,4-difluoronon-6-en-3-ol,
7-[3-(3,4-Bis-hydroxymethylbenzyloxy)phenyl]-3-ethyl-4,4-difluoro-7-methyloctan-3-ol,
(E)-6-[3-(3,4-Bis-hydroxymethylbenzyloxy)phenyl]-2-methyloct-5-en-3-ol,
(E)-4-[3-(3,4-Bis-hydroxymethylbenzyloxy)phenyl]-1-cyclopropylhex-3-en-1-ol,
(E)-7-[3-(3,4-Bis-hydroxymethylbenzyloxy)phenyl]-3-ethyl-4-methylnon-6-en-3-ol,
(E)-7-[3-(3,4-Bis-hydroxymethylbenzyloxy)phenyl]-3-ethyl-4-methyldec-6-en-3-ol,
(4E,6E)-7-[3-(3,4-Bis-hydroxymethylphenoxymethyl)phenyl]-3-ethylnona-4,6-dien-3-ol, (4E,6E)-7-{3-[2-(3,4-Bis-hydroxymethylphenyl)ethyl]-phenyl}-3-ethylnona-4,6-dien-3-ol, (E)-7-{3-[2-(3,4-Bis-hydroxymethylphenyl)ethyl]phenyl}-3-ethylnon-6-en-3-ol, (E)-3-Ethyl-7-[3-(3-hydroxymethylphenoxymethyl) phenyl]non-6-en-3-ol, (E)-3-Ethyl-7-[3-(4-hydroxymethylphenoxymethyl) phenyl]-non-6-en-3-ol, (E)-3-Ethyl-7-[(E)-3-(3-hydroxymethyl-4-methylphenoxymethyl)phenyl]non-6-en-3-ol, (E)-3-Ethyl-7-[(E)-3-(4-hydroxymethyl-3-methylphenoxymethyl)phenyl]non-6-en-3-ol, 2-{4-[3-(3,4-Bis-hydroxymethylbenzyloxy)phenyl]-4-methylpentyl}-1,1,1,3,3,3-hexafluoropropan-2-ol, 7-[3-(3,4-Bis-hydroxymethylbenzyloxy)phenyl]-3-ethyl-4,4-difluoro-7-methyl-octan-3-ol, 7-{3-[2-(3,4-Bis-hydroxymethylphenyl)ethyl]phenyl}-3,7-diethylnonan-3-ol 7-[3-(3,4-Bis-hydroxymethylbenzyloxy)phenyl]-3-ethyl-7-methyloctane-3,4-diol 7-{3-[2-(3,4-Bis-hydroxymethylphenyl)ethyl]phenyl}-3,7-diethylnonane-3,4-diol 7-{3-[2-(3,4-Bis-hydroxymethylphenyl)ethyl]phenyl}-3-ethyl-7-methyloctane-3,4-diol (E)-4-{3-[2-(3,4-Bis-hydroxymethylphenyl)ethyl] phenyl}-1-cyclopropylhex-3-en-1-ol (4E,6E)-7-{3-[2-(3,4-Bis-hydroxymethylphenyl)ethyl] phenyl}-3-ethyl-4-methylnona-4,6-dien-3-ol (4E,6E)-7-[3-(3,4-Bis-hydroxymethylbenzyloxy) phenyl]-3-ethyl-4-methylnona-4,6-dien-3-ol (E)-3-Ethyl-7-[3-(4-hydroxymethyl-3-methylphenoxymethyl)phenyl]non-6-en-3-ol, (E)-3-Ethyl-7-[3-(3-hydroxymethyl-4-methylphenoxymethyl)phenyl]non-6-en-3-ol, (E)-7-[3-(3,4-Bis-hydroxymethylphenoxymethyl) phenyl]-3-ethyloct-6-en-3-ol, (E)-3-Ethyl-7-[3-(3-hydroxymethylphenoxymethyl) phenyl]-non-6-en-3-ol, (E)-3-Ethyl-7-[3-(4-hydroxymethylphenoxymethyl) phenyl]-non-6-en-3-ol.

According to the present invention, the compounds of formula (I) which are more particularly preferred are those for which at least one, and preferably all the conditions below are observed:

$R_1$ represents the radical —$(CH_2)_n$OH, $R_2$ represents the radical —$(CH_2)_n$OH, X—Y represents a bond of formula (a) or (c), $R_3$ represents a chain of 4 to 8 carbon atoms which is substituted with at least one hydroxyl radical and/or one lower alkyl radical.

The subject of the present invention is also the processes for the preparation of the compounds of formula (I).

FIGS. 1 to 4 represent the reaction schemes which may be used for the preparation of the compounds according to the invention.

Thus, the compounds of formula I(a) may be obtained (FIG. 1) by reacting a halogenated, preferably brominated, compound (1) with a phenol (W=OH), thiophenol (W=SH) or aniline (W=NH—COO-tert-butyl) derivative (3) in the presence of a base such as $K_2CO_3$ in a solvent such as acetone or methyl ethyl ketone.

The compounds of formula I(a) may also be obtained (FIG. 1) by reacting a halogenated, preferably brominated, compound (1) with a sodium or potassium salt of a phenol (W=OH), thiophenol (W=SH) or aniline (W=NH—COO-tert-butyl) derivative (3) in a solvent such as dimethylformamide (DMF).

The compounds of formula I(c) may be obtained (FIG. 1) by reacting a benzoic derivative (2) with a phenol (W=OH), thiophenol (W=SH) or aniline (W=NH$_2$) derivative (3) in the presence of carbonyldiimidazole or of dicyclohexylcarbodiimide in a solvent such as dichloromethane or tetrahydrofuran (THF).

The compounds of formula I(c) may also be obtained (FIG. 1) by reacting a benzoyl chloride (obtained by reacting a benzoic derivative (2) with thionyl chloride or oxalyl chloride) with a phenol (W=OH), thiophenol (W=SH) or aniline (W=NH$_2$) derivative (3) in the presence of a base such as triethylamine in a solvent such as dichloromethane or tetrahydrofuran (THF).

The compounds of formula I(b) may be obtained (FIG. 2) by a Horner-Emmons-type reaction between the phosphonate derivative (4) (obtained from the corresponding benzyl bromide by an Arbuzov-type reaction) and benzaldehyde (5).

The compounds of formula I(a) may be obtained from compounds I(b) by hydrogenation in the presence of palladium on carbon.

The compounds of formula I(b) may also be obtained (FIG. 3) by a Heck-type reaction between an ethylenic derivative (7) (obtained by reacting benzaldehyde (5) with methyl triphenyl phosphine bromide) and the triflate derivative (9) in the presence of a transition metal catalyst such as $Pd(Cl)_2(PPh_3)_2$ in a solvent such as triethylamine.

The compounds of formula I(d) may be obtained (FIG. 3) by the reaction between an acetylenic derivative (8) (obtained from benzaldehyde (5) by a Corey-Fuchs-type reaction) and a triflate derivative (9) in the presence of a transition metal catalyst $Pd(Cl)_2(PPh_3)_2$ and of CuI in a solvent such as triethylamine.

The chain $R_3$ may be introduced using, for example, the methods described in Medicinal Research Reviews, Vol 7, No. 2, 147–171 (1987) T. KAMETANI and H. FURUYAMA, Chem. Rev. Vol 78, No. 3, 199–241 (1978) D. M. PIATAK and J. WICHA, or in Chem. Rev. Vol 95, No. 6, 1877–1952 (1995) G. ZHU and W. H. OKAMURA.

Figure 4A:
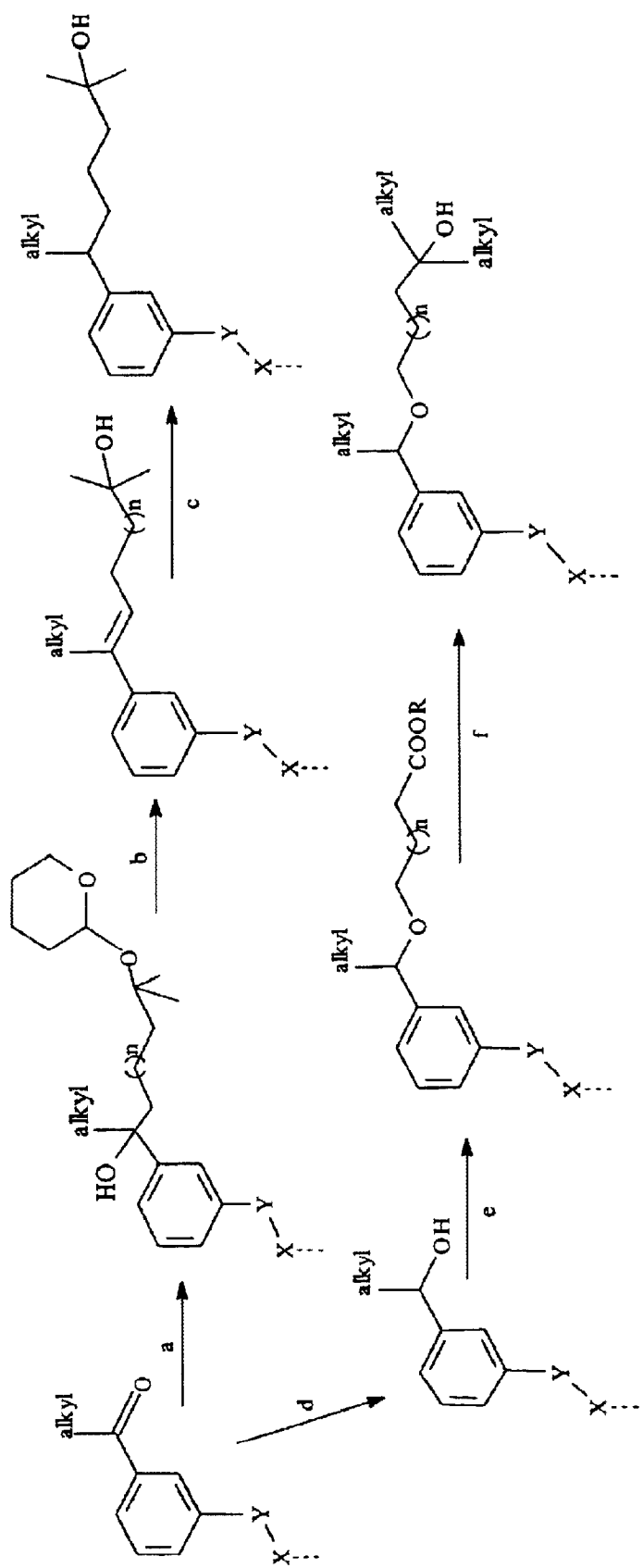
Figure 4B:
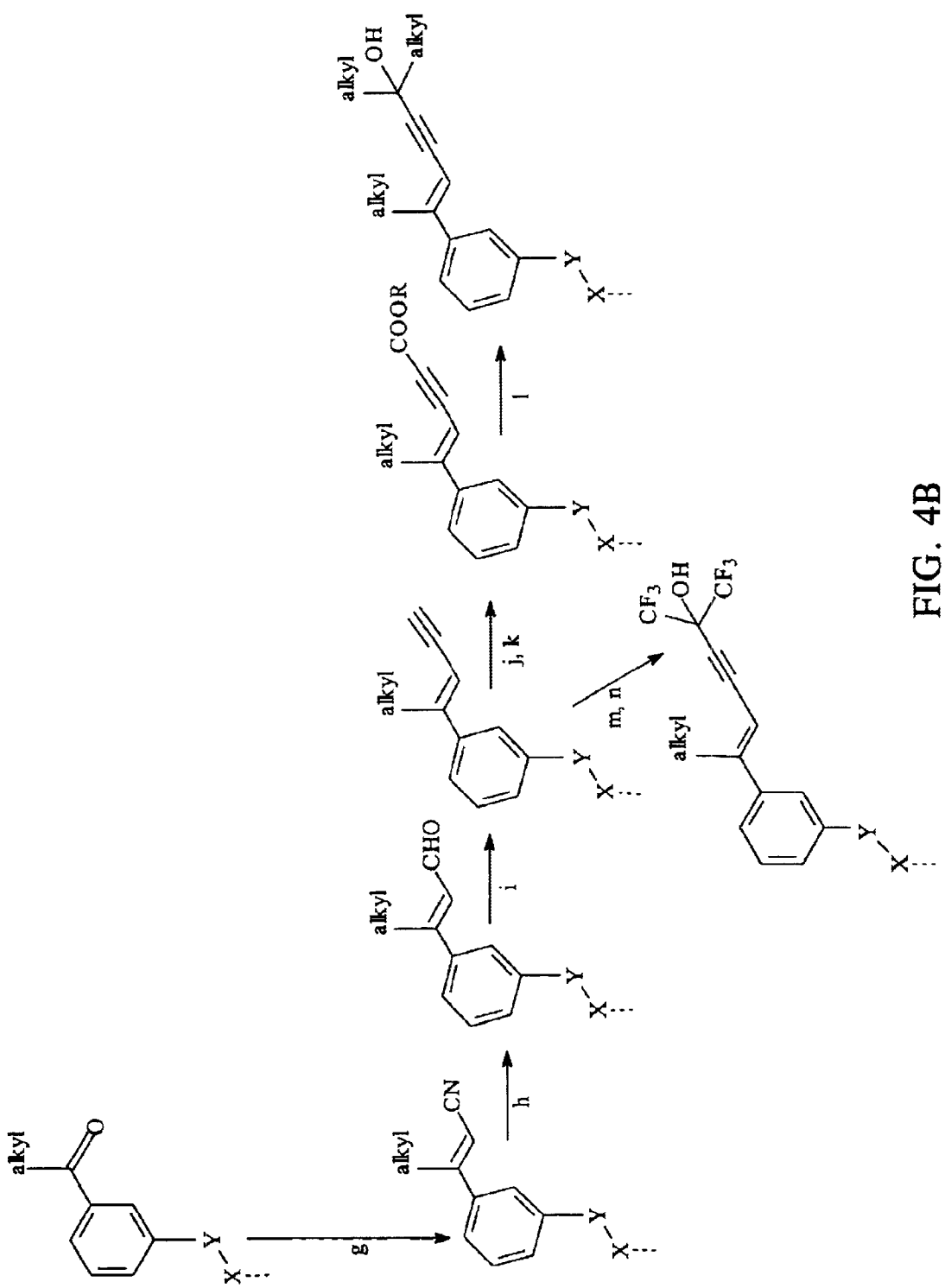
Figure 4C:
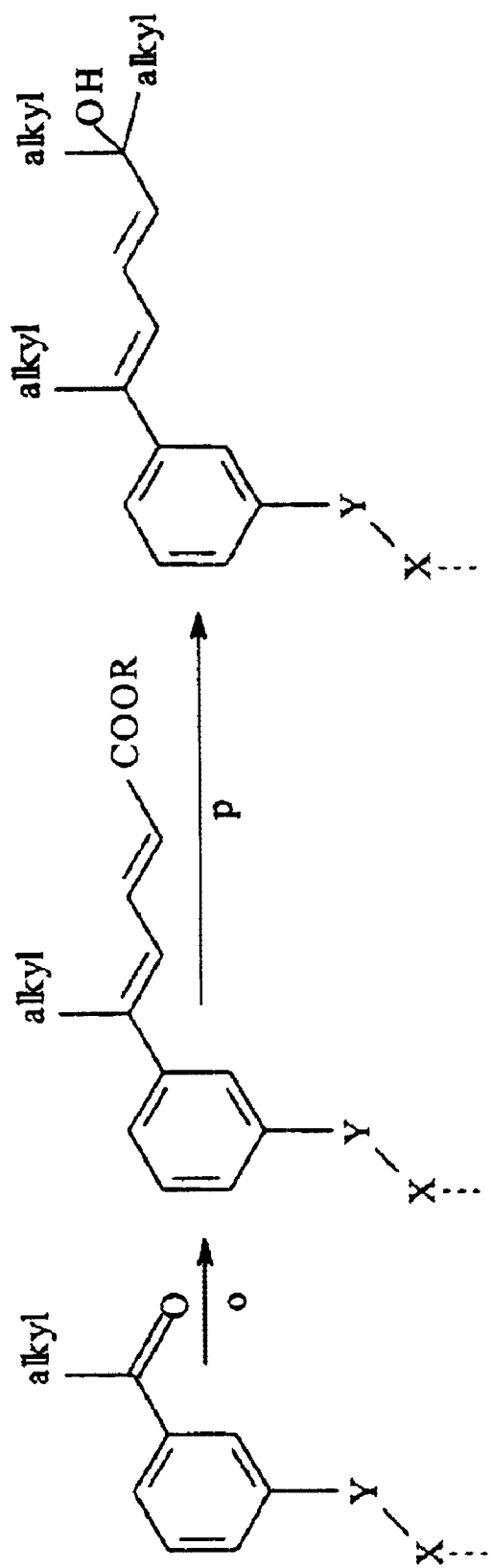

Thus, by way of examples, a few summarized methods are given in FIG. 4, in which (a) represents a reaction with MgBr—$CH_2$—$(CH_2)_n$—$C(CH_3)_2$—O-tetrahydropyran in a solvent such as tetrahydrofuran, (b) represents a reaction in the presence of para-toluenesulphonic acid or sulphuric acid, (c) represents a hydrogenation reaction in the presence of palladium-on-carbon catalyst, (d) represents a reduction reaction with sodium borohydride in a methanol-tetrahydrofuran solvent, (e) represents a reaction with Br—$CH_2(CH_2)_n$—$CH_2$—COOR in the presence of potassium hydride in a dimethylformamide solvent, (f) represents a reaction with MgXAlkyl, X representing a halogen atom, in a tetrahydrofuran solvent, (g) represents a reaction with NC—$CH_2$—$P(O)(OC_2H_5)_2$ in the presence of sodium hydride in a tetrahydrofuran solvent, (h) represents a reaction with diisobutylaluminium hydride in a tetrahydrofuran solvent, (i) represents a reaction with carbon tetrabromide in the presence of triphenylphosphine in a mixture of tetrahydrofuran followed by a reaction with n-butyllithium, (j) represents a reaction with n-butyllithium in tetrahydrofuran, (k) represents a reaction with the alkyl chloroformate Cl—COOR, (l) represents a reaction with MgXAlkyl, X representing a halogen atom, in a tetrahydrofuran solvent, (m) represents a reaction with n-butyllithium in tetrahydrofuran, (n) represents a reaction with $CF_3$—CO—$CF_3$, (o) represents a reaction with ROOC—CH=CH—$CH_2$—P(O) $(OC_2H_5)_2$ in the presence of lithium iisopropylamide in tetrahydrofuran, (p) represents a reaction with MgXAlkyl, X representing a halogen atom, n a tetrahydrofuran solvent.

The compounds of general formula (I) exhibit biological properties similar to those of vitamin D, in particular the vitamin D response element (VDRE) transactivating properties, such as an agonist or antagonist activity towards receptors for vitamin D or its derivatives. Vitamins D or their derivatives are understood to mean, for example, the derivatives of vitamin $D_2$ or $D_3$ and in particular 1,25-dihydroxy vitamin $D_3$ (calcitriol).

This agonist activity towards receptors for vitamin D or its derivatives may be demonstrated "in vitro" by methods recognized in the field of the study of gene transcription (Hansen et al., The Society for Investigative Dermatology, vol. 1, No. 1, April 1996).

By way of example, the VDR agonist activity may be tested on the HeLa cell line, by cotransfecting a human VDR receptor expression vector and the reporter plasmid p240Hase-CAT which contains the region—1399 to +76 of the promoter of rat 24-hydroxylase, cloned upstream of the coding phase of the chloramphenicol acetyl transferase (CAT) gene. 18 hours after cotransfection, the test product is added to the medium. After 18 hours of treatment, the assay of the CAT activity in the cell lysates is carried out by an Elisa test. The results are expressed as percentage of the effect normally observed with $10^{-7}$ M calcitriol.

The agonist activity may also be characterized in this cotransfection system by the determination of the dose necessary to reach 50% of the maximum activity of the product (AC50).

The biological properties which are similar to vitamin D may also be measured by the capacity of the product to inhibit the proliferation of normal human keratinocytes (NHK in culture). The product is added to NHKs cultured under conditions promoting the proliferative state. The product is left in contact with the cells for 5 days. The number of proliferative cells is measured by incorporation of bromodeoxyuridine (BRdU) into DNA.

The agonist activity towards the vitamin D receptors of the compounds of the invention may also be evaluated "in vivo" by induction of 24-Hydroxylase in SKH mice (Voorhees et al. 1997.108: 513–518). The test protocol used is described in Example 54 of the present application.

The subject of the present invention is also, as a medicament, the compounds of formula (I) as described above.

The compounds according to the invention are particularly suitable in the following fields of treatment:

1) For treating dermatological conditions linked to a keratinocyte or sebocyte differentiation or proliferation disorder, in particular for treating acne vulgaris, comedo-type acne, polymorphic acne, acne rosacea, nodulocystic acne, acne conglobata, senile acne, secondary acne such as solar acne, acne medicamentosa or occupational acne.

2) For treating other types of keratinization disorders, in particular ichthyosis, ichthyosiform states, Darier's disease, keratosis palmaris et plantaris, leukoplasia, leukoplasiform states, cutaneous or mucosal (buccal) lichen.

3) For treating other dermatological conditions linked to a keratinization disorder with an inflammatory and/or immunoallergic component, and in particular all the forms of psoriasis, whether cutaneous, mucosal or ungual, and even psoriatic rheumatism or cutaneous atopy, such as eczema or respiratory atopy or gingival hypertrophy; the compounds may also be used in certain inflammatory conditions which do not exhibit keratinization disorders.

4) For treating any dermal or epidermal proliferations whether benign or malignant, whether of viral origin or not, such as verruca vulgaris, verruca plana and epidermodysplasia verruciformis, oral or florid papillomatoses and proliferations which may be induced by ultraviolet radiation in particular in the case of baso- and spinocellular epithelioma.

5) For treating other dermatological disorders such as bullous dermatoses and collagen diseases.

6) For repairing or combating skin ageing, whether photoinduced or chronologic, or for reducing pigmentations and actinic keratoses, or any pathologies associated with chronologic or actinic ageing.

7) For preventing or treating cicatrization disorders or for preventing or repairing vibices.

8) For combating disorders of the sebaceous function, such as hyperseborrhoea of acne or simple seborrhoea or seborrhoeic eczema.

9) For treating certain ophthalmological disorders, in particular corneopathies.

10) In the treatment or prevention of cancerous or precancerous states of cancers exhibiting or capable of being induced so as to exhibit vitamin D receptors, such as, but without limitation, breast cancer, leukaemia, myelodysplasic syndromes and lymphomas, carcinomas of the cells of the Malpighian epithelium and gastrointestinal cancers, melanomas and osteosarcoma.

11) In the treatment of inflammatory conditions such as arthritis or rheumatoid arthritis.

12) In the treatment of any condition of viral origin at the cutaneous level or in general.

13) In the prevention or treatment of alopecia of various origins, in particular alopecia due to chemotherapy or to radiation.

14) In the treatment of dermatological or general conditions with an immunological component.

15) In the treatment of immunological conditions such as autoimmune diseases (such as, but without limitation, type 1 diabetes mellitus, multiple sclerosis, lupus and lupus-type conditions, asthma, glomerulonephritis and the like), selective dysfunctions of the immune system (for example AIDS) and the prevention of immune rejection [such as the rejection of grafts (for example the kidney, heart, bone marrow, liver, pancreatic islets or the whole pancreas, the skin and the like) or the prevention of graft-versus-host disease].

16) In the treatment of hormonal conditions given that the vitamin D analogues can modulate hormonal secretion such as the increase in the secretion of insulin or the selective suppression of the secretion of the parathyroid hormone (for example in chronic renal insufficiency and secondary hyperparathyroidism).

17) In the treatment of conditions characterized by an abnormal management of intracellular calcium.

18) In the treatment and/or prevention of vitamin D deficiencies and of other conditions of the homeostasis of the minerals in the plasma and the bones, such as rickets, osteomalacia, osteoporosis, in particular in the case of menopausal women, renal osteodystrophy, parathyroid function disorders.

In the abovementioned therapeutic fields, the compounds according to the invention may be advantageously used in combination with retinoids, with corticosteroids or oestrogens, in combination with antioxidants, with α-hydroxy or α-keto acids or derivatives thereof, with potassium channel blockers, or alternatively in combination with other medicaments known to interfere with the immune system (for example cyclosporin, FK 506, glucocorticoids, monoclonal antibodies, cytokines or growth factors and the like).

Retinoids are understood to mean ligands for the RAR or RXR receptors, either natural or synthetic.

Anti-free radicals are understood to mean, for example, α-tocopherol, Super Oxide Dismutase, Ubiquinol or some metal chelators.

α-Hydroxy or α-keto acids or derivatives thereof are understood to mean, for example, lactic, malic, citric, glycolic, mandelic, tartaric, glyceric or ascorbic acids, or salicylic acid derivatives, as well as their salts, amides or esters.

Potassium channel blockers are understood to mean, for example, Minoxidil (2,4-diamino-6-piperidinopyrimidine 3-oxide) and its derivatives.

The subject of the present invention is also a pharmaceutical composition comprising at least one compound of formula (I) as defined above.

The subject of the present invention is therefore also such a pharmaceutical composition intended in particular for the treatment of the abovementioned conditions.

The administration of the compounds according to the invention may be carried out by the enteral, parenteral, topical or ocular route.

By the enteral route, the pharmaceutical compositions may be provided in the form of tablets, gelatin capsules, sugar-coated tablets, syrups, suspensions, solutions, powders, granules, emulsions, lipid or polymeric microspheres or nanospheres or vesicles which allow a controlled release. By the parenteral route, the compositions may be provided in the form of solutions or suspensions for infusion or for injection.

The compounds according to the invention are generally administered at a daily dose of about 0.001 µg/kg to 1000 µg/kg and preferably about 0.01 µg/kg to 100 µg/kg as bodyweight, in 1 to 3 doses.

By the topical route, the pharmaceutical compositions based on compounds according to the invention are intended for the treatment of the skin and the mucous membranes and are provided in the form of salves, creams, milks, ointments, powders, impregnated pads, solutions, gels, sprays, lotions or suspensions. They may also be provided in the form of lipid or polymeric microspheres or nanospheres or vesicles or of polymeric patches and hydrogels allowing a controlled release. These compositions for the topical route may be provided either in anhydrous form or in an aqueous form, depending on the clinical indication.

By the ocular route, they are mainly collyria

These compositions for the topical or ocular route contain at least one compound of formula (I) as defined above at a concentration preferably of between 0.0001 and 5% and preferably between 0.001 to 1% relative to the total weight of the composition.

The compounds of formula (I) according to the invention also find application in the cosmetic field, in particular in body and hair care and in particular for the treatment of skins with a tendency towards acne, for hair regrowth, against hair loss, for combating the greasy appearance of the skin or the hair, in protecting against the harmful effects of the sun and in the treatment of physiologically dry skins, for preventing and/or for combating photoinduced or chronologic ageing.

In the cosmetic field, the compounds according to the invention may be advantageously used in combination with retinoids, with corticosteroids, in combination with anti-free radicals, with α-hydroxy or α-keto acids or derivatives thereof, or alternatively with ion-channel blockers.

The various products taken in combination with the compounds of the present invention are as defined above.

The present invention therefore also relates to a cosmetic composition containing, in a cosmetically acceptable carrier, at least one compound of formula I as defined above. This cosmetic composition may be provided in particular in the form of a cream, a milk, a lotion, a gel, lipid or polymeric microspheres or nanospheres or vesicles, a soap or a shampoo.

The concentration of compound of formula I in the cosmetic compositions may be between 0.001 and 3% by weight relative to the total weight of the composition.

The pharmaceutical and cosmetic compositions according to the invention may, in addition, contain inert or even pharmacodynamically or cosmetically active additives or combinations of these additives, and in particular: wetting agents; depigmenting agents such as hydroquinone, azelaic acid, caffeic acid or kojic acid; emollients; moisturizing agents such as glycerol, PEG 400, thiamorpholinone, and its derivatives or urea; antiseborrhoeic or antiacne agents, such as S-carboxymethylcysteine, S-benzylcysteamine, their salts or their derivatives, or benzoyl peroxide; antibiotics such as erythromycin and its esters, neomycin, clindamycin and its esters, tetracyclines; antifungal agents such as ketoconazole or 4,5-polymethylene-3-isothiazolinones; agents promoting hair regrowth, such as Minoxidil (2,4-diamino-6-piperidinopyrimidine 3-oxide) and its derivatives, Diazoxide (7-chloro 3-methyl-1,2,4-benzothiadiazine 1,1-dioxide) and Phenytoin (5,4-diphenyl-2,4-imidazolidinedione); non-steroidal anti-inflammatory agents; carotenoids and, in particular, β-carotene; antipsoriatic agents such as anthralin and its derivatives; and finally 5,8,11,14-eicosatetraynoic and 5,8,11-eicosatrynoic acids, their esters and amides.

The compositions according to the invention may also contain taste-enhancing agents, preservatives such as parahydroxybenzoic acid esters, stabilizing agents, moisture-regulating agents, pH-regulating agents, osmotic pressure-modifying agents, emulsifying agents, UV-A and UV-B screening agents, antioxidants such as α-tocopherol, butylated hydroxyanisole or butylated hydroxytoluene.

Several examples of producing active compounds of formula (I) according to the invention, as well as various concrete formulations based on such compounds as well as an example of a test for evaluating the biological activity of the compounds of formula (I) according to the invention will now be given, by way of illustration and without any limitation.

EXAMPLE 1

3-Hydroxymethyl-5-{2-[3-(5-hydroxy-5-methylhexyl)phenyl]vinyl}phenol a) Methyl 5-Hydroxyisophthalate.

30 ml of concentrated sulphuric acid are added, dropwise, to a solution of 54.6 g (0.3 mol) of 5-hydroxyisophthalic acid in 500 ml of methanol. The reaction medium is heated under reflux for 24 hours. After evaporation, the residue is taken up in ethyl acetate and extracted with water. The organic phase is dried over anhydrous magnesium sulphate and then concentrated. The residue is triturated in heptane.

White solid. m=59.8 g. Y=95%. m.p.=162–4° C. $^1$H NMR (CDCl$_3$): 3.91 (6H, s) 7.71 (2H, d), 8.15–8.16 (1H, t).

b) 5-Hydroxyisophthalic Acid Monomethyl Ester.

119 g (2.8 mol) of lithium hydroxide monohydrate are added to a solution of 59.7 g (0.28 mol) of methyl 5-hydroxyisophthalate in 500 ml of THF. The mixture is heated under reflux for 24 hours. At room temperature, it is gently poured into concentrated hydrochloric acid, extracted with ethyl acetate and washed with water. After decantation, the organic phase is dried over magnesium sulphate and concentrated. The residue is purified on a silica column (dichloromethane 93-heptane 7).

White crystals. m=40 g. Y=78%. m.p.=238–40° C. $^1$H NMR (DMSO): 3.87 (3H, s), 7.54–7.58 (2H, m), 7.95–7.96 (1H, t).

c) Methyl 3-Hydroxy-5-hydroxymethylbenzoate.

375 ml of borane 1M/THF are added, dropwise, at 0° C., to a solution of 37 g (0.19 mol) of 5-hydroxyisophthalic acid monomethyl ester in 200 ml of THF. At the end of the addition, the medium is heated at 40° C. for 12 hours. 200 ml of a THF/water solution (1/1) are added very slowly. After having evaporated the THF, the remaining aqueous phase is extracted with dichloromethane and then potassium carbonate is added. After decantation, the organic phase is washed with water and then dried over magnesium sulphate and concentrated. The residue is filtered on silica with ethyl acetate.

White crystals. m=27 g. Y=78%. $^1$H NMR (CDCl$_3$): 3.87 (3H, s), 4.62–4.64 (2H, d), 7.09 (1H, s), 7.39–7.41 (1H, t), 7.51 (1H, s), 8.96 (1H, s).

d) Methyl 3-Ethoxymethoxy-5-ethoxymethoxymethylbenzoate.

26 g (143 mmol) of methyl 3-hydroxy-5-hydroxymethylbenzoate in 200 ml of dimethylformamide are added, dropwise, to a solution of 11 g (344 mmol) of sodium hydride (75%) in 100 ml of DMF. The medium is stirred for 1 hour and then 29.1 ml (314 mmol) of methoxymethyl chloride are added slowly. The stirring is continued overnight. The medium is then poured into ice-cold water and extracted with ethyl acetate. The organic phase is dried over magnesium sulphate and then concentrated. The residue is purified on a silica column (dichloromethane 90-heptane 10).

Yellow oil. m=26.5 g. Y=63%. $^1$H NMR (CDCl$_3$): 1.19–1.26 (6H, m), 3.61–3.77 (4H, m), 3.91 (3H, s), 4.61 (2H, s), 4.77 (2H, s), 5.26 (2H, s), 7.23 (1H, s), 7.61–7.62 (1H, c), 7.67 (1H, s).

e) (3-Ethoxymethoxy-5-ethoxymethoxymethylphenyl)methanol.

203 ml of diisobutylaluminium hydride 1M/toluene are added, at −78° C., dropwise, to a solution of 20 g (68 mmol) of methyl 3-ethoxymethoxy-5-ethoxymethoxymethylbenzoate in 150 ml of toluene. This solution is stirred for 2 hours at −78° C. A solution of 32 g of sodium tartrate in 300 ml of water is then added. The white solid formed is filtered and the filtrate is evaporated. The residue is taken up in ethyl acetate and poured into ice. The organic phase is washed several times with water and then dried over magnesium sulphate and then concentrated. The residue is purified on a silica column (ethyl acetate 30-heptane 70).

Yellow oil. m=14.5 g. Y=79%. $^1$H NMR (CDCl$_3$): 1.19–1.26 (6H, m), 1.94–1.98 (1H, OH, t), 3.59–3.76 (4H, m), 4.56 (2H, s), 4.64–4.66 (2H, d), 4.75 (2H, s), 5.22 (2H, s), 6.96–6.99 (3H, m).

f) 3-Ethoxymethoxy-5-ethoxymethoxymethylbenzaldehyde.

4.9 ml of acetic acid are added, dropwise, at 10° C., to a solution of 13.5 g (0.05 mol) of (3-ethoxymethoxy-5-ethoxymethoxymethylphenyl)methanol, 28.2 g (0.075 mol) of pyridinium dichromate and 30 g of ground molecular sieve in 250 ml of anhydrous dichloromethane. After stirring for 15 minutes at room temperature, 300 ml of ether are added. The precipitate formed is filtered on silica, rinsed with ether and then the filtrate is evaporated. The residue is purified on a silica column (dichloromethane 20-heptane 80).

Yellow oil. m=10 g. Y=75%. $^1$H NMR (CDCl$_3$): 1.19–1.27 (6H, m), 3.62–3.78 (4H, m), 4.65 (2H, s), 4.79 (2H, s), 5.28 (2H, s), 7.29 (1H, s), 7.47 (1H, s), 7.52 (1H, s), 9.97 (1H, s).

g) 3-Bromo-[2-(3-ethoxymethoxy-5-ethoxymethoxymethylphenyl)vinyl]phenyl.

290 mg (8.9 mmol) of sodium hydride 75% are added, in small quantities, to a solution of 2 g (7.4 mmol) of 3-ethoxymethoxy-5-ethoxymethoxymethylbenzaldehyde and 2.7 g (8.8 mmol) of ethyl (3-bromobenzyl)phosphonate in 60 ml of THF with one drop of 15-Crown-5. The mixture is stirred overnight at room temperature. It is then concentrated, taken up in ethyl ether and washed several times with water. After decantation, the organic phase is dried over magnesium sulphate and concentrated. The residue is purified on a silica column (ethyl acetate 10-heptane 90).

Yellow oil. m=2.8 g. Y=89%. $^1$H NMR (CDCl$_3$): 1.18–1.28 (6H, m), 3.63–3.79 (4H, m), 4.60 (2H, s), 4.79 (2H, s), 5.26 (2H, s), 6.96 (1H, s), 7.03–7.04 (2H, d), 7.11–7.16 (1H, d, J=12.1 Hz), 7.22–7.25 (1H, d, J=7.8 Hz), 7.36–7.42 (2H, m), 7.65–7.76 (1H, t).

h) Methyl 5-{3-[2-(3-ethoxymethoxy-5-ethoxymethoxymethylphenyl)vinyl]phenyl}pentanoate.

A solution of 1.4 g (5.7 mmol) of 9-borabicyclo[3.3.1]nonane in 15 ml of THF is added, dropwise, at 0° C., to 420 mg (3.7 mmol) of methyl pent-4-enoate. It is stirred for 5 hours at room temperature. 1.25 g (3 mmol) of 3-bromo-[2-(3-ethoxymethoxy-5-ethoxymethoxymethylphenyl)vinyl]phenyl in 10 ml of dimethylformamide, 850 mg (6 mmol) of potassium carbonate and 150 mg (0.18 mmol) of [1,1'-bis(diphenylphosphino)ferrocene]dichloropalladium are then added. The mixture is stirred at 50° C. overnight. Dichloromethane is added and the organic phase is then washed several times with water. After decantation, it is dried over magnesium sulphate and concentrated. The residue is purified on a silica column (ethyl acetate 8-heptane 92).

Yellow oil. m=830 mg. Y=61%. $^1$H NMR (CDCl$_3$): 1.21–1.28 (6H, m), 1.69 (4H, m), 2.35 (2H, m), 2.65 (2H, t), 3.67 (3H, s), 3.63–3.79 (4H, m), 4.60 (2H, s), 4.79 (2H, s), 5.26 (2H, s), 7.07–7.16 (5H, m), 7.25–7.32 (3H, m).

i) 6-{3-[2-(3-Ethoxymethoxy-5-ethoxymethoxymethylphenyl)vinyl]phenyl}-2-methylhexan-2-ol.

3.6 ml (10.8 mmol) of methylmagnesium bromide 3M/ether are added, dropwise, to 820 mg (1.8 mmol) of methyl 5-{3-[2-(3-ethoxymethoxy-5-ethoxymethoxymethylphenyl)vinyl]phenyl}pentanoate in 20 ml of ethyl ether. The mixture is stirred for 1 hour at room temperature. A saturated aqueous ammonium chloride solution is then very slowly added as well as ether. The organic phase is washed several times with water and, after decantation, it is dried over magnesium sulphate and concentrated. The residue is purified on a silica column (ethyl acetate 25-heptane 75).

Yellow oil. m=600 mg. Y=73%. $^1$H NMR (CDCl$_3$): 1.22 (6H, s), 1.18–1.25 (6H, m), 1.50–1.60 (6H, m), 2.58–2.66 (2H, m), 3.57–3.86 (4H, m, 4.60 (2H, s), 4.79 (2H, s), 5.27 (2H, s), 6.94 (1H, c), 7.08–7.17 (6H, m), 7.33 (2H, c).

j) 3-Hydroxymethyl-5-{2-[3-(5-hydroxy-5-methylhexyl)phenyl]vinyl}phenol.

A solution of 0.3 ml of concentrated sulphuric acid in 5 ml of methanol is added to 600 mg (1.3 mmol) of 6-{3-[2-(3-ethoxymethoxy-5-ethoxymethoxyphenyl)vinyl]phenyl}2-methylhexan-2-ol in 5 ml of methanol and 5 ml of THF. After 4 hours at room temperature, water and ethyl acetate are added. The organic phase is washed several times with water and then dried over magnesium sulphate and concentrated. The residue is purified on a silica column (ethyl acetate 50-heptane 50).

White crystals m=300 mg. Y=67%. m.p.=108–10° C. $^1$H NMR (CDCl$_3$): 1.20 (6H, s), 1.38–1.54 (4H, m), 1.59–1.71 (2H, m), 2.61–2.67 (2H, t), 4.61 (2H, s), 6.80 (1H, s), 6.90 (1H, s), 7.04–7.08 (4H, m), 7.21–7.29 (3H, m), 8.74 (1H, OH, s).

EXAMPLE 2

3-Hydroxymethyl-5-{2-[2-(6-hydroxy-6-methylphenyl)phenyl]vinyl}phenol a) Methyl 6-{3-[2-(3-ethoxymethoxy-5-ethoxymethoxymethyl)vinyl]phenyl}hexanoate.

In a manner similar to Example 1(h), by reacting 1.3 g (3 mmol) of 3-bromo-[2-(3-ethoxymethoxy-5-ethoxymethoxymethylphenyl)vinyl]phenyl in 10 ml of dimethylformamide with the solution, at 0° C., of 1.4 g (5.7 mmol) of 9-borabicyclo[3.3.1]nonane and 475 mg (3.7 mmol) of methyl hex-5-enoate in 15 ml of THF, a yellow oil (m=1.08 g; Y=74%) is obtained, after purification on a silica column (ethyl acetate 8-heptane 92).

$^1$H NMR (CDCl$_3$): 1.21–1.28 (6H, m), 1.64–1.67 (2H, m), 1.85 (4H, m), 2.29–2.35 (2H, t), 2.60–2.66 (2H, t), 3.66 (3H, s), 3.63–3.79 (4H, m), 4.60 (2H, s), 4.79 (2H, s), 5.26 (2H, s), 6.94 (1H, s), 7.08–7.16 (5H, m), 7.23–7.32 (3H, m).

b) 7-{3-[2-(3-Ethoxymethoxy-5-ethoxymethoxymethylphenyl)vinyl]phenyl}-2-methylheptan-2-ol.

In a manner similar to Example 1(i), by reacting 3.8 ml (11.4 mmol) of methylmagnesium bromide 3M/ether with 1.08 g (2.3 mmol) of methyl 6-{3-[2-(3-ethoxymethoxy-5-ethoxymethoxymethylphenyl)vinyl]phenyl}hexanoate in 20 ml of ethyl ether, a yellow oil (m=480 mg; Y=44%) is obtained after purification on a silica column (ethyl acetate 30-heptane 70).

$^1$H NMR (CDCl$_3$): 1.21 (6H, s), 1.22–1.28 (6H, m), 1.40–1.66 (8H, m), 2.60–2.66 (2H, t), 3.63–3.79 (4H, m), 4.60 (2H, s), 4.79 (2H, s), 5.26 (2H, s), 6.93 (1H, s), 7.07–7.16 (5H, s), 7.29–7.32 (3H, m).

c) 3-Hydroxymethyl-5-{2-[3-(6-hydroxy-6-methyl-heptyl)phenyl]vinyl}phenol.

In a manner similar to Example 1(j), by reacting 0.3 ml of concentrated sulphuric acid in 5 ml of methanol with 470 mg (1.0 mmol) of 7-{3-[2-(3-ethoxymethoxy-5-ethoxymethoxymethylphenyl)vinyl]phenyl}-2-methylheptan-2-ol in 5 ml of methanol and 5 ml of THF, a colourless oil (m=109 mg; Y=31%) is obtained after purification on a silica column (ethyl acetate 40-heptane 60).

$^1$H NMR (CDCl$_3$): 1.21 (6H, s), 1.39–1.66 (8H, m) 2.59–2.65 (2H, t), 4.66 (2H, s), 6.76 (1H, s), 6.90 (1H, s), 7.03–7.09 (4H, m), 7.26–7.30 (3H, m).

EXAMPLE 3

3-[3-(5-Hydroxy-1,5-dimethylhexyl)phenoxymethyl]-5-hydroxymethylphenol a) (3-Ethoxymethoxy-5-ethoxymethoxymethylphenyl)methanol.

135 mg (3.55 mmol) of sodium borohydride are added, in small quantities, to a solution of 1.9 g (7.1 mmol) of 3-ethoxymethoxy-5-ethoxymethoxymethylbenzaldehyde in 30 ml of methanol and 20 ml of THF. After having been stirred for 15 minutes at room temperature, the medium is poured into water and extracted with ethyl acetate. After decantation, the organic phase is dried over magnesium sulphate and concentrated.

Yellow oil. m=1.9 g. Y=100%. $^1$H NMR (CDCl$_3$): 1.19–1.26 (6H, m), 3.61–3.77 (4H, m), 4.57 (2H, s), 4.66 (2H, s), 4.85 (2H, s), 5.23 (2H, s), 6.96–7.00 (3H, m).

b) 1-Bromomethyl-3-ethoxymethoxy-5-ethoxymethoxymethylbenzene.

At 0° C., 6.9 ml (15.4 mmol) of trioctylphosphine are added to a solution of 1.9 g (7 mmol) of (3-ethoxymethoxy-5-ethoxymethoxymethylphenyl)methanol and 5.1 g (15.4 mmol) of carbon tetrabromide in 50 ml of ethyl ether. After 15 minutes at 0° C., ether is added and the medium is washed several times with water. After decantation, the organic phase is dried over magnesium sulphate and concentrated. The residue is purified on a silica column (AcOEt8-heptane 92).

Yellow oil. m=1.5 g. Y=64%. $^1$H NMR (CDCl$_3$): 1.19–1.26 (6H, s), 3.61–3.77 (4H, m), 4.45 (2H, s), 4.54–4.57 (2H, m), 4.76 (2H, s), 5.22 (2H, s), 6.97–7.02 (3H, m).

c) 1-[3-(tert-Butyldimethylsilanyloxy)phenyl]-ethanone.

45.2 g (0.3 mol) of tert-butyldimethylsilane chloride in 250 ml of dimethylformamide are added, dropwise, to a solution of 34 g (0.25 mol) of 3-hydroxyacetophenone in 200 ml of DMF with 38.2 ml (0.27 mol) of triethylamine and 1.2 g (9.8 mmol) of dimethylaminopyridine. The mixture is stirred for 2 hours 30 minutes at room temperature. It is then poured into ice-cold water and extracted with ether. The organic phase is dried over magnesium sulphate and concentrated. The residue is purified on a silica column (dichloromethane 40-heptane 60).

Orange-coloured oil. m=57 g. Y=91%. $^1$H NMR (CDCl$_3$): 0.01 (6H, s), 0.79 (9H, s), 2.38 (3H, s), 6.82–6.85 (1H, dd), 7.06–7.15 (1H, m), 7.20–7.22 (1H, t), 7.33–7.36 (1H, d, J=7.6 Hz).

d) 3-[3-tert-Butyldimethylsilanyloxy)phenyl]but-2-enenitrile.

62 ml (0.38 mol) of diethylcyanomethylphosphonate in 200 ml of THF are added, dropwise, at 0° C., to a solution of 12.2 g (0.38 mol) of sodium hydride in 50 ml of THF. The mixture is stirred for 2 hours at room temperature. 57 g (0.23 mol) of 1-[3-(tert-butyldimethylsilanyloxy)phenyl]ethanone in 200 ml of THF are then added at 0C. The temperature is allowed to rise and the mixture is stirred for 4 hours. After evaporation of the THF, the product is taken up in ethyl ether. The ethereal phase is washed several times with water. After decantation, the organic phase is dried over magnesium sulphate and concentrated. The residue is purified on a silica column (heptane).

Yellow oil. m=58.3 g. Y=94%. $^1$H NMR (CDCl$_3$): 0.01 (6H, s), 0.79 (9H, s), 2.24 (3H, d, J=1 Hz), 5.38–5.39 (1H, d, J=1 Hz), 6.67–6.70 (2H, m), 6.83–6.87 (1H, dd), 7.02–7.08 (1H, m).

e) 3-[3-(tert-Butyldimethylsilanyloxy)phenyl]but-2-enal.

In a manner similar to Example 1(e), by reacting 280 ml of diisobutylaluminium hydride 1M/toluene, at –78° C., with 58.2 g (0.21 mol) of 3-[3-(tert-butyldimethylsilanyloxy)phenyl]but-2-enenitrile, an orange-coloured oil (m=28.5 g; Y=48%) is obtained after purification on a silica column (dichloromethane 50-heptane 50).

$^1$H NMR (CDCl$_3$): 0.01 (6H, s), 0.79 (9H, s), 2.34 (3H, d, J=1.1 Hz), 6.14–6.18 (1H, d, J=6.7 Hz), 6.67–6.71 (1H, dd), 6.79–6.80 (1H, t), 6.92–6.95 (1H, d), 7.03–7.10 (1H, m), 9.96–9.99 (1H, d, J=7.9 Hz).

f) Ethyl 5-[3-(tert-butyldimethylsilanyloxy)phenyl]-hexa-2,4-dienoate.

62 ml (154 mmol) of n-butyllithium 2.5 M/hexane are added, dropwise, at 0° C., to 150 ml of THF and 150 ml of HMPA. Rapidly, at –30° C., 21.5 ml (154 mmol) of diisopropylamine are added, followed, at –60° C. and dropwise, by 28.5 ml (144 mmol) of triethylphosphonoacetate. The mixture is stirred for 1 hour at –60° C. and then a solution of 28.4 g (103 mmol) of 3-[3-(tert-butyldimethylsilanyloxy)phenyl]but-2-enal in 60 ml of THF is added dropwise. The temperature is allowed to rise to room temperature. The solvents are evaporated and the residue is taken up in ethyl ether. The organic phase is extracted with a saturated aqueous ammonium chloride solution and then washed several times with water. After decantation, it is dried over magnesium sulphate and concentrated. The residue is purified on a silica column (heptane).

Orange-coloured oil. m=24 g. Y=67%. $^1$H NMR (CDCl$_3$): 0.21 (6H, s), 0.99 (9H, s), 1.29–1.34 (3H, t), 2.26–2.27 (3H, d), 4.19–4.27 (2H, q), 5.95–6.01 (1H, d, J=15 Hz), 6.79–6.81 (1H, m), 6.93–6.94 (1H, t), 7.06–7.10 (1H, dd), 7.18–7.21 (1H, d), 7.68–7.79 (1H, q).

g) Ethyl 5-[3-(tert-butyldimethylsilanyloxy)phenyl]-hexanoate.

In a reactor, 15 g (43.3 mmol) of ethyl 5-[3-(tert-butyldimethylsilanyloxy)phenyl]hexa-2,4-dienoate are dissolved in 200 ml of ethyl acetate and 800 mg of 5% palladium/carbon are added. The solution is stirred at room temperature and under a hydrogen pressure of 4 bar. 2 hours later, it is filtered on celite and evaporated. The residue is purified on a silica column (ethyl acetate 3-heptane 97).

Yellow oil. m=11.7 g. Y=77%. $^1$H NMR (CDCl$_3$): 0.08 (6H, s), 0.79 (9H, s), 1.01–1.07 (6H, t), 1.32–1.39 (4H, m), 2.03–2.08 (2H, m), 2.40–2.45 (1H, m), 3.86–3.95 (2H, q), 6.45–6.48 (2H, m), 6.56–6.59 (1H, d, J=7.6 Hz), 6.90–6.97 (1H, t).

h) 6-[3-(tert-Butyldimethylsilanyloxy)phenyl]-2-methylheptan-2-ol.

In a manner similar to Example 1(i), by reacting 55 ml (165 mmol) of methylmagnesium bromide 3M/ether with 11.6 g (33 mmol) of ethyl 5-[3-tert-butyldimethylsilanyloxy)phenyl]hexanoate in 100 ml of ether, a yellow oil (m=10.65 g; Y=96%) is obtained.

$^1$H NMR (CDCl$_3$): 0.00 (6H, s), 0.79 (9H, s), 1.01, (3H, s), 1.03–1.08 (3H, d), 1.20–1.39 (6H, m), 2.40–2.48 (1H, m), 6.45–6.47 (2H, m), 6.56–6.59 (1H, d, J=7.6 Hz), 6.90–6.97 (1H, t).

i) 3-(5-Hydroxy-1,5-dimethylhexyl)phenol.

38 ml of tetrabutylammonium fluoride 1M/THF are added to 10.6 g (31.5 mmol) of 6-[3-(tert-butyldimethylsilanyloxy) phenyl]-2-methylheptan-2-ol in 100 ml of THF. The solution is stirred at room temperature. 2 hours later, the solvent is evaporated. The residue is taken up in ethyl ether and washed with water. The organic phase is dried over magnesium sulphate and concentrated. The product is purified on a silica column (ethyl acetate 25-heptane 75).

Yellow oil. m=6 g. Y=85%. $^1$H NMR (CDCl$_3$): 1.17 (6H, s), 1.20–1.23 (3H, d), 1.40–1.66 (6H, m), 2.60–2.69 (1H, m), 5.19 (1H, OH, s), 6.62–6.66 (2H, m), 6.73–6.76 (1H, d, J=7.7 Hz), 7.11–7.17 (1H, t).

j) 6-[3-(3-Ethoxymethoxy-5-ethoxymethoxymethylbenzyloxy)phenyl]-2-methylheptan-2-ol.

A solution of 514 mg (2.3 mmol) of 3-(5-hydroxy-1,5-dimethylhexyl)phenol, 81 mg (2.5 mmol) of sodium hydride 75% in 10 ml of dimethylformamide is stirred for 30 minutes at room temperature. 700 mg (2.1 mmol) of 1-bromomethyl-3-ethoxymethoxy-5-ethoxymethoxymethylbenzene in 5 ml of dimethylformamide are then added. The medium is stirred overnight at room temperature. It is then poured into water and extracted with ether. The organic phase is dried over magnesium sulphate and concentrated. The product is purified on a silica column (ethyl acetate 25-heptane 75).

Yellow oil. m=871 mg. Y=87%. $^1$H NMR (CDCl$_3$): 1.15 (6H, s), 1.19–1.24 (6H, m), 1.39–1.55 (4H, m), 2.62–2.71 (2H, m), 3.61–3.77 (4H, m), 4.59 (2H, s), 4.76 (2H, s), 5.00 (2H, s), 5.23 (2H, s), 6.77–6.80 (3H, m), 6.99 (1H, s), 7.05–7.08 (2H, d), 7.17–7.23 (1H, t).

k) 3-[3-(5-Hydroxy-1,5-dimethylhexyl)phenoxymethyl]-5-hydroxymethylphenol.

In a manner similar to Example 1(j), by reacting 0.4 ml of concentrated sulphuric acid in 5 ml of methanol with 860 mg (1.8 mmol) of 6-[3-(3-ethoxymethoxy-5-ethoxymethoxymethylbenzyloxy)phenyl]-2-methylheptan-2-ol in 5 ml of methanol and 5 ml of THF, after purification on a silica column (ethyl acetate 60-heptane 40), a colourless oil (m=510 mg. Y=79%) is obtained.

$^1$H NMR (CDCl$_3$): 1.14 (6H, s), 1.20–1.23 (3H, d), 1.34–1.57 (6H, m), 2.30 (1H, OH, s), 2.61–2.69 (1H, m), 4.60 (2H, s), 5.02 (2H, s), 6.73–6.78 (5H, s), 6.91 (1H, s), 7.14–7.20 (1H, t)

EXAMPLE 4

6-[3-(3,4-bis-Hydroxymethylbenzyloxy)phenyl]-2-methylhepta-3,5-dien-2-ol a) (2-Hydroxymethyl-5-iodophenyl)methanol.

A solution of 2.55 g (37 mmol) of sodium nitrite in 10 ml of water is added, dropwise, at 0° C., to 5 g (27.6 mmol) of 4-aminophthalic acid in 30 ml of 20% sulphuric acid. This solution is added to 7.26 g (43.7 mmol) of potassium iodide, 7.35 g (38.6 mmol) of copper iodide in 30 ml of 20% sulphuric acid. The stirring is continued for 2 hours at room temperature and then for 3 hours at 50° C. The medium is then poured into ethyl acetate. It is extracted with a saturated aqueous sodium thiosulphate solution and then with a saturated aqueous sodium hydrogen carbonate solution. The aqueous phase is then acidified with hydrochloric acid up to pH 1 and extracted with ethyl acetate. The organic phase is dried over magnesium sulphate and concentrated. The product obtained is dissolved in anhydrous THF and cooled to 0° C. 110 ml of borane 1M/THF are added dropwise. 3 hours later, a solution of 250 ml of a THF/water mixture (1/1) is added very slowly. After decantation, the aqueous phase is extracted with ether. The organic phase is washed several times with water and then dried over magnesium sulphate and concentrated. The residue is purified on a silica column (ethyl acetate 80-heptane 20).

Colourless oil. m=4.9 g. Y=69%. $^1$H NMR (DMSO): 4.56–4.61 (4H, m), 5.25–5.35 (2H, OH, m), 7.28–7.31 (1H, d, J=8 Hz), 7.68–7.72 (1H, dd, J=6.5 Hz, J'=1.5 Hz), 7.84 (1H, s)

b) 4-iodo-1-(tert-Butyldimethylsilanyloxy)-3-(tert-butyldimethylsilanyloxymethyl)phenyl.

In a manner similar to Example 3(c), by reacting 3.86 g (14.6 mmol) of (2-hydroxymethyl-5-iodophenyl)methanol with 5.08 ml of triethylamine, 4.63 g (30.7 mmol) of tert-butyldimethylsilane chloride and 95 mg (0.78 mmol) of dimethylaminopyridine in 30 ml of dimethylformamide, a colourless oil (m=7 g. Y=98%) is obtained.

c) 4-(tert-Butyldimethylsilanyloxy)-3-(tert-butyldimethylsilanyloxymethyl)benzaldehyde.

6.3 ml (15.75 mmol) of n-butyllithium 2.5 M/hexane are added, dropwise, at −78° C., to 7 g (14.2 mmol) of 4-iodo-1-(tert-butyldimethylsilanyloxy)-3-(tert-butyldimethylsilanyloxymethyl)phenyl in 50 ml of THF. 10 minutes later, 1.2 ml (15.6 mmol) of anhydrous dimethylformamide are added. The mixture is allowed to return to room temperature over 1 hour. Water and ether are then added. After decantation, the ethereal phase is extracted with a saturated aqueous ammonium chloride solution and then with water. The organic phase is dried over magnesium sulphate and concentrated. The residue is purified on a silica column (dichloromethane 50-heptane 50).

Yellowish solid. m=3.07 g. Y=55%. $^1$H NMR (CDCl$_3$): 0.00 (12H, s), 0.83 (18H, s), 4.64 (2H, s), 4.69 (2H, s), 7.52–7.56 (1H, d, J=7.8 Hz), 7.66–7.70 (1H, dd, J=7.8 Hz, J'=1.4 Hz), 7.80 (1H, s), 9.89 (1H, s).

d) [4-(tert-Butyldimethylsilanyloxy)-3-(tert-butyldimethylsilanyloxymethyl)phenyl]methanol.

In a manner similar to Example 3(a), by reacting 290 mg (7.6 mmol) of sodium borohydride with 3 g (7.6 mmol) of 4-(tert-butyldimethylsilanyloxy)-3-(tert-butyldimethylsilanyloxymethyl)benzaldehyde in 30 ml of methanol and 20 ml of THF, after purification on a silica column (ethyl acetate 20-heptane 80), a yellow oil (m=2.6 g; Y=87%) is obtained.

$^1$H NMR (CDCl$_3$): 0.00 (6H, s), 0.01 (6H, s), 0.843 (9H, s), 0.849 (9H, s), 4.58–4.60 (2H, d, J=5.8 Hz), 4.651 (2H, s), 4.659 (2H, s), 7.15–7.18 (1H, m), 7.31–7.33 (2H, m).

e) 4-Bromomethyl-1-(tert-butyldimethylsilanyloxy)-2-(tert-butyldimethylsilanyloxymethyl)benzene In a manner similar to Example 3(b), by reacting 4.2 ml (9.4 mmol) of trioctylphosphine, 3.1 g (9.4 mmol) of carbon tetrabromide with 1.7 g (4.3 mmol) of [4-(tert-butyldimethylsilanyloxy)-3-(tert-butyldimethylsilanyloxymethyl)phenyl]methanol in 30 ml of ethyl ether, after purification on a silica column (AcOEt 10-Heptane 90), a yellow oil (m=1.7 g; Y=86%) is obtained.

f) 6-[3-(tert-Butyldimethylsilanyloxy)phenyl]-2-methylhepta-3,5-dien-2-ol.

In a manner similar to Example 1(i), by reacting 31 ml (93 mmol) of methylmagnesium bromide 3M/ether with 8 g (23 mmol) of ethyl 5-[3-tert-butyldimethylsilanyloxy)phenyl] hexa-2,4-dienoate in 100 ml of ether, after purification on a silica column (dichloromethane 70-heptane 30), a yellow oil (m=4.6 g; Y=60%) is obtained.

$^1$H NMR (CDCl$_3$): 0.20 (6H, s), 0.99 (9H, s), 1.39 (6H, s), 2.15 (3H, s), 5.92–5.98 (1H, d, J=15.1 Hz), 6.38–6.42 (1H, d, J=10.9 Hz), 6.58–6.68 (1H, q), 6.73–6.74 (1H, dd), 6.89–6.90 (1H, t), 7.01–7.04 (1H, dd), 7.14–7.20 (1H, t).

g) 3-(5-Hydroxy-1,5-dimethylhexa-1,3-dienyl)phenol.

In a manner similar to Example 3(i), by reacting 16 ml of tetrabutylammonium fluoride 1M/THF with 4.5 g (13.5 mmol) of 6-[3-(tert-butyldimethylsilanyloxy)phenyl]-2-methylhepta-3,5-dien-2-ol in 50 ml of THF, after purification on a silica column (ethyl acetate 30-heptane 70), a yellow oil (m=2.2 g; Y=74%) is obtained.

$^1$H NMR (CDCl$_3$): 1.38 (6H, s), 2.32 (3H, s), 5.90–5.96 (1H, d, J=15 Hz), 6.39–6.44 (1H, d, J=11.5 Hz), 6.57–6.68 (1H, q), 6.73–6.76 (1H, dd), 6.91–6.94 (2H, m), 7.11–7.17 (1H, t), 8.36 (1H, s).

h) 6-{3-[3,4-bis(tert-Butyldimethylsilanyloxymethyl) benzyloxy]phenyl}-2-methylhepta-3,5-dien-2-ol.

In a manner similar to Example 3(j), by reacting 218 mg (1 mmol) of 3-(5-hydroxy-1,5-dimethylhexa-1,3-dienyl) phenol, 39 mg (1.2 mmol) of 75% sodium hydride in 5 ml of dimethylformamide with 460 mg (1 mmol) of 4-bromomethyl-1-(tert-butyldimethylsilanyloxy)-2-(tert-butyldimethylsilanyloxymethyl)benzene in 5 ml of dimethylformamide, after purification on a silica column (ethyl acetate 20-heptane 70), a yellow oil (m=440 mg, Y=74%) is obtained.

$^1$H NMR (CDCl$_3$): –0.007 (6H, s), 0.000 (6H, s), 0.84 (18H, s), 1.29 (3H, s), 4.65–4.66 (4H, d), 4.98 (2H, s), 5.82–5.88 (1H, d), 6.31–6.35 (1H, d), 6.49–6.59 (1H, m), 6.93–6.96 (2H, m), 7.10–7.13 (1H, d), 7.21–7.24 (1H, d), 7.32–7.36 (1H, d), 7.41 (1H, s).

i) 6-[3-(3,4-bis-Hydroxymethylbenzyloxy)phenyl]-2-methylhepta-3,5-dien-2-ol.

In a manner similar to Example 3(i), by reacting 1.6 ml of tetrabutylammonium fluoride 1M/THF with 424 mg (0.71 mmol) of 6-{3-[3,4-bis-(tert-butyldimethylsilanyloxymethyl)benzyloxy]phenyl}-2-methylhepta-3,5-dien-2-ol in 15 ml of THF, after purification on a silica column (ethyl acetate 90-heptane 10), a yellow oil (m=206 mg; Y=79%) is obtained.

$^1$H NMR (CDCl$_3$): 1.38 (6H, s), 2.15 (3H, s), 4.33–4.35 (2H, m), 4.70–4.74 (2H, m), 5.07 (2H, s), 5.92–5.98 (1H, d, J=15 Hz), 6.40–6.44 (1H, d, J=10.9 Hz), 6.58–6.68 (1H, q), 6.82–6.85 (1h, d, J=6.2 Hz), 7.03–7.05 (2H, m), 7.19–7.26 (1H, m), 7.37 (2H, s), 7.45 (1H, s).

EXAMPLE 5

6-[3-(3,4-bis-Hydroxymethylbenzyloxy)phenyl]-2-methylhexan-2-ol a) 3-Bromo-[3,4-bis-(tert-butyldimethylsilanyloxymethyl) benzyloxy]phenyl.

In a manner similar to Example 3(j), by reacting 260 mg (1.5 mmol) of 3-bromophenol, 58 mg (1.8 mmol) of 75% sodium hydride in 5 ml of dimethylformamide with 690 mg (1.5 mmol) of 4-bromomethyl-1-(tert-butyldimethylsilanyloxy)-2-(tert-butyldimethylsilanyloxymethyl)benzene in 10 ml of dimethylformamide, after purification on a silica column (ethyl acetate 7-heptane 93), a yellow oil (m=790 mg; Y=95%) is obtained.

$^1$H NMR (CDCl$_3$): 0.00 (12H, s), 0.84 (18H, s), 4.65–4.66 (4H, d), 4.95 (2H, s), 6.78–6.81 (1H, dd), 6.97–7.07 (3H, m), 7.16–7.18 (1H, d), 7.33–7.39 (2H, m).

b) Methyl 5-{3-[3,4-bis-(tert-Butyldimethylsilanyloxymethyl)benzyloxy] phenyl}pentanoate.

In a manner similar to Example 1(h), by reacting 780 mg (1.4 mmol) of 3-bromo-[3,4-bis-(tert-butyldimethylsilanyloxymethyl)benzyloxy]phenyl in 10 ml of dimethylformamide with the solution, at 0° C., of 750 mg (3 mmol) of 9-borabicyclo[3.3.1]nonane and 230 mg (2 mmol) of methyl pent-4-enoate in 20 ml of THF, after purification on a silica column (ethyl acetate 5-heptane 95), a yellow oil (m=515 mg; Y=62%) is obtained.

$^1$H NMR (CDCl$_3$): 0.000 (s, 6H), 0.006 (s, 6H), 0.84 (s, 18H), 1.55–1.58 (m, 4H), 2.21–2.24 (t, 2H), 2.50–2.53 (t, 2H), 3.57 (s, 3H), 4.65–4.66 (d, 4H), 4.95 (s, 2H), 6.66–6.71 (m, 3H), 7.06–7.12 (t, 1H), 7.21–7.24 (d, 1H), 7.31–7.36 (d, 1H), 7.40 (s, 1H).

c) 6-{3-[3,4-bis-(tert-Butyldimethylsislanyloxymethyl) benzyloxy]phenyl}-2-methylhexan-2-ol.

In a manner similar to Example 1(I), by reacting 1.4 ml (4.2 mmol) of methylmagnesium bromide 3M/ether with 509 mg (0.87 mmol) of 5-{3-[3,4-bis-(tert-butyldimethylsilanyloxymethyl)benzyloxy]-phenyl}pentanoate in 15 ml of ether, a yellow oil (m=503 mg; Y=99%) is obtained.

$^1$H NMR (CDCl$_3$): 0.000 (s, 6H); 0.005 (s, 6H); 0.847 (s, 18H); 1.115 (s, 6H); 1.29–1.56 (m, 6H); 2.47–2.54 (t, 2H); 4.65 (s, 2H); 4.66 (s, 2H); 4.95 (s, 2H); 6.67–6.72 (m, 3H); 7.06–7.12 (t, 1H); 7.21–7.24 (d, 1H); 7.32–7.40 (m, 2H).

d) 6-[3-(3,4-bis-Hydroxymethylbenzyloxy)phenyl]-2-methylhexan-2-ol.

In a manner similar to Example 3(I), by reacting 2 ml of tetrabutylammonium fluoride 1M/THF with 490 mg (0.83 mmol) of 6-{3-[3,4-bis-(tert-butyldimethylsilanyloxymethyl)benzyloxy]phenyl}-2-methylhexan-2-ol in 15 ml of THF, after purification on a silica column (ethyl acetate 90-heptane 10), a yellow oil (m=196 mg; Y=66%) is obtained.

$^1$H NMR $^1$H (CDCl$_3$): 1.17 (s, 6H); 1.31–1.64 (m, 4H); 2.56–2.62 (t, 2H); 3.16–3.18 (m, 2H); 4.71 (s, 2H); 4.72 (s, 2H); 5.05 (s, 2H); 6.77–6.79 (m, 3H); 7.15–7.21 (m, 1H); 7.35–7.41 (m, 3H).

EXAMPLE 6

6-[3-(3,4-bis-Hydroxymethylphenoxymethyl) phenyl]-2-methylheptan-2-ol a) 4-Aminophthalic Acid 1 g (4.73 mmol) of 4-nitrophthalic acid is dissolved in 10 ml of anhydrous ethanol. The solution is stirred at room temperature and degassed under argon. 50 mg of 5% palladium/carbon are added all at once and hydrogen is bubbled through the solution. After 3 hours, the solution is filtered on celite and then evaporated.

Orange-coloured oil. m=820 mg. Y=96%. $^1$H NMR (DMSO): 3.32 (1H, s), 5.95 (1H, s), 6.49–6.53 (2H, m), 7.46–7.50 (1H, d, J=8.8 Hz), 12.33 (2H, COOH, s).

b) Dimethyl 4-Hydroxyphthalate.

A solution of 5 g (27.6 mmol) of 4-aminophthalic acid in 50 ml of 1M sulphuric acid is cooled to 0° C. and a solution of 2.27 g of sodium nitrite in 6 ml of water is then slowly added. After 15 minutes at 0° C., 15 ml of concentrated sulphuric acid are added and the mixture is heated at 100° C., with vigorous stirring, for 1 hour. At room temperature, the reaction medium is extracted with ethyl acetate and washed with water. After decantation, the organic phase is dried over magnesium sulphate and concentrated. The residue is purified on a silica column (dichloromethane 80-methanol 20). It is then dissolved in 100 ml of methanol and refluxed with 2 ml of acetic acid. After the disappearance of the diacid, the methanol is evaporated and the product is taken up in ethyl acetate and washed with water.

M=5.2 g. Y=90%. $^1$H NMR (DMSO): 3.64 (3H, s), 3.67 (3H, s), 6.79–6.86 (2H, m), 7.56–7.60 (1H, d, J=8.4 Hz), 10.51 (1H, OH, s).

c) 1-(3-Chloromethylphenyl)ethanone.

30 ml of methyllithium are added, dropwise, at 0° C., to 4 g (23.4 mmol) of 3-chloromethylbenzoic acid in 250 ml of anhydrous ethyl ether. At the end of the addition, the solution is again stirred at 0° C. for 30 minutes. Water is then slowly added and then the mixture is acidified with hydrochloric acid. The organic phase is washed several times with water, dried over magnesium sulphate and then concentrated. The residue is purified on a silica column (ethyl acetate 5-heptane 95).

M=2.7 g. Y=69%. ¹H NMR (CDCl₃): 2.62 (3H, s), 4.63 (2H, s), 7.44–7.50 (1H, t), 7.59–7.62 (1H, d, J=7.6 Hz), 7.89–7.93 (1H, d, J=6.5 Hz), 7.97 (1H, s).

d) 2-(3-Chloromethylphenyl)-2-methyl[1,3]dioxolane.

In a three-necked flask equipped with a Dean-Stark system, 2.5 g (14.8 mmol) of 1-(3-chloromethylphenyl) ethanone are dissolved in 20 ml of toluene. 4 ml (74 mmol) of ethylene glycol and 250 mg (1.48 mmol) of para-toluenesulphonic acid are added. The mixture is heated under reflux overnight. 200 mg of potassium carbonate are added and the medium is poured into water and extracted with dichloromethane. The organic phase is dried over magnesium sulphate and concentrated. The product is purified on a silica column (ethyl acetate 10-heptane 90).

Oil. m=1.9 g. Y=59%. ¹H NMR (CDCl₃): 1.65 (3H, s), 3.71–3.84 (2H, m), 3.97–4.11 (2H, m), 4.59 (2H, s), 7.32–7.37 (2H, m), 7.42–7.46 (1H, m), 7.50 (1H, s).

e) 4-[3-(2-Methyl-[1,3]dioxolan-2-yl)benzyloxy)phthalate.

A solution of 1.83 g (8.6 mmol) of 2-(3-chloromethylphenyl)-2-methyl-[1,3]dioxolane, 1.9 g (9.03 mmol) of dimethyl 4-hydroxyphthalate, 1.25 g (9.03 mmol) of potassium carbonate and 200 mg of potassium iodide in 75 ml of 2-butanone is heated under reflux. After 3 hours and at room temperature, the mixture is filtered, concentrated and purified on a silica column (ethyl acetate 20-heptane 80).

Colourless oil. m=3.2 g. Y=97%. ¹H NMR (CDCl₃): 1.66 (3H, s), 3.70–3.84 (2H, m), 3.87 (3H, s), 3.91 (3H, s), 4.01–4.11 (2H, m), 5.12 (2H, s), 7.04–7.08 (1H, dd, J=6 Hz, J'=2.6 Hz), 7.16–7.17 (1H, d, J=2.5 Hz), 7.35–7.41 (2H, m), 7.45–7.49 (1H, m), 7.53 (1H, s), 7.79–7.82 (1H, d, J=8.6 Hz).

f) {2-Hydroxymethyl-5-[3-(2-methyl-[1,3]dioxolan-2-yl) benzyloxy]phenyl}methanol.

3.2 g (8.3 mmol) of dimethyl 4-[3-(2-methyl-[1,3]-dioxolan-2-yl)benzyloxy)phthalate are dissolved in 10 ml of THF and 3 ml of toluene. 460 mg (21 mmol) of lithium borohydride are then added and the mixture is heated under reflux for 1 hour 30 minutes. The reaction medium is evaporated and taken up in water, acidified with 1N hydrochloric acid and then extracted with ethyl acetate. The organic phase is dried over magnesium sulphate and concentrated.

Colourless oil. m=2.7 g. Y=99%. ¹H NMR (CDCl₃): 1.66 (3H, s), 3.74–3.80 (2H, m), 4.01–4.10 (2H, m), 5.07 (2H, s), 6.90 (1H, m), 6.99 (1H, m), 7.22 (1H, m), 7.35–7.37 (2H, m), 7.45 (1H, m), 7.54 (1H, s).

g) 1-[3-(3,4-bis-Hydroxymethylphenoxymethyl)phenyl] ethanone.

2.7 g (8.3 mmol) of (2-hydroxymethyl-5-[3-(2-methyl-[1,3]dioxolan-2-yl)-benzyloxyl]phenyl}-methanol and 200 mg (0.8 mmol) of pyridinium para-toluenesulphonic in 5 ml of water and 20 ml of acetone are heated under reflux for 6 hours. At room temperature, the mixture is taken up in ethyl acetate and washed with a saturated aqueous sodium bicarbonate solution. The organic phase is dried over magnesium sulphate and concentrated.

h) 1-{3-[3,4-bis-(tert-Butyldimethylsilanyloxymethyl) phenoxymethyl]phenyl}ethanone.

In a manner similar to Example 3(c), by reacting 3 g (20 mmol) of tert-butyldimethylsilane chloride with 2.3 g (8 mmol) of 1-[3-(3,4-bis-hydroxymethylphenoxymethyl) phenyl]ethanone, 50 mg of dimethylaminopyridine in 3.5 ml (24 mmol) of triethylamine and 50 ml of dimethylformamide, 3 g of a colourless oil are obtained.

¹H NMR (CDCl₃): 0.00 (6H, s), 0.01 (6H, s), 0.84 (9H, s), 0.86 (9H, s), 2.54 (3H, s), 4.57 (2H, s), 4.68 (2H, s), 5.05 (2H, s), 6.72–6.77 (1H, dd, J=5.7 Hz, J'=2.6 Hz), 7.06–7.07 (1H, d, J=2.6 Hz), 7.17–7.20 (1H, m), 7.37–7.43 (1H, t), 7.56–7.59 (1H, d, J=7.6 Hz), 7.82–7.85 (1H, d, J=7.8 Hz), 7.94 (1H, s).

i) Ethyl 5-{3-[3,4-bis-(tert-Butyldimethylsilanyloxymethyl) phenoxymethyl]phenyl}hexa-2,4-dienoate.

2.48 ml (11 mmol) of ethyl 4-(diethoxyphosphoryl)but-2-enoate in 5 ml of THF are added, at 0° C., to a solution of 360 mg (11.25 mmol) of sodium hydride in 5 ml of THF and 10 ml of 1,3-dimethyl-3,4,5,6-tetrahydro-2(1H)-pyrimidinone. The mixture is stirred at 0° C. for 1 hour and then 2.89 g (5.6 mmol) of 1-{3-(3,4-bis-tert-butyldimethylsilanyloxymethyl)phenoxymethyl] phenyl}ethanone in 20 ml of THF are added dropwise. The mixture is kept stirring at room temperature for 24 hours. Water is then added and the mixture is acidified with 1N hydrochloric acid and extracted with dichloromethane. The organic phase is washed with water, dried over sodium sulphate and concentrated. The residue is purified on a silica column (ethyl acetate 5-heptane 95).

Oil. m=1.2 g. Y=36%. ¹H NMR (CDCl₃): 0.00 (6H, s), 0.01 (6H, s), 0.84 (9H, s), 0.86 (9H, s), 1.19 (3H, s), 1.21–1.27 (3H, t), 4.57 (2H, s), 4.68 (2H, s), 5.01 (2H, s), 5.88–5.94 (1H, d, J=15 Hz), 6.48–6.53 (1H, d, J=11.6 Hz), 6.74–6.77 (1H, dd, J=8.3 Hz). 7.08 (1H, d), 7.17–7.20 (2H, m), 7.31 (2H, m), 7.47 (1H, s), 7.62–7.72 (1H, q).

j) Ethyl 5-{3-[3,4-bis-(tert-Butyldimethylsilanyloxymethyl) phenoxymethyl]phenyl}hexanoate 350 mg of 5% rhodium/alumina are added to 750 mg (1.22 mmol) of ethyl 5-{3-[3,4-bis-(tert-butyldimethylsilanyloxymethyl)phenoxymethyl]phenyl}-hexa-2,4-dienoate in 50 ml of ethyl acetate. Hydrogen is bubbled through the medium for 1 hour 30 minutes. The mixture is then filtered on celite and concentrated.

Colourless oil. m=665 mg. Y=88%.

k) 6-{3-[3,4-bis-(tert-Butyldimethylsilanyloxymethyl) phenoxymethyl]phenyl}-2-methylheptan-2-ol.

In a manner similar to Example 1(i), by reacting 0.53 ml (1.6 mmol) of methylmagnesium bromide with 320 mg (0.52 mmol) of ethyl 5-{3-[3,4-bis-(tert-butyldimethylsilanyloxymethyl)phenoxymethyl]-phenyl}hexanoate in 10 ml of THF, after purification on a silica column (ethyl acetate 10-heptane 90), a colourless oil (m=265 mg; Y=85%) is obtained.

¹H NMR (CDCl₃): 0.00 (6H, s), 0.01 (6H, s), 0.85 (9H, s), 0.87 (9H, s), 1.08 (6H, s), 1.15–1.18 (3H, d), 1.15–1.48 (6H, m), 2.63–2.66 (1H, m), 4.58 (2H, s), 4.68 (2H, s), 4.96 (2H, s), 6.73–6.77 (1H, dd, J=5.6 Hz, J'=2.6 Hz), 7.05–7.07 (2H, m), 7.16–7.23 (4H, m).

l) 6-[3-(3,4-bis-Hydroxymethylphenoxymethyl)phenyl]-2-methylheptan-2-ol.

In a manner similar to Example 3(i), by reacting 1.25 ml of tetrabutylammonium fluoride with 250 mg (0.41 mmol) of 6-{3-[3,4-bis-(tert-butyldimethylsilanyloxymethyl) phenoxymethyl]phenyl}-2-methylheptan-2-ol in 7 ml of THF, after purification on a silica column (ethyl acetate 30-heptane 70), a colourless oil (m=130 mg; Y=85%) is obtained.

¹H NMR (CDCl₃): 1.11 (6H, s), 1.22–1.25 (3H, d), 1.16–1.42 (4H, m), 1.51–1.60 (2H, q), 2.66–2.74 (1H, m), 4.63 (2H, s), 4.65 (2H, s), 5.07 (2H, s), 6.83–6.88 (1H, dd, J=5.6 Hz, J'=2.6 Hz), 6.97–6.98 (1H, d, J=2.5 Hz), 7.11–7.14 (1H, d, J=7.26 Hz), 7.20–7.32 (4H, m).

EXAMPLE 7

7-[3-{3,4-bis-Hydroxymethylphenoxymethyl) phenyl]-3-ethyloctan-3-ol a) 7-{3-[3,4-bis-(tert-Butyldimethylsilanyloxymethyl) phenoxymethyl]phenyl}-3-ethyloctan-3-ol.

In a manner similar to Example 1(i), by reacting 370 mg (0.6 mmol) of ethyl 5-{3-[3,4-bis-(tert-butyldimethylsilanyloxymethyl)phenoxymethyl]-phenyl}hexanoate with 1.8 ml (1.8 mmol) of ethylmagnesium bromide, a colourless oil (m=265 mg; Y=70%) is obtained.

¹H NMR (CDCl₃): 0.00 (6H, s), 0.01 (6H, s), 0.70–0.76 (6H, t), 0.84 (9H, s), 0.87 (9H, s), 1.15–1.18 (3H, d), 1.15–1.53 (10H, m), 2.63–2.66 (1H, m), 4.58 (2H, s), 4.69 (2H, s), 4.96 (2H, s), 6.74–6.77 (1H, dd, J=5.6 Hz, J'=2.6 Hz), 7.05–7.07 (2H, m), 7.16–7.22 (4H, m).

b) 7-[3-(3,4-bis-Hydroxymethylphenoxymethyl)phenyl]-3-ethyloctan-3-ol.

In a manner similar to Example 3(i), by reacting 230 mg (0.36 mmol) of 7-{3-[3,4-bis-(tert-butyldimethylsilanyloxymethyl)phenoxymethyl]phenyl}-3-ethyloctan-3-ol with 1.2 ml of tetrabutylammonium fluoride, a colourless oil (m=110 mg; Y=75%) is obtained.

¹H NMR (CDCl₃): 0.75–0.81 (6H, t), 1.22–1.25 (3H, d), 1.22–1.69 (10H, m), 2.66–2.75 (1H, m), 4.64 (2H, s), 4.66 (2H, s), 5.07 (2H, s), 6.84–6.89 (1H, dd, J=5.6 Hz, J'=2.6 Hz), 6.98–6.99 (1H, d, J=2.5 Hz), 7.11–7.14 (1H, d, J=7.3 Hz), 7.21–7.32 (4H, m).

EXAMPLE 8

5-{2-[4-(5-Hydroxy-5-methylhexyl)phenyl]vinyl}-benzene-1,3-diol a) 6-Bromo-2-methylhexan-2-ol.

340 ml (476 mmol) of methylmagnesium bromide 1.4 M/THF are added, dropwise, at −78° C., to a solution of 25 g (120 mmol) of ethyl 5-bromovalerate in 150 ml of THF. The mixture is stirred for 3 hours at a temperature of between −78 and −30° C. At −30° C., a saturated aqueous ammonium chloride solution is added slowly. At room temperature, the medium is extracted with ether. The ethereal phase is washed with water, dried over magnesium sulphate and concentrated. The residue is purified on a silica column (dichloromethane).

Yellow oil. m=21.5 g, Y=92%. ¹H NMR (CDCl₃): 1.23 (6H, s), 1.45–1.59 (4H, m), 1.82–1.93 (2H, m), 3.40–3.45 (2H, t).

b) 2-(5-Bromo-1,1-dimethylpentyloxy)tetrahydropyran.

A solution of 21.5 g (0.11 mol) of 6-bromo-2-methylhexan-2-ol in 150-ml of ethyl ether with 15 ml (0.16 mol) of dihydropyran and 100 mg of para-toluenesulphonic acid is stirred overnight at room temperature. A saturated aqueous sodium bicarbonate solution is then added and the mixture is extracted with ether. The organic phase is washed with water, dried over sodium sulphate and concentrated. The residue is purified on a silica column (dichloromethane 70-heptane 30).

Yellow oil. m=29.2 g. Y=95%.

c) 7-Bromo-2-methylheptan-2-ol.

In a manner similar to Example 8(a), by reacting 160 ml (0.48 mol) of methylmagnesium bromide with 26.8 g (0.12 mol) of ethyl 6-bromohexanoate, a yellowish oil (m=25.2 g; Y=100%) is obtained.

¹H NMR (CDCl₃): 1.21 (6H, s), 1.37–1.50 (6H, m), 1.82–1.93 (2H, m), 3.39–3.44 (2H, t).

d) 2-(6-Bromo-1,1-dimethylhexyloxy)tetrahydropyran.

In a manner similar to Example 8(b), by reacting 14.11 g (0.168 mol) of dihydropyran with 25.2 g (0.12 mol) of 7-bromo-2-methylheptan-2-ol, a yellowish oil (m=34.8 g; Y=90%). is obtained.

¹H NMR (CDCl₃): 1.18–1.20 (6H, d), 1.39–1.90 (14H, m), 3.38–3.44 (2H, t), 3.38–3.48 (1H, m), 3.92–3.96 (1H, m), 4.69–4.71 (1H, d).

e) Ethyl (4-Bromobenzyl)phosphonate.

A solution of 25 g (0.1 mol) of 4-bromobenzyl bromide and 19 ml (0.11 mol) of triethylphosphite is heated at 100° C. for 24 hours. At room temperature, the residue is purified on a silica column (dichloromethane and then ethyl acetate).

Yellow oil. m=31 g. Y=100%. ¹H NMR (CDCl₃): 1.22–1.28 (6H, t), 3.05–3.13 (2H, d), 3.96–4.08 (4H, q), 7.15–7.19 (2H, dd, J=6 Hz, J'=2.4 Hz), 7.42–7.45 (2H, d, J=8 Hz).

f) 3-(Tetrahydropyran-2-yl)-5-(tetrahydropyran-2-yloxy)benzaldehyde.

30.25 ml (0.33 mol) of dihydropyran are added, dropwise, to a solution of 11.5 g (0.083 mol) of 3,5-dihydroxybenzaldehyde and 1.05 g (4.18 mmol) of pyridinium para-toluenesulphonate in 250 ml of dichloromethane. The mixture is stirred for 2 hours at room temperature. The reaction medium is poured into a saturated aqueous sodium hydrogen carbonate solution. The organic phase is washed with water, dried over magnesium sulphate and concentrated. The residue is purified on a silica column (dichloromethane).

Yellow oil. m=22.8 g. Y=90%. ¹H NMR (CDCl₃): 1.57–1.71 (6H, m), 1.83–2.06 (6H, m), 3.60–3.65 (2H, m), 3.83–3.93 (2H, m), 5.46–5.49 (2H, m), 7.02 (1H, s), 7.20–7.21 (2H, c), 9.90 (1H, s).

g) Ethyl (3-Bromobenzyl)phosphonate.

In a manner similar to Example 8(e), by reacting 25.2 g (0.1 mol) of 3-bromobenzyl bromide with 19 ml (0.11 mol) of triethylphosphite, a yellowish oil (m=32.6 g; Y=100%) is obtained.

¹H NMR (CDCl₃): 1.26–1.31 (6H, t), 3.06–3.15 (2H, d), 3.97–4.09 (4H, q), 7.14–7.23 (2H, m), 7.36–7.44 (2H, m).

h) 4-Bromo-{2-[3-(tetrahydropyran-2-yl-5-(tetrahydropyran-2-yloxy)phenyl]vinyl}phenyl.

In a manner similar to Example 1(g), by reacting 157 mg (5.2 mmol) of sodium hydride with a solution of 1.32 g (4.3 mmol) of 3-(tetrahydropyran-2-yl)-5-(tetrahydropyran-2-yloxy)benzaldehyde and 1.59 g (5.2 mmol) of ethyl (4-bromobenzyl)phosphonate in 30 ml of THF, after purification on a silica column (dichloromethane 60-heptane 40), a yellowish oil (m=1.78 g; Y=90%) is obtained. m.p.=77–9° C.

¹H NMR (CDCl₃): 1.57–1.76 (6H, m), 1.83–2.07 (6H, m), 3.60–3.65 (2H, m), 3.88–3.97 (2H, m), 5.44–5.45 (2H, d), 6.72 (1H, s), 6.86 (2H, s), 6.99 (2H, s), 7.32–7.35 (2H, d, J=8.5 Hz), 7.44–7.47 (2H, d, J=8.4 Hz).

i) 3-Bromo-{2-[3-(tetrahydropyran-2-yl)-5-(tetrahydropyran-2-yloxy)phenyl]vinyl}phenyl.

In a manner similar to Example 1(g), by reacting 3.08 g (0.01 mol) of 3-tetrahydropyran-2-yl)-5-(tetrahydropyran-2-yloxy)benzaldehyde and 3.68 g (0.12 mol) of ethyl (3-bromobenzyl)phosphonate with 362 mg (0.012 mol) of sodium hydride, a yellowish oil (m=4.43; Y=96%) is obtained.

¹H NMR (CDCl₃): 1.58–1.77 (6H, m), 1.83–2.07 (6H, m), 3.61–3.65 (2H, m), 3.88–3.97 (2H, m), 5.44–5.45 (2H, m), 6.72 (1H, s), 6.86 (2H, s), 6.92–7.06 (2H, q), 7.17–7.23 (1H, m), 7.34–7.40 (2H, m), 7.63 (1H, s).

j) 2-[5-(4-{2-[3-(Tetrahydropyran-2-yl)-5-(tetrahydropyran-2-yloxy)phenyl]vinyl}phenyl)-1,1-dimethylpentyloxy] tetrahydropyran.

2.17 g (7.8 mmol) of 2-(5-bromo-1,1-dimethylpentyloxy) tetrahydropyran are added, at 35° C., to a solution of 208 mg (8.6 mmol) of magnesium in 8 ml of anhydrous THF with an iodine crystal. The magnesium compound is heated at 35° C. for 4 hours. At room temperature, 1.43 g (3.11 mmol) of 4-bromo-{2-[3-(tetrahydropyran-2-yl)-5-(tetrahydropyran-2-yloxy)phenyl]vinyl}phenyl, 63 mg (0.12 mmol) of (1,2-bis(diphenylphosphino)ethane]dichloronickel and 6 ml of anhydrous ether are added and the mixture is heated at 35° C. overnight. The reaction medium is poured into a saturated aqueous ammonium chloride solution and extracted with ether. The organic phase is washed with water, dried over magnesium sulphate and concentrated. The product is purified on a silica column (ethyl acetate 10-heptane 90).

Yellowish oil. m=1.75 g. Y=97%. $^1$H NMR (CDCl$_3$): 1.18–1.20 (6H, d), 1.26 (6H, s), 1.37–2.05 (24H, m), 2.58–2.64 (2H, t), 3.40–3.45 (1H, m), 3.60–3.65 (2H, m), 3.90–3.97 (3H, m), 4.68 (1H, m), 5.44–5.46 (2H, d), 6.69 (1H, s), 6.86 (2H, s), 6.93–7.09 (2H, q), 7.14–7.17 (2H, d, J=8 Hz), 7.38–7.41 (2H, d, J=8 Hz).

k) 5-{2-[4-(5-Hydroxy-5-methylhexyl)phenyl]vinyl}-benzene-1,3-diol.

A solution of 1.74 g (3 mmol) of 2-[5-(4-{2-[3-(tetrahydropyran-2-yl)-5-(tetrahydropyran-2-yloxy)phenyl]vinyl}phenyl-1,1-dimethylpentyloxy]tetrahydropyran in 50 ml of acetic acid, 25 ml of THF and 12 ml of water is stirred overnight at room temperature. It is then evaporated to dryness and the residue thus obtained is triturated in a mixture of ethyl ether and hexane. After filtration, the product is dried.

White crystals. m=423 mg. Y=55%. m.p.=177–8° C. $^1$H NMR (DMSO): 1.23 (6H, s), 1.53 (4H, m), 1.72 (2H, m), 2.72–2.75 (2H, t), 4.24 (1H, OH, s), 6.33 (1H, s), 6.61 (2H, s), 7.17 (2H, s), 7.34–7.37 (2H, d, J=7.6 Hz), 7.64–7.67 (2H, d, J=7.7 Hz), 9.42 (2H, OH, s).

EXAMPLE 9

5-{2-[4-(5-Hydroxy-5-methylhexyl)phenyl]ethyl}benzene-1,3-diol 414 mg (1.27 mmol) of 5-{2-[4-(5-hydroxy-5-methylhexyl)phenyl]vinyl}benzene-1,3-diol in 40 ml of dioxane and 42 mg of 10% palladium/carbon are placed in a reactor. A hydrogen pressure of 7 bar is exerted for 4 hours at room temperature. The reaction medium is filtered on celite and the filtrate is evaporated. The product is crystallized from an ethyl acetate/hexane mixture.

Whitish powder m=227 mg. Y=69%. m.p.=144–5° C. $^1$H NMR (CDCl$_3$): 1.19 (6H, s), 1.28–1.66 (6H, m), 2.55–2.61 (2H, t), 2.72–2.83 (4H, m), 6.20–6.24 (3H, m), 7.07 (4H, s), 8.12 (2H, OH, s).

EXAMPLE 10

5-{2-[4-(6-Hydroxy-6-methylheptyl)phenyl]vinylbenzene-1,3-diol a) 2-[6-(4-{2-[3-(Tetrahydropyran-2-yl)-5-(tetrahydropyran-2-yloxy)phenyl]vinyl}phenyl)-1,1-dimethylhexyloxy]tetrahydropyran.

In a manner similar to Example 8(j), by reacting 4.33 g (9.42 mmol) of 4-bromo-{2-[3-(tetrahydropyran-2-yl)-5-(tetrahydropyran-2-yloxy)phenyl]vinyl}phenyl in 12 ml of ether with the solution of 630 mg (26 mmol) of magnesium, 7 g (23.8 mmol) of 2-(6-bromo-1,1-dimethylhexyloxy)tetrahydropyran in 20 ml of THF and catalysed with 193 mg (0.36 mmol) of [1,2-bis-(diphenylphosphino)ethane]dichloronickel, a yellowish oil (m=5 g; Y=90%) is obtained.

$^1$H NMR (CDCl$_3$): 1.18–1.20 (6H, d), 1.26–1.63 (20H, m), 1.84–1.87 (4H, m), 1.97–2.01 (2H, m), 2.57–2.63 (2H, t), 3.41–3.45 (1H, m), 3.60–3.65 (2H, m), 3.90–3.97 (3H, m), 4.69 (1H, m), 5.45–5.46 (2H, m), 6.69 (1H, s), 6.86 (2H, s), 6.93–7.09 (2H, q), 7.13–7.17 (2H, d, J=8 Hz), 7.38–7.41 (2H, d, J=8 Hz).

b) 5-{2-[4-(6-Hydroxy-6-methylheptyl)phenyl]vinyl}-benzene-1,3-diol.

In a manner similar to Example 8(k), by reacting 4.98 g (8.4 mmol) of 2-[6-(4-{2-[3-(tetrahydropyran-2-yl)-5-(tetrahydropyran-2-yloxy)phenyl]-vinyl}phenyl)-1,1-dimethylhexyloxy]tetrahydropyran with the solution of 100 ml of acetic acid, 50 ml of THF and 25 ml of water, whitish crystals (m=1.85 g; Y=65%) are obtained. m.p.=158–60° C.

$^1$H NMR (CDCl$_3$): 1.19 (6H, s), 1.35–1.43 (6H, m), 1.63 (2H, m), 2.08 (1H, OH, s), 2.56–2.62 (2H, t), 6.33 (1H, s), 6.52–6.53 (2H, d), 6.86–7.03 (2H, q), 7.12–7.15 (2H, d, J=8 Hz), 7.36–7.39 (2H, d, J=8 Hz), 8.40 (2H, OH, s).

EXAMPLE 11

5-{2-[3-(6-Hydroxy-6-methylheptyl)phenyl]vinyl}-benzene-1,3-diol a) 2-[6-(3-{2-[3-(Tetrahydropyran-2-yl)-5-(tetrahydropyran-2-yloxy)phenyl]vinyl}phenyl}-1,1-dimethylhexyloxy]tetrahydropyran In a manner similar to Example 8(j), by reacting 4.39 g (9.56 mmol) of 3-bromo-{2-[3-(tetrahydropyran-2-yl)-5-(tetrahydropyran-2-yloxy)pheny]vinyl}phenyl in 12 ml of ether with the solution of 630 mg (26 mmol) of magnesium, 7 g (23.8 mmol) of 2-(6-bromo-1,1-dimethylhexyloxy)tetrahydropyran in 20 ml of THF and catalysed by 193 mg (0.36 mmol) of [1,2-bis-(diphenylphosphino)ethane]dichloronickel, a yellowish oil (m=4.5 g; Y=79%) is obtained.

$^1$H NMR (CDCl$_3$): 1.18–1.20 (6H, d), 1.26–1.67 (20H, m), 1.84–1.87 (4H, m), 2.01 (2H, m), 2.58–2.64 (2H, t), 3.41–3.45 (1H, m), 3.61–3.65 (2H, m), 3.90–3.97 (3H, m), 4.69 (1H, m), 5.45–5.46 (2H, m), 6.70 (1H, s), 6.87 (2H, s), 6.96–7.08 (3H, m), 7.21–7.30 (3H, m).

b) 5-{2-[3-(6-Hydroxy-6-methylheptyl)phenyl]vinyl}-benzene-1,3-diol.

In a manner similar to Example 8(k), by reacting 4.50 g (7.6 mmol) of 2-[6-(3-{2-[3-(tetrahydropyran-2-yl)-5-(tetrahydropyran-2-yloxy)phenyl]-vinyl}phenyl)-1,1-dimethylhexyloxy]tetrahydropyran with the solution of 100 ml of acetic acid, 50 ml of THF and 25 ml of water, and after purification on a silica column (ethyl acetate 50-heptane 50), beige crystals (m=1.23 g; Y=48%) are obtained. m.p.=98–100° C.

$^1$H NMR (CDCl$_3$): 1.20 (6H, s), 1.35–1.44 (6H, m), 1.64–1.67 (2H, m), 2.57–2.63 (2H, t), 6.35 (1H, s), 6.55 (2H, s),. 6.96–6.97 (2H, d), 7.03–7.06 (1H, d, J=6.6 Hz), 7.19–7.29 (3H, m), 8.22 (2H, OH, s).

EXAMPLE 12

5-{2-[4-(6-Hydroxy-6-methylheptyl)phenyl]ethyl}benzene-1,3-diol

In a manner similar to Example 9(a), by reacting 1 g (2.9 mmol) of 5-{2-[4-(6-hydroxy-6-methylheptyl)phenyl]vinyl}benzene-1,3-diol with 100 mg of 10% palladium/carbon, whitish crystals (m=728 mg; Y=91%) are obtained. m.p.=128–30° C.

$^1$H NMR (CDCl$_3$): 1.19 (6H, s), 1.33–1.42 (6H, m), 1.61–1.63 (2H, m), 1.99 (1H, OH, s), 2.53–2.59 (2H, t), 2.73–2.86 (4H, m), 6.24 (3H, s), 7.05–7.12 (4H, dd, J=8.8 Hz), 8.08 2H, OH, s).

EXAMPLE 13

5-{2-[3-(6-Hydroxy-6-methylheptyl)phenyl]ethyl)benzene-1,3-diol

In a manner similar to Example 9(a), by reacting 600 mg (1.76 mmol) of 5-{2-[3-(6-hydroxy-6-methylheptyl)phenyl]vinyl}benzene-1,3-diol with 60 mg of 10% palladium/carbon, pinkish crystals (m=368 mg; Y=61%) are obtained. m.p.=102–3° C.

$^1$H NMR (CDCl$_3$): 1.20 (6H, s), 1.23–1.56 (8H, m), 1.99 (1H, OH, s), 2.46–2.52 (2H, t), 2.74–2.82 (4H, m), 6.14–6.18 (3H, m), 6.47 (2H, OH, s), 6.79 (1H, s), 6.92–697 (2H, m), 7.11–7.17 (1H, t).

EXAMPLE 14

2-Hydroxymethyl-4-{2-[3-(5-hydroxy-5-methylhexyl)phenyl]vinyl}phenol a) 4-Bromo-2-hydroxymethylphenol.

In a manner similar to Example 3(a), by reacting 190 mg (5 mmol) of sodium borohydride with 1 g (5 mmol) of 5-bromosalicylilaldehyde in 10 ml of methanol and 15 ml of THF, beige crystals (m=900 mg; Y=89%) are obtained.

$^1$H NMR (CDCl$_3$)+DMSO) 4.47 (1H, OH, s), 4.71 (2H, s), 6.73–6.76 (1H, d, J=9.2 Hz), 7.19–7.22 (2H, m), 8.82 (1H, OH, s).

b) 6-Bromo-2,2-dimethyl-4H-benzo[1,3]dioxin.

59 ml (0.48 mol) of dimethoxypropane and 2 g (0.01 mol) of para-toluenesulphonic acid are added to 42.5 g (0.2 mol) of 4-bromo-2-hydroxymethylphenol in 400 ml of dimethylformamide. The reaction medium is stirred overnight at room temperature. It is poured into ice-cold water and extracted with ether. The organic phase is dried over magnesium sulphate and concentrated. The product is purified on a silica column (dichloromethane).

Yellow oil. m=47.2 g. Y=93%. $^1$H NMR (CDCl$_3$): 1.52 (6H, s), 4.80 (2H, s), 6.68–6.72 (1H, d, J=8.7 Hz), 7.09–7.10 (1H, d, J=2.2 Hz), 7.22–7.27 (1H, m).

c) 2,2-Dimethyl-4H-benzo[1,3]dioxin-6-carbaldehyde.

In a manner similar to Example 4(c), by reacting 49 ml of n-butyllithium 2.5 M/hexane, at −78° C., with 27 g (111 mmol) of 6-bromo-2,2-dimethyl-4H-benzo[1,3]dioxin in 200 ml of THF and 30 minutes later, with 8.5 ml (111 mmol) of dimethylformamide, after purification on a silica column (dichloromethane 70-heptane 30), white crystals (m=7.7 g; Y=36%) are obtained. (Low yield, the product very rapidly becomes degraded). m.p.=49–51° C.

$^1$H NMR (CDCl$_3$): 1.57 (6H, s), 4.90 (2H, s), 6.91–6.94 (1H, d, J=8.4 Hz), 7.55 (1H, t), 7.68–7.72 (1H, dd, J=6.5 Hz, J'=1.9 Hz).

d) 6-[2-(3-Bromophenyl)vinyl]-2,2-dimethyl-4H-benzo[1,3]dioxin.

In a manner similar to Example 1(g), by reacting 78 mg (2.59 mmol) of sodium hydride with 410 mg (2.14 mmol) of 2,2-dimethyl-4H-benzo[1,3]dioxin-6-carbaldehyde and 775 mg (2.52 mmol) of ethyl (3-bromobenzyl)phosphonate in 20 ml of THF, yellowish crystals (m=596 mg; Y=81%) are obtained. m.p.=128–9° C.

$^1$H NMR (CDCl$_3$): 1.56 (6H, s), 4.87 (2H, s), 6.80–6.89 (2H, m), 6.98–7.04 (1H, d, J=16.3 Hz), 7.11 (1H, s), 7.16–7.22 (1H, m), 7.31–7.38 (3H, m), 7.62 (1H, s).

e) 2,2-Dimethyl-6-(2-{3-[5-methyl-5-(tetrahydropyran-2-yloxy)hexyl]phenyl}vinyl)-4H-benzo[1,3]dioxin.

In a manner similar to Example 8(j) by reacting 500 mg (1.45 mmol) of 6-[2-(3-bromophenyl)vinyl]-2,2-dimethyl-4H-benzo[1,3]dioxin in 2 ml of ether with the solution of 97 mg (4 mmol) of magnesium, 2.02 g (7.24 mmol) of 2-(5-bromo-1,1-dimethylpentyloxy)tetrahydropyran in 7 ml of THF and catalysed by 31 mg (0.058 mmol) of [1,2-bis-(diphenylphosphino)ethane]dichloronickel, a yellow oil (m=323 mg; Y=48%) is obtained.

$^1$H NMR (CDCl$_3$): 1.19–1.21 (6H, d), 1.56 (6H, s), 1.48–1.82 (12H, m), 2.60–2.66 (2H, t), 3.43–3.45 (1H, m), 3.91 (1H, m), 4.69 (1H, m), 4.87 (2H, s), 6.79–6.83 (1H, d, J=8.4 Hz), 6.96–6.99 (1H, d, J=7.2 Hz), 7.05–7.07 (1H, d, J=4.95 Hz), 7.12 (1H, s), 7.21–7.35 (4H, m).

f) 2-Hydroxymethyl-4-{2-[3-(5-hydroxy-5-methylhexyl)phenyl]vinyl}phenol.

In a manner similar to Example 8(k), by reacting 313 mg (0.67 mmol) of 2,2-dimethyl-6-(2-{3-[5-methyl-5-(tetrahydropyran-2-yloxy)hexyl]phenyl}vinyl)-4H-benzo [1,3]dioxin in 10 ml of acetic acid, 5 ml of THF and 2.5 ml of water, and after purification on a silica column (ethyl acetate 40-heptane 60), white crystals (m=91 mg; Y=40%) are obtained. m.p.=130–1° C.

$^1$H NMR (CDCl$_3$): 1.01 (6H, s), 1.32 (4H, m), 1.51 (2H, m), 2.50–2.56 (2H, t), 4.04 (1H, OH, s), 4.44–4.46 (2H, d, J=4.4 Hz), 4.98 (1H, OH, m), 6.70–6.74 (1H, d, J=8.3 Hz), 6.88–7.34 (7H, m), 7.50 (1H, s), 9.51 (1H, OH,

EXAMPLE 15

2-Hydroxymethyl-4-{2-[4-(5-hydroxy-5-methylhexyl)phenyl]vinyl}-phenol a) 6-[2-(4-Bromophenyl)vinyl]-2,2-dimethyl-4H-benzo[1,3]dioxin.

In a manner similar to Example 1(g), by reacting 188 mg (6.24 mmol) of sodium hydride with 1 g (5.2 mmol) of 2,2-dimethyl-4H-benzo[1,3]dioxin-6-carbaldehyde and 1.52 g (5.2 mmol of ethyl (4-bromobenzyl)phosphonate in 10 ml of THF, a white solid (m=1.4 g; Y=78%) is obtained.

$^1$H NMR (CDCl$_3$): 1.55 (6H, s), 4.86 (2H, s), 6.79–6.96 (3H, m), 7.03 (1H, s), 7.30–7.33 (3H, m), 7.43–7.46 (2H, d, J=8.5 Hz).

b) 2,2-Dimethyl-6-(2-{4-[5-methyl-5-(tetrahydropyran-2-yloxy)hexyl]phenyl]}vinyl)-4H-benzo[1,3]-dioxin.

In a manner similar to Example 8(j) by reacting 500 mg (1.45 mmol) of 6-[2-(4-bromophenyl)vinyl]-2,2-dimethyl-4H-benzo[1,3]dioxin in 2 ml of ether with the solution of 97 mg (4 mmol) of magnesium, 2.02 g (7.24 mmol) of 2-(5-bromo-1,1-dimethylpentyloxy)tetrahydropyran in 7 ml of THF and catalysed by 31 mg (0.058 mmol) of [1,2-bis-(diphenylphosphino)ethane]dichloronickel, a yellowish solid (m=654 mg; Y=97%) is obtained. m.p.=86–7° C.

$^1$H NMR (CDCl$_3$): 1.18–1.20 (6H, d), 1.50–1.83 (18H, m), 2.58–2.61 (2H, t), 3.45 (1H, m), 3.93 (1H, m), 4.71 (1H, m), 4.87 (2H, m), 6.79–6.82 (1H, m), 6.96 (2H, m), 7.12–7.17 (3H, m), 7.31–7.40 (3H, m).

c) 2-Hydroxymethyl-4-{2-[4-(5-hydroxy-5-methylhexyl) phenyl]vinyl}phenol.

In a manner similar to Example 8(k), by reacting 640 mg (1.38 mmol) of 2,2-dimethyl-6-(2-{4-[5-methyl-5-tetrahydropyran-2-yloxy)hexyl]phenyl]}vinyl)-4H-benzo[1,3]dioxin in 24 ml of the solution (20 ml of acetic acid+10 ml of THF+5 ml of water), a white powder (m=140 mg; r=50%) is obtained. m.p.=139–40° C.

$^1$H NMR (DMSO): 1.11 (6H, s), 1.42 (4H, m), 1.60 (2H, m), 2.57–2.63 (2H, t), 4.14 (1H, s), 4.55–4.57 (2H, d, J=4.6 Hz), 5.09 (1H, OH, m), 6.81–6.84 (1H, d, J=8.3 Hz), 6.98–7.14 (2H, m), 7.21–7.24 (2H, d, J=8.1 Hz), 7.32–7.35 (1H, d, J=8.9 Hz), 7.50–7.53 (2H, d, J=7.8 Hz), 7.60 (1H, s), 9.61 (1H, s).

EXAMPLE 16

2-Hydroxymethyl-4-{2-[3-(6-hydroxy-6-methylheptyl)phenyl]vinyl}phenol a) 2,2-Dimethyl-6-(2-{3-[6-methyl-6-(tetrahydropyran-2-yloxy)heptyl]phenyl}vinyl)-4H-benzo[1,3]dioxin.

In a manner similar to Example 8(j), by reacting 467 mg (1.35 mmol) of 6-[2-(3-bromophenyl)vinyl]-2,2-dimethyl-4H-benzo[1,3]dioxin in 2 ml of ether with the solution of 90 mg (3.71 mmol) of magnesium, 990 mg (3.37 mmol) of 2-(6-bromo-1,1-dimethylhexyloxy)tetrahydropyran in 3.5 ml of THF and catalysed by 29 mg (0.05 mmol) of [1,2-bis (diphenylphosphino)ethane]dichloronickel, a yellowish oil (m=363 mg; Y=56%) is obtained.

$^1$H NMR (CDCl$_3$): 1.18–1.20 (6H, d), 1.56 (6H, s), 1.35–1.83 (14H, m), 2.58–2.64 (2H, t), 3.41–3.45 (1H, m), 3.92–3.96 (1H, m), 4.69 (1H, m), 4.87 (2H, s), 6.79–6.83 (1H, d, J=8.5 Hz), 6.90–7.04 (2H, dd, J=16.3 Hz, J'=7.4 Hz), 7.04–7.07 (1H, m), 7.13 (1H, s), 7.21–7.35 (4H, m).

b) 2-Hydroxymethyl-4-{2-[3-(6-hydroxy-6-methylheptyl) phenyl]vinyl}phenol.

In a manner similar to Example 8(k), by reacting 350 mg (0.73 mmol) of 2,2-dimethyl-6-(2-{3-[6-methyl-6-

(tetrahydropyran-2-yloxy)heptyl]phenyl}vinyl)-4H-benzo[1,3]dioxin in 15 ml of the solution (20 ml of acetic acid+10 ml of THF+5 ml of water), a whitish powder (m=165 mg; Y=70%) is obtained. m.p.=120–22° C.

$^1$H NMR (DMSO): 0.85 (6H, s), 1.12 (6H, m), 1.40 (2H, m), 2.35–2.41 (2H, t), 3.87 (1H, OH, s), 4.29–4.31 (2H, d, J=4.8 Hz), 4.83 (1H, t), 6.55–6.59 (1H, d, J=8.2 Hz), 6.73–7.18 (7H, m), 7.35 (1H, s), 9.36 (1H, s).

EXAMPLE 17

2-Hydroxymethyl-4-{2-[4-(6-hydroxy-6-methylheptyl)phenyl]vinyl}phenol a) 2,2-Dimethyl-6-(2-{4-[6-methyl-6-(tetrahydropyran-2-yloxy)heptyl]phenyl}vinyl)-4H-benzo[1,3]dioxin.

In a manner similar to Example 8(j), by reacting 467 mg (1.35 mmol) of 6-[2-(4-bromophenyl)vinyl]-2,2-dimethyl-4H-benzo[1,3]dioxin in 2 ml of ether with the solution of 90 mg (3.71 mmol) of magnesium, 990 mg (3.37 mmol) of 2-(6-bromo-1,1-dimethylhexyloxy)tetrahydropyran in 3.5 ml of THF and catalysed by 29 mg (0.05 mmol) of [1,2-bis-(diphenylphosphino)ethane]dichloronickel, whitish crystals (m=563 mg; Y=87%) are obtained.

m.p.=72° C. $^1$H NMR (CDCl$_3$): 1.18–1.20 (6H, d), 1.55 (6H, s), 1.25–1.83 (14H, m), 2.56–2.63 (2H, t), 3.41–3.45 (1H, m), 3.92–3.96 (1H, m), 4.69–4.71 (1H, m), 4.87 (2H, s), 6.79–6.82 (1H, d, J=8.5 Hz), 6.88–7.02 (2H, dd, J=16.4 Hz, J'=2.3 Hz), 7.11–7.16 (3H, m), 7.30–7.33 (1H, d, J=8.5 Hz), 7.37–7.40 (2H, d, J=8.1 Hz).

b) 2-Hydroxymethyl-4-{2-[4-(6-hydroxy-6-methylheptyl)phenyl]vinyl}phenol.

In a manner similar to Example 8(k), by reacting 548 mg (1.14 mmol) of 2,2-dimethyl-6-(2-{4-[6-methyl-6-(tetrahydropyran-2-yloxy)heptyl]-phenyl}vinyl)-4H-benzo[1,3]dioxin in 20 ml of the solution (20 ml of acetic acid+10 ml of THF+5 ml of water), a white powder (m=290 mg; Y=72%) is obtained. m.p.=145–6° C.

$^1$H NMR (DMSO): 0.87 (6H, s), 1.13 (6H, m), 1.39 (2H, m), 2.37–2.40 (2H, t), 3.88 (1H, OH, s), 4.30–4.32 (2H, d, J=5.1 Hz), 4.83–4.85 (1H, t), 6.57–6.6 (1H, d, J=8.25 Hz), 6.74–6.89 (2H, m), 6.96–6.99 (2H, d, J=8.2 Hz), 7.07–7.11 (1H, d, J=8.3 Hz), 7.26–7.29 (2H, d, J=8 Hz), 7.35 (1H, s), 9.36 (1H, s).

EXAMPLE 18

2-Hydroxymethyl-4-{2-[3-(5-hydroxy-5-methylheptyl)phenyl]ethyl}phenol

In a manner similar to Example 9(a), by reacting 50 mg (0.147 mmol) of 2-hydroxymethyl-4-{2-[3-(5-hydroxy-5-methylhexyl)phenyl]vinyl}phenol with 10 mg of 10% palladium/carbon, whitish crystals (m=26 mg; Y=52%) are obtained. m.p.=101–4° C.

$^1$H NMR (DMSO): 0.93 (6H, s), 1.23 (4H, m), 1.40 (2H, m), 2.39–2.44 (6H, m), 3.96 (1H, OH, s), 4.32–4/34 (2H, d), 4.78–4.83 (1H, t), 6.51–6.55 (1H, d, J=8.1 Hz), 6.74–7.07 (6H, m), 8.97 (1H, OH, s).

EXAMPLE 19

2-Hydroxy-4-{2-[4-(5-hydroxy-5-methylhexyl)phenyl]-ethyl}phenol

In a manner similar to Example 9(a), by reacting 110 mg (0.32 mmol) of 2-hydroxymethyl-4-{2-[4-(5-hydroxy-5-methylhexyl)phenyl]vinyl}phenol with 30 mg of 10% palladium/carbon, crystals (m=81 mg; Y=74%) are obtained. m.p.=124–6° C.

$^1$H NMR (DMSO): 1.12 (6H, s), 1.42 (4H, m), 1.59 (2H, m), 2.58 (6H, m), 4.52–4.54 (2H, d), 4/98–5.03 (1H, OH, t), 5.84 (1H, s), 6.71–6.74 (1H, d, J=8.1 Hz), 6.94–6.97 (1H, d, J=8.3 Hz), 7.14–7.24 (5H, m), 9.17 (1H, OH, s).

EXAMPLE 20

2-Hydroxymethyl-4-{2-[3-(6-hydroxy-6-methylheptyl)phenyl]ethyl}phenol

In a manner similar to Example 9(a), by reacting 97 mg (0.27 mmol) of 2-hydroxymethyl-4-{2-[3-(6-hydroxy-6-methylheptyl)phenyl]vinyl}phenol with 27 mg of 10% palladium/carbon, yellowish crystals (m=70 mg; Y=73%) are obtained. m.p.=73–5° C.

$^1$H NMR (CDCl$_3$): 1.21 (6H, s), 1.23–1.61 (8H, m), 2.51–2.57 (3H, t), 2.82 (4H, s), 4.80 (2H, s), 6.75–7.00 (6H, m), 7.15–7.21 (1H, t), 7.36 (1H, OH, s).

EXAMPLE 21

2-Hydroxymethyl-4-{2-[4-(6-hydroxy-6-methylheptyl)phenyl]ethyl}phenol

In a manner similar to Example 9(a), by reacting 150 mg (0.42 mmol) of 2-hydroxymethyl-4-{2-[4-(6-hydroxy-6-methylheptyl)phenyl]vinyl}phenol with 42 mg of 10% palladium/carbon, crystals (m=65 mg; Y=43%) are obtained. m.p.=110–1° C.

$^1$H NMR (DMSO): 0.85 (6H, s), 1.10 (6H, m), 1.34 (2H, m), 2.29–2.35 (6H, m), 3.86 (1H, s), 4.24–4.26 (2H, d), 4.70–4.74 (1H, t), 6.43–6.46 (1H, d, J=8.09 Hz), 6.66–6.70 (1H, d, J=8.1 Hz), 6.86–6.96 (5H, s), 8.89 (1H, s).

EXAMPLE 22

2-Hydroxymethyl-5-{2-[4-(5-hydroxy-5-methylhexyl)phenyl]vinyl}phenol a) 2-Hydroxy-4-iodobenzoic Acid.

40 g (1 mol) of sodium hydroxide are added to 55.6 g (0.2 mol) of methyl 4-iodosalicylate in 600 ml of THF, 10 ml of methanol and 10 ml of water. The solution is heated at 40° C. overnight. It is then evaporated. The residue is taken up in water. It is acidified to pH 1 with concentrated hydrochloric acid and extracted with ethyl acetate. The organic phase is washed several times with water, dried over magnesium sulphate and concentrated. The product is triturated in a dichloromethane-hexane mixture and then filtered.

Orange-coloured powder. m=48.53 g. Y=92%. $^1$H NMR (CDCl$_3$): 7.20–7.24 (1H, dd, J=6.8 Hz, J'=1.5 Hz), 7.36–7.37 (1H, d, J=1.5 Hz), 7.52–7.56 (1H, d, J=8.3 Hz), 11.29 (1H, s).

b) 5-Hydroxymethyl-5-iodophenol.

In a manner similar to Example 1(c), by reacting 300 ml of borane 1M THF with 48.45 g (0.183 mol) of 2-hydroxy-4-iodobenzoic acid in one liter of THF, after purification on a silica column (dichloromethane and then ethyl acetate), beige crystals (m=26.82 g; Y=59%) are obtained.

$^1$H NMR (CDCl$_3$): 4.69 (2H, s), 6.80–6.83 (1H, d, J=7.9 Hz), 7.12–7.16 (1H, dd, J=6.3 Hz, J'=1.6 Hz), 7.21–7.22 (1H, d, J=1.6 Hz), 8.94 (1H, s).

c) 7-iodo-2,2-Dimethyl-4H-benzo[1,3]dioxin.

In a manner similar to Example 14(b), by reacting 22.7 g (0.218 mol) of 2,2-dimethoxypropane, 554 mg (2.9 mmol) of para-toluenesulphonic acid with 24.25 g (0.097 mol) of 5-hydroxymethyl-5-iodophenol in 500 ml of DMF, after purification on a silica column (dichloromethane 50-heptane 50), white crystals (m=21.88 g; Y=78%) are obtained. m.p.=50–2° C.

$^1$H NMR (CDCl$_3$): 1.52 (6H, s), 4.77 (2H, s), 6.70 (1H, m), 7.19–7.22 (2H, m).

d) 2,2-Dimethyl-4H-benzo[1,3]dioxin-7-carbaldehyde.

In a manner similar to Example 4(c), by reacting 31 ml of n-butyllithium 2.5 M/hexane, at −78° C., with 20.4 g (70 mmol) of 7-iodo-2,2-dimethyl-4H-benzo[1,3]dioxin in 300 ml of THF and, 30 minutes later, with 6 ml (77 mmol of dimethylformamide, after purification on a silica column (dichloromethane 60-heptane 40), yellowish crystals (m=10.38 g; Y=85%) are obtained. m.p.=53–4° C.

$^1$H NMR (CDCl$_3$): 1.56 (6H, s), 4.90 (2H, s), 7.11–7.14 (1H, d, J=7.8 Hz), 7.31–7.32 (1H, d, J=1.26 Hz), 7.40–7.44 (1H, dd, J=6.4 Hz, J'=1.4 Hz), 9.91 (1H, e) 7-[2-(4-Bromophenyl)vinyl]-2,2-dimethyl-4H-benzo[1,3]dioxin.

In a manner similar to Example 1(g), by reacting 724 mg (24 mmol) of sodium hydride with 3.84 g (20 mmol) of 2,2-dimethyl-4H-benzo[1,3]dioxin-7-carbaldehyde and 7.37 g (24 mmol) of ethyl (4-bromobenzyl)phosphonate in 110 ml of THF, a white solid (m=6.5 g; Y=.94%) is obtained. m.p.=137–9° C.

$^1$H NMR (CDCl$_3$): 1.55 (6H, s), 4.85 (2H, s), 6.93–7.05 (5H, m), 7.32–7.35 (2H, d, J=8.5 Hz), 7.44–7.47 (2H, d, J=8.5 Hz).

f) 2,2-Dimethyl-7-(2-{4-[5-methyl-5-(tetrahydropyran-2-yloxy)hexyl]phenyl}vinyl)-4H-benzo[1,3]dioxin.

In a manner similar to Example 8 (j), by reacting 1.7 g (4.9 mmol) of 7-[2-(4-bromophenyl)vinyl]-2,2-dimethyl-4H-benzo[1,3]dioxin in 6 ml of ether with the solution of 330 mg (13.5 mmol) of magnesium, 3.43 g (12.3 mmol) of 2-(5-bromo-1,1-dimethylpentyloxy)tetrahydropyran in 12 ml of THF and catalysed by 105 mg (0.199 mmol) of [1,2-bis-(diphenylphosphino)ethane]dichloronickel, after purification on a silica column (ethyl acetate 10-heptane 90), white crystals (m=2.02 g; Y=89%) are obtained. m.p.=70–4° C.

$^1$H NMR (CDCl$_3$): 1.11–1.14 (6H, d), 1.49 (6H, s), 1.19–1.76 (12H, m), 2.52–2.58 (2H, t), 3.34–3.38 (1H, m), 3.85–3.89 (1H, m), 4.62–4.64 (1H, m), 4.78 (2H, s), 6.85–7.02 (6H, m), 7.08–7.11 (2H, d, J=8 Hz), 7.32–7.35 (2H, d, J=8 Hz).

g) 2-Hydroxymethyl-5-{2-[4-(5-hydroxy-5-methylhexyl)phenyl]vinyl}phenol.

In a manner similar to Example 8(k), by reacting 2 g (4.3 mmol) of 2,2-dimethyl-7-(2-{4-[5-methyl-5-(tetrahydropyran-2-yloxy)hexyl]phenyl}vinyl-4H-benzo[1,3]dioxin in a solution of 50 ml of acetic acid+25 ml of THF+12.5 ml of water, after purification on a silica column (ethyl acetate 50-heptane 50), a white powder (m=44 mg; Y=3%) is obtained. m.p.=163–5° C.

$^1$H NMR (DMSO): 0.87 (6H, s), 1.18 (4H, m), 1.36 (2H, m), 2.40 (2H, t), 3.89 (1H, s), 4.30 (2H, s), 6.77 (1H, s), 6.88 (3H, m), 6.99–7.02 (2H, d, J=7.6 Hz), 7.08–7.11 (1H, d, J=7.9 Hz), 7.30–7.33 (2H, d, J=7.8 Hz), 9.24 (1H, s).

EXAMPLE 23

6-[3-(3,4-bis-Hydroxymethylbenzyloxy)phenyl]-2-methylheptan-2-ol a) 6-{3-[3-(tert-Butyldimethylsilanyloxymethyl)-4-(1,1,2,2-tetramethylpropoxymethyl)benzyloxy]phenyl}-2-methylheptan-2-ol.

In a manner similar to Example 3(j), by reacting 24 mg (0.1 mmol) of 3-(5-hydroxy-1,5-dimethylhexyl)phenol, 3.4 mg (0.11 mmol) of 80% sodium hydride in 2 ml of dimethylformamide with 50 mg (0.1 mmol) of 4-bromomethyl-1-(tert-butyldimethylsilanyloxy)-2-(tert-butyldimethylsilanyloxymethyl)benzene in 4 ml of dimethylformamide, after purification on a silica column (ethyl acetate 20-heptane 80), a yellow oil (m=50 mg; Y=77%) is obtained.

$^1$H NMR (CDCl$_3$): 0.00 (12H, s), 0.84 (18H, s), 1.06 (6H, s), 1.11–1.14 (3H, d), 1.19–1.48 (6H, m), 2.56–2.58 (1H, m), 4.65 (2H, s), 4.66 (2H, s), 4.95 (2H, s), 6.67–6.71 (3H, m), 7.07–7.13 (1H, m), 7.21–7.25 (1H, d, J=8.4 Hz), 7.32–7.35 (1H, d, J=7.8 Hz), 7.41 (1H, s).

b) 6-[3-(3,4-bis-Hydroxymethylbenzyloxy)phenyl]-2-methylheptan-2-ol.

In a manner similar to Example 3(i), by reacting 50 mg (0.08 mmol) of 6-{3-[3-(tert-butyldimethylsilanyloxymethyl)-4-(1,1,2,2-tetramethylpropoxymethyl)benzyloxy]phenyl}-2-methylheptan-2-ol with 0.17 ml of tetrabutylammonium fluoride 1M/THF, a colourless oil (m=29 mg; Y=94%) is obtained.

$^1$H NMR (CDCl$_3$): 1.11 (6H, s), 1.20–1.23 (3H, d), 1.33–1.56 (6H, m), 2.60–2.69 (1H, m), 3.64 (2H, OH, s), 4.66 (4H, s), 5.04 (2H, s), 6.76–6.78 (3H, m), 7.15–7.38 (4H, m).

EXAMPLE 24

4-[3-(5-Hydroxy-1,5-dimethylhexyl)phenoxymethyl]-2-hydroxymethylphenol a) (2,2-Dimethyl-4H-benzo[1,3]dioxin-6-yl)methanol.

In a manner similar to Example 3(a), by reacting 115 mg (3 mmol) of sodium borohydride with 580 mg (3 mmol) of 2,2-dimethyl-4H-benzol[1,3]dioxin-6-carbaldehyde in 15 ml of methanol and 10 ml of THF, after purification on a silica column (ethyl acetate 30-heptane 70), a white solid (m=500 mg; Y=85%) is obtained. m.p.=42–4° C.

b) 6-Bromomethyl-2,2-dimethyl-4H-benzo[1,3]dioxin.

In a manner similar to Example 3(b), by reacting 2.5 ml (5.6 mmol) of trioctylphosphine, 1.9 g (5.6 mmol) of carbon tetrabromide with 500 mg (2.6 mmol) of (2,2-dimethyl-4H-benzo[1,3]dioxin-6-yl)methanol in 20 ml of ethyl ether, after purification on a silica column (AcOEt 8-heptane 92), a colourless oil (m=445 mg; Y=67%) is obtained.

c) 6-[3-(2,2-Dimethyl-4H-benzo[1,3]dioxin-6-ylmethoxy)phenyl]-2-methylheptan-2-ol.

In a manner similar to Example 3(j), by reacting 44 mg (0.2 mmol) of 3-(5-hydroxy-1,5-dimethylhexyl)phenol, 6.2 mg (0.22 mmol) of 80% sodium hydride in 5 ml of dimethylformamide with 52 mg (0.2 mmol) of 6-bromomethyl-2,2-dimethyl-4H-benzo[1,3]dioxin in 5 ml of dimethylformamide, after purification on a silica column (ethyl acetate 20-heptane 80), a colourless oil (m=43 mg; Y=55%) is obtained.

$^1$H NMR (CDCl$_3$): 1.15 (6H, s), 1.21–1.23 (3H, d), 1.23–1.54 (6H, m), 2.65 (1H, m), 4.86 (2H, s), 4.93 (2H, s), 2H, s), 6.78–6.85 (4H, m), 7.07 (1H, s), 7.20–7.26 (2H, m).

d) 4-[3-(5-Hydroxy-1,5-dimethylhexyl)phenoxymethyl]-2-hydroxymethylphenol.

In a manner similar to Example 8(k), by reacting 43 mg (0.1 mmol) of 6-[3-(2,2-dimethyl-4H-benzo[1,3]dioxin-6-ylmethoxy)phenyl]-2-methylheptan-2-ol in 2 ml of the solution (5 ml of acetic acid+2.5 ml of THF+1.25 ml of water), a colourless oil (m=12 mg; Y=31%) is obtained.

$^1$H NMR (CDCl$_3$): 1.12 (6H, s), 1.19–1.22 (3H, d), 1.32–1.56 (6H, m), 2.59–2.68 (1H, m), 4.81 (2H, s), 4.96 (2H, s), 6.74–6.79 (3H, m), 6.85–6.89 (1H, d, J=8.2 Hz), 7.07 (1H, s), 7.15–7.22 (2H, m), 7.69 (1H, OH, s).

EXAMPLE 25

6-{3-[2-(3,4-bis-Hydroxymethylphenyl)vinyl]phenyl}-2-methylhexan-2-ol a) 3-Bromo-[2-{3,4-bis-(tert-butyldimethylsilanyloxymethyl)phenyl}vinyl]phenyl.

In a manner similar to Example 1(g), by reacting 53 mg (1.8 mmol) of sodium hydride with 600 mg (1.5 mmol) of 4-(tert-butyldimethylsilanyloxy)-3-(tert-butyldimethylsilanyloxymethyl)benzaldehyde and 560 mg (1.8 mmol) of ethyl (3-bromobenzyl)phosphonate in 30 ml of THF, a colourless oil (m=830 mg; Y=100%) is obtained.

$^1$H NMR (CDCl$_3$): 0.00, (6H, s), 0.02 (6H, s), 0.84 (9H, s), 086 (9H, s), 4.64 (2H, s), 4.66 (2H, s), 6.86–7.04 (2H, dd,

J=16.3 Hz, J'=11.6 Hz), 7.08–7.14 (1H, m), 7.24–7.32 (4H, m), 7.48 (1H, s), 7.55 (1H, s).

b) 2-[5-(3-{3,4-bis-(tert-Butyldimethylsilanyloxymethyl) phenyl]vinyl}phenyl)-1,1-dimethylpentyloxy]-tetrahydropyran.

In a manner similar to Example 8(j), by reacting 236 mg (0.43 mmol) of 3-bromo-[2-{3,4-bis(tert-butyldimethylsilanyloxymethyl)phenyl}vinyl]-phenyl in 1 ml of ether with the solution of 29 mg (1.18 mmol) of magnesium, 300 mg (1.07 mmol) of 2-(5-bromo-1,1-dimethylpentyloxy)tetrahydropyran in 2 ml of THF and catalysed by 10 mg (0.019 mmol) of [1,2-bis-(diphenylphosphino)ethane]dichloronickel, after purification on a silica column (ethyl acetate 3-heptane 97), a yellowish oil (m=34 mg; Y=12%) is obtained.

$^1$H NMR (CDCl$_3$): −0.02 (6H, s), 0.00 (6H, s), 0.82 (9H, s), 0.84 (9H, s), 0.84 (9H, s), 1.06–1.08 (6H, d), 1.13–1.70 (12H, m), 2.48–2.54 (2H, t), 3.27–3.36 (2H, m), 3.79 (1H, m), 4.62 (2H, s), 4.64 (2H, s), 6.93–6.97 (3H, m), 7.10–7.19 (3H, m), 7.27 (2H, s), 7.46 (1H, s).

c) [2-Hydroxymethyl-5-(2-{3-[5-methyl-5-(tetrahydropyran-2-yloxy)hexyl]phenyl}vinyl)phenyl] methanol.

In a manner similar to Example 3(i), by reacting 67 mg (0.1 mmol) of 2-[5-(3-{3,4-bis-(tert-butyldimethylsilanyloxymethyl)phenyl]vinyl}phenyl)-1,1-dimethylpentyloxy]tetrahydropyran with 0.2 ml of tetrabutylammonium fluoride 1M/THF, a yellowish oil (m=44 mg; Y=100%) is obtained.

$^1$H NMR (CDCl$_3$): 1.19–1.20 (6H, d), 1.43–1.82 (12H, m), 2.61–2.67 (2H, t), 3.42 (1H, m), 3:91 (1H, m), 4.69 (1H, m), 4.75 (2H, s), 4.78 (2H, s), 7.09 (3H, m), 7.26 (2H, m), 7.29–7.35 (2H, m), 7.42–7.45 (1H, m), 7.51 (1H, s).

d) 6-{3-[2-(3,4-bis-Hydroxymethylphenyl)vinyl]-phenyl}-2-methylhexan-2-ol.

0.09 ml of concentrated sulphuric acid are added to 44 mg (0.1 mmol) of [2-hydroxymethyl-5-(2-{3-[5-methyl-5-(tetrahydropyran-2-yloxy)hexyl]-phenyl}vinyl)phenyl] methanol in 1 ml of THF and 1 ml of water. The solution is heated at 40° C. for 48 hours. Water is added and the mixture is extracted with ether. The organic phase is dried over magnesium sulphate and concentrated. The product is triturated in an ether-hexane mixture and is then filtered and dried.

Whitish crystals. m=15 mg. Y=42%. m.p. 115–7° C. $^1$H NMR (CDCl$_3$): 1.21 (6H, s), 1.49–1.66 (6H, m), 2.62–2.65 (2H, t), 4.74 (2H, s), 4.77 (2H, s), 7.10–7.51 (9H, m).

EXAMPLE 26

7-{4-[2-(3,4-bis-Hydroxymethylphenyl)vinyl] phenyl}-2-methylheptan-2-ol a) 4-Bromo-[2-{3,4-bis(tert-butyldimethylsilanyloxymethyl)phenyl}vinyl]phenyl.

In a manner similar to Example 1(g), by reacting 61 mg (2.03 mmol) of sodium hydride with 667 mg (1.69 mmol) of 4-(tert-butyldimethylsilanyloxy)-3-(tert-butyldimethylsilanyloxymethyl)benzaldehyde and 623 mg (2.03 mmol) of ethyl ($_4$-bromobenzyl)phosphonate in 15 ml of THF, after purification on a silica column (dichloromethane 10-heptane 90), white crystals (m=790 mg; Y=85%) are obtained. m.p.=80–1° C.

$^1$H NMR (CDCl$_3$): 0.00 (6H, s), 0.02 (6H, s), 0.84 (9H, s), 0.86 (9H, s), 4.64 (2H, s), 4.66 (2H, s), 6.88–7.04 (2H, q), 7.25–7.30 (4H, m), 7.35–7.38 (2H, d), 7.48 (1H, s).

b) 2-[6-(4-{2-[3,4-bis(tert-Butyldimethylsilanyloxy-methyl) phenyl]vinyl}phenyl)-1,1-dimethylhexyloxy]-tetrahydropyran.

In a manner similar to Example 8(j), by reacting 390 mg (0.71 mmol) of 4-bromo-[2-{3,4-bis(tert-butyldimethylsilanyloxymethyl)phenyl}vinyl]phenyl in 1 ml of ether with the solution of 48 mg (1.96 mmol) of magnesium, 520 mg (1.77 mmol) of 2-(6-bromo-1,1-dimethylhexyloxy)tetrahydropyran in 2 ml of THF and catalysed by 15 mg (0.028 mmol) of [1,2-bis (diphenylphosphino)ethane]dichloronickel, after purification on a silica column (ethyl acetate 3-heptane 97), a yellowish oil (m=347 mg; Y=72%) is obtained.

$^1$H NMR (CDCl$_3$): 0.00 (6H, s), 0.02 (6H, s), 0.84 (9H, s), 0.87 (9H, s), 1.08–1.10 (6H, d), 1.13–1.74 (14H, m), 2.48–2.54 (2H, t), 3.31–3.39 (1H, m), 3.82 (1H, m), 4.59 (1H, m), 4.64 (2H, s), 4.67 (2H, s), 6.97 (2H, s), 7.04–7.08 (2H, d, J=8 Hz), 7.29–7.34 (4H, m), 7.49 (1H, s).

c) 7-{4-[2-(3,4-bis-Hydroxymethylphenyl)vinyl]-phenyl}-2-methylheptan-2-ol.

In a manner similar to Example 25(d), by reacting 5 drops of concentrated sulphuric acid with 335 mg (0.49 mmol) of 2-[6-(4-{2-[3,4-bis(tert-butyldimethylsilanyloxymethyl) phenyl]vinyl}phenyl)-1,1-dimethylhexyloxy] tetrahydropyran in 5 ml of THF and 5 ml of water, white crystals (m=94 mg; Y=52%) are obtained. m.p. 112–4° C.

$^1$H NMR (CDCl$_3$): 1.20 (6H, s), 1.38 (6H, m), 1.64 (2H, m), 2.61 (2H, t), 4.72 (2H, s), 4.75 (2H, s), 7.06–7.25 (4H, m), 7.347.49 (5H, m).

EXAMPLE 27

6-{4-[2-(3,4-bis-Hydroxymethylphenyl)vinyl]-phenyl}-2-methylhexan-2-ol a) 2-[5-(4-{2-[3,4-bis(tert-Butyldimethylsilanyloxymethyl) phenyl]vinyl}phenyl)-1,1-dimethylpentyloxy] tetrahydropyran.

In a manner similar to Example 8(j), by reacting 375 mg (0.68 mmol) of 4-bromo-[2-{3,4-bis(tert-butyldimethylsilanyloxymethyl)phenyl}vinyl]phenyl in 1 ml of ether with the solution of 46 mg (1.88 mmol) of magnesium, 478 mg (1.71 mmol) of 2-(5-bromo-1,1-dimethylpentyloxy)tetrahydropyran in 2 ml of THF and catalysed by 15 mg of (0.028 mmol) of [1,2-bis (diphenylphosphino)ethane]dichloronickel, after purification on a silica column (ethyl acetate 3-heptane 97), a yellowish oil (m=278 mg; Y=61%) is obtained.

$^1$H NMR (CDCl$_3$): 0.00 (6H, s), 0.02 (6H, s), 0.84 (9H, s), 0.86 (9H, s), 1.08–1.10 (6H, d), 1.18–1.73 (12H, m), 2.49–2.55 (2H, t), 3.36–3.39 (1H, m), 3.81 (1H, m), 4.59 (1H, m), 4.64 (2H, s), 4.67 (2H, s), 6.97 (2H, s), 7.05–7.08 (2H, d, J=8 Hz), 7.29–7.34 (4H, m), 7.48 (1H, s).

b) 6-{4-[2-(3,4-bis-Hydroxymethylphenyl)vinyl]-phenyl}-2-methylhexan-2-ol.

In a manner similar to Example 25(d), by reacting 10 drops of concentrated sulphuric acid with 265 mg (0.4 mmol) of 2-[5-(4-{2-[3,4-bis(tert-butyldimethylsilanyloxymethyl)phenyl]vinyl}phenyl)-1,1-dimethylpentyloxy]tetrahydropyran in 5 ml of THF and 5 ml of water, white crystals (m=73 mg; Y=51%) are obtained. m.p.=102–4° C.

$^1$R NMR (CDCl$_3$): 1.20 (6H, s), 1.47 (4H, m), 1.63 (2H, m), 2.63 (2H, t), 4.72 (2H, s), 4.74 (2H, s), 6.99–7.15 (2H, dd, J=16.5 Hz, J'=5 Hz), 7.15–7.18 (2H, d, J=8 Hz), 7.31–7.34 (1H, m), 7.40–7.44 (3H, d, J=8 Hz), 7.50 (1H, s).

EXAMPLE 28

5-{2-[3-(6-Hydroxy-6-methylheptyl)phenyl]-1-methylvinyl}benzene-1,3-diol a) 1-[3,5-bis(tert-Butyldimethylsilanyloxy)phenyl] ethanone.

In a manner similar to Example 3(c), by reacting 34.7 g (0.22 mmol) of tert-butyldimethylsilane chloride with 15.68 g (0.1 mmol) of 3,5-dihydroxyacetophenone at 611 mg of dimethylaminopyridine in 30.7 ml (0.22 mmol) of triethylamine and 160 ml of dimethylformamide, after purification on a silica column (ethyl acetate 10-heptane 90), an orange oil (m=33 22 g; Y=87%) is obtained.

$^1$H NMR (CDCl$_3$): 0.01 (12H, s), 0.78 (18H, s), 2.33 (3H, s), 6.32–6.33 (1H, t), 6.82 (1H, s), 6.83 (1H, s).

b) 3-Bromo-{2-[3,5-bis(tert-butyldimethylsilanyloxy) phenyl]propenyl}phenyl.

In a manner similar to Example 1(g), by reacting 362 mg (12 mmol) of sodium hydride with 3.8 g (10 mmol) of 1-[3,5-bis(tert-butyldimethylsilanyloxy)phenyl]ethanone and 3.68 g (12 mmol) of ethyl (3-bromobenzyl)phosphonate in 75 ml of THF, after purification on a silica column (ethyl acetate 10-heptane 90), crystals are obtained (m=2.12 g; Y=52%).

$^1$H NMR (CDCl$_3$): 0.00 (12H, s), 0.84 (18H, s), 2.03 (3H, d), 6.14 (3H, s), 6.22 (1H, s), 6.77–6.89 (2H, m), 7.00–7.08 (2H, m).

c) 2-[6-(3-{2-[3,5-bis(tert-Butyldimethylsilanyloxy)phenyl] propenyl}phenyl)-1,1-dimethylhexyloxy]-tetrahydropyran.

In a manner similar to Example 8(j), by reacting 1.04 g (2 mmol) of 3-bromo-{2-[3,5-bis(tert)-butyldimethylsilanyloxy)phenyl]propenyl}phenyl in 2.5 ml of ether with the solution of 134 mg (5.5 mmol) of magnesium, 1.47 g (5 mmol) of 2-(6-bromo-1,1-dimethylhexyloxy)tetrahydropyran in 5 ml of THF and catalysed by 43 mg (0.08 mmol) of [1,2-bis-(diphenylphosphino)ethane]dichloronickel, after purification on a silica column (ethyl acetate 3-heptane 97), a yellowish oil (m=1.08 g; Y=66%) is obtained.

$^1$H NMR (CDCl$_3$): 0.00 (12H, s), 0.85 (18H,s), 1.10–1.76 (20H, m), 2.04 (3H, d), 2.31–2.37 (2H, t), 3.36 (1H, m), 3.84 (1H, m), 4.62 (1H, m), 6.14–6.31 (4H, m), 6.67–6.93 (4H, m).

d) 7-(3-{2-[3,5-bis(tert-Butyldimethylsilanyloxy)phenyl] propenyl}phenyl)-2-methylheptan-2-ol.

In a manner similar to Example 25(d), by reacting 0.28 ml of concentrated sulphuric acid with 1.06 g (1.1 mmol) of 2-[6-(3-{2-[3,5-bis(tert-butyldimethylsilanyloxy)phenyl] propenyl}phenyl)-1,1-dimethylhexyloxy]tetrahydropyran in 25 ml of THF and 25 ml of water, after purification on a silica column (ethyl acetate 10-heptane 90), a yellow oil (m=420 mg; Y=43%) is obtained.

$^1$H NMR (CDCl$_3$): 0.00 (12H, s), 0.85 (18H, s), 1.12 (6H, s), 1.19–1.51 (8H, m), 2.04 (3H, d), 2.31–2.38 (2H, t), 6.14–6.19 (3H, m), 6.31 (1H, s), 6.68–6.79 (3H, m), 6.88–6.94 (1H, t).

e) 5-{2-[3-(6-Hydroxy-6-methylheptyl)phenyl]-1-methylvinyl}benzene-1,3-diol.

In a manner similar to Example 3(i), by reacting 402 mg (0.69 mmol) of 7-(3-{2-[3,5-bis(tert-butyldimethylsilanyloxy)phenyl]propenyl}phenyl)-2-methylheptan-2-ol with 1.4 ml of tetrabutylammonium fluoride 1M/THF, after purification on a silica column (ethyl acetate 40-heptane 60), white crystals (m=176 mg; Y=72%) are obtained. m.p. 113–4° C.

$^1$H NMR (CDCl$_3$): 1.20 (6H, s), 1.20–1.44 (8H, m), 2.12–2.13 (3H, d), 2.33–2.39 (2H, t), 2.89 (1H, OH, s), 6.19–6.20 (2H, d, J=2 Hz), 6.30–6.35 (2H, m), 6.80–6.90 (3H, m), 7.01–7.07 (1H, t), 7.98 (2H, OH, s).

EXAMPLE 29

5-{2-[3-(5-Hydroxy-5-methylhexyl)phenyl] vinyl}benzene-1,3-diol a) 2-[5-(3-{3,5-bis(Tetrahydropyran-2-yloxy)phenyl]-vinyl}phenyl)-1,1-dimethylpentyloxy]tetrahydropyran.

In a manner similar to Example 8(j), by reacting 2.59 g (5.64 mmol) of 3-bromo-{2-[3-(tetrahydropyran-2-yl)-5-(tetrahydropyran-2-yloxy)phenyl]vinyl}phenyl in 7 ml of ether with the solution of 377 mg (15.5 mmol) of magnesium, 3.94 g (14.1 mmol) of 2-(5-bromo-1,1-dimethylpentyloxy)tetrahydropyran in 14 ml of THF and catalysed by 121 mg (0.23 mmol) of [1,2-bis-(diphenylphosphino)ethane]-dichloronickel, after purification on a silica column (ethyl acetate 10-heptane 90), a yellowish oil (m=2.65 g; Y=81%) is obtained.

$^1$H NMR (CDCl$_3$): 1.19–1.21 (6H, d), 1.48–1.63 (18H, m), 1.87–2.01 (6H, m), 2.60–2.66 (2H, t), 3.41–3.45 (1H, m), 3.61–3.65 (2H, m), 3.90–3.97 (3H, m), 4.69 (1H, m), 5.45–5.46 (2H, d), 6.70 (1H, s), 6.87 (2H, s), 7.03–7.08 (3H, m), 7.21–7.30 (3H, m).

b) 5-{2-[3-(5-Hydroxy-5-methylhexyl)phenyl]vinyl}-benzene-1,3-diol.

In a manner similar to Example 25(d), by reacting 0.75 ml of concentrated sulphuric acid with 2.58 g (4.46 mmol) of 2-[5-(3-{3,5-bis(tetrahydropyran-2-yloxy)phenyl] vinyl}phenyl)-1,1-dimethylpentyloxy]tetrahydropyran in 15 ml of THF and 15 ml of water, after purification on a silica column (ethyl acetate 40-heptane 60), white crystals (m=680 mg; Y=47%) are obtained. m.p. 145–7° C.

$^1$H NMR (CDCl$_3$): 1.20 (6H, s), 1.31–1.64 (6H, m), 2.59–2.65 (2H, t), 2.83 (1H, OH, s), 6.34 (1H, s), 6.54 (2H, s), 6.96 (2H, m), 7.04–7.06 (1H, d, J=7 Hz), 7.20–7.36 (3H, m), 8.64 (2H, OH, s).

EXAMPLE 30

5-[3-(6-Hydroxy-6-methylheptyl)phenoxymethyl] benzene-1,3-diol a) Methyl 3,5-Dihydroxybenzoate.

In a manner similar to Example 1(a), by reacting 44 ml (0.8 mol) of concentrated sulphuric acid with 61.65 g (0.4 mol) of 3,5-dihydroxybenzoic acid in 600 ml of methanol, a white powder (m=63.86 g, Y=95%) is obtained. m.p.= 162–3° C.

$^1$H NMR (CDCl$_3$): 3.85 (3H, s), 6.59–6.61 (1H, t), 7.02–7.03 (2H, d), 8.67 (2H, s).

b) 3,5-bis(tert-Butyldimethylsilanyloxy)benzoate.

In a manner similar to Example 3(c), by reacting 126 9 (836 mmol) of tert-butyldimethylsilane chloride with 63.86 g (380 mmol) of methyl 3,5-dihydroxybenzoate, 2.32 g of dimethylaminopyridine in 116.5 ml (836 mmol) of triethylamine and 600 ml of dimethylformamide, after purification on a silica column (dichloromethane 30-heptane 90), a yellow oil (m=113.46 g; Y=75%) is obtained.

$^1$H NMR (CDCl$_3$): 0.00 (12H, s), 0.78 (18H, s), 3.68 (3H, s), 6.31–6.32 (1H, t), 6.91–6.92 (2H, d).

c) [3,5-bis(tert-Butyldimethylsilanyloxy)phenyl]-methanol.

In a manner similar to Example 1(e), by reacting 144 ml of diisobutylaluminium hydride 1M/toluene, at –78° C., with 18.86 g (47 mmol) of methyl 3,5-bis(tert-butyldimethylsilanyloxy)benzoate, a colourless oil (m=16.97 g; Y=98%) is obtained.

$^1$H NMR (CDCl$_3$): 0.00 (12H, s), 0.78 (18H, s), 4.36–4.38 (2H, d), 6.05–6.07 (1H, t), 6.27–6.28 (2H, d).

d) 1-Bromomethyl-3,5-bis(tert-butyldimethylsilanyloxy) benzene.

In a manner similar to Example 3(b), by reacting 45.6 ml (92 mmol) of trioctylphosphine, 33.56 g (101 mmol) of carbon tetrabromide with 16.95 g (46 mmol) of [3,5-bis(tert-butyldimethylsilanyloxy)phenyl]methanol in 300 ml of ethyl ether, after purification on a silica column (dichloromethane 10-heptane 90), a colourless oil (m=15.61 g; Y=79%) is obtained.

$^1$H NMR (CDCl$_3$): 0.00 (12H, s), 0.78 (18H, s), 4.16 (2H, s), 6.05–6.07 (1H, t), 6.28–6.29 (2H, d).

e) 3-Bromo-3,5-bis(tert-butyldimethylsilanyloxy) benzyloxy]phenyl.

1.04 g (7.5 mmol) of potassium carbonate and 166 mg (1 mmol) of potassium iodide are added to a solution of 865 mg (5 mmol) of 3-bromophenol and 3.24 g (7.5 mmol) of 1-bromomethyl-3,5-bis(tert-butyldimethylsislanyloxy) benzene in 80 ml of 2-butanone. The reaction medium is heated for 6 hours under reflux and then stirred at room temperature overnight. It is then poured into a saturated aqueous ammonium chloride solution and extracted with ether. The organic phase is washed with water, dried over magnesium sulphate and concentrated. The residue is purified on a silica column (dichloromethane 15-heptane 85).

Yellowish oil. m=1.09 g. Y=42%. $^1$H NMR (CDCl$_3$): 0.00 (12H, s), 0.78 (18H, s), 4.76 (2H, s), 6.09–6.11 (1H, t), 6.31–6.32 (2H, d), 6.67–6.71 (1H, m), 6.87–6.98 (3H, m).

f) 2-(6-[3-[3,5-bis(tert-Butyldimethylsilanyloxy)benzyloxy]phenyl}-1,1-dimethylhexyloxy)tetrahydropyran.

In a manner similar to Example 8(j), by reacting 1.06 g (2 mmol) of 3-bromo[3,5-bis(tert-butyldimethylsilanyloxy) benzyloxy]phenyl in 2.5 ml of ether with the solution of 135 mg (5.56 mmol) of magnesium, 1.47 g (5 mmol) of 2-(6-bromo-1,1-dimethylhexyloxy)tetrahydropyran in 5 ml of THF and catalysed by 45 mg (85 mmol) of [1,2-bis-(diphenylphosphino)ethane]dichloronickel, after purification on a silica column (ethyl acetate 3-heptane 97), a yellow oil (m=793 mg; Y=60%) is obtained.

$^1$H NMR (CDCl$_3$): 0.00 (12H, s), 0.79 (18H, s), 1.00–1.02 (6H, d), 1.08–1.66 (14H, m), 2.35–2.42 (2H, t), 3.23–3.28 (1H, m), 3.74–3.78 (1H, m), 4.51 (1H, m), 4.76 (2H, s), 6.08–6.09 (1H, t), 6.34–6.35 (2H, d), 6.57–6.60 (3H, m), 6.95–7.02 (1H, t).

g) 5-{3-[6-Methyl-6-(tetrahydropyran-2-yloxy)heptyl]-phenoxymethyl}benzene-1,3-diol.

In a manner similar to Example 3(i), by reacting 777 mg (1.18 mmol) of 2-(6-{3-[3,5-bis(tert-butyldimethylsilanyloxy)benzyloxy]phenyl}-1,1-dimethylhexyloxy)tetrahydropyran with 2.4 ml of tetrabutylammonium fluoride 1M/THF, after purification on a silica column (ethyl acetate 30-heptane 70), a yellow oil (m=505 mg; Y=99%) is obtained.

$^1$H NMR (CDCl$_3$): 1.17–1.19 (6H, d), 1.29–1.84 (14H, m), 2.51–2.57 (2H, t), 3.50 (1H, m), 3.96 (1H, m), 4.73 (1H, m), 4.98 (2H, s), 6.29 (1H, s), 6.45 (2H, s), 6.72–6.75 (3H, m), 7.12–7.18 (1H, t).

h) 5-[3-(6-Hydroxy-6-methylheptyl)phenoxymethyl]-benzene-1,3-diol.

In a manner similar to Example 25(d), by reacting 0.07 ml of concentrated sulphuric acid with 505 mg (1.18 mmol) of 5-{3-[6-methyl-6-tetrahydropyran-2-yloxy)heptyl]phenoxymethyl}benzene-1,3-diol in 4 ml of THF and 2 ml of water, after purification on a silica column (ethyl acetate 40-heptane 60), a yellowish paste (m=342 mg; Y=84%) is obtained.

$^1$H NMR (CDCl$_3$): 1.05 (6H, s), 1.30–1.55 (8H, m), 2.50 (2H, m), 4.07 (1H, OH, s), 4.89 (2H, s), 6.12 (1H, s), 6.26 (2H, s), 6.74–6.78 (3H, m), 7.13–7.16 (1H, t).

EXAMPLE 31

5-{2-[3-(7-Hydroxy-7-methyloct-1-enyl)phenyl] vinyl}-benzene-1,3-diol a) Methyl hept-6-Enoate.

320 mg (2.6 mmol) of dimethylaminopyridine and 8 ml (197 mmol) of methanol are added to 4 g (31.2 mmol) of heptenoic acid in 100 ml of dichloromethane. The solution is cooled to 0° C., and 7.2 g (34.9 mmol) of N,N'-dicyclohexylcarbodiimide are added and the mixture is allowed to return to room temperature. After 5 h, the precipitate is filtered, the filtrate is evaporated and taken up in ether. The ethereal phase is washed with 0.5N hydrochloric acid and then with a saturated aqueous sodium hydrogen carbonate solution. After decantation, it is dried over magnesium sulphate and concentrated. The residue is purified on a silica column (dichloromethane); the product is very volatile.

Colourless oil. m=4.1 g. Y=92%. $^1$H NMR: 1.36–1.47 (2H, m), 1.58–1.70 (2H, m), 2.02–2.11 (2H, m), 2.29–2.34 (2H, t), 3.67 (3H, s), 4.93–5.04 (2H, m), 5.71–5.87 (1H, m).

b) Methyl 7-(3-{2-[3,5-bis(Tetrahydropyran-2-yloxy) phenyl]vinyl}phenyl)hept-6-enoate.

In a manner similar to Example 1(h), by reacting 1.41 g (3.07 mmol) of 3-bromo-{2-[3-(tetrahydropyran-2-yl)-5-(tetrahydropyran-2-yloxy)phenyl]vinyl}phenyl in 15 ml of dimethylformamide with the solution, at 0° C., of 8 ml (4 mmol) of 9-borabicyclo[3.3.1]nonane 0.5M/THF and 567 mg (4 mmol) of methyl hept-6-enoate in 6 ml of THF, after purification on a silica column (ethyl acetate 10-heptane 90), a yellow oil (m=971 mg; Y=61%) is obtained.

$^1$H NMR (CDCl$_3$): 1.46–1.93 (20H, m), 3.67 (3H, s), 3.61–3.67 (2H, m), 3.89–3.98 (2H, m), 5.45–5.46 (2H, d), 6.18–6.43 (2H, m), 6.70 (1H, s), 6.87–6.89 (2H, t), 6.97–7.04 (2H, m), 7.20–7.34 (3H, m), 7.45 (1H, s).

c) 8-(3-{2-[3,5-bis(Tetrahydropyran-2-yloxy)phenyl] vinyl}phenyl)-2-methyloct-7-en-2-ol.

In a manner similar to Example 1(i), by reacting 2.2 ml (6.6 mmol) of methylmagnresium bromide 3M/ether with 859 mg (1.65 mmol) of 7-(3-{2-[3,5-bis-(tetrahydropyran-2-yloxy)phenyl]vinyl}phenyl)hept-6-enoate in 10 ml of ether, after purification on a silica column (ethyl acetate 20-heptane 80), a yellow oil (m=306 mg; Y=36%) is obtained.

$^1$H NMR (CDCl$_3$): 1.22 (6H, s), 1.46–1.87 (20H, m), 3.61–3.67 (2H, m), 3.89–3.98 (2H, m), 5.45–5.46 (2H, m), 6.20–6.43 (2H, m), 6.70 (1H, s), 6.87–6.88 (2H, m), 7.04–7.06 (2H, m), 7.21–7.34 (3H, m), 7.45 (1H, s).

d) 5-{2-[3-(7-Hydroxy-7-methyloct-1-enyl)phenyl]-vinyl}benzene-1,3-diol.

In a manner similar to Example 25(d), by reacting 0.037 ml of concentrated sulphuric acid with 374 mg (0.72 mmol) of 8-(3-{2-[3,5-bis(tetrahydropyran-2-yloxy)phenyl] vinyl}phenyl)-2-methyloct-7-en-2-ol in 4 ml of THF and 2 ml of water, after purification on a silica column (ethyl acetate 40-heptane 60), a beige powder (m=40 mg; Y=16%) is obtained. m.p.=152–4° C.

$^1$H NMR (CDCl$_3$): 1.21 (6H, s), 1.48 (6H, m), 2.24–2.26 (2H, m), 2.36 (1H, OH, s), 6.23–6.42 (3H, m), 6.53–6.54 (2H, d), 6.97 (2H, d), 7.23–7.29 (3H, m), 7.42 (1H, s), 8.57 (2H, OH, s).

EXAMPLE 32

5-{2-[3-(7-Hydroxy-7-methyloctyl)phenyl] vinyl}benzene-1,3-diol a) Methyl 7-(3-{2-[3,5-bis-(Tetrahydropyran-2-yloxy) phenyl]vinyl}phenyl)heptanoate.

In a manner similar to Example 1(h), by reacting 1.51 g (3.28 mmol) of 3-bromo-{2-[3-(tetrahydropyran-2-yl)-5-(tetrahydropyran-2-yloxy)phenyl]-vinyl}phenyl in 15 ml of dimethylformamide with the solution at 0° C., 9.85 ml (4.92 mmol) of 9-borabicyclo[3.3.1]nonane 0.5 M/THF and 520 mg (3.61 mmol) of methyl hept-6-enoate in 5 ml of THF, after purification on a silica column (ethyl acetate 20-heptane 80), a yellow oil (m=1.75 g; Y=100%) is obtained.

$^1$H NMR (CDCl$_3$): 1.34–1.92 (22H, m), 2.57–2.64 (2H, t), 3.66 (3H, s), 3.61–3.66 (2H, m), 3.89–3.98 (2H, m), 5.45–5.46 (2H, d), 6.69–6.70 (1H, d), 6.87–6.88 (2H, t), 7.03–7.10 (3H, m), 7.21–7.35 (3H, m).

b) 8-(3-{2-(3,5-bis(Tetrahydropyran-2-yloxy)phenyl]-vinyl}phenyl)-2-methyloctan-2-ol.

In a manner similar to Example 1(i), by reacting 4.45 ml (13.3 mmol) of methylmagnesium bromide 3M/ether with 1.73 g (3.31 mmol) of methyl 7-(3-{2-[3,5-bis (tetrahydropyran-2-yloxy)phenyl]-vinyl}phenyl)heptanoate in 20 ml of ether, after purification on a silica column (ethyl acetate 20-heptane 80), a yellow oil (m=1.2 g; Y=69%) is obtained.

¹H NMR (CDCl₃): 1.20 (6H, s), 1.28–1.87 (22H, m), 2.57–2.60 (2H, t), 3.65 (2H, m), 3.93 (2H, m), 5.46 (2H, m), 6.50–6.78 (2H, m), 6.88 (1H, s), 6.98–7.08 (3H, m), 7.25–7.29 (3H, m).

c) 5-{2-[3-(7-Hydroxy-7-methyloctyl)phenyl]vinyl}-benzene-1,3-diol.

In a manner similar to Example 25(d), by reacting 0.06 ml of concentrated sulphuric acid with 1.15 g (2.21 mmol) of 8-(3-{2-[3,5-bis(tetrahydropyran-2-yloxy)phenyl]vinyl}phenyl)-2-methyloctan-2-ol in 20 ml of THF and 10 ml of water, after purification on a silica column (ethyl acetate 40-heptane 60), pinkish crystals (m=331 mg; Y=42%) are obtained.

m.p.=127–8° C. ¹H NMR (CDCl₃): 1.16 (6H, s), 1.40 (8H, m), 1.70 (2H, m), 2.66–2.69 (2H, t), 4.16 (1H, OH, s), 6.27 (1H, s), 6.55 (2H, s), 7.13–7.20 (3H, m), 7.33–7.39 (1H, t), 7.47–7.51 (2H, m), 9.37 (2H, OH, s).

EXAMPLE 33

4-{2-[3-(6-Hydroxy-6-methylheptyl)phenyl]vinyl}benzene-1,2-diol a) 3,4-bis(tert-Butyldimethylsilanyloxy)benzaldehyde.

In a manner similar to Example 3(c), by reacting 68.36 g (0.44 mol) of tributyldimethylsilane chloride with 27.62 g (0.2 mol) of 3,4-dihydroxybenzaldehyde, 1.23 g of dimethylaminopyridine in 61.5 ml (0.44 mmol) of triethylamine and 900 ml of dimethylformamide, after purification on a silica column (ethyl acetate 5-heptane 95), an orange-coloured oil (m=69.82 g; Y=95%) is obtained.

¹H NMR (CDCl₃): 0.01 (6H, s), 0.02 (6H, s), 0.79 (18H, s), 6.72–6.75 (1H, dd, J=5 Hz, J'=1.9 Hz), 7.14–7.18 (2H, m), 9.60 (1H, s).

b) 3-Bromo-[2-{3,4-bis-(tert-butyldimethylsilanyloxy)phenyl}vinyl]phenyl

In a manner similar to Example 1(g), by reacting 543 mg (18 mmol) of sodium hydride with 5.5 g (15 mmol) of 3,4-bis(tert-butyldimethylsilanyloxy)benzaldehyde and 5.53 g (18 mmol) of ethyl (3-bromobenzyl)phosphonate in 120 ml of THF, after purification on a silica column (dichloromethane 10-heptane 90), a colourless oil (m=5.38 g; Y=69%) is obtained.

¹H NMR (CDCl₃): 0.20 (6H, s), 0.21 (6H, s), 0.99 (9H, s), 1.01 (9H, s), 6.76–6.83 (2H, m), 6.94–7.00 (3H, m), 7.15–7.25 (1H, m), 7.32–7.39 (2H, m), 7.61–7.62 (1H, m).

c) 2-[6-(3-{2-[3,4-bis(tert-Butyldimethylsilanyloxy)phenyl]vinyl}phenyl)-1,1-dimethylhexyloxy]-tetrahydropyran.

In a manner similar to Example 8(j), by reacting 1.73 g (3.32 mmol) of 3-bromo-[2-{3,4-bis(tert-butyldimethylsilanyloxy)phenyl}vinyl]phenyl in 4 ml of ether with the solution of 222 mg (9.13 mmol) of magnesium, 2.43 g (8.3 mmol) of 2-(6-bromo-1,1-dimethylhexyloxy)tetrahydropyran in 8 ml of THF and catalysed by 72 mg (0.14 mmol) of [1,2-bis-(diphenylphosphino)ethane]dichloronickel, after purification on a silica column (ethyl acetate 3-heptane 97), a colourless oil (m=1.4 g; Y=65%) is obtained.

¹H NMR (CDCl₃): 0.21 (6H, s), 0.23 (6H, s), 0.99 (9H, s), 1.01 (9H, s), 1.18–1.20 (6H, d), 1.26–1.83 (14H, m), 2.58–2.64 (2H, t), 3.38–3.47 (1H, m), 3.92–3.98 (1H, m), 4.69–4.71 (1H, m), 6.78–7.06 (6H, m), 7.20–7.32 (3H, m).

d) 4-{2-[3-(6-Hydroxy-6-methylheptyl)phenyl]vinyl}-benzene-1,2-diol.

In a manner similar to Example 25(d), by reacting 0.118 ml of concentrated sulphuric acid with 1.38 g (2.11 mmol) of 2-[6-(3-{2-[3,4-bis(tert-butyldimethylsilanyloxy)phenyl]vinyl}phenyl)-1,1-dimethylhexyloxy]tetrahydropyran in 20 ml of THF and 10 ml of water, after purification on a silica column (ethyl acetate 45-heptane 55), a solid having a cottony appearance (m=522 mg; Y=77%) is obtained.

m.p.=138–9° C. ¹H NMR (CDCl₃): 1.20 (6H, s), 1.37–1.44 (6H, m), 1.62–1.68 (2H, m), 2.58–2.64 (2H, t), 6.82–6.95 (4H, m), 7.01–7.08 (2H, m), 7.19–7.30 (3H, m), 7.58 (1H, OH, s), 7.69 (1H, OH, s).

EXAMPLE 34

3-{2-[3-(6-Hydroxy-6-methylheptyl)phenyl]vinyl}phenol a) 3-(tert-Butyldimethylsilanyloxy)benzaldehyde.

In a manner similar to Example 3(c), by reacting 42.72 g (0.275 mol) of tert-butyldimethylsilane chloride with 30.53 g (0.2 mol) of 3-hydroxybenzaldehyde, 1.52 g of dimethylaminopyridine in 38.5 ml (0.275 mmol) of triethylamine and 300 ml of dimethylformamide, after purification on a silica column (dichloromethane 20-heptane 80), a yellow oil (m=55.86 g; Y=95%) is obtained.

¹H NMR (CDCl₃): 0.20 (6H, s), 0.98 (9H, s) 7.06–7.10 (1H, m), 7.24–7.48 (3H, m), 9.93 (1H, s).

b) {3-[2-(3-Bromophenyl)vinyl]phenoxy}-tert-butyldimethylsilane.

In a manner similar to Example 1(g), by reacting 543 mg (18 mmol) of sodium hydride with 3.55 g (15 mmol) of 3-(tert-butyldimethylsilanyloxy)benzaldehyde and 5.53 g (18 mmol) of ethyl (3-bromobenzyl)phosphonate in 100 ml of THF, after purification on a silica column (dichloromethane 10-heptane 90), a colourless oil (m=3.73 g; Y=64%) is obtained.

¹H NMR (CDCl₃): 0.22 (6H, s), 1.00 (9H, s), 6.74–6.78 (1H, dd, J=4.7 Hz, J'=1.5 Hz), 6.92–7.01 (3H, m), 7.08–7.25 (3H, m), 7.35–7.42 (2H, t), 7.65–7.66 (1H, t).

c) tert-Butyldimethyl-[3-(2-{3-[6-methyl-6-(tetrahydropyran-2-yloxy)heptyl]phenyl}vinyl)phenoxy]silane.

In a manner similar to Example 8(j), by reacting 1.30 g (3.32 mmol) of {3-[2-(3-bromophenyl)vinyl]phenoxy}-tert-butyldimethylsilane in 4 ml of ether with the solution of 222 mg (9.13 mmol) of magnesium, 2.43 g (8.3 mmol) of 2-(6-bromo-1,1-dimethylhexyloxy)tetrahydropyran in 8 ml of THF and catalysed by 72 mg (0.14 mmol) of [1,2-bis-(diphenylphosphino)ethane]dichloronickel, after purification on a silica column (ethyl acetate 3-heptane 97), a colourless oil (m=1.28 g; Y=74%) is obtained.

¹H NMR (CDCl₃): 0.22 (6H, s), 1.00 (9H, s), 1.18–1.20 (6H, d), 1.25–1.83 (14H, m), 2.59–2.65 (2H, t), 3.38–3.47 (1H, m), 3.92–3.98 (1H, m), 4.69–4.71 (1H, m), 6.71–6.76 (1H, dd), 6.97–6.99 (1H, t), 7.06–7.34 (6H, m).

d) 3-{2-[3-(6-Hydroxy-6-methylheptyl)phenyl]vinyl}-phenol.

In a manner similar to Example 25(d), by reacting 0.133 ml of concentrated sulphuric acid with 1.25 g (2.39 mmol) of tert-butyldimethyl-[3-(2-{3-[6-methyl-6-(tetrahydropyran-2-yloxy)heptyl]phenyl}-vinyl)phenoxy]silane in 20 ml of THF and 10 ml of water, after crystallization from a heptane/ethyl acetate mixture, white crystals (m=697 mg; Y=90%) are obtained. m.p.=96–7° C.

¹H NMR (CDCl₃): 1.22 (6H, s), 1.31–1.45 (6H, m), 1.60–1.70 (2H, m), 2.59–2.65 (2H, t), 5.46 (1H, OH, s), 6.71–6.75 (1H, dd, J=6.2 Hz, J'=1.7 Hz), 6.99–7.08 (5H, m), 7.18–7.33 (4H, m).

EXAMPLE 35

6-{3-[2-(3,5-bis-Hydroxymethylphenyl)vinyl]phenyl}-2-methylhexan-2-ol a) 5-Bromoisophthalic Acid.

33.23 g (0.2 mol) of isophthalic acid and 37.42 g (0.12 mol) of silver sulphate are dissolved in 330 ml of sulphuric acid. 13.3 ml (0.26 mol) of bromine are then added over 1 h. The solution is heated at 55° C. for 24 h. The medium is then poured into ice, the insoluble material is filtered and taken up in ethyl acetate. The remaining solid is taken up in water and basified with a saturated aqueous sodium hydrogen carbonate solution. The insoluble material is filtered and the filtrate is acidified and then extracted with ethyl acetate. The organic phase is washed with water and then dried over magnesium sulphate and concentrated.

White powder. m=42.1 g. Y=86%. m.p.=285–7° C. $^1$H NMR (DMSO): 8.40 (2H, s), 8.57 (1H, t), 13.76 (2H, COOH, s).

b) (3-Bromo-5-hydroxymethylphenyl)methanol.

In a manner similar to Example 1(c), by reacting 690 ml of boran 1M/THF with 42.06 g (0.172 mol) of 5-bromoisophthalic acid in 420 ml of THF, after trituration in heptane, a white powder (m=28.19 g; Y=76%) is obtained. m.p.=85–8° C.

$^1$H NMR (DMSO): 4.65 (4H, s), 5.48 (2H, OH, s), 7.41 (1H, s), 7.52 (2H, s).

c) 1-Bromo-3,5-bis-(tert-butyldimethylsilanyloxymethyl) benzene.

In a manner similar to Example 3(c), by reacting 44.43 g (0.286 mol) of tert-butyldimethylsilane chloride with 28.18 g (0.13 mol) of (3-bromo-5-hydroxymethylphenyl) methanol, 794 mg of dimethylaminopyridine in 40 ml of (0.286 mmol) of triethylamine and 700 ml of dimethylformamide, after purification on a silica column (dichloromethane 10-heptane 90), a yellowish oil (m=50.84 g; Y=98%) is obtained.

$^1$H NMR (CDCl$_3$): 0.00 (12H, s), 0.84 (18H, s), 4.59 (4H, s), 7.10 (1H, s), 7.22 (2H, s).

d) 3,5-bis-(tert-Butyldimethylsilanyloxymethyl) benzaldehyde.

In a manner similar to Example 4(c), by reacting 13.5 ml (33.75 mmol) of n-butyllithium 2.5M/hexane, at −78° C., with 13.4 g (30 mmol) of 1-bromo-3,5-bis-(tert-butyldimethylsilanyloxymethyl)benzene in 140 ml of THF and 30 minutes later, with 2.55 ml (33 mmol) of dimethylformamide, after purification on a silica column (dichloromethane 60-heptane 40), a yellowish oil (m=9.5 g; Y=80%) is obtained.

$^1$H NMR (CDCl$_3$): 0.00 (12H, s), 0.84 (18H, s), 4.68 (4H, s), 7.48 (1H, s), 7.58 (2H, s), 9.89 (1H, s).

e) 3-Bromo-[2-{3,5-bis-(tert-butyldimethylsilanyloxymethyl)phenyl]vinyl}phenyl.

In a manner similar to Example 1(g), by reacting 362 mg (12 mmol) of sodium hydride with 3.95 g (10 mmol) of 3,5-bis-(tert-butyldimethylsilanyloxymethyl)benzaldehyde and 3.61 g (12 mmol) of ethyl (3-bromobenzyl)phosphonate in 80 ml of THF, after purification on a silica column (dichloromethane 10-heptane 90), a yellowish oil (m=4.93 g; Y=90%) is obtained.

$^1$H NMR (CDCl$_3$): 0.00 (12H, s), 0.84 (18H, s), 4.63 (4H, s), 6.84–7.01 (2H, q), 7.05–7.12 (2H, m), 7.21–7.30 (4H, m), 7.52–7.53 (1H, t).

f) Methyl 5-(3-{2-[3,5-bis-(tert-Butyldimethylsilanyloxymethyl)phenyl]vinyl}phenyl) pentanoate.

In a manner similar to Example 1(h), by reacting 1.64 g (3 mmol) of 3-bromo-[2-{3,5-bis-(tert-butyldimethylsilanyloxymethyl)phenyl]vinyl}phenyl in 20 ml of dimethylformamide with the solution, at 0° C., of 9 ml (4.5 mmol) of 9-borabicyclo[3.3.1]nonane 0.5 M/THF and 397 mg (3.3 mmol) of methyl pent-4-enoate in 5 ml of THF, after purification on a silica column (dichloromethane 40-heptane 80), a yellowish oil (m=1.14 g; Y=65%) is obtained.

$^1$H NMR (CDCl$_3$): 0.00 (12H, s), 0.84 (18H, s), 1.37–1.77 (6H, m), 2.50–2.55 (2H, t), 3.54 (3H, s), 4.63 (4H, s), 6.93–6.96 (3H, m), 7.08–7.22 (6H, m).

g) 6-(3-{2-[3,5-bis-(tert-Butyldimethylsilanyloxymethyl) phenyl]vinyl}phenyl)-2-methylhexan-2-ol.

In a manner similar to Example 1(i), by reacting 2.6 ml (7.73 mmol) of methylmagnesium bromide 3M/ether with 1.13 g (1.93 mmol) of methyl 5-(3-{2-[3,5-bis(tert-butyldimethylsilanyloxymethyl)phenyl]-vinyl}phenyl) pentanoate in 10 ml of ether, after purification on a silica column (ethyl acetate 15-heptane 85), a yellow oil (m=886 mg; Y=79%) is obtained.

$^1$H NMR (CDCl$_3$): 0.00 (12H, s), 0.84 (18H, s), 1.09 (6H, s), 1.14–1.60 (6H, m), 2.50–2.56 (2H, t), 4.63 (4H, s), 6.94–6.96 (3H, m), 7.08–7.22 (6H, m).

h) 6-{3-[2-(3,5-bis-Hydroxymethylphenyl)vinyl]-phenyl}-2-methylhexan-2-ol.

In a manner similar to Example 3(i), by reacting 858 mg (1.47 mmol) of 6-(3-{2-[3,5-bis-(tert-butyldimethylsilanyloxymethyl)phenyl]vinyl}phenyl)-2-methylhexan-2-ol with 3.25 ml of tetrabutylammonium fluoride 1M/THF, after purification on a silica column (ethyl acetate), a white paste (m=460 mg; Y=88%) is obtained.

$^1$H NMR (CDCl$_3$): 1.20 (6H, s), 1.37–1.71 (6H, m), 2.61–2.67 (2H, t), 4.69 (4H, s), 7.03–7.17 (3H, m), 7.23–7.34 (4H, m), 7.42 (2H, s).

EXAMPLE 36

3-{2-[3-(7-Hydroxy-7-methyloctyl)phenyl] vinyl}phenol a) Methyl 7-(3-{2-[tert-Butyldimethylsilanyloxy)phenyl] vinyl}phenyl)heptanoate.

In a manner similar to Example 1(h), by reacting 1.17 g (3 mmol) of {3-[2-(3-bromophenyl)vinyl]phenoxy}-tert-butyldimethylsilane in 12 ml of dimethylformamide with the solution at 0° C., of 9 ml (4.5 mmol) of 9-borabicyclo[3.3.1] nonane 0.5 M/THF and 470 mg (3.3 mmol) of methyl hex-5-enoate in 5 ml of THF, after purification on a silica column (dichloromethane 40-heptane 80), a yellowish oil (m=270 mg; Y=20%) is obtained.

$^1$H NMR (CDCl$_3$): 0.22 (6H, s), 1.00 (9H, s), 1.33–1.39 (4H, m), 1.55–1.63 (4H, m), 2.27–2.33 (2H, t), 2.58–2.64 (2H, t), 3.66 (3H, s), 6.72–6.76 (1H, m), 6.97–6.99 (1H, t), 7.08–7.34 (8H, m).

b) 8-(3-{2-[3-(tert-Butyldimethylsilanyloxy)phenyl]-vinyl}phenyl)-2-methyloctan-2-ol.

In a manner similar to Example 1(i), by reacting 0.77 ml (2.29 mmol) of methylmagnesium bromide 3M/ether with 259 mg (0.57 mmol) of methyl 7-(3-{2-[tert-butyldimethylsilanyloxy)phenyl]vinyl}phenyl)heptanoate in 3 ml of ether, after purification on a silica column (ethyl acetate 20-heptane 80), a yellowish paste (m=219 mg; Y=81%) is obtained.

$^1$H NMR (CDCl$_3$): 0.21 (6H, s), 1.00 (9H, s), 1.20 (6H, s), 1.28–1.43 (8H, m), 1.61–1.65 (2H, m), 2.59–2.65 (2H, t), 6.72–6.76 (1H, m), 6.97–6.99 (1H, t), 7.06–7.35 (8H, m)

c) 3-{2-[3-(7-Hydroxy-7-methyloctyl)phenyl]vinyl}-phenol.

In a manner similar to Example 3(i), by reacting 207 mg (0.46 mmol) of 8-(3-{2-[3-(tert-butyldimethylsilanyloxy) phenyl]vinyl}phenyl)-2-methyloctan-2-ol with 0.5 ml of tetrabutylammonium fluoride 1M/THF, after purification on a silica column (ethyl acetate 30-heptane 70), a white powder (m=203 mg; Y=32%) is obtained. m.p.=142–3° C.

$^1$H NMR (DMSO): 1.05 (6H, s), 1.30 (8H, m), 1.59 (2H, m), 2.55–2.61 (2H, t), 4.03 (1H, OH, s), 6.66–6.69 (1H, dd, J=6.3 Hz, J'=1.6 Hz), 6.96–7.28 (7H, m), 7.36–7.39 (2H, d, J=7.7 Hz).

EXAMPLE 37

7-{3-[2-(3,5-bis-Hydroxymethylphenyl)vinyl]phenyl}-2-methylheptan-2-ol a) 2-[6-(3-{2-[3,5-bis-(tert-Butyldimethylsilanyloxymethyl)phenyl]vinyl}phenyl)-1,1-dimethylhexyloxy]-tetrahydropyran.

In a manner similar to Example 8(j), by reacting 2.40 g (4.38 mmol) of 3-bromo-[2-{3,5-bis-(tert-butyldimethylsilanyloxymethyl)phenyl]vinyl}phenyl with the solution of 293 mg (12 mmol) of magnesium, 3.12 g (10.6 mmol) of 2-(6-bromo-1,1-dimethylhexyloxy)tetrahydropyran in 10 ml of THF and catalysed by 94 mg (0.178 mmol) of [1,2-bis-(diphenylphosphino)ethane]-dichloronickel, after purification on a silica column (ethyl acetate 3-heptane 97), a colourless oil (m=2.05 g; Y=69%) is obtained.

$^1$H NMR (CDCl$_3$): 0.00 (12H, s), 0.84 (18H, s), 1.06–1.08 (6H, d), 1.13–1.71 (14H, m), 2.47–2.53 (2H, t), 3.29–3.33 (1H, m), 3.80–3.84 (1H, m), 4.57–4.59 (1H, m), 4.63 (4H, s), 6.94–6.97 (3H, m), 7.08–7.22 (6H, m).

b) 7-{3-[2-(3,5-bis-Hydroxymethylphenyl)vinyl]-phenyl}-2-methylheptan-2-ol.

In a manner similar to Example 25(d), by reacting 0.5 ml of concentrated sulphuric acid with 2.04 g (3 mmol) of 2-[6-(3-{2-[3,5-bis-(tert-butyldimethylsilanyloxymethyl)phenyl]vinyl}phenyl)-1,1-dimethylhexyloxy]tetrahydropyran in 30 ml of THF and 10 ml of water, after purification on a silica column (ethyl acetate 80-heptane 20), white crystals (m=646 mg; Y=58%) are obtained. m.p.=108–9° C.

$^1$H NMR (CDCl$_3$): 1.18 (6H, s), 1.37–1.43 (6H, m), 1.63–1.68 (2H, m), 2.59–2.65 (2H, t), 4.29–4.34 (2H, OH, t), 4.64 (2H, s), 4.67 (2H, s), 7.06–7.11 (3H, m), 7.18–7.30 (4H, m), 7.42–7.43 (2H, d).

EXAMPLE 38

7-{3-[2-(3,4-bis-Hydroxymethylphenyl)vinyl]phenyl}-2-methylheptan-2-ol a) 2-[6-(3-{2-[3,4-bis-(tert-Butyldimethylsilanyloxymethyl)phenyl]vinyl}phenyl)-1,1-dimethylhexyloxy]-tetrahydropyran.

In a manner similar to Example 8(j), by reacting 2.40 g (4.38 mmol) of 3-bromo-[2-{3,4-bis-(tert-butyldimethylsilanyloxymethyl)phenyl}vinyl]phenyl with the solution of 293 mg (12 mmol) of magnesium, 3.12 g (10.6 mmol) of 2-(6-bromo-1,1-dimethylhexyloxy)tetrahydropyran in 10 ml of THF and catalysed by 94 mg (0.178 mmol) of [1,2-bis-(diphenylphosphino)ethane]dichloronickel, after purification on a silica column (ethyl acetate 3-heptane 97), a colourless oil (m=2.31 g; Y=77%) is obtained.

$^1$H NMR (CDCl$_3$): −0.02 (6H, s), 0.00 (6H, s), 0.83 (9H, s), 0.84 (9H, s), 1.06–1.08 (6H, d), 1.13–1.71 (14H, m), 2.47–2.53 (2H, t), 3.28–3.33 (1H, m), 3.80–3.84 (1H, m), 4.57 (1H, m), 4.62 (2H, s), 4.64 (2H, s), 6.93–6.97 (3H, m), 7.10–7.27 (5H, m), 7.46 (1H, s).

b) 7-{3-[2-(3,4-bis-Hydroxymethylphenyl)vinyl]-phenyl}-2-methylheptan-2-ol.

In a manner similar to Example 25(d), by reacting 0.56 ml of concentrated sulphuric acid with 2.30 g (3.37 mmol) of 2-[6-(3-{2-[3,4-bis-(tert-butyldimethylsilanyloxymethyl)phenyl]vinyl}phenyl)-1,1-dimethylhexyloxy]tetrahydropyran in 30 ml of THF and 10 ml of water, after purification on a silica column (ethyl acetate 80-heptane 20), white crystals (m=475 mg; Y=38%) are obtained. m.p.=93–5° C.

$^1$H NMR (CDCl$_3$): 1.19 (6H, s), 1.28–1.42 (6H, m), 1.62–1.68 (2H, m), 2.59–2.65 (2H, t), 3.50 (2H, OH, s), 4.66 (2H, s), 4.70 (2H, s), 7.00–7.14 (3H, m), 7.22–7.32 (4H, m), 7.39–7.44 (1H, dd, J=6.2 Hz, J'=1.55 Hz), 7.47 (1H, s).

EXAMPLE 39

7-{3-[2-(4-Hydroxymethylphenyl)vinyl]phenyl}-2-methylheptan-2-ol a) (4-Bromobenzyloxy)-tert-butyldimethylsilane.

In a manner similar to Example 3(c), by reacting 54.3 g (0.36 mol) of tert-butyldimethylsilane chloride with 56.1 g (0.3 mol) of (4-bromophenyl)methanol, 8.8 g (72 mmol) of dimethylaminopyridine in 100 ml of triethylamine and 150 ml of dimethylformamide, after purification on a silica column (heptane), a greenish-yellow oil (m=81 g; Y=90%) is obtained.

$^1$H NMR (CDCl$_3$): 0.00 (6H, s), 0.84 (9H, s), 4.58 (2H, s), 7.08–7.11 (2H, d, J=8.3 Hz), 7.33–7.37 (2H, d, J=8.4 Hz).

b) 4-(tert-Butyldimethylsilanyloxymethyl)benzaldehyde.

In a manner similar to Example 4(c), by reacting 13.2 [lacuna] of n-butyllithium 2.5 M/hexane, at −78° C., with 9.04 g (30 mmol) of (4-bromobenzyloxy)tert-butyldimethylsilane in 90 ml of THF and 30 minutes later, with 2.55 ml (33 mmol) of dimethylformamide, after purification on a silica column (ethyl acetate 5-heptane 60), a yellowish oil (m=3.64 g; Y=48%) is obtained.

$^1$H NMR (CDCl$_3$): 0.00 (6H, s), 0.83 (9H, s), 4.69 (2H, s), 7.35–7.38 (2H, d, J=8.07 Hz), 7.71–7.75 (2H, d, J=8.2 Hz).

c) {4-[2-(3-Bromophenyl)vinyl]benzyloxy}-tert-butyldimethylsilane.

In a manner similar to Example 1(g), by reacting 513 mg (17 mmol) of sodium hydride with 3.64 g (14 mmol) of 4-(tert-butyldimethylsilanyloxymethyl)benzaldehyde and 5.36 g (17 mmol) of ethyl (3-bromobenzyl)phosphonate in 90 ml of THF, after purification on a silica column (dichloromethane 5-heptane 95), white crystals (m=4.61 g; Y=82%) are obtained.

m.p.=65–7° C. $^1$H NMR (CDCl$_3$): 0.10 (6H, s), 0.93 (9H, s), 4.74 (2H, s), 6.95–7.13 (2H, dd, J=11.9 Hz, J'=16.3 Hz), 7.17–7.25 (1H, m), 7.30–7.48 (6H, m), 7.64–7.66 (1H, t).

d) tert-Butyldimethyl-[4-(2-{3-[6-methyl-6-(tetrahydropyran-2-yloxy)heptyl]phenyl}vinyl)benzyloxy]-silane.

In a manner similar to Example 8(j), by reacting 1.77 g (4.38 mmol) of {4-[2-(3-bromophenyl)vinyl]benzyloxy}-tert-butyldimethylsilane with the solution of 293 mg (12 mmol) of magnesium, 3.12 g (10.6 mmol) of 2-(6-bromo-1,1-dimethylhexyloxy)tetrahydropyran in 10 ml of THF and catalysed by 94 mg (0.178 mmol) of [1,2-bis-(diphenylphosphino)ethane]-dichloronickel, after purification on a silica column (ethyl acetate 3-heptane 97), a colourless oil (m=1 g; Y=43%) is obtained.

$^1$H NMR (CDCl$_3$): 0.00 (6H, s), 0.84 (9H, s), 1.07–1.09 (6H, d), 1.24–1.53 (14H, m), 2.48–2.54 (2H, t), 3.30–3.34 (1H, m), 3.81–3.85 (1H, m), 4.58 (1H, m), 4.63 (2H, s), 6.94–6.97 (3H, m), 7.11–7.21 (5H, m), 7.35–7.38 (2H, d, J=8.2 Hz).

e) 7-{3-[2-(4-Hydroxymethylphenyl)vinyl]phenyl}-2-methylheptan-2-ol.

In a manner similar to Example 25(d), by reacting 0.2 ml of concentrated sulphuric acid with 1 g (1.86 mmol) of tert-butyldimethyl-[4-(2-{3-[6-methyl-6-(tetrahydropyran-2-yloxy)heptyl]phenyl}vinyl)benzyloxy]silane in 20 ml of THF and 10 ml of water, after purification on a silica column (ethyl acetate 50-heptane 50), white crystals (m=350 mg; Y=56%) are obtained. m.p.=105–7° C.

$^1$H NMR (CDCl$_3$): 1.19 (6H, s), 1.28–1.43 (6H, m), 1.63–1.69 (2H, m), 2.59–2.65 (2H, t), 4.67 (2H, s), 7.06–7.09 (3H, m), 7.23–7.36 (5H, m), 7.48–7.51 (2H, d, J=8.2 Hz).

EXAMPLE 40

4-{2-[3-(7-Hydroxy-7-methyloct-1-enyl)phenyl] vinyl}-benzene-1,2-diol a) Methyl 7-(3-{2-[3,4-bis-(tert-Butyldimethylsilanyloxy) phenyl]vinyl}phenyl)hept-6-enoate.

0.43 ml of triethylamine and 72 mg (0.077 mmol) of [1,1'-bis(diphenylphosphino)ferrocene]dichloropalladium are added to a solution of 1.33 g (2.56 mmol) of 3-bromo-[2-{3,4-bis-(tert-butyldimethylsilanyloxy)phenyl}vinyl] phenyl and 444 mg (3.1 mmol) of methyl hept-6-enoate in 20 ml of dimethylformamide. The medium is heated at 75° C. for 3 days. It is then poured into a saturated aqueous ammonium chloride solution and extracted with ether. The organic phase is washed with a saturated aqueous sodium chloride solution and then with water. After decantation, it is dried over magnesium sulphate and concentrated. The residue is purified on a silica column (ethyl acetate 5-heptane 95).

Yellow oil. m=318 mg. Y=21%. $^1$H NMR (CDCl$_3$): 0.21 (6H, s), 0.23 (6H, s), 1.00 (9H, s), 1.03 (9H, s), 1.48–1.55 (2H, m), 1.64–1.78 (2H, m), 2.21–2.29 (2H, m), 2.32–2.41 (2H, t), 3.67 (3H, s), 6.18–6.30 (1H, m), 6.37–6.44 (1H, d, J=15.9 Hz), 6.79–7.02 (6H, m), 7.14–7.43 (2H, m), 7.62 (1H, s).

b) 8-(3-{2-[3,4-bis-(tert-Butyldimethylsilanyloxy)phenyl] vinyl}phenyl)-2-methyloct-7-en-2-ol.

In a manner similar to Example 1(i), by reacting 1 ml (3 mmol) of methylmagnesium bromide 3M/ether with 305 mg (0.52 mmol) of methyl 7-(3-{2-[3,4-bis-(tert-butyldimethylsilanyloxy)phenyl]-vinyl}phenyl)hept-6-enoate in 6 ml of ether, after purification on a silica column (ethyl acetate 20-heptane 80), a yellow oil (m=190 mg; Y=63%) is obtained.

$^1$H NMR (CDCl$_3$): 0.21 (6H, s), 0.23 (6H, s), 0.99 (9H, s), 1.01 (9H, s), 1.23 (6H, s), 1.38–1.62 (6H, m), 2.24–2.26 (2H, m), 6.20–6.32 (1H, m), 6.37–6.44 (1H, d, J=15.9 Hz), 6.79–7.02 (5H, s), 7.20–7.34 (3H, m), 7.44 (1H, s).

c) 4-{2-[3-(7-Hydroxy-7-methyloct-1-enyl)phenyl]-vinyl}benzene-1,2-diol.

In a manner similar to Example 3(i), by reacting 166 mg (0.286 mmol) of 8-(3-{2-[3,4-bis-(tert-butyldimethylsilanyloxy)phenyl]vinyl}phenyl)-2-methyloct-7-en-2-ol with 0.63 ml of tetrabutylammonium fluoride 1M/THF, after purification on a silica column (ethyl acetate 45-heptane 55), white crystals (m=65 mg; Y=64%) are obtained. m.p.=116–8° C.

$^1$H NMR (CDCl$_3$): 1.21 (6H, s), 1.47–1.54 (6H, m), 2.23–2.25 (2H, m), 6.19–6.31 (1H, m), 6.36–6.42 (1H, d, J=15.9 Hz), 6.82–7.33 (8H, m), 7.41 (1H, s).

EXAMPLE 41

7-[3-(3,4-bis-Hydroxymethylphenylethynyl)phenyl]-2-methylheptan-2-ol a) 1,2-bis-(tert-Butyldimethylsilanyloxymethyl)-4-ethynylbenzene.

7.5 ml (18.4 mmol) of n-butyllithium 2.5M/hexane are added, at −78° C., to 2.62 ml (18.4 mmol) of diisopropylamine in 50 ml of THF. The solution is stirred for 1 hour and then, still at −78° C., 9.2 ml (18.4 mmol) of (trimethylsilyl) diazomethane 2M/hexane are added dropwise. After 40 min, 3.64 g (9.2 mmol) of 4-(tert-butyldimethylsilanyloxy)-3-(tert-butyldimethylsilanyloxymethyl)benzaldehyde in 40 ml of THF are added. The medium is further stirred for 1 hour at −78° C. and then it is allowed to return to room temperature over 12 hours. It is then poured into a saturated aqueous ammonium chloride solution and extracted with ether. The organic phase is washed with water, dried over magnesium sulphate and then concentrated. The residue is purified on a silica column (dichloromethane 20-heptane 80).

Yellowish oil. m=952 mg. Y=26%. $^1$H NMR (CDCl$_3$): 0.00 (6H, s), 0.01 (6H, s), 0.83 (18H, s), 2.94 (1H, s), 4.59 (2H, s), 4.63 (2H, s), 7.29–7.30 (2H, d), 7.44 (1H, s).

b) 3-Bromo-[3,4-bis-(tert-butyldimethylsilanyloxymethyl) phenylethynyl]phenyl.

949 mg (2.42 mmol) of 1,2-bis-(tert-butyldimethylsilanyloxymethyl)-4-ethynylbenzene and 707 mg (2.42 mmol) of 3-iodo-1-bromobenzene are dissolved in 20 ml of triethylamine. The solution is degassed with nitrogen for 1 hour 30 minutes and then 136 mg (0.19 mmol) of PdCl$_2$(PPh$_3$)$_2$ and 56 mg (0.29 mmol) of copper iodide are added. The mixture is kept stirring for 12 hours at room temperature. The triethylamine is then evaporated and the residue is purified on a silica column (dichloromethane 20-heptane 80).

Yellow oil. m=1.27 g. Y=96%. $^1$H NMR (CDCl$_3$): 0.00 (6H, s), 0.01 (6H, s), 0.84 (18H, s), 4.61 (2H, s), 4.65 (2H, s), 7.07–7.14 (1H, t), 7.33–7.37 (4H, m), 7.45 (1H, s), 7.57–7.58 (1H, t).

c) Methyl 6-{3-[3,4-bis-(tert-Butyldimethylsilanyloxymethyl)phenylethynyl] phenyl}hexanoate.

In a manner similar to Example 1(h), by reacting 663 mg (1.21 mmol) of 3-bromo-[3,4-bis-(tert-butyldimethylsilanyloxymethyl)phenylethynyl]phenyl in 12 ml of dimethylformamide with the solution at 0° C., 985 mg (4.04 mmol) of 9-borabicyclo[3.3.1]nonane in 10 ml of THF and 259 mg (2.02 mmol) of methyl hex-5-enoate in 5 ml of THF, after purification on a silica column (ethyl acetate 5-heptane 95), a yellow oil (m=326 mg; Y=45%) is obtained.

$^1$H NMR (CDCl$_3$): −0.01 (6H, s), 0.00 (6H, s), 0.83 (18H, s), 1.21–1.81 (6H, m), 2.17–2.23 (2H, t), 2.46–2.52 (2H, t), 3.55 (3H, s), 4.61 (2H, s), 4.65 (2H, s), 7.00–7.03 (1H, d), 7.10–7.17 (1H, t), 7.23–7.24 (2H, t), 7.31–7.32 (2H, d), 7.44 (1H, s).

d) 7-{3-[3,4-bis-(tert-Butyldimethylsilanyloxymethyl) phenylethynyl]phenyl}-2-methylheptan-2-ol.

In a manner similar to Example 1(i), by reacting 0.7 ml (2.11 mmol) of methylmagnesium bromide 3M/ether with 314 mg (0.53 mmol) of 6-{3-[3,4-bis-(tert-butyldimethylsilanyloxymethyl)phenylethynyl]-phenyl}hexanoate in 6 ml of ether, after purification on a silica column (ethyl acetate 10-heptane 90), a yellow oil (m=252 mg; Y=80%) is obtained.

$^1$H NMR (CDCl$_3$): −0.01 (6H, s), 0.00 (6H, s), 0.83 (18H, s), 1.14–1.66 (8H, m), 2.46–2.53 (2H, t), 4.61 (2H, s), 4.65 (2H, s), 7.01–7.04 (1H, d), 7.11–7.17 (1H, m), 7.23–7.25 (2H, d), 7.31–7.32 (2H, d), 7.44 (1H, s).

e) 7-[3-(3,4-bis-Hydroxymethylphenylethynyl)phenyl]-2-methylheptan-2-ol.

In a manner similar to Example 3(i), by reacting 250 mg (0.42 mmol) of 7-{3-[3,4-bis-(tert-butyldimethylsilanyloxymethyl)phenylethynyl]phenyl}-2-methylheptan-2-ol with 0.93 ml of tetrabutylammonium fluoride 1M/THF, after purification on a silica column (ethyl acetate 70-heptane 30), white crystals (m=132 mg; Y=86%) are obtained. m.p.=52–5° C.

$^1$H NMR (CDCl$_3$): 1.19 (6H, s), 1.37–1.64 (8H, m), 2.57–2.63 (2H, t), 3.18 (2H, OH, s), 4.71 (4H, s), 7.13–7.16 (1H, d, J=7.4 Hz), 7.22–7.35 (4H, m), 7.45–7.51 (2H, m).

EXAMPLE 42

5-{2-[3-(6-Hydroxy-6-methylhept-1-enyl)phenyl] vinyl}-benzene-1,3-diol a) Methyl 3,5-bis-Ethoxymethoxybenzoate.

In a manner similar to Example 1(d), by reacting 42.04 g (0.25 mol) of methyl 3,5-dihydroxybenzoate in 400 ml of dimethylformamide with 18.09 g (0.6 mol) of sodium hydride and 51.26 g (0.515 mol) of methoxymethyl chloride, after purification on a silica column (dichloromethane), a yellow oil (m=37.72 g; Y=62%) is obtained.

$^1$H NMR (CDCl$_3$): 1.19–1.25 (6H, t), 3.68–3.77 (4H, q), 3.89 (3H, s), 5.23 (4H, s), 6.92–6.94 (1H, t), 7.35–7.36 (2H, d).

b) (3,5-bis-Ethoxymethoxyphenyl)methanol.

In a manner similar to Example 1(e), by reacting 400 ml of diisobutylaluminium hydride 1M/toluene, at −78° C., with 37.7 g (0.133 mol) of methyl 3,5-bis-ethoxymethoxybenzoate, after purification on a silica column (ethyl acetate 20-heptane 80), a yellow oil (m=38.1 g; Y=86%) is obtained.

$^1$H NMR (CDCl$_3$): 1.19–1.24 (6H, t), 3.67–3.76 (4H, q), 4.61 (2H, s), 5.19 (4H, s), 6.64–6.66 (1H, t), 6.69–6.70 (2H, d).

c) 3,5-bis-Ethoxymethoxybenzaldehyde.

97 g (1.11 mol) of manganese dioxide are added to a solution of 40.78 g (0.159 mol) of (3,5-bis-ethoxymethoxyphenyl)methanol in 400 ml of dichloromethane. The medium is stirred at room temperature for 5 days. It is then filtered on silica and the solid is washed with dichloromethane. The filtrate is evaporated.

Yellow oil. m=36.51 g. Y=90%. $^1$H NMR (CDCl$_3$): 1.20–1.25 (6H, t) 3.69–3.78 (4H, q), 5.25 (4H, s), 6.98–6.99 (1H, t), 7.20–7.21 (2H, d).

d) 3-Bromo-[2-(3,5-bis-ethoxymethoxyphenyl)vinyl] phenyl.

In a manner similar to Example 1(g), by reacting 2.05 g (68 mmol) of sodium hydride with 14.5 g (57 mmol) of 3,5-bis-ethoxymethoxybenzaldehyde and 20.88 g (68 mmol) of ethyl 3-bromobenzylphosphonate in 350 ml of THF, after purification on a silica column (dichloromethane 30-heptane 70), a yellow oil (m=22.83 g; Y=98%) is obtained.

$^1$H NMR (CDCl$_3$): 1.21–1.27 (6H, t), 3.70–3.79 (4H, q), 5.23 (4H, s), 6.68–6.69 (1H, t), 6.85–6.86 (2H, d), 6.93–7.07 (2H, dd, J=16.3 Hz, J'=2.55 Hz), 7.17–7.24 (1H, t), 7.35–7.41 (2H, t), 7.64–7.65 (1H, t).

e) Methyl 6-{3-[2-(3,5-bis-Ethoxymethoxyphenyl)vinyl] phenyl}-hex-5-enoate.

In a manner similar to Example 40(a), by reacting 4.07 g (0.01 mol) of 3-bromo-[2-(3,5-bis-ethoxymethoxyphenyl) vinyl]phenyl in 50 ml of triethylamine with 1.54 g (0.012 mol) of methyl hex-5-enoate and as catalyst 112 mg (0.5 mmol) of palladium acetate and 262 mg (1 mmol) of triphenylphosphine, after purification on a silica column (ethyl acetate 10-heptane 90), a yellow oil (m=2 g; Y=44%) is obtained.

$^1$H NMR (CDCl$_3$): 1.22–1.27 (6H, t), 1.78–1.89 (2H, m), 2.23–2.41 (4H, m), 3.67 (3H, s), 3.63–3.79 (4H, m), 5.24 (4H, s), 6.17–6.28 (1H, m), 6.38–6.45 (1H, d, J=15.9 Hz), 6.67 (1H, s), 6.87 (2H, d), 7.05–7.07 (2H, d), 7.22–7.36 (3H, m), 7.47 (1H, s).

f) 7-{3-[2-(3,5-bis-Ethoxymethoxyphenyl)vinyl]-phenyl}-2-methylhept-6-en-2-ol.

In a manner similar to Example 1(i), by reacting 6.9 ml (21 mmol) of methylmagnesium bromide 3M/ether with 935 mg (2.06 mmol) of methyl 6-{3-[2-(3,5-bis-ethoxymethoxyphenyl)vinyl]phenyl}hex-5-enoate in 20 ml of ether, after purification on a silica column (ethyl acetate 30-heptane 70), a yellow oil (m=352 mg; Y=36%) is obtained.

$^1$H NMR (CDCl$_3$): 1.23 (6H, s), 1.18–1.28 (6H, m), 1.51–1.69 (4H, m), 2.21–2.26 (2H, m), 3.71–3.79 (4H, q), 5.24 (4H, s), 6.21–6.33 (1H, m), 6.38–6.44 (1H, d, J=15.9 Hz), 6.66–6.67 (1H, t), 6.87–6.88 (2H, d), 7.04–7.05 (2H, d), 7.22–7.36 (3H, m), 7.47 (1H, s).

g) 5-{2-[3-(6-Hydroxy-6-methylhept-1-enyl)phenyl]-vinyl}benzene-1,3-diol.

In a manner similar to Example 1(j), by reacting 0.15 ml of concentrated sulphuric acid in 3 ml of methanol with 314 mg (0.67 mmol) of 7-{3-[2-(3,5-bis-ethoxymethoxyphenyl) vinyl]phenyl}-2-methylhept-6-en-2-ol in 3 ml of methanol and 3 ml of THF, after purification on a silica column (ethyl acetate 50-heptane 50), white crystals (m=206 mg; Y=91%) are obtained. m.p.=60–4° C.

$^1$H NMR (CDCl$_3$): 1.24 (6H, s), 1.53–1.61 (4H, m), 2.17–2.22 (2H, m), 6.18–6.30 (1H, m), 6.35–6.36 (2H, d), 6.57 (2H, d), 6.89–7.03 (2H, m), 7.21–7.30 (3H, m), 7.40 (1H, s), 7.96 (2H, OH, s).

EXAMPLE 43

5-{2-[3-(7-Ethyl-7-hydroxynon-1-enyl)phenyl] vinyl}-benzene-1,3-diol a) Methyl 7-{3-[2-(3,5-bis-Ethoxymethoxyphenyl)vinyl] phenyl}hept-6-enoate.

In a manner similar to Example 40(a), by reacting 1.03 g (2.5 mmol) of 3-bromo-[2-(3,5-bis-ethoxymethoxyphenyl) vinyl]phenyl in 30 ml of dimethylformamide with 430 mg (3 mmol) of methyl hept-6-enoate and 700 mg (5 mmol) of potassium carbonate and as catalyst 82 mg (0.1 mmol) of [1,1'-bis-(diphenylphosphino)ferrocene]dichloropalladium, after purification on a silica column (ethyl acetate 10-heptane 90), a yellowish oil (m=843 mg; Y=72%) is obtained.

$^1$H NMR (CDCl$_3$): 1.22–1.27 (6H, t), 1.47–1.85 (4H, m), 2.21–2.42 (4H, m), 3.66 (3H, s), 3.67–3.79 (4H, q), 5.24 (4H, s), 6.19–6.30 (1H, m), 6.37–6.44 (1H, d, J=15.9 Hz), 6.66–6.67 (1H, t), 6.87 (2H, d), 7.05–7.07 (2H, m), 7.21–7.41 (3H, m), 7.47 (1H, s).

b) 9-{3-[2-(3,5-bis-Ethoxymethoxyphenyl)vinyl]-phenyl}-3-ethylnon-8-en-3-ol.

In a manner similar to Example 1(i), by reacting 7 ml of ethylmagnesium bromide 1M/THF with 824 mg (1.76 mmol) of methyl 7-{3-[2-(3,5-bis-ethoxymethoxyphenyl) vinyl]phenyl}hept-6-enoate in 20 ml of ether, after purification on a silica column (ethyl acetate 15-heptane 85), a yellow oil (m=728 mg; Y=83%) is obtained.

$^1$H NMR (CDCl$_3$): 0.81–0.89 (6H, m), 1.22–1.27 (6H, m), 1.34–1.51 (10H, m), 2.17–2.29 (2H, m), 3.71–3.79 (4H, q), 5.24 (4H, s), 6.21–6.32 (1H, m), 6.37–6.43 (1H, d, J=15.9 Hz), 6.66–6.67 (1H, t), 6.87 (2H, d), 7.05–7.07 (2H, m), 7.22–7.36 (3H, m), 7.47 (1H, s).

c) 5-{2-[3-(7-Ethyl-7-hydroxynon-1-enyl)phenyl]-vinyl}benzene-1,3-diol.

In a manner similar to Example 1(j), by reacting 0.3 ml of concentrated sulphuric acid in 7 ml of methanol with 700 mg (1.41 mmol) of 9-{3-[2-(3,5-bis-ethoxymethoxyphenyl) vinyl]phenyl}-3-ethylnon-8-en-3-ol in 7 ml of methanol and 7 ml of THF, after purification on a silica column (ethyl acetate 40-heptane 60), beige crystals (m=477 mg; Y=77%) are obtained. m.p.=98–102° C.

$^1$H NMR (CDCl$_3$): 0.67–0.73 (6H, m), 1.25–1.31 (8H, m), 2.10–2.12 (2H, m), 2.76–2.79 (2H, m, 1H, OH, s), 6.16–6.35 (3H, m), 6.45 (2H, s), 6.96 (2H, s), 7.14–7.15 (2H, m), 7.27 (1H, m), 7.45 (1H, s), 8.16 (1H, s).

EXAMPLE 44

5-{2-[3-(7-Hydroxy-1-methoxy-1,7-dimethyloctyl) phenyl]-vinyl}benzene-1,3-diol a) 1,3-bis-Ethoxymethoxy-5-vinylbenzene.

At 0° C., 18 ml (36 mmol) of phenyllithium 2M/cyclohexane-ether are added, dropwise, to 14.3 g (0.04 mol) of methyltriphenylphosphonium bromide. The solution is stirred at room temperature for 4 h 30 min. It is then cooled to −70° C. and 5.10 g (0.02 mol) of 3,5-bis-ethoxymethoxybenzaldehyde in 50 ml of THF are added dropwise. The medium is stirred for 2 h at −70° C. and then at room temperature for 12 h. It is then poured into a saturated aqueous ammonium chloride solution and extracted with ether. The organic phase is washed with water, dried over magnesium sulphate and concentrated. The residue is purified on a silica column (dichloromethane 30-heptane 70).

Yellow oil. m=4.4 g. Y=87%. $^1$H NMR (CDCl$_3$): 1.20–1.25 (6H, t), 3.68–3.77 (4H, q), 5.22 (4H, s), 5.69–5.76 (1H, dd, J=16.9 Hz, J'=0.55 Hz), 6.58–6.69 (2H, m), 6.75–6.76 (2H, d).

b) 1-{3-[2-{3,5-bis-Ethoxymethoxyphenyl)vinyl]-phenyl}ethanone.

In a manner similar to Example 40(a), by reacting 2.5 g (12.5 mmol) of 3-bromoacetophenone in 100 ml of dimethylformamide with 3.47 g (13.7 mmol) of 1,3-bis-ethoxymethoxy-5-vinylbenzene and 3.47 g (25 mmol) of potassium carbonate and as catalyst 408 mg (0.5 mmol) of [1,1'-bis-(diphenylphosphino)ferrocene]-dichloropalladium, after purification on a silica column (ethyl acetate 15-heptane 85), a yellow oil (m=3.88 g; Y=84%) is obtained.

$^1$H NMR (CDCl$_3$): 1.22–1.28 (6H, t), 2.64 (3H, s), 3.71–3.80 (4H, m), 5.25 (4H, s), 6.68–6.70 (1H, t), 6.88–6.89 (2H, d), 7.11 (2H, s), 7.42–7.48 (1H, t), 7.68–7.71 (1H, d, J=7.8 Hz), 7.82–7.85 (1H, d, J=20 7.7 Hz), 8.08 (1H, s)

c) 2-{3-[2-(3,5-bis-Ethoxymethoxyphenyl)vinyl]-phenyl}-8-methyl-8-(tetrahydropyran-2-yloxy)nonan-2-ol.

In a manner similar to Example 8(j), by reacting 1.85 g (5 mmol) of 1-{3-[2-(3,5-bis-ethoxymethoxyphenyl)vinyl] phenyl}ethanone with the solution of 344 mg (13.7 mmol) of magnesium, 3.67 g (12.5 mmol) of 2-(6-bromo-1,1-dimethylhexyloxy)tetrahydropyran in 12 ml of THF and catalysed by 107 mg (0.2 mmol) of [1,2-bis-(diphenylphosphino)ethane]-dichloronickel, after purification on a silica column (ethyl acetate 15-heptane 85), a yellow oil (m=1.16 g; Y=40%) is obtained.

$^1$H NMR (CDCl$_3$): 1.14–1.16 (6H, d), 1.22–1.27 (6H, m), 1.58 (3H, s), 1.39–1.81 (16H, m), 3.38–3.43 (1H, m), 3.71–3.79 (4H, m), 4.89–4.94 (1H, m), 4.66 (1H, m), 5.24 (4H, s), 6.65–6.67 (1H, t), 6.87–6.88 (2H, d), 7.01–7.15 (2H, dd, J=16.3 Hz, J'=2.4 Hz), 7.30–7.39 (3H, m), 7.58 (1H, s).

d) 5-{2-[3-(7-Hydroxy-1-methoxy-1,7-dimethyloctyl) phenyl]vinyl}benzene-1,3-diol In a manner similar to Example 1(j), by reacting 0.2 ml of concentrated sulphuric acid in 3 ml of methanol with 350 mg (0.6 mmol) of 2-{3-[2-(3,5-bis-ethoxymethoxyphenyl) vinyl]phenyl}-8-methyl-8-(tetrahydropyran-2-yloxy)nonan-2-ol in 3 ml of methanol and 3 ml of THF, after purification on a silica column (ethyl acetate 60-heptane 40), white crystals (m=76 mg; Y=32%) are obtained. m.p.=65–75° C.

$^1$H NMR (acetone): 0.91 (6H, s), 1.03–1.16 (8H, m), 1.34 (3H, s), 1.59 (2H, m), 2.70 (2H, OH, s), 2.88 (3H, s), 6.11 (1H, s), 6.40–6.41 (2H, d), 6.93 (2H, s), 7.12–07.18 (2H, m), 7.26–7.29 (1H, d, J=6.8 Hz), 7.39 (1H, s), 8.11 (1H, s).

EXAMPLE 45

5-{2-[3-(6-Hydroxy-1-methoxy-1,6-dimethylheptyl) phenyl]vinyl}benzene-1,3-diol a) 2-{3-[2-(3,5-bis-Ethoxymethoxyphenyl)vinyl]-phenyl}-7-methyl-7-(tetrahydropyran-2-yloxy)octan-2-ol.

In a manner similar to Example 8(j), by reacting 1.18 g (3.18 mmol) of 1-{3-[2-(3,5-bis-ethoxymethoxyphenyl) vinyl]phenyl}ethanone with a solution of 213 mg (8.75 mmol) of magnesium, 2.15 g (7.7 mmol) of 2-(5-bromo-1, 1-dimethylpentyloxy)tetrahydropyran in 8 ml of THF and catalysed by 68 mg (0.13 mmol) of [1,2-bis-(diphenylphosphino)ethane]-dichloronickel, after purification on a silica column (ethyl acetate 25-heptane 75), a yellow oil (m=768 mg; Y=42%) is obtained.

$^1$H NMR (CDCl$_3$): 0.94–0.96 (6H, d), 1.02–1.09 (6H, m), 1.38 (3H, s), 1.21–1.64 (14H, m), 3.18–3.25 (1H, m), 3.51–3.60 (4H, m), 3.69–3.74 (1H, m), 4.46–4.48 (1H, m), 5.04 (4H, s), 6.46–6.47 (1H, t), 6.67–6.68 (2H, d), 6.81–6.95 (2H, dd, J=16.4 Hz, J'=2.4 Hz), 7.11–7.19 (3H, m), 7.38 (1H, s).

b) 5-{2-[3-(6-Hydroxy-1-methoxy-1,6-dimethylheptyl) phenyl]vinyl}benzene-1,3-diol In a manner similar to Example 1(j), by reacting 0.2 ml of concentrated sulphuric acid in 3 ml of methanol with 340 mg (0.6 mmol) of 2-{3-[2-(3,5-bis-ethoxymethoxyphenyl) vinyl]phenyl}-7-methyl-7-(tetrahydropyran-2-yloxy)octan-2-ol in 3 ml of methanol and 3 ml of THF, after purification on a silica column (ethyl acetate 60-heptane 40), white crystals (m=72 mg; Y=32%) are obtained. m.p.=65–75° C.

$^1$H NMR (CDCl$_3$): 1.17 (6H, s), 1.26–1.40 (6H, m), 1.55 (3H, s), 1.76–1.82 (2H, t), 3.10 (3H, s), 6.35 (1H, t), 6.60–6.61 (2H, d), 6.93–7.09 (2H, dd, J=16.3 Hz, J'=5 Hz), 7.20–7.39 (5H, m), 7.47 (1H, s).

EXAMPLE 46

5-{2-[3-(5-Hydroxypentyl)phenyl]vinyl}benzene-1,3-diol a) Methyl 5-{3-[2-(3,5-bis-Ethoxymethoxyphenyl)vinyl] phenyl}pentanoate.

In a manner similar to Example 1(h), by reacting 1.54 g (3.77 mmol) of 3-bromo-[2-(3,5-bis-ethoxymethoxyphenyl) vinyl]phenyl in 15 ml of dimethylformamide with the solution, at 0° C., of 1.61 g (6.6 mmol) of 9-borabicyclo [3.3.1]nonane in 40 ml of THF and 502 mg (4.4 mmol) of methyl pent-4-enoate in 10 ml of THF, after purification on a silica column (ethyl acetate 15-heptane 85), a yellow oil (m=1.19 g; Y=71%) is obtained.

$^1$H NMR (CDCl$_3$): 1.21–1.27 (6H, t), 1.33–1.87 (4H, m), 2.32–2.38 (2H, t), 2.64 (2H, t), 3.66 (3H, s), 3.70–3.84 (4H, m), 5.24 (4H, s), 6.65–6.67 (1H, t), 6.86–6.87 (2H, d), 7.03–7.09 (3H, m), 7.23–7.34 (3H, m).

b) 5-{3-[2-(3,5-bis-Ethoxymethoxyphenyl)vinyl]-phenyl}pentan-1-ol.

In a manner similar to Example 1(e), by reacting 5 ml of diisobutylaluminium hydride 1M/toluene, at −78° C., with 738 mg (1.67 mmol) of methyl 5-{3-[2-(3,5-bis-ethoxymethoxyphenyl)vinyl]phenyl}-pentanoate, after purification on a silica column (ethyl acetate 40-heptane 60), a yellow oil (m=259 mg; Y=37%) is obtained.

$^1$H NMR (CDCl$_3$): 1.21–1.27 (6H, t), 1.38–1.84 (6H, m), 2.61–2.67 (2H, t), 3.62–3.67 (2H, t), 3.70–3.85 (4H, m), 5.24 (4H, s), 6.65–6.67 (1H, t), 6.86–6.87 (2H, d), 7.03–7.09 (3H, m), 7.22–7.31 (3H, m).

c) 5-{2-[3-(5-Hydroxypentyl)phenyl]vinyl}benzene-1,3-diol.

In a manner similar to Example 1(j), by reacting 0.1 ml of concentrated sulphuric acid in 1 ml of methanol with 90 mg (0.2 mmol) of 5-{3-[2-(3,5-bis-ethoxymethoxyphenyl) vinyl]phenyl}pentan-1-ol in 1 ml of methanol and 1 ml of THF, after purification on a silica column (ethyl acetate 60-heptane 40), a white powder (m=33 mg; Y=55%) is obtained.

m.p.=144–6° C. $^1$H NMR (CDCl$_3$): 1.46–1.80 (6H, m), 2.68–2.74 (2H, t), 3.58–3.63 (2H, m), 6.38–6.39 (1H, t), 6.66 (2H, d), 7.16 (3H, s), 7.30–7.36 (1H, t), 7.44–7.50 (2H, m), 8.37 (1H, OH, s).

EXAMPLE 47

5-{2-[3-(5-Hydroxy-6-methylheptyl)phenyl] vinyl}benzene-1,3-diol a) 5-{3-[2-(3,5-bis-Ethoxymethoxyphenyl)vinyl]-phenyl}pentanal.

586 mg (1.55 mmol) of pyridinium dichromate are added to a solution of 162 mg (0.39 mmol) of 5-{3-[2-(3,5-bisethoxymethoxyphenyl)vinyl]phenyl}pentan-1-ol in 2 ml of dichloromethane. The reaction medium is stirred overnight at room temperature. After evaporation, the residue is purified on a silica column (dichloromethane).

Yellowish oil. m=76 mg. Y=47%. $^1$H NMR (CDCl$_3$): 1.21–1.27 (6H, t), 1.66–1.72 (4H, m), 2.47 (2H, m), 2.65 (2H, m), 3.71–3.79 (4H, m), 5.24 (4H, s), 6.65–6.67 (1H, t), 6.86–6.87 (2H, d), 7.04–7.08 (3H, m), 7.20–7.35 (3H, m), 9.76–9.77 (1H, t).

b) 7-{3-[2-(3,5-bis-Ethoxymethoxyphenyl)vinyl]-phenyl}-2-methylheptan-3-ol.

0.18 ml (0.38 mmol) of 2M isopropylmagnesium chloride are added to 74 mg (0.18 mmol) of 5-{3-[2-(3,5-bis-ethoxymethoxyphenyl)vinyl]phenyl}pentanal in 1.5 ml of ether. The medium is heated at 30–35° C. overnight. It is then poured into an ether/water mixture. After decantation, the organic phase is washed with a 1N hydrochloric acid solution and then with water. It is then dried over magnesium sulphate and concentrated. The residue is purified on a silica column (ethyl acetate 20-heptane 80).

Yellowish oil. m=62 mg. Y=75%. $^1$H NMR (CDCl$_3$): 0.89–0.93 (6H, dd), 1.22–1.27 (6H, t), 1.39–1.69 (6H, m), 2.61–2.67 (2H, t), 3.37 (1H, m), 3.71–3.79 (4H, m), 5.24 (4H, s), 6.66–6.67 (1H, t), 6.86–6.87 (2H, d), 6.97–7.09 (3H, m), 7.23–7.31 (3H, m).

c) 5-{2-[3-(5-Hydroxy-6-methylheptyl)phenyl]vinyl}-benzene-1,3-diol.

In a manner similar to Example 1(j), by reacting 0.1 ml of concentrated sulphuric acid in 1 ml of methanol with 60 mg (0.13 mmol) of 7-{3-[2-(3,5-bis-ethoxymethoxyphenyl)vinyl]phenyl}-2-methylheptan-3-ol in 1 ml of methanol and 1 ml of THF, after purification on a silica column (ethyl acetate 40-heptane 60), a yellowish oil (m=7 mg; Y=16%) is obtained.

$^1$H NMR (CDCl$_3$): 0.90–0.93 (6H, d), 1.43–1.81 (6H, m), 2.60–2.66 (2H, t), 3.38 (1H, m), 6.32–6.38 (3H, m), 6.58 (2H, s), 6.90–7.05 (2H, dd, J=16.3 Hz, J'=4.8 Hz), 7.05–7.08 (1H, d, J=7.8 Hz), 7.21–7.27 (3H, m).

EXAMPLE 48

5-{2-[3-(6-Hydroxy-7-methyloctyl)phenyl] vinyl}benzene-1,3-diol a) Methyl 6-{3-[2-(3,5-bis-Ethoxymethoxyphenyl)vinyl] phenyl}hexanoate.

In a manner similar to Example 1(h), by reacting 1.50 g (3.68 mmol) of 3-bromo-[2-{3,5-bis-ethoxymethoxyphenyl) vinyl]phenyl in 30 ml of dimethylformamide with the solution, at 0° C., of 1.61 g (6.6 mmol) of 9-borabicyclo [3.3.1]nonane in 30 ml of THF and 564 mg (4.4 mmol) of methyl hex-5-enoate in 10 ml of THF, after purification on a silica column (ethyl acetate 10-heptane 90), a yellowish oil (m=430 mg; Y=26%) is obtained.

$^1$H NMR (CDCl$_3$): 1.22–1.27 (6H, t), 1.34–1.87 (6H, m), 2.29–2.35 (2H, t), 2.59–2.65 (2H, t), 3.66 (3H, s), 3.71–3.81 (4H, m), 5.24 (4H, s), 6.65–6.67 (1H, t), 6.86–6.87 (2H, d), 6.97–7.11 (3H, m), 7.23–7.34 (3H, m).

b) 6-{3-[2-(3,5-bis-Ethoxymethoxyphenyl)vinyl]-phenyl}hexan-1-ol.

In a manner similar to Example 1(e), by reacting 2.1 ml of diisobutylaluminium hydride 1M/toluene, at −78° C., with 315 mg (0.69 mmol) of methyl 6-{3-[2-(3,5-bis-ethoxymethoxyphenyl)vinyl]-phenyl}hexanoate, after purification on a silica column (ethyl acetate 40-heptane 60), a yellow paste (m=198 mg; Y=66%) is obtained.

$^1$H NMR (CDCl$_3$): 1.21–1.27 (6H, t), 1.38–1.40 (4H, m), 1.52–1.68 (4H, m), 2.59–2.65 (2H, t), 3.61–3.66 (2H, t), 3.70–3.85 (4H, m), 5.24 (4H, s), 6.66–6.67 (1H, t), 6.86–6.87 (2H, d), 6.97–7.11 (3H, m), 7.22–7.33 (3H, m).

c) 6-{3-[2-(3,5-bis-Ethoxymethoxyphenyl)vinyl]-phenyl}hexanal.

In a manner similar to Example 47(a), by reacting 692 mg (1.83 mmol) of pyridinium dichromate with 197 mg (0.46 mmol) of 6-{3-[2-(3,5-bis-ethoxymethoxyphenyl)vinyl] phenyl}hexan-1-ol in 3 ml of dichloromethane, after purification on a silica column (dichloromethane), a yellow paste (m=76 mg; Y=75%) is obtained.

$^1$H NMR (CDCl$_3$): 1.22–1.27 (6H, t), 1.39–1.45 (2H, m), 1.62–1.73 (4H, m), 2.40–2.46 (2H, m), 2.60–2.66 (2H, t), 3.71–3.80 (4H, m), 5.24 (4H, s), 6.65–6.67 (1H, t), 6.86–6.87 (2H, d), 6.97–7.12 (3H, m), 7.20–7.34 (3H, m), 9.76 (1H, t).

d) 8-{3-[2-(3,5-bis-Ethoxymethoxyphenyl)vinyl]-phenyl}-2-methyloctan-3-ol.

In a manner similar to Example 47(b), by reacting 0.35 ml (0.7 mmol) of isopropylmagnesium chloride 2M/ether with 148 mg (0.35 mmol) of 6-{3-[2-(3,5-bis-ethoxymethoxyphenyl)vinyl]phenyl}hexanal in 2 ml of ether, after purification on a silica column (ethyl acetate 15-heptane 85), a yellow oil (m=130 mg; Y=79%) is obtained.

$^1$H NMR (CDCl$_3$): 0.88–0.92 (6H, dd), 1.22–1.27 (6H, t), 1.37–1.68 (8H, m), 2.60–2.66 (2H, t), 3.35 (1H, m), 3.71–3.79 (4H, m), 5.24 (4H, s), 6.66–6.67 (1H, t), 6.86–6.87 (2H, d), 6.97–7.09 (3H, m), 7.23–7.31 (3H, m).

e) 5-{2-[3-(6-Hydroxy-7-methyloctyl)phenyl]vinyl}-benzene-1,3-diol.

In a manner similar to Example 1(j), by reacting 0.2 ml of concentrated sulphuric acid in 1 ml of methanol with 130 mg (0.27 mmol) of 8-{3-[2-(3,5-bis-ethoxymethoxyphenyl) vinyl]phenyl}-2-methyloctan-3-ol in 1 ml of methanol and 1 ml of THF, after purification on a silica column (ethyl acetate 40-heptane 60), a yellowish oil (m=12 mg; Y=13%) is obtained.

$^1$H NMR (CDCl$_3$): 0.90–0.93 (6H, d), 1.36–2.17 (8H, m), 2.57–2.63 (2H, t), 3.38 (1H, m), 6.34–6.38 (1H, t), 6.58–6.59 (2H, d), 6.89–7.04 (2H, dd, J=16.3 Hz, J'=3.6 Hz), 7.04–7.06 (1H, d, J=6.9 Hz), 7.14–7.29 (3H, m).

EXAMPLE 49

5-{2-[3-(5-Hydroxy-6-methylhept-1-enyl)phenyl] vinyl}-benzene-1,3-diol a) Methyl 5-{3-[2-(3,5-bis-Ethoxymethoxyphenyl)vinyl] phenyl}pent-4-enoate.

In a manner similar to Example 40(a), by reacting 1.5 g (3.68 mmol) of 3-bromo-[2-(3,5-bis-ethoxymethoxyphenyl) vinyl]phenyl in 30 ml of dimethylformamide with 502 mg (4.4 mmol) of methyl pent-4-enoate and 1.02 g (7.36 mmol) of potassium carbonate and as catalyst 120 mg (0.15 mmol) of [1,1'-bis(diphenylphosphino)ferrocene] dichloropalladium, after purification on a silica column (ethyl acetate 10-heptane 90), a yellow paste (m=883 mg; Y=54%) is obtained.

$^1$H NMR (CDCl$_3$): 1.22–1.27 (6H, t), 2.47–2.59 (4H, m), 3.70 (3H, s), 3.67–3.79 (4H, q), 5.24 (4H, s), 6.19–6.30 (1H, m), 6.42–6.48 (1H, d, J=15.9 Hz), 6.66–6.67 (1H, t), 6.86–6.87 (2H, d, J=2.1 Hz), 7.04 (2H, s), 7.21–7.37 (3H, m), 7.46 (1H, s).

b) 5-{3-[2-(3,5-bis-Ethoxymethoxyphenyl)vinyl]-phenyl}pent-4-en-1-ol.

In a manner similar to Example 1(e), by reacting 6 ml of diisobutylaluminium hydride 1M/toluene, at −78° C., with 869 mg (1.97 mmol) of methyl 5-{3-[2-(3,5-bis-ethoxymethoxyphenyl)vinyl]phenyl}pent-4-enoate in 20 ml of toluene, after purification on a silica column (ethyl acetate 30-heptane 70), a yellow paste (m=381 mg; Y=47%) is obtained.

$^1$H NMR (CDCl$_3$): 1.22–1.27 (6H, t), 1.72–1.83 (2H, m), 2.29–2.38 (2H, m), 3.71–3.79 (6H, m), 5.24 (4H, s), 6.22–6.34 (1H, m), 6.41–6.47 (1H, d, J=15.9 Hz), 6.66–6.67

(1H, t), 6.86–6.87 (2H, d, J=1.94 Hz), 7.05 (2H, s), 7.22–7.36 (3H, m), 7.47 (1H, s).

c) 5-{3-[2-(3,5-bis-Ethoxymethoxyphenyl)vinyl]-phenyl}pent-4-enal.

In a manner similar to Example 47(a), by reacting 1.38 g (3.68 mmol) of pyridinium dichromate with 380 mg (0.92 mmol) of 5-{3-[2-(3,5-bis-ethoxymethoxyphenyl)vinyl] phenyl}pent-4-en-1-ol in 10 ml of dichloromethane, after purification on a silica column (dichloromethane), a yellow paste (m=245 mg; Y=65%) is obtained.

$^1$H NMR (CDCl$_3$): 1.22–1.27 (6H, t), 2.56–2.66 (4H, m), 3.71–3.79 (4H, q), 5.24 (4H, s), 6.19–6.31 (1H, m), 6.42–6.48. (1H, d, J=15.9 Hz), 6.66–6.68 (1H, t), 6.86–6.87 (2H, d, J=2.1 Hz), 7.04 (2H, s), 7.20–7.37 (3H, m), 7.46 (1H, s), 9.84 (1H, s).

d) 7-{3-[2-(3,5-bis-Ethoxymethoxyphenyl)vinyl]-phenyl}-2-methylhept-6-en-3-ol.

In a manner similar to Example 47(b), by reacting 0.58 ml (1.16 mmol) of isopropylmagnesium chloride 2M/ether with 239 mg (0.58 mmol) of 5-{3-[2-(3,5-bis-ethoxymethoxyphenyl)vinyl]phenyl}pent-4-enal in 2.5 ml of ether, after purification on a silica column (ethyl acetate 15-heptane 85), a yellow oil (m=137 mg; Y=52%) is obtained.

$^1$H NMR (CDCl$_3$): 0.92–0.94 (6H, m), 1.25 (6H, s), 1.62–1.73 (2H, m), 2.26–2.45 (2H, m), 3.44 (1H, m), 3.71–3.79 (4H, q), 5.24 (4H, s), 6.24–6.35 (1H, m), 6.42–6.48 (1H, d, J=15.9 Hz), 6.66–6.67 (1H, t), 6.86–6.87 (2H, d, J=2.08 Hz), 7.05 (2H, s), 7.22–7.36 (3H, m), 7.47 (1H, s).

e) 5-{2-[3-(5-Hydroxy-6-methylhept-1-enyl)phenyl]-vinyl}benzene-1,3-diol.

In a manner similar to Example 1(j), by reacting 0.3 ml of concentrated sulphuric acid in 2.8 ml of methanol with 140 mg (0.31 mmol) of 7-{3-[2-(3,5-bis-ethoxymethoxyphenyl) vinyl]phenyl}-2-methylhept-6-en-3-ol in 2.8 ml of THF, after purification on a silica column (ethyl acetate 40-heptane 60), a white powder (m=80 mg; Y=77%) is obtained. m.p.=51–60° C.

$^1$H NMR (CDCl$_3$): 0.85–0.88 (6H, d), 1.58–1.63 (2H, m), 2.23–2.37 (2H, m), 3.37–3.46 (1H, m), 6.16–6.37 (3H, m), 6.52 (2H, s), 6.88 (2H, m), 7.13–7.22 (3H, m), 7.31 (2H, s).

EXAMPLE 50

5-{2-[3-(6-Hydroxy-7-methyloct-1-enyl)phenyl]-vinyl}benzene-1,3-diol a) 6-{3-[2-(3,5-bis-Ethoxymethoxyphenyl)vinyl]-phenyl}hex-5-en-1-ol.

In a manner similar to Example 1(e), by reacting 3.9 ml of diisobutylaluminium hydride 1M/toluene, at −78° C., with 581 mg (1.28 mmol) of methyl 6-{3-[2-(3,5-bis-ethoxymethoxyphenyl)vinyl]phenyl}hex-5-enoate in 15 ml of toluene, after purification on a silica column (ethyl acetate 30-heptane 70), a yellow oil (m=290 mg; Y=53%) is obtained.

$^1$H NMR (CDCl$_3$): 1.22–1.27 (6H, t), 1.57–1.68 (4H, m), 2.23–2.31 (2H, m), 3.71–3.79 (6H, m), 5.24 (4H, s), 6.20–6.32 (1H, m), 6.38–6.45 (1H, d, J=15.9 Hz), 6.66–6.67 (1H, t), 6.86–6.87 (2H, d, J=2 Hz), 7.05 (2H, s), 7.22–7.36 (3H, m), 7.47 (1H, s).

b) 6-{3-[2-(3,5-bis-Ethoxymethoxyphenyl)vinyl]-phenyl}hex-5-enal.

In a manner similar to example 47(a), by reacting 1.02 g (2.7 mmol) of pyridinium dichromate with 290 mg (0.68 mmol) of 6-{3-[2-(3,5-bis-ethoxymethoxyphenyl)vinyl] phenyl}hex-5-en-1-ol in 10 ml of dichloromethane, after purification on a silica column (dichloromethane), a yellowish paste (m=202 mg; Y=70%) is obtained.

$^1$H NMR (CDCl$_3$): 1.22–1.27 (6H, t), 1.78–1.90 (2H, m), 2.24–2.33 (2H, m), 2.49–2.54 (2H, m), 3.71–3.79 (4H, q), 5.24 (4H, s), 6.16–6.28 (1H, m), 6.39–6.45 (1H, d, J=15.9 Hz), 6.66–6.68 (1H, t), 6.87 (2H, d, J=2.1 Hz), 7.05 (2H, s), 7.20–7.37 (3H, m), 7.47 (1H, s), 9.80 (1H, s).

c) 8-{3-[2-(3,5-bis-Ethoxymethoxyphenyl)vinyl]-phenyl}-2-methyloct-7-en-3-ol.

In a manner similar to Example 47(b), by reacting 0.47 ml (0.94 mmol) of isopropylmagnesium chloride 2M/ether with 198 mg (0.47 mmol) of 6-{3-[2-(3,5-bis-ethoxymethoxyphenyl)vinyl]phenyl}hex-5-enal in 2 ml of ether, after purification on a silica column (ethyl acetate 15-heptane 85), a yellow oil (m=107 mg; Y=49%) is obtained.

$^1$H NMR (CDCl$_3$): 0.90–0.94 (6H, dd) 1.22–1.27 (6H, t) 1.42–1.74 (4H, m), 2.23–2.28 (2H, m), 3.40 (1H, s), 3.71–3.79 (4H, q), 5.24 (4H, s), 6.21–6.33 (1H, m), 6.38–6.44 (1H, d, J=15.9 Hz), 6.66–6.67 (1H, t), 6.86–6.87 (2H, d, J=2.1 Hz), 7.05 (2H, s), 7.22–7.36 (3H, m), 7.47 (1H, s).

d) 5-{2-[3-(6-Hydroxy-7-methyloct-1-enyl)phenyl]-vinyl}benzene-1,3-diol.

In a manner similar to Example 1(j), by reacting 0.3 ml of concentrated sulphuric acid in 2.5 ml of methanol with 126 mg (0.27 mmol) of 8-{3-[2-(3,5-bis-ethoxymethoxyphenyl) vinyl]phenyl}-2-methyloct-7-en-3-ol in 2.5 ml of THF, after purification on a silica column (ethyl acetate 40-heptane 60), a beige powder (m=60 mg; Y=63%) is obtained.

m.p.=115–20° C. $^1$H NMR (CDCl$_3$): 0.91–0.94 (6H, d), 1.50–1.69 (4H, m), 2.24 (2H, m), 3.43–3.54 (1H, m), 6.17–6.40 (3H, m), 6.59 (2H, s), 6.95 (2H, s), 7.20–7.31 (3H, m), 7.38 (1H, s), 7.59 (2H, s).

EXAMPLE 51

5-{2-[3-(1,6-Dihydroxy-1,6-dimethylheptyl)phenyl]-vinyl}benzene-1,3-diol

In a manner similar to Example 1(j), by reacting 0.6 ml of concentrated sulphuric acid in 7.5 ml of methanol with 369 mg (0.65 mmol) of 2-{3-[2-(3,5-bis-ethoxymethoxyphenyl) vinyl}phenyl}-7-methyl-7-(tetrahydropyran-2-yloxy)octan-2-ol in 7.4 ml of THF, after purification on a silica column (ethyl acetate 70-heptane 30), a yellowish paste (m=220 mg; Y=92%) is obtained.

$^1$H NMR (CDCl$_3$): 1.16 (6H, s), 1.28–1.39 (6H, m), 1.57 (3H, s), 1.77–1.84 (2H, m), 6.35–6.37 (1H, t), 6.58–6.59 (2H, d), 6.92–7.06 (2H, dd, J=16.4 Hz), 2.4 Hz), 7.27–7.38 (3H, m), 7.59 (1H, s), 7.83 (2H, OH, s).

EXAMPLE 52

5-{2-[3-(6-Hydroxy-1,6-dimethylhept-1-enyl) phenyl]-vinyl}benzene-1,3-diol

In a manner similar to Example 1(j), by reacting 0.09 ml of concentrated sulphuric acid in 3 ml of THF with 152 mg (0.41 mmol) of 5-{2-[3-(1,6-dihydroxy-1,6-dimethylheptyl) phenyl]vinyl}benzene-1,3-diol in 1.5 ml of THF, after purification on a silica column (ethyl acetate 50-heptane 50), a yellow powder (m=65 mg; Y=45%) is obtained. m.p.= 55–60° C.

$^1$H NMR (CDCl$_3$): 1.21 (3H, s), 1.24 (6H, s), 1.45–1.55 (4H, m), 2.23 (1H, m), 2.54 (1H, m), 5.80 (1H, t), 6.34 (1H, s), 6.59 (2H, s), 6.92–7.08 (2H, dd, J=16.3 Hz, J'=6 Hz), 7.28–7.33 (3H, m), 7.45 (1H, m).

EXAMPLE 53

6-{[3-(3,4-bis-Hydroxymethylbenzyloxy)phenyl]-methylamino}-2-methylhexan-2-ol a) Ethyl 6-{[3-(p-Toluenesulphonyloxy)phenyl]carbomethoxyamino}pentanoate.

1 g (3.1 mmol) of 3-p-toluenesulphonyloxy-N-carbomethoxyaniline and 1.9 ml (12 mmol) of ethyl 5-bromovalerate are dissolved in 25 ml of anhydrous DMF. 140 mg (4.5 mmol) of 75% sodium hydride are then added and the reaction medium is stirred for 6 hours. After treating with a saturated ammonium chloride solution and extracting with dichloromethane and then drying and evaporating the solvents of the organic phase, the residue is purified by chromatography on a silica column. A colourless oil is obtained (m=1.35 g; Y=97%).

b) 6-{[3-(p-Toluenesulphonyloxy)phenyl]carbomethoxyamino}-2-methylhexan-2-ol.

500 mg of ethyl 6-{[3-(p-toluenesulphonyloxy)phenyl]carbomethoxyamino}pentanoate (1.2 mmol) are dissolved in 20 ml of THF. 1 ml of a 3.0 M solution of methylmagnesium bromide (3.0 mmol) is then added and the reaction medium is stirred for 1 hour at room temperature. After treating with a saturated ammonium chloride solution, drying and evaporating the solvents of the organic phase and then purifying by chromatography on a silica column, a colourless oil is obtained (m=480 mg; Y=92%).

c) 6-[(3-Hydroxyphenyl)methylamino]-2-methylhexan-2-ol.

300 mg of 6-{[3-(p-toluenesulphonyloxy)phenyl]carbomethoxyamino}-2-methylhexan-2-ol (0.69 mmol) are dissolved in 10 ml of anhydrous THF. 80 mg (2.1 mmol) of lithium aluminium hydride are then added, and the reaction medium is heated under reflux for two hours. After cooling, 80 l of water and then 80 l of a 15% NaOH solution and then 240 l of water are added sequentially; after stirring for 1 h, the reaction medium is then filtered and then the solvent is evaporated. The residue obtained is then dissolved in a mixture composed of 5 ml of water and 5 ml of ethanol, and 200 mg of KOH are added. The reaction medium is then heated for 12 hours at 70° C. and then cooled and treated with a mixture of 1N HCl and dichloromethane. After separation, the organic phase is then dried and the solvents are evaporated. After purification by chromatography on a silica column, a colourless oil (m=125 mg; Y=79%) is obtained.

d) 6-{[3-(3,4-bis-Carboxymethylbenzyloxy)phenyl]-methylamino}-2-methylhexan-2-ol.

90 mg (0.38 mmol) of 6-[(3-hydroxyphenyl)methylamino-2-methylhexan-2-ol are added to a solution of 3-(3,4-dicarboxymethyl)benzyl bromide (132 mg, 0.46 mmol) in 2-butanone. 64 mg (0.46 mmol) of potassium carbonate are then added before heating the reaction medium under reflux for 6 hours. After filtration and evaporation of the solvent and purification by chromatography on a silica gel (heptane 60-ethyl acetate 40), a yellow oil is obtained (m=67 mg; Y=40%).

e) 6-{[3-(3,4-bis-Hydroxymethylbenzyloxy)phenyl]-methylamino}-2-methylhexan-2-ol.

30 mg of 6-{[3-(3,4-bis-carboxymethylenzyloxy)phenyl]methylamino}-2-methylhexan-2-ol (0.07 mmol) are dissolved in 3 ml of anhydrous THF and then 20 mg (1 mmol) of lithium borohydride are added before heating the reaction medium under reflux for 3 hours. After treating the reaction medium with a saturated ammonium chloride solution and then drying, evaporating and purifying by chromatography on a silica column (heptane 30-ethyl acetate 70), a clear oil is obtained (m=19 mg; Y=72%).

$^1$H NMR (CDCl$_3$): 1.19 (s, 6H), 1.26–1.59 (m, 6H), 2.89 (s, 3H), 3.27 (t, 2H, J=7.2 Hz), 4.70 (s, 4H), 5.04 (s, 2H), 6.28–6.34 (m, 3H), 7.11 (t, 1H, J=7.9 Hz), 7.34 (s, 2H), 7.40 (s, 1H).

EXAMPLE 54

5-{[3-(3,4-bis-Hydroxymethylbenzyloxy)phenyl]-methylamino}-2-methylpentan-2-ol

In a manner similar to Example 53(e), by reacting 80 mg (0.18 mmol) of 5-{[3-(3,4-bis-carboxymethylbenzyloxy)phenyl]methylamino}-2-methylpentan-2-ol (prepared in a manner similar to Examples 53(a–d)) with 16 mg (0.75 mmol) of lithium borohydride and after purification on a silica column, a colourless oil is obtained (m=50 mg; Y=76%).

$^1$H NMR (CDCl$_3$): 1.18 (s, 6H), 1.37–1.43 (m, 2H), 1.54–1.63 (m, 2H), 1.70 (bs, 1H), 2.89 (s, 3H), 3.25 (t, 2H, J=7.4 Hz), 3.38 (bs, 2H), 4.69 (s, 4H), 5.05 (s, 2H), 6.28–6.34 (m, 3H), 7.11 (t, 1H, J=8.0 Hz), 7.35 (s, 2H), 7.39 (s, 1H).

EXAMPLE 55

6-{[3-(3,4-bis-Hydroxymethylbenzyloxy)phenyl]-methylamino}-3-ethylhexan-3-ol

In a manner similar to Example 53(e), by reacting 250 mg (0.45 mmol) of 6-{[3-(3,4-bis-carboxymethylbenzyloxy)phenyl]methylamino}-3-ethylhexan-3-ol (prepared in a manner similar to Examples 53 (a–d)) with 40 mg (1.8 mmol) of lithium borohydride and after purification on a silica column, a colourless oil is obtained (m=160 mg; Y=88%).

$^1$H NMR (CDCl$_3$): 0.82 (t, 6H, J=7.6 Hz), 1.26–1.56 (m, 8H), 2.89 (s, 3H), 3.25 (t, 2H, J=6.9 Hz), 3.46 (bs, 2H), 4.67 (s, 4H), 5.04 (s, 2H), 6.27–6.33 (m, 3H), 7.11 (t, 1H, J=8.1 Hz), 7.33 (m, 2H), 7.38 (s, 1H).

EXAMPLE 56

7-{[3-(3,4-bis-Hydroxymethylbenzyloxy)phenyl]methylamino}-3-ethylheptan-3-ol

In a manner similar to Example 53(e), by reacting 370 mg (0.8 mmol) of 7-{[3-(3,4-bis-carboxymethylbenzyloxy)phenyl]methylamino}-3-ethylheptan-3-ol (prepared in a manner similar to Examples 53 (a–d)) with 80 mg (3.5 mmol) of lithium borohydride and after purification on a silica column, a colourless oil is obtained (m=266 mg; Y=80%).

$^1$H NMR (CDCl$_3$): 0.84 (t, 6H, J=7.6 Hz), 1.23–1.55 (m, 10H), 1.7 (bs, 1H), 2.89 (s, 3H), 3.26 (t, 2H, J=7.6 Hz), 3.35 (bs, 2H), 4.69 (s, 2H), 4.69 (s, 2H), 5.04 (s, 2H), 6.29–6.34 (m, 3H), 7.11 (t, 1H, J=8.0 Hz), 7.34 (m, 2H), 7.39 (s, 1H).

EXAMPLE 57

5-{[3-(3,4-bis-Hydroxymethylbenzyloxy)phenyl]ethylamino}-2-methylpentan-2-ol a) 5-[(3-tert-Butyldimethylsilyloxyphenyl)ethylamino]-5-oxopentan-2-one.

1 g (4 mmol) of (3-tert-butyldimethylsilyloxy)-N-ethylaniline is dissolved in 40 ml of dichloromethane at 0° C. and then 511 mg (4.4 mmol) of levulinic acid and 595 mg (4.4 mmol) of 1-hydroxybenzotriazole are added to the reaction medium. 908 mg (4.4 mmol) of dicyclohexylcarbodiimide are then added in portions. The reaction medium is heated to room temperature, stirred for 1 hour and then filtered. The filtrate is then stirred for 12 h and then treated with a saturated ammonium chloride solution and extracted with dichloromethane. After drying and purifying on a silica column, a colourless oil is obtained (m=1.27 g; Y=91%).

b) 5-[(3-tert-Butyldimethylsilyloxyphenyl)ethylamino]-5-oxo-2-methylpentan-2-ol.

700 mg (2 mmol) of 5-[(3-tert-butyldimethylsilyloxyphenyl)ethylamino]-5-oxopentan-2-one are dissolved in 20 ml of anhydrous THF and the reaction medium is cooled to 0° C. 0.66 ml (2 mmol) of a methylmagnesium bromide solution is then slowly added and the reaction medium is stirred for 4 hours at this temperature. After treating with a saturated ammonium chloride solution, extracting with ethyl acetate, drying and then evaporating, the residue is purified by chromatography on a silica column in order to obtain a colourless oil (m=610 mg; Y=86%).

c) 5-{[3-(3,4-bis-Carboxymethylbenzyloxy)phenyl]-ethylamino}-5-oxo-2-methylpentan-2-ol.

710 mg of 5-[(3-tert-butyldimethylsilyloxyphenyl)ethylamino]-5-oxo-2-methylpentan-2-ol (2 mmol) are dissolved in 20 ml of THF and then 2.4 ml of a tetrabutylammonium fluoride solution (1M in THF) are added dropwise. After stirring for 1 hour at room temperature, the reaction medium is treated with an ammonium chloride solution and then extracted with ethyl acetate. After concentrating under reduced pressure, the residue obtained is added to a solution of 3-(3,4-dicarboxymethyl)benzyl bromide (750 mg, 2.6 mmol) in 2-butanone (25 ml). 305 mg (2.2 mmol) of potassium carbonate are then added before heating the reaction medium under reflux for 6 hours. After filtration, evaporation of the solvent and purification by chromatography on a silica gel (heptane 60-ethyl acetate 40), a yellow oil is obtained (m=760 mg; Y=83%).

d) 5-{[3-(3,4-bis-Hydroxymethylbenzyloxy)phenyl]-ethylamino}-2-methylpentan-2-ol.

350 mg (0.76 mmol) of 5-{[3-(3,4-bis-carboxymethylbenzyloxy)phenyl]ethylamino}-5-oxo-2-methylpentan-2-ol are dissolved in 10 ml of anhydrous THF and then 120 mg of lithium aluminium hydride (3.1 mmol) are added in two equal portions. After heating under reflux for 4 hours, the reaction medium is cooled and then sequentially treated with 120 l of water, 120 l of a 15% NaOH solution and then 360 l of water. After stirring for 1 hour, the reaction medium is filtered, concentrated and then purified by chromatography on a silica gel. A colourless oil is obtained (m=280 mg; Y=95%).

$^1$H NMR (CDCl$_3$): 1.12 (t, 3H, J=7.0 Hz), 1.18 (s, 6H), 1.38–1.45 (m, 2H), 1.56–1.63 (m, 3H), 3.20 (t, 2H, J=7.5 Hz), 3.31 (q, 2H, J=7.0 Hz), 4.69 (s, 2H), 4.70 (s, 2H), 5.05 (s, 2H), 6.24–6.32 (m, 3H), 7.10 (t, 1H, J=8.1 Hz), 7.34 (m, 2H), 7.40 (s, 1H).

EXAMPLE 58

6-{[3-(3,4-bis-Hydroxymethylbenzyloxy)phenyl]amino}-3-ethylhexan-3-ol a) 6-{[3-(3,4-bis-Carboxymethylbenzyloxy)phenyl]-N-benzoylamino}-3-ethylhexan-3-ol.

In a manner similar to Example 53(d), by reacting 130 mg (0.38 mmol) of 6-[(3-hydroxyphenyl)-N-benzoylamino-3-ethylhexan-3-ol (prepared in a manner similar to Examples 53(a–c)) with a solution of 3-(3,4-dicarboxymethyl)benzyl bromide (133 mg, 0.46 mmol) in 2-butanone (5 ml) and 60 mg (0.42 mmol) of potassium carbonate, after filtration and evaporation of the solvent and purification by chromatography on a silica gel (heptane 60-ethyl acetate 40), a yellow oil is obtained (m=104 mg; Y=50%).

b) 6-{[3-(3,4-bis-Hydroxymethylbenzyloxy)phenyl]-amino}-3-ethylhexan-3-ol.

In a manner similar to Example 57(d), by treating 6-{[3-(3,4-bis-carboxymethylbenzyloxy)phenyl]-N-benzoylamino}-3-ethylhexan-3-ol (100 mg, 0.18 mmol) with 40 mg (1 mmol) of lithium aluminium hydride and after purification on a silica column, a colourless oil is obtained (m=75 mg; Y=87%).

$^1$H NMR (CDCl$_3$): 0.86 (t, 6H, J=7.5 Hz), 1.43–1.70 (m, 9H), 3.1 (bs, 1H), 3.2 (bs, 1H), 3.90 (t, 2H, J=6.3 Hz), 4.31 (s, 2H), 4.70 (s, 4H), 6.14–6.28 (m, 3H), 7.04 (t, 1H, J=8.1 Hz), 7.30 (s, 2H), 7.34 (s, 1H).

EXAMPLE 59

(4E,6E)-7-{3-[2-(3,4-bis-Hydroxymethylphenyl)ethyl]-phenyl}-3-ethylocta-4,6-dien-3-ol a) 3-(2-Methyl-[1,3]dioxolan-2-yl)benzaldehyde.

5 g (25 mmol) of 3-bromoacetophenone are dissolved in 40 ml of toluene and then 15 ml of ethylene glycol and 500 mg of para-toluenesulphonic acid are added. The reaction medium is then heated under reflux equipped with a Dean-Stark distillation assembly. After 12 h, the medium is cooled and then treated with water and extracted with dichloromethane. After drying and concentrating, the residue is purified on a silica column in order to obtain the desired 3-(2-methyl-[1,3]dioxolan-2-yl)-1-bromobenzene (Y=85%). This product (4 g, 16.4 mmol) is then dissolved in anhydrous THF and the mixture is cooled to –78° C. 7.2 ml (18 mmol) of a 2.5M solution of butyllithium are then added dropwise. After stirring for 1 hour at the same temperature, 1.9 ml (18 mmol) of dimethylformamide are added. The mixture is maintained at –78° C. for 30 minutes and then brought to room temperature. The reaction medium is then treated with a saturated ammonium chloride solution and extracted with dichloromethane. After purification by chromatography on a silica column (ethyl acetate 10-heptane 90), a colourless oil is obtained (m=3.09 g; Y=98%).

b) Dimethyl 4-{(E)-2-[3-(2-Methyl-[1,3]dioxolan-2-yl)phenyl]vinyl}phthalate.

Dimethyl 4-(diethoxyphosphorylmethyl)phthalate (2 g, 5.8 mmol) is dissolved in 30 ml of anhydrous THE and then cooled to 0° C. 2.8 ml (5.6 mmol) of a 2M solution of lithium diisopropylamide are then added dropwise and then the reaction medium is stirred at this temperature for 30 minutes. Next, a solution of 3-(2-methyl-[1,3]dioxolan-2-yl)benzaldehyde (1.02 g, 5.3 mmol) in 10 ml of THF is added using a small tube. The medium is then brought to room temperature and then stirred for 12 hours. After treating with a saturated ammonium chloride solution and extracting with ethyl acetate, the organic phase is dried and the solvents are evaporated. After purification on a silica column (ethyl acetate 30-heptane 70), a colourless oil is obtained (m=1.68 g; Y=83%).

c) Dimethyl 4-{2-[3-(2-Methyl-[1,3]dioxolan-2-yl)phenyl]ethyl}phthalate.

1.8 g (4.7 mmol) of dimethyl 4-{(E)-2-[3-(2-methyl-[1,3]dioxolan-2-yl)phenyl]vinyl}phthalate are dissolved in 50 ml of ethyl acetate. The solution is degassed for 30 minutes and then 5% Pd/C (200 mg) are added. A hydrogen flask (1 bar) is then attached to the assembly and the reaction medium is stirred for 4 hours. The loss of fluorescence during the TLC analyses (=254 nm) indicates the end of the reaction: the reaction medium is then filtered and then concentrated under reduced pressure to give a colourless oil (m=1.78 g; Y=98%).

d) 1-{3-[2-(3,4-bis-Hydroxymethylphenyl)ethyl]-phenyl}ethanone.

Dimethyl 4-{2-[3-(2-methyl-[1,3]dioxolan-2-yl)phenyl]ethyl}phthalate (1.78 g, 4.6 mmol) is dissolved in 20 ml of anhydrous THF. 530 mg of lithium aluminium hydride (14 mmol) are then added in three equal fractions and then the reaction medium is heated under reflux for 4 hours. The medium is then cooled and then sequentially treated with 530 l of water, 530 l of 15% NaOH and then 1.6 ml of water. After stirring for 1 hour, the mixture is filtered and then concentrated under reduced pressure. The residue obtained is then dissolved in 10 ml of acetone to which 5 ml of water and 100 mg of para-toluenesulphonic acid are added. The reaction medium is stirred at 70° C. for 12 h, and then poured into 50 ml of ethyl acetate. After separating and drying the organic phase, the solvents are evaporated and then the residue purified by chromatography on a silica gel (ethyl acetate 50-heptane 50) in order to obtain a white semisolid (m=1.18 g; Y=90%).

e) 1-(3-{2-[3,4-bis(tert-Butyldimethylsilanyloxymethyl)phenyl]ethyl}phenyl)ethanone.

1.15 g of 1-{3-[2-(3,4-bis-hydroxymethylphenyl)ethyl]phenyl}ethanone (4.04 mmol) are dissolved in 20 ml of DMF and 20 ml of dichloromethane. The mixture is cooled to 0° C. and then 1.7 ml of triethylamine (12 mmol) are added, followed by 1.35 g of tert-butyldimethylsilane chloride (8.9 mmol). The medium is stirred at room temperature for 12 h and then treated with a saturated ammonium chloride solution and extracted with ethyl ether. The organic phase is washed with water and then dried and concentrated under reduced pressure to give a colourless oil (m=2.07 g; Y=100%).

f) Ethyl (2E,4E)-5-(3-{2-[3,4-bis(tert-Butyldimethylsilanyloxymethyl)phenyl]ethyl}phenyl)hexa-2,4-dienoate.

850 ml (3.9 mmol) of ethyl 4-diethylphosphonocrotonate are dissolved in 5 ml of THF. To this mixture there are added 10 ml of DMPU (1,3-dimethyl-3,4,5,6-tetrahydro-2(1H)-pyrimidinone) and then, after cooling to 0° C., 1.85 ml (3.7 mmol) of a 2M solution of lithium diisopropylamide. The mixture is stirred for 30 minutes at this same temperature and then a solution of 1 g (1.95 mmol) of 1-(3-{2-[3,4-bis-(tert-butyldimethylsilanyloxymethyl)phenyl]ethyl}phenyl) ethanoate in 5 ml of THF is added dropwise. The mixture is then brought to room temperature and then stirred for 48 hours. After treating with a solution of ammonium chloride and extracting with ethyl acetate, the organic phase is dried and concentrated under reduced pressure. After chromatography on a silica column, a light-yellow oil is obtained (m=1.46 g; Y=81%).

g) (4E,6E)-7-(3-{2-[3,4-bis(tert-Butyldimethylsilanyloxymethyl)phenyl]ethyl}phenyl)-3-ethylocta-4,6-dien-3-ol.

500 mg of ethyl (2E,4E)-5-(3-{2-[3,4-bis-(tert-butyldimethylsilanyloxymethyl)phenyl]ethyl}-phenyl) hexa-2,4-dienoate (0.82 mmol) are dissolved in 10 ml of anhydrous THF and the mixture is cooled to −78° C. 5.4 ml (4 mmol) of a freshly prepared ethyllithium solution (0.75 M) are then added dropwise and then the mixture is brought to 0° C. After stirring for 1 hour, the reaction medium is treated with a saturated ammonium chloride solution and extracted with ethyl acetate. After purification by chromatography on a silica column (ethyl acetate 5-heptane 95), the pure all-trans isomer is obtained in the form of a colourless oil (m=350 mg; Y=70%).

h) (4E,6E)-7-{3-[2-(3,4-bis-Hydroxymethylphenyl)ethyl]phenyl}-3-ethylocta-4,6-dien-3-ol.

340 mg of (4E,6E)-7-(3-{2-[3,4-bis-(tert-butyldimethylsilanyloxymethyl)phenyl]ethyl}phenyl)-3-ethylocta-4,6-dien-3-ol (0.5 mmol) are dissolved in 10 ml of THF and 1.5 ml (1.5 mmol) of a tetrabutylammonium fluoride solution (1M in THF) are added dropwise. After 30 minutes, 10 ml of methanol are added and the mixture is concentrated under reduced pressure. After purification of the residue by chromatography on a silica column, a colourless oil is obtained (m=163 mg; Y=88%).

$^1$H NMR (CDCl$_3$): 0.90 (t, 6H, J=7.4 Hz), 1.61 (q, 4H, J=7.5 Hz), 2.17 (s, 3H), 2.92 (bs, 2H), 2.92 (s, 4H), 4.71 (s, 4H), 5.77 (d, 1H, J=15.1 Hz), 6.42 (d, 1H, J=11 Hz), 6.63 (dd, 1H, J1=15.1 Hz, J2=11 Hz), 7.08–7.29 (m, 7H).

EXAMPLE 60

(3E,5E)-6-{3-[2-(3,4-bis-Hydroxymethylphenyl)ethyl]-phenyl}-2-methylhepta-3,5-dien-2-ol In a manner similar to Example 59(h), by reacting 410 mg (0.7 mmol) of (3E,5E)-6-{3-[2-(3,4-bis-(tert-butyldimethylsilanyloxymethyl)phenyl)ethyl]-phenyl}-2-methylhepta-3,5-dien-2-ol (prepared in a manner similar to Examples 53(a–g)) with 2 ml (2 mmol) of a tetrabutylammonium fluoride solution (1M in THF), a colourless oil is obtained (m=230 mg; Y=96%).

$^1$H NMR (CDCl$_3$): 1.39 (s, 6H), 2.15 (s, 3H), 2.91 (s, 4H), 2.92 (bs, 2H), 4.69 (s, 2H), 4.70 (s, 2H), 5.94 (d, 1H, J=15.1 Hz), 6.36 (d, 1H, J=10.9 Hz), 6.62 (dd, 1H, J1=15.1 Hz, J2=10.9 Hz), 7.06–7.28 (m, 7H).

EXAMPLE 61

(4E-6E)-7-{3-[2-(3,4-bis-Hydroxymethylphenyl}vinyl]-phenyl)-3-ethylocta-4,6-dien-3-ol In a manner similar to Example 59(h), by reacting 320 mg (0.5 mmol) of (4E,6E)-7-(3-{2-[3,4-bis(tert-butyldimethylsilanyloxymethyl)phenyl]-vinyl}phenyl)-3-ethylocta-4,6-dien-3-ol (prepared in a manner similar to Examples 53(a–b, d–g)) with 1.5 ml (1.5 mmol) of a 1M solution of tetrabutylammonium fluoride, a colourless oil is obtained (m=184 mg; Y=100%).

$^1$H NMR (CDCl$_3$): 0.91 (t, 6H, J=7.4 Hz), 1.62 (q, 4H, J=7.4 Hz), 2.22 (s, 3H), 4.13 (bs, 1H), 4.21 (bs, 1H), 4.72 (s, 2H), 4.75 (s, 2H), 5.82 (d, 1H, J=14.9 Hz), 6.52 (d, 1H, J=11 Hz), 6.65 (dd, 1H, J1=14.9 Hz, J2=11 Hz), 7.13 (s, 2H), 7.29–7.57 (m, 7H).

EXAMPLE 62

(3E,5E)-6-{3-[2-(3,4-bis-Hydroxymethylphenyl) vinyl]-phenyl}-2-methylhepta-3,5-dien-2-ol In a manner similar to Example 59(h), by reacting 450 mg (0.75 mmol) of (3E,5E)-6-{3-[2-(3,4-bis(tert-butyldimethylsilanyloxymethyl)phenyl)vinyl]phenyl}-2-methylhepta-3,5-dien-2-ol (prepared in a manner similar to Examples 59(a–b, d–g)) with 2 ml (2 mmol) with a tetrabutylammonium fluoride solution (1M in THF), a colourless oil is obtained (m=270 mg; Y=99%).

$^1$H NMR (CDCl$_3$): 1.40 (s, 6H), 2.21 (s, 3H), 2.35 (bs, 1H), 4.20–4.40 (bs, 2H), 4.71 (s, 2H), 4.74 (s, 2H), 5.98 (d, 1H, J=15 Hz), 6.47 (d, 1H, J=10.9 Hz), 6.67 (dd, 1H, J1=15.0 Hz, J2=10.9 Hz), 7.13 (s, 2H), 7.31–7.55 (m, 7H).

EXAMPLE 63

(4E,6E)-7-[3-(3,4-bis-Hydroxymethylphenylethynyl) phenyl]-3-ethylocta-4,6-dien-3-ol a) 1-(3-Ethynylphenyl)ethanone 4 g of 3-bromoacetophenone (20 mmol) and 4.23 ml (30 mmol) of trimethylsilylacetylene are dissolved in 50 ml of triethylamine. CuI (760 mg, 4 mmol) are added and the reaction medium is degassed for 10 minutes by an argon stream. Tetrakis(triphenylphosphine)palladium (1.4 g, 2 mmol) is then added in one fraction, and the reaction medium is stirred for 12 hours at room temperature. The medium is then treated with water and extracted with dichloromethane. After drying and concentrating under reduced pressure, the residue is dissolved in 100 ml of THF, to which 100 ml of ethanol and 10 ml of water are added. Two fractions of 1.4 g (24 mmol) of potassium fluoride are added at an interval of 9 hours and then the reaction medium is stirred for 24 h before being concentrated under reduced pressure. The residue is then taken up in a mixture of dichloromethane and a saturated ammonium chloride solution. The organic phase is dried and then concentrated. After chromatography on a silica column (ethyl acetate 10-heptane 90), a clear oil is obtained (m=2.68 g; Y=93%).

b) 1-{3-[3,4-bis(tert-Butyldimethylsilanyloxymethyl) phenylethynyl]phenyl}ethanone.

100 mg (0.1 mmol) of tetrakis(triphenylphosphine) palladium, 35 mg (0.2 mmol) of CuI and 250 mg (1.7 mmol) of 1-(3-ethynylphenyl)ethanone are successively added to 850 mg (1.7 mmol) of 1,2-bis(tert-butyldimethylsilanyloxymethyl)-4-iodobenzene in 6 ml of pyrrolidine. After 30 minutes at room temperature, the reaction medium is filtered and then the filtrate is taken up in dichloromethane and washed with water. A yellow oil is obtained (m=770 mg; Y=89%).

c) Ethyl (2E,4E)-5-{3-[3,4-bis(tert-Butyldimethylsilanyloxymethyl)phenylethynyl]phenyl}hexa-2,4-dienoate.

0.6 ml (2.7 mmol) of ethyl 4-diethylphosphonocrotonate is dissolved in 20 ml of anhydrous THF and the mixture is cooled to 0° C. 1.27 ml (2.54 mmol) of a 2M solution of lithium diisopropylamide are added dropwise. After stirring for 1 hour at the same temperature, a solution of 680 mg (1.34 mmol) of 1-{3-[3,4-bis(tert-butyldimethylsilanyloxymethyl)phenylethynyl]phenyl}ethanone in 5 ml of THF is slowly added by means of a small tube. The reaction medium is brought to room temperature and then stirred for 18 hours. After treating with a saturated ammonium chloride solution and extracting with ethyl acetate, the organic phase is dried and concentrated under reduced pressure. The residue is purified by chromatography on a silica column: a yellow oil is obtained (m=480 mg; Y=60%).

d) (4E,6E)-7-[3-(3,4-bis-Hydroxymethylphenylethynyl)phenyl]-3-ethylocta-4,6-dien-3-ol.

470 mg of ethyl (2E,4E)-5-{3-[3,4-bis(tert-butyldimethylsilanyloxymethyl)phenylethynyl]phenyl}hexa-2,4-dienoate (0.77 mmol) are dissolved in 10 ml of anhydrous THF. 0.8 ml (2.4 mmol) of a 3M solution of ethylmagnesium bromide are added dropwise. After 30 minutes at room temperature, the reaction medium is treated with an ammonium chloride solution and then extracted with ethyl acetate. The residue, obtained after drying and concentrating the organic phase, is then dissolved in 10 ml of THF and 3 ml (3 mmol) of a tetrabutylammonium fluoride solution (1M in THF) are added. After 15 minutes, the reaction medium is diluted with 10 ml of ethanol and then concentrated under reduced pressure. The residue is purified by chromatography on a silica gel (ethyl acetate 40-heptane 60). A colourless oil is obtained (m=55 mg; Y=18%).

$^1$H NMR (CDCl$_3$): 0.93 (t, 6H, J=6.7 Hz), 1.58 (q, 4H, J=6.7 Hz), 2.07 (s, 3H), 2.92 (bs, 2H), 4.75 (s, 4H), 5.81 (d, 1H, J=14.8 Hz), 6.51 (d, 1H, J=10.9 Hz), 6.65 (dd, 1H, J1=14.8 Hz, J2=10.9 Hz), 7.26–7.62 (m, 7H).

EXAMPLE 64

7-[3-(3,4-bis-Hydroxymethylbenzyloxy)phenyl]-3-ethyl-3-octanol a) Ethyl 5-[3-(tert-Butyldimethylsilanyloxy)phenyl]-hexa-2,4-dienoate.

4.3 g of ethyl 4-diethylphosphonocrotonate are added dropwise to a solution of 19 mmol of lithium diisopropylamide in 150 ml of anhydrous THF cooled to 0° C. After stirring for 1 hour at this temperature, 2 g (8 mmol) of 3-(tert-butyldimethylsilanyloxy)acetophenone dissolved in 20 ml of THF are added dropwise by means of a small tube. The reaction medium is brought to room temperature and stirred for 15 hours. After treating with a saturated ammonium chloride solution and extracting with dichloromethane, the organic phase is dried and concentrated under reduced pressure. The residue is purified by chromatography on a silica column. A yellow oil is obtained (m=1.39 g; Y=50%).

b) Ethyl 5-[3-(tert-Butyldimethylsilanyloxy)phenyl]-hexanoate.

600 mg (1.7 mmol) of ethyl 5-[3-(tert-butyldimethylsilanyloxy)phenyl]hexa-2,4-dienoate are dissolved in 40 ml of ethyl acetate and the solution is degassed with an argon stream for 10 minutes. 100 mg of 5% Pd/C are then added and the reaction medium is equipped with a hydrogen flask (1 bar). After 6 hours at room temperature, the reaction medium is filtered on a celite pad and then the filtrate is concentrated under reduced pressure to give a colourless oil (m=580 mg; Y=97%).

c) 3-(5-Ethyl-5-hydroxy-1-methylheptyl)phenol.

580 mg (1.66 mmol) of ethyl 5-[3-(tert-butyldimethylsilanyloxy)phenyl]hexanoate are dissolved in 25 ml of ethyl ether and the mixture is cooled to 0° C. 1.9 ml of a 3M ethylmagnesium bromide solution (5.8 mmol) are then added dropwise and the medium is stirred for 3 hours. After treating with a saturated ammonium chloride solution and extracted with ethyl ether, the organic phase is dried and then concentrated under reduced pressure. The reaction medium is then dissolved in 20 ml of THF and then 2.5 ml (2.5 mmol) of a tetrabutylammonium fluoride solution (1M in THF) are added in one portion and the reaction medium is stirred for 1 hour at room temperature. The reaction medium is then concentrated under reduced pressure and the residue is purified by chromatography on a silica column. A colourless oil is obtained (m=400 mg; Y=96%).

d) Dimethyl 4-[3-(5-Ethyl-5-hydroxy-1-methylheptyl)phenoxymethyl]phthalate.

450 mg of 3-(5-ethyl-5-hydroxy-1-methylheptyl)phenol (1.8 mmol) and 620 mg (2.16 mmol) of dimethyl 4-bromomethylphthalate are dissolved in 20 ml of 2-butanone. A catalytic quantity of 18-crown-6 is added, followed by 300 mg (2.16 mmol) of potassium carbonate. The reaction medium is heated under reflux for 15 h and then cooled and filtered. The filtrate is concentrated under reduced pressure and then the residue is purified by chromatography on a silica column. A yellow oil is obtained (m=220 mg; Y=27%).

e) 7-[3-(3,4-bis-Hydroxymethylbenzyloxy)phenyl]-3-ethyl-3-octanol.

220 mg (0.48 mmol) of dimethyl 4-[3-(5-ethyl-5-hydroxy-1-methylheptyl)phenoxymethyl]phthalate are dissolved in 15 ml of anhydrous THF. 42 mg (1.9 mmol) of lithium borohydride are then added and the reaction medium is heated under reflux for 12 hours. After cooling, treating with a saturated ammonium chloride solution and extracting with ethyl acetate, the organic phase is dried and concentrated under reduced pressure. The residue is then purified by chromatography on a silica column. A colourless oil is obtained (m=132 mg; Y=75%).

$^1$H NMR (CDCl$_3$): 0.79 (t, 6H, J=7.5 Hz), 1.13–1.57 (m, 13H), 1.72 (bs, 1H), 1.65 (m, 1H), 3.44 (bs, 2H), 4.69 (s, 2H), 4.70 (s, 2H), 5.06 (s, 2H), 6.77–6.79 (m, 3H), 7.19 (t, 1H, J=8.5 Hz), 7.31–7.35 (m, 2H), 7.40 (s, 1H).

EXAMPLE 65

(4E,6E)-7-[3-(3,4-bis-Hydroxymethylbenzyloxy) phenyl]-3-ethylocta-4,6-dien-3-ol a) 7-[3-(tert-Butyldimethylsilanyloxy)phenyl]-3-ethylocta-4,6-dien-3-ol.

In a manner similar to Example 63(d), by reacting 700 mg (2 mmol) of ethyl 5-[3-(tert-butyldimethylsilanyloxy) phenyl]hexa-2,4-dienoate (prepared in Example 64(a)) with 2.7 ml (8 mmol) of an ethylmagnesium bromide solution (3M), 121 mg (17%) of (Z)-7-[3-(tert-butyldimethylsilanyloxy)phenyl]-3-ethylocta-4,6-dien-3-ol and 146 mg (20%) of (E)-7-[3-(tert-butyldimethylsilanyloxy)phenyl]-3-ethylocta-4,6-dien-3-ol are obtained after purification on a silica column (pentane-ethyl acetate 90-10).

b) (4E,6E)-7-[3-Hydroxyphenyl]-3-ethylocta-4,6-dien-3-ol.

In a manner similar to Example 59(h), starting with 205 mg (0.57 mmol) of (E)-7-[3-(tert-butyldimethylsilanyloxy)

phenyl]-3-ethylocta-4,6-dien-3-ol, 140 mg (100%) of expected product are obtained in the form of an oil.

c) Dimethyl 4-[3-((1E,3E)-5-Ethyl-5-hydroxy-1-methylhepta-1,3-dienyl)phenoxymethyl]phthalate.

In a manner similar to Example 64(d), by reacting 140 mg (0.57 mmol) of the previous product with 196 mg (0.68 mmol) of dimethyl 4-bromomethylphthalate, 154 mg (60%) of expected product are obtained in the form of an oil.

d) (4E,6E)-7-[3-(3,4-bis-Hydroxymethylbenzyloxy)phenyl]-3-ethylocta-4,6-dien-3-ol.

In a manner similar to Example 53(e), by reacting 150 mg (0.34 mmol) of dimethyl 4-[3-((1E,3E)-5-ethyl-5-hydroxy-1-methylhepta-1,3-dienyl)phenoxymethyl]phthalate with 30 mg (1.35 mmol) of lithium borohydride, a colourless oil is obtained (m=56 mg; Y=42%).

$^1$H NMR (CDCl$_3$): 0.89 (t, 6H, J=7.5 Hz), 1.59 (q, 4H, J=7.5 Hz), 2.15 (s, 3H), 3.57 (bs, 2H), 4.66 (s, 2H), 4.67 (s, 2H), 5.03 (s, 2H), 5.76 (d, 1H, J=14.9 Hz), 6.46 (d, 1H, J=10.9 Hz), 6.62 (dd, 1H, J1=14.9 Hz, J2=10.9 Hz), 6.82 (dd, 1H, J1=1.9 Hz, J2=7.6 Hz), 7.05 (m, 2H), 7.22 (t, 1H, J=8.2 Hz), 7.30–7.38 (m, 3H).

EXAMPLE 66

(4E,6Z)-7-[3-(3,4-bis-Hydroxymethylbenzyloxy)phenyl]-3-ethylocta-4,6-dien-3-ol a) (4E,6Z)-7-[3-Hydroxyphenyl]-3-ethylocta-4,6-dien-3-ol.

In a manner similar to Example 59(h), starting with 202 mg (0.56 mmol) of (Z)-7-[3-(tert-butyldimethylsilanyloxy)phenyl]-3-ethylocta-4,6-dien-3-ol (obtained in Example 66(a), 138 mg (100%) of expected product are recovered in the form of an oil.

b) Dimethyl 4-[3-((1Z,3E)-5-Ethyl-5-hydroxy-1-methylhepta-1,3-dienyl)phenoxymethyl]phthalate In a manner similar to Example 64(d), by reacting 138 mg (0.56 mmol) of the previous product with 196 mg (0.68 mmol) of dimethyl 4-bromomethylphthalate, 152 mg (60%) of expected product are obtained in the form of an oil.

c) (4E,6Z)-7-[3-(3,4-bis-Hydroxymethylbenzyloxy)phenyl]-3-ethylocta-4,6-dien-3-ol.

In a manner similar to Example 53(e), by reacting 106 mg (0.23 mmol) of dimethyl 4-[3-((1Z,3E)-5-ethyl-5-hydroxy-1-methylhepta-1,3-dienyl)phenoxymethyl]phthalate with 20 mg (0.94 mmol) of lithium borohydride, a colourless oil is obtained (m=50 mg; Y=55%).

$^1$H NMR (CDCl$_3$): 0.80 (t, 6H, J=7.5 Hz), 1.49 (q, 4H, J=7.5 Hz), 2.10 (s, 3H), 3.21 (bs, 1H), 4.73 (s, 4H), 5.10 (s, 2H), 5.61 (d, 1H, J=14.9 Hz), 6.12 (d, 1H, J=10.9 Hz), 6.24 (dd, 1H, J1=14.9 Hz, J2=10.9 Hz), 6.83–6.98 (m, 3H), 7.18–7.42 (m, 4H).

EXAMPLE 67

7-[4-(3,4-bis-Hydroxymethylbenzyloxy)phenyl]-3-ethyl-3-octanol

In a manner similar to Example 53(e), by reacting 607 mg (1.33 mmol) of dimethyl 4-[4-(5-ethyl-5-hydroxy-1-methylheptyl)phenoxymethyl]phthalate (prepared in a manner similar to Examples 64(a–d)) with 116 mg (5.32 mmol) of lithium borohydride, a colourless oil is obtained (m=421 mg; Y=79%).

$^1$H NMR (CDCl$_3$): 0.73 (t, 6H, J=7.5 Hz), 1.09–1.47 (m, 13H), 2.56 (m, 1H), 3.2 (bs, 1H), 4.62 (s, 4H), 4.94 (s, 2H), 6.80 (d, 2H, J=8.6 Hz), 7.01 (d, 2H, J=8.6 Hz), 7.24–7.30 (m, 3H).

EXAMPLE 68

(4E,6E)-7-[3-(3,4-bis-Hydroxymethylbenzyloxy)phenyl]-3-ethylnona-4,6-dien-3-ol

In a manner similar to Example 53(e), by reacting 122 mg (0.26 mmol) of dimethyl 4-[3-((1E,3E)-5-ethyl-5-hydroxy-1-ethylhepta-1,3-dienyl)phenoxymethyl]phthalate (prepared in a manner similar to Examples 65(a–c)) with 17 mg (0.78 mmol) of lithium borohydride, a colourless oil is obtained (m=91 mg; Y=85%).

$^1$H NMR (CDCl$_3$): 0.81 (t, 6H, J=7.6 Hz), 0.96 (t, 3H, J=7.5 Hz), 1.52 (q, 4H, J=7.6 Hz), 2.56 (q, 2H, J=7.5 Hz), 3.21 (bs, 2H), 4.57 (s, 2H), 4.58 (s, 2H), 4.95 (s, 2H), 5.67 (d, 1H, J=15.1 Hz), 6.25 (d, 1H, J=11 Hz), 6.53 (dd, 1H, J'=15.1 Hz, J2=11 Hz), 6.75 (dd, 1H, J1=1.7 Hz, J2=8.0 Hz), 6.94–6.96 (m, 2H), 7.14 (t, 1H, J=8.1 Hz), 7.26–7.30 (m, 3H).

EXAMPLE 69

(4E,6Z)-7-[3-(3,4-bis-Hydroxymethylbenzyloxy)phenyl]-3-ethylnona-4,6-dien-3-ol

In a manner similar to Example 53(e), by reacting 72 mg (0.15 mmol) of dimethyl 4-[3-((1Z,3E)-5-ethyl-5-hydroxy-1-ethylhepta-1,3-dienyl)phenoxymethyl]phthalate (prepared in a manner similar to Examples 66(a–b)) with 10 mg (0.46 mmol) of lithium borohydride, a colourless oil is obtained (m=62 mg; Y=100%).

$^1$H NMR (CDCl$_3$): 0.80 (t, 6H, J=7.6 Hz), 0.99 (t, 3H, J=7.5 Hz), 1.48 (q, 4H, J=7.6 Hz), 2.41 (q, 2H, J=7.5 Hz), 3.71 (bs, 2H), 4.64 (s, 4H), 5.06 (s, 2H), 5.63 (d, 1H, J=14.7 Hz), 6.08 (d, 1H, J=10.8 Hz), 6.19 (dd, 1H, J1=14.7 Hz, J2=10.8 Hz), 6.78–6.88 (m, 3H), 7.23 (t, 1H, J=8.2 Hz), 7.29–7.37 (m, 3H).

EXAMPLE 70

(E)-6-[3-(3,4-bis-Hydroxymethylbenzyloxy)phenyl]-2-methylhept-3-en-2-ol a) Ethyl 3-[3-(tert-Butyldimethylsilanyloxy)phenyl]-butyrate.

3 g (12 mmol) of 3-(tert-butyldimethylsilanyloxy)acetophenone in 20 ml are added dropwise to a solution, at 0° C., of 5 g (26.4 mmol) of ethyl diethylphosphonoacetate and 24 mmol of lithium diisopropylamide in 100 ml of THF. The reaction medium is stirred for 15 hours at room temperature and then treated with an ammonium chloride solution and extracted with ethyl acetate. The organic phase is dried and then concentrated under reduced pressure. The residue obtained is then dissolved in 100 ml of ethyl acetate. The mixture is degassed with an argon stream and then 300 mg of 5% Pd/C are added. The assembly is then equipped with a hydrogen flask (1 bar), and the reaction medium is stirred for 4 hours. After filtration and concentration, the residue is purified by chromatography on a silica column. A colourless oil is obtained (m=3.15 g; Y=82%).

b) Methyl (E)-5-[3-(tert-Butyldimethylsilanyloxy)phenyl]hex-2-enoate 3.15 g (9.8 mmol) of ethyl 3-[3-(tert-butyldimethylsilanyloxy)phenyl]butyrate are dissolved in 150 ml of anhydrous ethyl ether. The mixture is cooled to 0° C. and then lithium aluminium hydride (1.12 g, 29.4 mmol) is added in 4 equal portions. The reaction medium is heated under reflux for 4 h, and then brought to room temperature. After treating with 1.12 ml of water, 1.12 ml of a 15% NaOH solution and then 3.4 ml of water, the medium is stirred for 1 h and then filtered. The filtrate is concentrated under reduced pressure. The residue obtained is then dissolved in 50 ml of dichloromethane.

In a 500 ml round-bottomed flask, 2.28 g of oxalyl chloride (18 mmol) are dissolved in 100 ml of dichloromethane and the mixture is cooled to −78° C. 2.6 ml (36 mmol) of DMSO in 10 ml of dichloromethane are then added, and then the mixture is stirred for 15 minutes at −78° C. The solution of the alcohol obtained above is then slowly added by means of a small tube and then the reaction medium is again stirred for 30 minutes. 10 ml (72 mmol) of triethylamine are then added and the reaction medium is brought to room temperature. After stirring for 1 hour, the medium is treated with a saturated ammonium chloride solution and extracted with ethyl ether. The organic phase is rinsed with water and then dried and concentrated under reduced pressure. The aldehyde obtained is immediately used as it is.

The residue is dissolved in 120 ml of anhydrous THF and then 6.4 g (19 mmol) of methyl (triphenylphosphanylidene) acetate are added. The reaction mixture is stirred for 12 hours under reflux and is then treated with a saturated ammonium chloride solution and extracted with ethyl acetate. After purification by chromatography on a silica column, a yellow oil is obtained (m=2.67 g; Y=82%).

c) 3-((E)-5-Hydroxy-1,5-dimethylhex-3-enyl)phenol.

800 mg (2.4 mmol) of methyl (E)-5-[3-(tert-butyldimethylsilanyloxy)phenyl]hex-2-enoate are dissolved in 50 ml of anhydrous THF. The mixture is cooled to 0° C. and then 4.5 ml (7.2 mmol) of a 1.6M solution of methyllithium are added dropwise. The reaction medium is stirred for 2 hours at 0° C. and is then treated with a saturated ammonium chloride solution and extracted with ethyl acetate. After drying and concentrating the organic phase under reduced pressure, the residue is purified by chromatography on a silica column. The alcohol obtained (600 mg; 1.8 mmol) is then dissolved in 10 ml of THF, and 2 ml (2 mmol) of a tetrabutylammonium fluoride solution (1M in THF) are added. After 15 min, the reaction medium is concentrated under reduced pressure and the residue is purified by chromatography on a silica column. A yellow oil is obtained (m=358 mg; Y=68%).

d) (E)-6-[3-(3,4-bis-Hydroxymethylbenzyloxy)phenyl]-2-methylhept-3-en-2-ol.

In a manner similar to Example 53(e), by reacting 517 mg (1.2 mmol) of dimethyl 4-[3-((E)-5-hydroxy-1,5-dimethylhex-3-enyl)phenoxymethyl]phthalate (prepared by reacting the previous product with dimethyl 4-bromomethylphthalate, in a manner similar to Example 64(d)) with 80 mg (3.6 mmol) of lithium borohydride, a colourless oil is obtained (m=430 mg; Y=97%).

$^1$H NMR (CDCl$_3$): 1.18 (s, 6H), 1.22 (d, 3H, J=3.7 Hz), 2.19–2.25 (m, 2H), 2.69 (m, 1H), 4.55 (s, 2H), 4.56 (s, 2H), 4.97 (s, 2H), 5.43–5.46 (m, 2H), 6.71–6.77 (m, 3H), 7.14 (t, 1H, J=7.8 Hz), 7.28–7.34 (m, 3H).

EXAMPLE 71

(E)-7-[3-(3,4-bis-Hydroxymethylbenzyloxy)phenyl]-3-ethyloct-4-en-3-ol

In a manner similar to Example 53(e), by treating 63 mg (0.14 mmol) of dimethyl 4-[3-((E)-5-ethyl-5-hydroxy-1-methylhept-3-enyl)phenoxymethyl]phthalate (prepared in a manner similar to Example 70) with 10 mg (0.4 mmol) of lithium borohydride, a colourless oil is obtained (m=54 mg; Y=97%).

$^1$H NMR (CDCl$_3$): 0.70 (t, 3H, J=7.5 Hz), 0.73 (t, 3H, J=7.5 Hz), 1.25 (d, 3H, J=3.7 Hz), 1.42 (m, 4H), 2.29 (t, 2H, J=7 Hz), 2.74 (m, 1H), 3.8 (bs, 2H), 4.65 (s, 2H), 4.66 (s, 2H), 5.03 (s, 2H), 5.23–5.47 (m, 2H), 6.74–6.78 (m, 3H), 7.17 (t, 1H, J=7.8 Hz), 7.30–7.38 (m, 3H).

EXAMPLE 72

(E)-7-[3-(3,4-bis-Hydroxymethylbenzyloxy)phenyl]-3-ethyloct-6-en-3-ol a) Methyl 5-(3-Hydroxyphenyl)hex-4-enoate.

3.54 g of (3-carboxypropyl)triphenylphosphonium bromide (8.25 mmol) are added to a sodium hydride solution (400 mg, 16.5 mmol) in 15 ml of DMSO. After 20 min, 1 g (5.5 mmol) of 1-(3-methoxymethoxyphenyl)ethanone in 5 ml of DMSO are added by means of a small tube, and then the reaction medium is stirred for 15 hours at room temperature. After treating with 50 ml of water and 50 ml of toluene, the aqueous phase is separated and then acidified with a 2M solution of HCl and finally extracted with ethyl acetate. The organic phase is then dried and then concentrated under reduced pressure. The residue obtained is then dissolved in 50 ml of ethanol and then the mixture is heated to reflux temperature after addition of 1 ml of sulphuric acid. After stirring for 2 hours, the reaction medium is poured into a water/dichloromethane mixture and the phases are separated. The organic phase is dried and concentrated under reduced pressure and the residue is purified by chromatography on a silica column. A colourless oil is obtained (m=260 mg; Y=22%).

b) 3-Ethyl-7-(3-hydroxyphenyl)oct-6-en-3-ol.

In a manner similar to Example 65(a), starting with 443 mg (2 mmol) of the previous product, 237 mg (48%) of (Z)-3-ethyl-7-(3-hydroxyphenyl)oct-6-en-3-ol and 112 mg (23%) of (E)-3-ethyl-7-(3-hydroxyphenyl)-oct-6-en-3-ol are obtained.

c) Dimethyl 4-[3-((E)-5-Ethyl-5-hydroxy-1-methylhept-1-enyl)phenoxymethyl]phthalate.

In a manner similar to Example 64(d), by reacting 112 mg (0.39 mmol) of (E)-3-ethyl-7-(3-hydroxyphenyl)oct-6-en-3-ol with 145 mg (0.51 mmol) of dimethyl 4-bromomethylphthalate, 131 mg (74%) of expected product are obtained in the form of an oil.

d) (E)-7-[3-(3,4-bis-Hydroxymethylbenzyloxy)-phenyl]-3-ethyloct-6-en-3-ol.

In a manner similar to Example 53(e), by reacting 131 mg (0.29 mmol) of dimethyl 4-[3-((E)-5-ethyl-5-hydroxy-1-methylhept-1-enyl)phenoxymethyl]phthalate with 25 mg (1.15 mmol) of lithium borohydride, a colourless oil is obtained (m=89 mg; Y=78%).

$^1$H NMR (CDCl$_3$): 0.88 (t, 6H, J=7.5 Hz), 1.45–1.57 (m, 4H), 1.98 (s, 3H), 2.03–2.20 (m, 2H), 3.78 (bs, 2H), 4.63 (s, 2H), 4.64 (s, 2H), 5.02 (s, 2H), 5.76 (t, 1H, 7.1 Hz), 6.79 (m, 1H), 6.95–6.98 (m, 2H) 7.15–7.36 (m, 4H).

EXAMPLE 73

(Z)-7-[3-(3,4-bis-Hydroxymethylbenzyloxy)phenyl]-3-ethyloct-6-en-3-ol a) Dimethyl 4-[3-((Z)-5-Ethyl-5-hydroxy-1-methylhept-1-enyl)phenoxymethyl]phthalate.

In a manner similar to Example 64(d), by reacting 234 mg (0.95 mmol) of (Z)-3-ethyl-7-(3-hydroxyphenyl)oct-6-en-3-ol with 356 mg (1.24 mmol) of dimethyl 4-bromomethylphthalate, .398 mg (92%) of expected product are obtained in the form of an oil.

b) (Z)-7-[3-(3,4-bis-Hydroxymethylbenzyloxy)-phenyl]-3-ethyloct-6-en-3-ol.

In a manner similar to Example 53(e), by reacting 431 mg (0.95 mmol) of dimethyl 4-[3-((Z)-5-ethyl-5-hydroxy-1-methylhept-1-enyl)phenoxymethyl]-phthalate with 83 mg (3.8 mmol) of lithium borohydride, a colourless oil is obtained (m=286 mg; Y=76%).

$^1$H NMR (CDCl$_3$): 0.74 (t, 6H, J=7.5 Hz), 1.22–1.42 (m, 6H), 1.84–1.94 (m, 2H), 1.99 (s, 3H), 4 (bs, 2H), 4.59 (s, 2H), 4.60 (s, 2H), 5.01 (s, 2H), 5.41 (t, 1H, 7.1 Hz), 6.75–6.84 (m, 3H), 7.17–7.35 (m, 4H).

EXAMPLE 74

(E)-8-[3-(3,4-bis-Hydroxymethylbenzyloxy)phenyl]-2-methylnon-7-en-2-ol

In a manner similar to Example 53(e), by reacting 204 mg (0.46 mmol) of dimethyl 4-[3-((E)-7-hydroxy-1,7- dimethyloct-1-enyl)phenoxymethyl]-phthalate (prepared in a manner similar to Examples 72(a–c)) with 30 mg (1.4 mmol) of lithium borohydride, a colourless oil is obtained (m=146 mg; Y=82%).

$^1$H NMR (CDCl$_3$): 1.18 (s, 6H), 1.18–1.51 (m, 6H), 1.99 (s, 3H), 2.16–2.22 (m, 2H), 3.7 (bs, 2H), 4.61 (s, 2H), 4.62 (s, 2H), 5.01 (s, 2H), 5.76 (t, 1H), 6.77–6.81 (m, 1H), 6.96–6.99 (m, 2H), 7.15–7.35 (m, 4H).

EXAMPLE 75

(Z)-8-[3-(3,4-bis-Hydroxymethylbenzyloxy)phenyl]-2-methylnon-7-en-2-ol

In a manner similar to Example 53(e), by reacting 790 mg (1.8 mmol) of dimethyl 4-[3-((Z)-7-hydroxy-1,7-dimethyloct-1-enyl)phenoxymethyl]phthalate (prepared in a manner similar to Example 73(a)) with 118 mg (5.4 mmol) of lithium borohydride, a colourless oil is obtained (m=621 mg; Y=86%).

$^1$H NMR (CDCl$_3$): 1.11 (s, 6H), 1.17–1.36 (m, 6H), 1.98 (s, 3H), 1.90–1.99 (m, 2H), 4.56 (s, 2H), 4.57 (s, 2H) 4.98 (s, 2H), 5.41 (t, 1H), 6.75–6.82 (m, 3H), 7.17–7.35 (m, 4H).

EXAMPLE 76

(E)-9-[3-(3,4-bis-Hydroxymethylbenzyloxy)phenyl]-3-ethyldec-8-en-3-ol

In a manner similar to Example 53(e), by reacting 397 mg (0.85 mmol) of dimethyl 4-[3-((E)-7-ethyl-7-hydroxy-1-methylnon-1-enyl)phenoxymethyl]phthalate (prepared in a manner similar to Examples 72(a–c)) with 55 mg (2.5 mmol) of lithium borohydride, a colourless oil is obtained (m=323 mg; Y=92%).

$^1$H NMR (CDCl$_3$): 0.78 (t, 6H, J=7.5 Hz), 1.20–1.42 (m, 10H), 1.99 (s, 3H), 1.91–1.99 (m, 2H), 4.38 (bs, 2H), 4.57 (s, 2H), 4.58 (s, 2H), 4.99 (s, 2H), 5.42 (t, 1H, J=6.9 Hz), 6.76–6.82 (m, 3H), 7.17–7.35 (m, 4H).

EXAMPLE 77

(Z)-9-[3-(3,4-bis-Hydroxymethylbenzyloxy)phenyl]-3-ethyldec-8-en-3-ol

In a manner similar to Example 53(e), by reacting 1.21 g (2.58 mmol) of dimethyl 4-(3-((Z)-7-ethyl-7-hydroxy-1-methylnon-1-enyl)phenoxymethyl]-phthalate (prepared in a manner similar to Example 73(a)) with 170 mg (7.76 mmol) of lithium borohydride, a colourless oil is obtained (m=865 mg; Y=81%).

$^1$H NMR (CDCl$_3$): 0.84 (t, 6H, J=7.5 Hz), 1.30–1.48 (m, 10H), 1.99 (s, 3H), 2.16–2.23 (m, 2H), 4.1 (bs, 2H), 4.60 (s, 2H), 4.61 (s, 2H), 5.00 (s, 2H), 5.76 (t, 1H, J=6.2 Hz), 6.76–6.82 (m, 2H), 6.95–6.99 (m, 1H), 7.15–7.35 (m, 4H).

EXAMPLE 78

8-[3-(3,4-bis-Hydroxymethylbenzyloxy)phenyl]-2-methyl-2-nonanol a) 3-(7-Hydroxy-1,7-dimethyloctyl)phenol.

125 mg (0.32 mmol) of (Z)-8-[3-(3,4-bis-hydroxymethylbenzyloxy)phenyl]-2-methylnon-7-en-2-ol (obtained in Example 75) are dissolved in 25 ml of methanol. NaNO$_2$ (620 mg, 9 mmol) is then added to the solution and then 50 mg of 5% Pd/C. The assembly is then equipped with a hydrogen flask (1 bar) and the reaction medium is stirred for 5 hours. The reaction medium is then filtered and then the filtrate is added to 50 ml of water and then extracted with dichloromethane. The organic phase is then dried and concentrated under reduced pressure. The residue is purified by chromatography on a silica column (ethyl acetate 20-heptane 80) and then ethyl acetate 50-heptate 50). A colourless oil is obtained (m=50 mg; Y=95%).

b) 8-[3-(3,4-bis-Hydroxymethylbenzyloxy)phenyl]-2-methyl-2-nonanol.

In a manner similar to Example 53(e), by reacting 97 mg (0.21 mmol) of dimethyl 4-[3-(7-hydroxy-1,7-dimethyloctyl)phenoxymethyl]phthalate (prepared from the previous product in a manner similar to Example 64(d) with 14 mg (0.63 mmol) of lithium borohydride, a colourless oil is obtained (m=83 mg; Y=99%).

$^1$H NMR (CDCl$_3$): 1.09 (s, 6H), 1.10–1.18 (m, 9H), 1.26–1.31 (m, 2H), 1.40–1.48 (m, 2H), 2.51–2.58 (m, 1H), 3.0 (bs, 2H), 4.60 (s, 2H), 4.61 (s, 2H), 4.96 (s, 2H), 6.68–6.73 (m, 3H), 7.08–7.32 (m, 4H).

EXAMPLE 79

9-[3-(3,4-bis-Hydroxymethylbenzyloxy)phenyl]-3-ethyldecan-3-ol

In a manner similar to Example 78, starting with (Z)-9-[3-(3,4-bis-hydroxymethylbenzyloxy)phenyl]-3-ethyldec-8-en-3-ol (prepared in Example 77), 9-[3-(3,4-bis-hydroxymethylbenzyloxy)phenyl]-3-ethyldecan-3-ol is obtained in the form of an oil.

$^1$H NMR (CDCl$_3$): 0.74 (t, 6H, J=7.6 Hz), 1.12–1.38 (m, 15H), 1.44–1.47 (m, 2H), 2.50–2.60 (m, 1H), 4.70 (bs, 2H), 4.56 (s, 2H), 4.57 (s, 2H), 4.93 (s, 2H), 6.66–6.72 (m, 3H), 7.07–7.29 (m, 4H).

EXAMPLE 80

(E)-7-[3-(3,4-bis-Hydroxymethylbenzyloxy)phenyl]-3-ethyloct-6-en-4-yn-3-ol a) 1-Methoxymethoxy-3-((E)-1-methylbut-1-en-3-ynyl) benzene.

2.47 g (9.9 mmol) of diethyl (3-trimethylsilanylprop-2-ynyl)phosphonate are dissolved in 20 ml of anhydrous THF and then the solution is cooled to −78° C. A solution of 1.94 g (10.6 mmol) of lithium bis-trimethylsilylamide in 10 ml of THF is added dropwise. After stirring for 30 minutes at −78° C., 1.2 g (6.6 mmol) of 3-methoxymethoxyacetophenone in 10 ml of THF are added dropwise by means of a small tube. The reaction medium is stirred for 30 minutes at −78° C. and is then brought to room temperature and stirred for 24 hours. The reaction medium is then treated with water and then extracted with ethyl acetate. The organic phase is dried and then concentrated under reduced pressure and then the residue is filtered on a silica pad. The residue obtained is then dissolved in 25 ml of THF and 8 ml (8 mmol) of a tetrabutylammonium fluoride solution (1M in THF) are added. After 15 minutes at room temperature, the reaction medium is concentrated and the residue purified by chromatography on a silica column (ethyl acetate 5-heptane 95). A yellow oil is obtained (m=1.11 g; Y=83%).

b) Ethyl (E)-5-(3-Methoxymethoxyphenyl)hex-4-en-2-ynoate 764 mg (3.78 mmol) of 1-methoxymethoxy-3-((E)-1-methylbut-1-en-3-ynyl)benzene are dissolved in 20 ml of anhydrous THF and the solution is cooled to −78° C. 1.8 ml (4.5 mmol) of a 2.5M butyllithium solution are then added dropwise and the reaction medium is stirred for 30 minutes at this temperature. 0.43 ml (4.5 mmol) of ethyl chloroformate are then added dropwise and then the reaction medium is brought to room temperature and stirred for 2 hours. After treating with a saturated ammonium chloride solution and extracting with ethyl acetate, the organic phase is dried and then concentrated under reduced pressure. After purification by chromatography on a silica column (ethyl acetate 10-heptane 90), a yellow oil is obtained (m=836 mg; Y=81%).

c) Ethyl (E)-5-(3-Hydroxyphenyl)hex-4-en-2-ynoate.

800 mg (2.9 mmol) of ethyl (E)-5-(3-methoxymethoxyphenyl)hex-4-en-2-ynoate are dissolved in 50 ml of ethanol and then 1 ml of sulphuric acid is added to the solution. The reaction medium is stirred for 14 h, treated with water and extracted with dichloromethane. The organic phase is dried, concentrated under reduced pressure and the residue is purified by chromatography (ethyl acetate 10-heptane 90) and then (ethyl acetate 20-heptane 80). A yellow oil is obtained (m=676 mg; Y=100%).

d) (E)-7-[3-(3,4-bis-Hydroxymethylbenzyloxy)-phenyl]-3-ethyloct-6-en-4-yn-3-ol.

In a manner similar to Example 53(e), by reacting 390 mg (0.87 mmol) of dimethyl 4-[3-((E)-5-ethyl-5-hydroxy-1-methylhept-1-en-3-ynyl)phenoxymethyl]phthalate (prepared from the previous product in a manner similar to Example 64(d)) with 56 mg (2.6 mmol) of lithium borohydride, a colourless oil is obtained (m=248 mg; Y=72%).

$^1$H NMR (CDCl$_3$): 1.09 (t, 6H, J=7.6 Hz), 1.70–1.79 (m, 4H), 2.27 (d, 3H, J=1 Hz), 3.14 (bs, 2H), 4.72 (s, 2H), 4.73 (s, 2H), 5.05 (s, 2H), 5.89 (d, 1H, J=1 HZ), 6.86–6.91 (m, 1H), 7.01–7.05 (m, 2H), 7.21–7.41 (m, 4H).

EXAMPLE 81

(3E,5E)-7-[3-(3,4-bis-Hydroxymethylbenzyloxy) phenyl]-2,7-dimethylocta-3, 5-dien-2-ol a) Methyl 2-[3-(tert-Butyldimethylsilanyloxy)phenyl]-2-methylpropionate.

2 g (7.1 mmol) of methyl [3-(tert-butyldimethylsilanyloxy)phenyl]acetate are added to a lithium diisopropylamide solution (20.6 mmol) in 100 ml of THF at 0° C. and then the medium is stirred for 30 minutes. 2.2 ml (35.5 mmol) of methyl iodide are then added dropwise and the reaction medium is brought to room temperature and stirred for 18 hours. The reaction medium is treated with a saturated ammonium chloride solution and then extracted with ethyl ether. The residue obtained is subjected to the same conditions described above. After 12 h, the reaction medium is treated with a saturated ammonium chloride solution and then extracted with ethyl ether. The organic phase is dried and then concentrated under reduced pressure. The residue obtained is then purified by chromatography on a silica column in order to obtain a colourless oil (m=1.526 g; Y=70%).

b) 2-[3-(tert-Butyldimethylsilanyloxy)phenyl]-2-methylpropionaldehyde.

1.53 g (4.9 mmol) of methyl 2-[3-(tert-butyldimethylsilanyloxy)phenyl]-2-methylpropionate are dissolved in 100 ml of anhydrous ethyl ether. The mixture is cooled to 0° C. and then lithium aluminium hydride (760 mg, 20 mmol) is added in 2 equal portions. The reaction medium is heated under reflux for 4 h and is then brought to room temperature. After treating with 0.76 ml of water, 0.76 ml of a 15% NaOH solution and then 2.3 ml of water, the medium is stirred for 1 h and then filtered. The filtrate is concentrated under reduced pressure. The residue obtained is then dissolved in 20 ml of dichloromethane.

In a 100 ml round-bottomed flask, 0.95 g of oxalyl chloride (7.5 mmol) is dissolved in 20 ml of dichloromethane and the mixture is cooled to −78° C. 1.06 ml (15 mmol) of DMSO in 5 ml of dichloromethane are then added and then the mixture is stirred for 15 minutes at −78° C. The solution of the alcohol previously obtained is then slowly added by means of a small tube and then the reaction medium is again stirred for 30 minutes. 4.2 ml (30 mmol) of triethylamine are then added and the reaction medium is brought to room temperature. After stirring for 1 hour, the medium is treated with a saturated ammonium chloride solution and extracted with ethyl ether. The organic phase is rinsed with water and then dried and concentrated under reduced pressure. The residue is purified by chromatography on a silica column (ethyl acetate 5-heptane 95). A colourless oil is obtained (m=1.08 g; Y=75%).

c) Ethyl (2E,4E)-6-[3-(tert-Butyldimethylsilanyloxy) phenyl]-6-methylhepta-2,4-dienoate.

1.7 ml (7.5 mmol) of ethyl 4-diethylphosphonocrotonate are dissolved in 50 ml of THF and then the mixture is cooled to 0 C. 3.4 ml (6.8 mmol) of a 2M solution of lithium diisopropylamide are added dropwise and the reaction medium is stirred for 30 minutes. 1 g (3.4 mmol) of 2-[3-(tert-butyldimethylsilanyloxy)-phenyl]-2-methylpropionaldehyde in 10 ml of THF is then slowly added by means of a small tube. The reaction medium is brought to room temperature and is then stirred for 4 hours. After treating with a saturated ammonium chloride solution, the organic phase is dried and concentrated under reduced pressure. The residue is filtered on a silica pad. A yellow oil is obtained (m=1.26 g; Y=99%).

c) Ethyl (2E,4E)-6-[3-Hydroxyphenyl]-6-methylhepta-2,4-dienoate.

In a manner similar to Example 59(h), starting with 568 mg (1.5 mmol) of the previous product, 284 mg (75%) of expected product are obtained in the form of an oil.

d) (3E,5E)-7-[3-(3,4-bis-Hydroxymethylbenzyloxy) phenyl]-2,7-dimethylocta-3,5-dien-2-ol.

In a manner similar to Example 53(e), by reacting 360 mg (0.8 mmol) of dimethyl 4-[3-((2E,4E)-6-hydroxy-1,1,6-trimethylhepta-2,4-dienyl)phenoxymethyl]phthalate (prepared from the previous product in a manner similar to Example 64(d)) with 70 mg (3.2 mmol) of lithium borohydride, a colourless oil is obtained (m=220 mg; Y=70%).

$^1$H NMR (CDCl$_3$): 1.33 (s, 6H), 1.40 (s, 6H), 2.27 (bs, 2H), 4.35 (bs, 1H), 4.71 (s, 4H), 5.04 (s, 2H), 5.75–10 5.87 (m, 2H), 6.02 (dd, 1H, J$_1$=15.3 Hz, J$_2$=10 Hz), 6.22 (dd, 1H, J$_1$=15.3 Hz, J$_2$=10 Hz), 6.78 (dd, 1H, J$_1$=1.6 Hz, J$_2$=8.2 Hz), 6.92–6.95 (m, 2H), 7.21 (t, 1H, J=8.2 Hz), 7.37 (s, 2H), 7.44 (s, 1H).

EXAMPLE 82

(4E,6E)-7-[3-(3,4-bis-Hydroxymethylphenoxy-methyl)phenyl]-3-ethylocta-4,6-dien-3-ol a) (4E,6E)-7-{3-[3,4-bis(tert-Butyldimethylsilanyloxymethyl)phenoxymethyl]phenyl}-3-ethylocta-4,6-dien-3-ol.

Ethyl 5-{3-[3,4-bis(tert-butyldimethylsilanyloxymethyl) phenoxymethyl]phenyl}hexa-2,4-dienoate (prepared in Example 6(i)) (800 mg, 1.3 mmol) is dissolved in 10 ml of THF and cooled to 0° C. 9 ml (13 mmol) of a 1.5M solution of ethyllithium are slowly added and then the stirring is continued for 3 hours. After treating with a saturated ammonium chloride solution and then extracting with ethyl ether, the organic phases are combined, dried and then concentrated under reduced pressure. After purification by chromatography on a silica column (heptane eluent), the expected product is obtained in the form of a colourless oil (m=410 mg, Y=50%).

b) (4E,6E)-7-[3-(3,4-bis-Hydroxymethylphenoxymethyl) phenyl]-3-ethylocta-4,6-dien-3-ol.

In a manner similar to Example 57(c) by reacting 520 mg (0.83 mmol) of (4E,6E)-7-{3-[3,4-bis-(tert-butyldimethylsilanyloxymethyl)phenoxymethyl]-phenyl}-3-ethylocta-4,6-dien-3-ol with 2.5 ml of a tetrabutylammonium fluoride solution (1N in THF), a colourless oil is obtained (m=164 mg; Y=50%).

$^1$H NMR (CDCl$_3$): 0.90 (t, 6H, J=7.4 Hz), 1.57 (q, 4H, J=7.4 Hz), 2.19 (s, 3H), 2.6 (bs, 2H), 4.69 (s, 2H), 4.71 (s, 2H), 5.08 (s, 2H), 5.79 (d, 1H, J=14.9 Hz), 6.49 (d, 1H,

J=10.9 Hz), 6.65 (dd, 1H, J₁=14.9 Hz, J₂=10.9 Hz), 6.90 (dd, 1H, J₁=2.6 Hz, J₂=8.2 Hz), 7.03 (m, 1H), 7.25–7.50 (m, 5H).

EXAMPLE 83

(3E,5E)-6-[3-(3,4-bis-Hydroxymethylphenoxymethyl)phenyl]-2-methylhepta-3,5-dien-2-ol a) (3E,5E)-6-{3-[3,4-bis(tert-Butyldimethylsilanyloxymethyl)phenoxymethyl]phenyl}-2-methylhepta-3,5-dien-2-ol.

Ethyl 5-{3-[3,4-bis(tert-butyldimethylsilanyloxymethyl)phenoxymethyl]phenyl}hexa-2,4-dienoate (prepared in Example 6(i)) (4.17 mg, 0.7 mmol) is dissolved in 6 ml of THF and cooled to 0° C. 2 ml (2.8 mmol) of a 1.4M solution of methyllithium are slowly added and then the stirring is continued for 3 hours. After treating with a saturated ammonium chloride solution and then extracting with ethyl ether, the organic phases are combined, dried and then concentrated under reduced pressure. After purification by chromatography on a silica column (heptane eluent), the expected product is obtained in the form of a colourless oil (m=120 mg, Y=30%).

b) (3E,5E)-6-[3-(3,4-bis-Hydroxymethylphenoxymethyl)phenyl]-2-methylhepta-3,5-dien-2-ol.

In a manner similar to Example 57(c), by reacting 120 mg (0.2 mmol) of (3E,5E)-6-{3-[3,4-bis-(tert-butyldimethylsilanyloxymethyl)phenoxymethyl]-phenyl}-2-methylhepta-3,5-dien-2-ol with 0.6 ml of a tetrabutylammonium fluoride solution (1N in THF), a colourless oil is obtained (m=30 mg; Y=41%).

¹H NMR (CDCl₃): 1.39 (s., 6H), 2.19 (s, 3H), 2.9 (bs, 2H), 4.67 (s, 2H), 4.69 (s, 2H), 5.07 (s, 2H), 5.96 (d, 1H, J=15 Hz), 6.44 (d, 1H, J=10.9 Hz), 6,64 (dd, 1H, J₁=15 Hz, J₂=10.9 Hz), 6.89 (dd, 1H, J₁=2.7 Hz, J₂=8.2 Hz), 7.02 (m, 1H), 7.24–7.49 (m, 5H).

EXAMPLE 84

(Z)-7-[3-(3,4-bis-Hydroxymethylbenzyloxy)-phenyl]-3-ethylnon-6-en-3-ol a) Ethyl (Z)-5-(3-Hydroxyphenyl)hex-4-enoate.

5.3 g (12.4 mmol) of (3-carboxypropyl)triphenylphosphonium bromide are dried under vacuum for 1 h by heating to 130° C. and then brought to room temperature and dissolved in 100 ml of anhydrous THF. 2.75 g (25 mmol) of potassium tert-butoxide in 50 ml of THF are then slowly added and then the orange-red mixture is stirred for 15 minutes. A solution of 1.2 g (6.2 mmol) of 1-(3-methoxymethoxyphenyl)-1-propanone in 50 ml of THF is then added dropwise and the reaction medium is stirred for 15 hours. After treating with a saturated ammonium chloride solution and extracting with ethyl acetate and then drying and evaporating the solvents of the organic phase, the residue is then dissolved in 50 ml of ethanol, and then 1 ml of sulphuric acid is added. The reaction medium is heated to reflux temperature and stirred for 2 hours. After treating with water, the medium is extracted with ethyl acetate and then the organic phases are combined, dried and concentrated under reduced pressure. The residue is purified by chromatography on a silica column (eluent heptane 95-ethyl acetate 5) in order to obtain a yellow oil (m=670 mg; Y=43%).

b) Ethyl (Z)-5-{3-[3,4-bis(1-Phenylmethanoyloxymethyl)]phenyl}hept-4-enoate.

670 mg (2.7 mmol) of ethyl (Z)-5-(3-hydroxyphenyl)hex-4-enoate, 1.42 g (3.2 mmol) of (3,4-bis-benzoyloxymethyl) benzyl bromide and 450 mg (3.2 mmol) of potassium carbonate are dissolved in 20 ml of 2-butanone. The mixture is heated under reflux (80° C.) and then stirred for 4 h. After cooling, the reaction medium is filtered and then concentrated under reduced pressure. The residue is purified by chromatography on a silica column (m=1.18 g; Y=73%).

c) (Z)-7-[3-(3,4-bis-Hydroxymethylbenzyloxy)phenyl]-3-ethylnon-6-en-3-ol.

800 mg (1.32 mmol) of ethyl (Z)-5-{3-[3,4-bis(1-phenylmethanoyloxymethyl)]phenyl}hept-4-enoate are dissolved in 30 ml of anhydrous THF and then the mixture is cooled to 0° C. 4.4 ml (13 mmol) of a 3M solution of ethylmagnesium bromide are then added and then the reaction medium is brought to room temperature and stirred for 1 h. After treating with a saturated ammonium chloride solution and then extracting with ethyl acetate, the organic phases are combined, dried and concentrated under reduced pressure. After purification by chromatography on a silica column, a colourless oil is obtained (m=309 mg; Y=57%).

¹H NMR (CDCl₃): 0.74 (t, 6H, J=7.5 Hz), 0.95 (t, 3H, 7.4 Hz), 1.25–1.40 (m, 6H), 1.78–1.90 (m, 2H), 2.29 (q, 2H, J=7.4 Hz), 3.5 (bs, 2H), 4.68 (s, 4H), 5.07 (s, 2H), 5.38 (t, 1H, J=7.3 Hz), 6.70–6.85 (m, 2H), 7.18–7.39 (m, 5H).

EXAMPLE 85

(Z)-6-[3-(3,4-bis-Hydroxymethylbenzyloxy)-phenyl]-2-methyloct-5-en-2-ol

In a manner similar to Example 84(c), by reacting 380 mg (0.63 mmol) of ethyl (Z)-5-{3-[3,4-bis-(1-phenylmethanoyloxymethyl)]phenyl}hept-4-enoate (prepared in a manner similar to Examples 84(a–b)) with 2.1 ml (6.3 mmol) of a 3.0M solution of methylmagnesium bromide, a colourless oil is obtained (m=178 mg; Y=74%).

¹H NMR (CDCl₃): 0.87 (t, 3H, 7.4 Hz) 0.98 (s, 6H), 1.32–1.39 (m, 2H), 1.78–1.85 (m, 2H), 2.17–2.24 (m, 2H), 3.7 (bs, 2H), 4.58 (s, 2H), 4.60 (s, 2H), 4.99 (s, 2H), 5.28 (t, 1H), 6.63–6.78 (m, 2H), 7.11–7.30 (m, 5H).

EXAMPLE 86

(Z)-7-[3-(3,4-bis-Hydroxymethylbenzyloxy)-phenyl]-3-ethyldec-6-en-3-ol

In a manner similar to Example 84(c), by reacting 1 g (1.6 mmol) of ethyl (Z)-5-[3-(3,4-bis-hydroxymethylbenzyloxy)phenyl]oct-4-enoate (prepared in a manner similar to Examples 84(a–b)) with 5.4 ml (16 mmol) of a 3.0M solution of ethylmagnesium bromide, a colourless oil is obtained (m=480 mg; Y=70%).

¹H NMR (CDCl₃): 0.70 (t, 6H, J=7.5 Hz), 0.81–0.91 (m, 5H), 1.25–1.37 (m, 6H), 1.45–1.54 (m, 2H), 1.70–1.90 (m, 2H), 2.40–2.45 (m, 2H), 3.5 (bs, 1H), 3.69 (bs, 1H), 4.66 (s, 4H), 5.06 (s, 2H), 5.39 (t, 1H, J=7.3 Hz), 6.70–6.85 (m, 2H), 7.18–7.39 (m, 5H).

EXAMPLE 87

(Z)-6-[3-(3,4-bis-Hydroxymethylbenzyloxy)-phenyl]-2-methylnon-5-en-2-ol

In a manner similar to Example 84(c), by reacting 1 g (1.6 mmol) of ethyl (Z)-5-[3-(3,4-bis-hydroxymethylbenzyloxy) phenyl]oct-4-enoate (prepared in a manner similar to Examples 84(a–b)) with 5.4 ml (16 mmol) of a 3.0M solution of methylmagnesium bromide, a colourless oil is obtained (m=516 mg; Y=81%).

¹H NMR (CDCl₃): 0.84 (t, 3H, J=7.4 Hz), 1.06 (s, 6H), 1.28–1.47 (m, 4H), 1.84–1.90 (m, 2H), 2.26 (t, 2H, J=6.7 Hz), 3.5 (bs, 2H), 4.69 (s, 4H), 5.08 (s, 2H), 5.38 (t, 1H), 6.70–6.85 (m, 2H), 7.18–7.40 (m, 5H).

EXAMPLE 88

(Z)-8-[3-(3,4-bis-Hydroxymethylbenzyloxy)-phenyl]-3-ethylnon-7-en-3-ol a) Ethyl 6-(3-Hydroxyphenyl)hept-5-enoate 21.6 g (48.7 mmol) of (4-carboxybutyl)triphenylphosphonium bromide are dried under vacuum for 1 h by heating to 130° C., and then brought to room temperature and dissolved in 300 ml of anhydrous THF. 10.9 g (97 mmol) of potassium tert-butoxide in 100 ml of THF are then slowly added and then the orange-red mixture is stirred for 15 minutes. A solution of 6.3 g (32.5 mmol) of 1-(3-methoxymethoxyphenyl)-1-ethanone in 50 ml of THF is then added dropwise and the reaction medium is stirred for 15 hours. After treating with a saturated ammonium chloride solution and extracting with ethyl acetate and then drying and evaporating the solvents of the organic phase, the residue is then dissolved in 50 ml of ethanol and then 1 ml of sulphuric acid is added. The reaction medium is heated to reflux temperature and stirred for 2 hours. After treating with water, the medium is extracted with ethyl acetate and then the organic phases are combined, dried and concentrated under reduced pressure. The residue is purified by chromatography on a silica column (eluent heptane 80-ethyl acetate 20) in order to obtain 1 g (12%) of ethyl (Z)-6-(3-hydroxyphenyl)hept-5-enoate and 1.3 g (16%) of ethyl (E)-6-(3-hydroxyphenyl)hept-5-enoate.

b) Ethyl (Z)-6-{3-[3,4-bis(1-Phenylmethanoyloxymethyl)]phenyl}hept-5-enoate.

1 g (4 mmol) of ethyl (Z)-6-(3-hydroxyphenyl)hept-5-enoate is dissolved in 20 ml of DMF and 180 mg of NaH (60% in oil) are added. The reaction medium is stirred until the gaseous emission ceases and then a solution of 1.9 g (4.4 mmol) of (3,4-bis-benzoyloxymethyl)benzyl bromide in 100 ml of DMF is added. The mixture is stirred for 14 h, extracted between water and ethyl acetate and separated after settling out. The organic phases are dried over magnesium sulphate and evaporated. The residue obtained is purified by chromatography on a silica column (heptane 80-ethyl acetate 20) (m=2.2 g; Y=90%).

c) (Z)-8-[3-(3,4-bis-Hydroxymethylbenzyloxy)phenyl]-3-ethylnon-7-en-3-ol.

In a manner similar to Example 84(c), by reacting 2.2 g (3.6 mmol) of ethyl (Z)-6-{3-[3,4-bis-(1-phenylmethanoyloxymethyl)]phenyl}hept-5-enoate with 9.7 ml (29 mmol) of a 3M solution of ethylmagnesium bromide, a colourless oil is obtained (m=1.1 g; Y=74%).

$^1$H NMR (CDCl$_3$): 0.82 (t, 6H, J=7.5 Hz), 1.23–1.28 (m, 4H), 1.41 (q, 4H, J=7.5 Hz), 1.87–1.90 (m, 2H), 2.00 (s, 3H), 3.1 (bs, 2H), 4.75 (s, 2H), 4.76 (s, 2H), 5.09 (s, 2H), 5.42 (t, 1H, J=5.9 Hz), 6.76–6.88 (m, 3H), 7.22–7.43 (m, 4H).

EXAMPLE 89

(E)-8-[3(3,4-bis-Hydroxymethylbenzyloxy)-phenyl]-3-ethylnon-7-en-3-ol a) Dimethyl 4-Hydroxymethylphthalate.

1,2,4-Benzenetricarboxylic anhydride (50 g, 260 mmol) is dissolved in 800 ml of anhydrous dioxane, at room temperature. BH$_3$.THF (260 mmol, 1 eq.) is then added dropwise by means of a dropping funnel, over a period of about 1 h 30 min. The stirring is maintained for 12 h and then the reaction medium is poured into a mixture containing 600 ml of a saturated NH$_4$Cl solution and 2 l of dichloromethane. After separating, the organic phase is dried and the solvents are evaporated under reduced pressure. The residue obtained is then dissolved in 1 l of methanol and heated to reflux temperature after addition of 5 ml of sulphuric acid. After refluxing for 18 h, the reaction medium is cooled to room temperature and directly poured into a water/ethyl ether mixture (1 1/2 l). After separating, the aqueous phase is again extracted with two fractions of ethyl ether (about 700 ml) and then the organic phases are combined and dried and then concentrated under reduced pressure. A triester-diester/alcohol mixture is obtained with a yield of 80%, containing 65% of the desired product.

b) Dimethyl 4-(tert-Butyldimethylsilanyloxymethyl)phthalate.

The mixture obtained above, containing about 135 mmol of desired product, is dissolved in 400 ml of anhydrous DMF. tert-Butyldimethylsilane chloride (22.5 g, 150 mmol) is then added in a single portion. Next, a total of 13.5 g (195 mmol) of imidazole is added in three portions (slight exothermicity). The reaction medium is stirred for 36 hours and then concentrated under reduced pressure. The residue is then dissolved in 500 ml of ethyl ether and then filtered in order to remove the imidazole hydrochloride formed. The salt is rinsed with 2 fractions of 150 ml of ethyl ether and then the organic phases are dried and concentrated under reduced pressure. The residue is then purified by chromatography: the first product collected (eluent AcOEt 10-heptane 90) is the desired dimethyl 4-(tert-butyldimethylsilanyloxymethyl)phthalate. Yield 87%, overall yield from the initial acid: 45%.

c) [5-(tert-Butyldimethylsilanyloxymethyl)-2-hydroxymethylphenyl]methanol.

The diester obtained above (75 g, 220 mmol) is dissolved in 1 l of ethyl ether and cooled to 0° C. under a positive nitrogen pressure., 4 fractions of 5 g of LiAlH$_4$ (527 mmol) are added with care and then the mixture is heated to 50° C. After stirring for 1 h 30 min, the reaction medium is again cooled to 0° C. and then treated successively with 20 ml of water, 20 ml of 15% NaOH and then 60 ml of water. The reaction medium is stirred for 30 minutes until the complete disappearance of the grey aluminium salts and their precipitation as white floccules are observed. The medium is then filtered and after rinsing the salts with three fractions of ethyl acetate (200 ml), the organic phases are combined, dried and concentrated under reduced pressure. The product obtained represents a yield of 97%.

d) 2-Benzoyloxymethyl-4-(tert-butyldimethylsilanyloxymethyl)benzyl Benzoate.

The crude diol obtained above (60 g, 212 mmol) is dissolved in 600 ml of anhydrous THF and cooled to 0° C. 74 ml (530 mmol) of triethylamine are then added, followed by 52 ml (448 mmol) of benzoyl chloride. DMAP (500 mg) is then added in a single portion and the mixture is stirred for 30 minutes at 0° C. and then for 12 hours at room temperature. The reaction medium is then filtered in order to remove the precipitated triethylammonium salts, the salts are rinsed with two fractions of 200 ml of ethyl acetate and then the mixture of the organic phases is concentrated under reduced pressure, taken up in dichloromethane, rinsed with a saturated NH$_4$Cl solution and finally with a fraction of water. After drying, the organic phase is concentrated under reduced pressure, giving a dark yellow residue which is used as it is for the next step.

e) 2-Benzoyloxymethyl-4-hydroxymethylbenzyl Benzoate.

The residue obtained above is dissolved in 600 ml of ethyl acetate and 220 ml of a tetrabutylammonium fluoride solution (1M in THF) are added in a single fraction. After stirring for 30 minutes at room temperature, the reaction medium is poured into a separating funnel containing 1 l of saturated NH$_4$Cl. After separating, the aqueous phase is again extracted with 500 ml of ethyl acetate and then the organic phases are combined, dried and evaporated. The product is then purified by chromatography (ethyl acetate 30-heptane 70). A white solid is obtained (m.p.: 91–93° C.).

f) (3,4-bis-Benzoyloxymethyl)benzyl Bromide.

The above alcohol (65 g, 172 mmol) is dissolved in 350 ml of dichloromethane and CBr$_4$ (67.7 g, 202 mmol) is added. The medium is cooled to 0° C. and then a solution of triphenylphosphine (53 g, 202 mmol) in 250 ml of dichloromethane is added dropwise. The reaction medium is then heated to room temperature and then stirred for 2 hours. The medium is then treated with 500 ml of water and then extracted with dichloromethane. After drying and concentrating the organic phases, the product is purified by chromatography (eluent $CH_2Cl_2$/EtOAc) in order to obtain a white solid (m.p.: 83° C.) with a yield of 93%.

g) Ethyl (E)-6-{3-[3,4-bis(1-Phenylmethanoyloxymethyl)]phenyl}hept-5-enoate 500 mg (2 mmol) of ethyl (E)-6-(3-hydroxyphenyl)hept-5-enoate (obtained in Example 88(a)) are dissolved in 20 ml of DMF and 90 mg of NaH (60% in oil) are added. The reaction medium is stirred until the gaseous emission ceases and then a solution of 950 mg (2.2 mmol) of (3,4-bis-benzoyloxymethyl)benzyl bromide (obtained above) in 50 ml of DMF is added. The mixture is stirred for 14 h, extracted between water and ethyl acetate and separated after settling out. The organic phases are dried over magnesium sulphate and evaporated. The residue obtained is purified by chromatography on a silica column (heptane 80-ethyl acetate 20) (m=1.1 g; Y=90%).

h) (E)-8-[3-(3,4-bis-Hydroxymethylbenzyloxy)phenyl]-3-ethylnon-7-en-3-ol.

In a manner similar to Example 84(c), by reacting 1.1 g (1.8 mmol) of ethyl (E)-6-{3-[3,4-bis-(1-phenylmethanoyloxymethyl)]phenyl}hept-5-enoate with 4.8 ml (14.5 mmol) of a 3M solution of ethylmagnesium bromide, a colourless oil is obtained (m=470 mg; Y=64%).

$^1$H NMR (CDCl$_3$): 0.86 (t, 6H, J=7.5 Hz), 1.38–1.57 (m, 8H), 2.00 (s, 3H), 2.16–2.22 (m, 2H), 2.8 (bs, 2H), 4.76 (s, 2H), 4.77 (s, 2H), 5.08 (s, 2H), 5.76 (t, 1H, J=7.2 Hz), 6.81–6.85 (m, 1H), 6.97–7.00 (m, 2H), 7.22 (t, 1H, J=8.2 Hz), 7.39 (s, 2H), 7.45 (s, 1H).

EXAMPLE 90

8-[3-(3,4-bis-Hydroxymethylbenzyloxy)phenyl]-3-ethyl-nonan-3-ol a) Ethyl 6-(3-Hydroxyphenyl)heptanoate.

In a manner similar to Example 64(b), starting with ethyl 6-(3-hydroxyphenyl)hept-5-enoate, ethyl 6-(3-hydroxyphenyl)heptanoate is obtained in the form of an oil.

b) Ethyl 6-{3-[3,4-bis(1-Phenylmethanoyloxymethyl)]phenyl}heptanoate.

In a manner similar to Example 89(a), by reacting ethyl 6-(3-hydroxyphenyl)heptanoate with (3,4-bis-benzoyloxymethyl)benzyl bromide, ethyl 6-{3-(3,4-bis(1-phenylmethanoyloxymethyl)]phenyl}heptanoate is obtained in the form of an oil b) 8-[3-(3,4-bis-Hydroxymethylbenzyloxy)phenyl]-3-ethylnonan-3-ol.

The product is obtained in a manner similar to Example 84(c) by addition of 4.5 ml of a 3.0M solution of ethylmagnesium bromide to 1 g (1.6 mmol) of ethyl 6-{3-[3,4-bis(1-phenylmethanoyloxymethyl)]-phenyl}heptanoate. A colourless oil is obtained (m=490 mg; Y=66%).

$^1$H NMR (CDCl$_3$): 0.82 (t, 6H, J=7.5 Hz), 1.14–1.33 (m, 9H), 1.42 (q, 4H, J=7.5 Hz), 1.46–1.62 (m, 2H), 2.64 (m, 1H), 3.08 (bs, 2H), 4.73 (s, 2H), 4.74 (s, 2H), 5.30 (s, 2H), 6.77–6.80 (m, 3H), 7.20 (t, 1H, J=8.2 Hz), 7.37 (s, 2H), 7.42 (s, 1H).

EXAMPLE 91

(4E,6E)-7-[5-(3,4-bis-Hydroxymethyl-benzyloxy)-2-methoxyphenyl]-3-ethylnona-4,6-dien-3-ol a) 5-Methoxymethoxy-2-methoxybenzaldehyde.

3 g (7.6 mmol) of NaH (60% in oil) are added to 9.6 g (63 mmol) of 5-hydroxy-2-methoxybenzaldehyde in 150 ml of DMF and the mixture is stirred until the gaseous emission ceases. 5.3 ml (70 mmol) of methoxymethyl chloride are then added and the mixture is stirred at room temperature for two hours. After the usual treatment and chromatography on silica, 12.3 g of the expected product are obtained (100%).

b) 3-(5-Methoxymethoxy-2-methoxyphenyl)-3-propanol.

12.3 g (63 mmol) of the above product in THF are reacted with 31 ml of a 3M solution of ethylmagnesium bromide (93 mmol). After stirring for one hour and the usual treatment, the residue is purified by chromatography on silica (ethyl acetate 20-heptane 80). 13.2 g (92%) of 3-(5-methoxymethoxy-2-methoxyphenyl)-3-propanol are obtained.

c) 3-(5-Methoxymethoxy-2-methoxyphenyl)-3-propanone.

4.04 ml (43.3 mmol) of oxalyl chloride are dissolved in 150 ml of dichloromethane and then the mixture is cooled to −78° C. A solution of 6.58 ml (92.7 mmol) of DMSO in 20 ml of dichloromethane is then slowly added. When the the gaseous emission is over (after about 15 minutes), a solution of 5.3 g (23.1 mmol) of 3-(5-methoxymethoxy-2-methoxyphenyl)-3-propanol and 3.3 ml of triethylamine (23 mmol) in 50 ml of dichloromethane is added dropwise. After 20 minutes, 22.5 ml (162 mmol) of triethylamine are added and then the reaction medium is brought to room temperature and stirred for one hour. The medium is then treated with a saturated ammonium chloride solution and then extracted with ethyl ether. The organic phase is washed with water, dried and concentrated under reduced pressure. The residue is purified by chromatography on silica (ethyl acetate 20-heptane 80); 5.2 g (100%) of expected ketone are recovered.

d) Ethyl 5-(5-Hydroxy-2-methoxyphenyl)hepta-2,4-dienoate.

In a manner similar to Example 63(c), by reacting 3.9 g (17 mmol) of 3-(5-methoxymethoxy-2-methoxyphenyl)-3-propanone with 8.7 g (34.8 mmol) of ethyl 4-diethylphosphonocrotonate, ethyl 5-(5-methoxymethoxy-2-methoxyphenyl)hepta-2,4-dienoate is obtained which is converted to ethyl 5-(5-hydroxy-2-methoxyphenyl)hepta-2,4-dienoate with concentrated sulphuric acid in ethanol 800 mg (17%).

e) (4E,6E)-7-(5-Hydroxy-2-methoxyphenyl)-3-ethylnona-4,6-dien-3-ol.

In a manner-similar to Example 82(a), starting with 520 mg (1.9 mmol) of ethyl 5-(5-hydroxy-2-methoxyphenyl)hepta-2,4-dienoate, 350 mg (64%) of (4E,6E)-7-(5-hydroxy-2-methoxyphenyl)-3-ethylnona-4,6-dien-3-ol are obtained in the form of an oil.

f) (4E,6E)-7-[5-(3,4-bis-Benzoyloxymethylbenzyloxy)-2-methoxyphenyl]-3-ethylnona-4,6-dien-3-ol.

In a manner similar to Example 89(g), by reacting 350 mg (1.2 mmol) of the above product with 630 mg (1.44 mmol) of (3,4-bis-benzoyloxymethyl)benzyl bromide, 581 mg (75%) of expected product are obtained.

g) (4E,6E)-7-[5-(3,4-bis-Hydroxymethylbenzyloxy)-2-methoxyphenyl]-3-ethylnona-4,6-dien-3-ol.

581 mg of 7-[5-(3,4-bis-benzoyloxymethylbenzyloxy)-2-methoxyphenyl]-3-ethylnona-4,6-dien-3-ol (0.89 mmol) are dissolved in 20 ml of a 2% potassium carbonate solution in methanol and then the reaction medium is stirred for 5 hours. After treating with a saturated ammonium chloride solution and extracting with ethyl acetate, the organic phases are combined, dried and concentrated under reduced pressure. The residue is purified by chromatography on a silica column. A yellow oil is obtained (m=284 mg; Y=72%).

$^1$H NMR (CDCl$_3$): 0.80 (t, 6H, J=7.6 Hz), 0.97 (t, 3H, J=7.4 Hz), 1.47 (q, 4H, J=7.6 Hz), 2.41 (q, 2H, J=7.4 Hz), 3.25 (bs, 1H), 3.35 (bs, 1H), 3.73 (s, 3H), 4.71 (s, 4H), 5.05 (s, 2H), 5.60 (d, 1H, J=15.3 Hz),. 5.94 (dd, 1H, J1=15.3 Hz, J2=10.7 Hz), 6.14 (d, 1H, J=10.7 Hz), 6.67–6.88 (m, 3H), 7.34–7.56 (m, 3H).

EXAMPLE 92

(4E,6E)-7-[5-(3,4-bis-Hydroxymethyl-benzyloxy)-2-methylphenyl]-3-ethylnona-4,6-dien-3-ol In a manner similar to Example 91, starting with 5-hydroxy-2-methylbenzaldehyde, (4E,6E)-7-[5-(3,4-bis-hydroxymethylbenzyloxy)-2-methylphenyl]-3-ethylnona-4,6-dien-3-ol is obtained in the form of a clear oil.

$^1$H NMR (CDCl$_3$): 0.83–0.97 (m, 9H), 1.60 (q, 4H, J=7.6 Hz), 2.20 (s, 3H), 2.49 (q, 2H, J=7.4 Hz), 2.83 (bs, 2H), 3.10 (bs, 1H), 4.75 (s, 4H), 5.03 (s, 2H), 5.65 (d, 1H, J=15.3 Hz), 5.87 (d, 1H, J=11 Hz), 6.58 (dd, 1H, J1=15.3 Hz, J2=11 Hz), 6.74–6.81 (m, 2H), 7.06–7.09 (m, 1H), 7.36–7.43 (m, 3H).

EXAMPLE 93

(4E,6E)-7-[3-(3,4-bis-Hydroxymethyl-benzyloxy)-5-methoxyphenyl]-3-ethylnona-4,6-dien-3-ol In a manner similar to Examples 91(c–g), starting with (3-methoxy-5-methoxymethoxyphenyl)ethanone, (4E,6E)-7-[3-(3,4-bis-hydroxymethyl-benzyloxy)-5-methoxyphenyl]-3-ethylnona-4,6-dien-3-ol is obtained in the form of a clear oil.

$^1$H NMR (CDCl$_3$): 0.87 (t, 6H, J=7.6 Hz), 1.60 (q, 4H, J=7.6 Hz), 2.16 (m, 3H), 2.88 (bs, 2H), 3.80 (s, 3H), 4.76 (s, 2H), 4.77 (s, 2H), 5.05 (s, 2H), 5.78 (d, 1H, J=15 Hz), 6.44–6.68 (m, 5H), 7.33–7.45 (m, 3H).

EXAMPLE 94

(4E,6E)-7-[3-(3,4-bis-Hydroxymethyl-benzyloxy)-2-methoxyphenyl]-3-ethylnona-4,6-dien-3-ol In a manner similar to Example 91, starting with 3-hydroxy-2-methoxybenzaldehyde, (4E,6E)-7-[3-(3,4-bis-hydroxymethylbenzyloxy)-2-methoxyphenyl]-3-ethylnona-4,6-dien-3-ol is obtained in the form of a clear oil.

$^1$H NMR (CDCl$_3$): 0.90–1.01 (m, 9H), 1.61 (q, 4H, J=7.6 Hz), 2.66 (q, 2H, J=7.6 Hz), 2.75 (bs, 2H), 3.79 (s, 3H), 4.78 (s, 4H), 5.12 (s, 2H), 5.68 (d, 1H, J=15.3 Hz), 6.09 (d, 1H, J=11 Hz), 6.62 (dd, 1H, J1=15.3 Hz, J2=11 Hz), 6.77–6.96 (m, 3H), 7.40–7.46 (m, 3H).

EXAMPLE 95

(4E,6E)-7-[3-(3,4-bis-Hydroxymethyl-benzyloxy)-4-methylphenyl]-3-ethylnona-4,6-dien-3-ol In a manner similar to Example 91(c–g), starting with (3-methoxymethoxy-4-methylphenyl)ethanone, (4E,6E)-7-[3-(3,4-bis-hydroxymethyl-benzyloxy)-4-methylphenyl]-3-ethylnona-4,6-diene-3-ol is obtained in the form of a clear oil.

$^1$H NMR (CDCl$_3$): 0.90 (t, 6H, J=7.5 Hz), 1.49 (bs, 1H), 1.60 (q, 4H, J=7.5 Hz), 2.04 (s, 3H), 2.26 (s, 3H), 3.08 (bs, 2H), 4.73 (s, 2H), 4.74 (s, 2H), 5.09 (s, 2H), 5.76 (d, 1H, J=15 Hz), 6.41 (d, 1H, 10.9 Hz), 6.62 (dd, 1H, J1=15 Hz, J2=10.9 Hz), 6.96–6.99 (m, 2H), 7.11 (d, 1H, J=8.0 Hz), 7.35–7.45 (m, 3H).

EXAMPLE 96

1-[3-(3,4-bis-Hydroxymethylbenzyloxy)-phenyl]ethanone O-(2-Hydroxy-2-methylpropyl)oxime a) 1-(3-Methoxymethoxyphenyl)ethanone Oxime.

360 mg (2 mmol) of 1-(3-methoxymethoxyphenyl)ethanone are dissolved in 30 ml of anhydrous ethanol. 417 mg (6 mmol) of hydroxylamine hydrochloride are added, followed by 6 ml of a 1N sodium hydroxide solution. The mixture is heated under reflux for 2 hours and then the reaction medium is concentrated under reduced pressure. The residue is taken up in a mixture of diethyl ether and a solution of ammonium chloride. After extracting with ether, the organic phases are combined, dried and concentrated under reduced pressure. The residue is purified by chromatography on a silica column. A yellow oil is obtained (m=342 mg; Y=88%).

b) 1-(3-Methoxymethoxyphenyl)ethanone O-(2-Hydroxy-2-methylpropyl)oxime.

330 mg of 1-(3-methoxymethoxyphenyl)ethanone oxime (1.7 mmol) are dissolved in 10 ml of anhydrous THF. 180 mg (1.87 mmol) of sodium tert-butoxide are then added and the mixture is stirred for 1 hour. 690 l (7.6 mmol) of isobutylene oxide are then added and the mixture is heated under reflux for 15 hours. After treating with water, the reaction medium is extracted with ethyl ether and then the organic phases are combined, dried and concentrated under reduced pressure. The residue is purified by chromatography on a silica column. A yellow oil is obtained (m=215 mg; Y=48%).

c) 1-(3-Hydroxyphenyl)ethanone O-(2-Hydroxy-2-methylpropyl)oxime.

210 mg (0.78 mmol) of 1-(3-methoxymethoxyphenyl)ethanone O-(2-hydroxy-2-methylpropyl)oxime are dissolved in 10 ml of methanol. 200 l of sulphuric acid are added and the reaction medium is stirred for 18 hours at room temperature. After treating with water and extracting with ethyl ether, the organic phases are combined, dried and then concentrated under reduced pressure. The residue is purified by chromatography on a silica column. A pale yellow oil is obtained (m=175 mg; Y=100%).

d) 1-[3-(3,4-bis-Hydroxymethylbenzyloxy)phenyl]-ethanone O-(2-Hydroxy-2-methylpropyl)oxime.

In a manner similar to Examples 84b and 91b, starting with 170 mg (0.76 mmol) of 1-(3-hydroxyphenyl)ethanone O-(2-hydroxy-2-methylpropyl)oxime, 197 mg (74%) of 1-[3-(3,4-bis-hydroxymethylbenzyloxy)phenyl]ethanone O-(2-hydroxy-2-methylpropyl)oxime are obtained in the form of a colourless oil.

$^1$H NMR (CDCl$_3$): 1.22 (s, 6H), 2.23 (s, 3H), 3.44 (bt, 1H), 3.58 (s, 1H), 4.71 (t, 4H, J=5.6 Hz), 5.15 (s, 2H), 6.99–7.15 (m, 3H), 7.25–7.39 (m, 4H).

EXAMPLE 97

1-{1-[3-(3,4-bis-Hydroxymethylbenzyloxy)-phenyl]-propoxy}-3-ethylpentan-3-ol a) 1-(3-Methoxymethoxyphenyl)propan-1-ol.

11.6 g (69.8 mmol) of 3-methoxymethoxybenzaldehyde are dissolved in 40 ml of anhydrous THF. The mixture is cooled to 0° C. and is then added to an ethylmagnesium bromide solution (139 mmol) in 100 ml of ethyl ether. The reaction medium is brought to room temperature and then stirred for 4 hours. After treating with an ammonium chloride solution and extracting with ethyl ether, the organic phases are combined, dried and concentrated under reduced pressure. The residue is filtered on a silica layer and then concentrated again in order to obtain a yellow oil (m=12.9 g; Y=94%).

b) Ethyl 3-[1-(3-Methoxymethoxyphenyl)propoxy]-propionate.

2.9 g (9.8 mmol) of 1-(3-methoxymethoxyphenyl)propan-1-ol and 4.24 ml (39 mmol) of ethyl acrylate are dissolved in 10 ml of anhydrous THF. This solution is then added to a 60% suspension of sodium hydride (390 mg, 9.8 mmol) in 5 ml of THF maintained at 0° C. The medium is brought to room temperature and then stirred for 48 hours. The medium is then treated with an ammonium chloride solution and extracted with ethyl acetate. The organic phases are combined, dried and then concentrated under reduced pressure. The residue is purified by chromatography on a silica column (heptane eluent). A yellow oil is obtained (m=700 mg; Y=24%).

c) Ethyl 3-[1-(3-Hydroxyphenyl)propoxy]propionate.

1.09 g (36.8 mmol) of ethyl 3-[1-(3-methoxymethoxyphenyl)propoxyl]propionate are dissolved in 30 ml of ethanol. 500 l of sulphuric acid are then added and the medium is stirred at room temperature for 15 minutes. After hydrolysis and extraction with ethyl acetate, the organic phases are combined, dried and concentrated under reduced pressure. The residue is purified by chromatography on a silica column. A yellow oil is obtained (m=520 mg; Y=56%).

d) 1-{-[3-(3,4-bis-Hydroxymethylbenzyloxy)phenyl]-propoxy}-3-ethylpentan-3-ol.

In a manner similar to Examples 84(b, c), 520 mg of ethyl 3-[1-(3-hydroxyphenyl)propoxy]-propionate (2.06 mmol) are converted to 1-{1-[3-(3,4-bis-hydroxymethylbenzyloxy) phenyl]propoxy}-3-ethylpentan-3-ol, in the form of a pale yellow oil (m=260 mg; Y=30%).

$^1$H NMR (CDCl$_3$): 0.64–0.74 (m, 9H), 1.24–1.42 (m, 4H), 1.47–1.63 (m, 4H), 3.16 (bs, 3H), 3.32–3.38 (m, 2H), 3.90–4.00 (m, 1H), 4.59 (s, 2H), 4.60 (s, 2H), 4.94 (s, 2H), 6.69–6.78 (m, 3H), 7.08–7.29 (m, 4H).

EXAMPLE 98

(E)-7-[3-(3,4-bis-Hydroxymethylphenoxy-methyl) phenyl]-3-ethylnon-6-en-3-ol a) Methyl (E)-5-(3-Bromophenyl)hex-4-enoate.

19.3 g (44.9 mmol) of (3-carboxypropyl) triphenylphosphonium bromide are dried under vacuum for 1 h and by heating 130° C. and then brought to room temperature and dissolved in 200 ml of anhydrous THF. 10.1 g (89.8 mmol) of potassium tert-butoxide in 100 ml of THF are then slowly added and then the orange-red mixture is stirred for 15 minutes. A solution of 6.4 g (29.9 mmol) of 1-(3-bromophenyl)propanone in 100 ml of THF is then added dropwise and the reaction medium is stirred for 15 hours. After treating with a saturated ammonium chloride solution and extracting with ethyl acetate and then drying and evaporating the solvents of the organic phase, the residue is purified by chromatography on a silica column. A yellow oil is obtained (m=6.2 g; Y=74%). This product is then dissolved in 100 ml of methanol and then 2 ml of sulphuric acid are added. The reaction medium is heated under reflux and stirred for 2 hours. After treating with water, the medium is extracted with ethyl acetate and then the organic phases are combined, dried and concentrated under reduced pressure. The residue is purified by chromatography on a silica column (eluent heptane 95-ethyl acetate 5) in order to obtain the pure trans isomer in the form of a yellow oil (m=6.5 g; Y=74% total).

b) (E)-7-(3-Bromophenyl)-3-ethylnon-6-en-3-ol.

6.49 g of ethyl (E)-5-(3-bromophenyl)hept-4-enoate (21.8 mmol) are dissolved in 100 ml of ethyl ether. 29 ml of a 3.0M solution of ethylmagnesium bromide (87 mmol) are then added dropwise and the reaction medium is stirred at room temperature for 1 hour. After treating with a saturated ammonium chloride solution, extracting with ethyl ether and then drying and evaporating the solvents of the organic phase, the residue is purified by chromatography on a silica column; a colourless oil is obtained (m=6.79 g; Y=97%).

c) ((E)-5-(3-Bromophenyl)-1,1-diethylhept-4-enyloxy]-triethylsilane.

6.79 g (20.9 mmol) of (E)-7-(3-bromophenyl)-3-ethylnon-6-en-3-ol are dissolved in 100 ml of dichloromethane. 75 mg (0.6 mmol) of 4-dimethyllaminopyridine and 14.5 ml of triethylamine (104 mmol) are added and the reaction medium is cooled to 0° C. 11.8 ml (52 mmol) of triethylsilyltrifluoromethanesulphonate are added dropwise. After the addition, the reaction medium is brought to room temperature and then treated with water and extracted with dichloromethane. After drying and concentrating the organic phases under reduced pressure, the residue is purified by chromatography on a silica column; a yellow oil is obtained (m=9.1 g; Y=99%).

d) [3-((E)-1,5-Diethyl-5-triethylsilanyloxyhept-1-enyl) phenyl]methanol.

9.1 g (20.5 mmol) of [(E)-5-(3-bromophenyl)-1,1-diethylhept-4-enyloxy]triethylsilane are dissolved in 130 ml of anhydrous THF and then the mixture is cooled to −78° C. 9.18 ml (23 mmol) of a 2.5M solution of butyllithium are then added and then the reaction medium is stirred for 15 minutes. 1.78 ml of anhydrous DMF (23 mmol) are then added and then the reaction medium is brought to room temperature and stirred for 1 h. After treating with a saturated ammonium chloride solution and then extracting with ethyl acetate, the organic phases are combined, dried and concentrated under reduced pressure. The residue containing the desired (E)-5-ethyl-1-ethyl-5-triethylsilanyloxyhept-1-enyl)benzene-2-carbaldehyde is then dissolved in 100 ml of anhydrous methanol and then 760 mg (20 mmol) of sodium borohydride are added in two portions. After stirring for 10 minutes, the medium is treated with a solution of ammonium chloride and extracted with ethyl ether. The organic phases are combined, dried and concentrated under reduced pressure. After purification by chromatography on a silica column, a yellow oil is obtained (m=2 g; Y=25%).

e) Dimethyl 4-[3-((E)-1,5-Diethyltriethylsilanyloxyhept-1-enyl)phenylmethoxy]phthalate.

300 mg (0.77 mmol) of [3-((E)-1,5-diethyl-5-triethylsilanyloxyhept-1-enyl)phenyl]-methanol are dissolved in 20 ml of dichloromethane and cooled to 0° C. 0.16 ml (1.1 mmol) of triethylamine is added, followed by 65 l of methylsulphonate chloride (0.85 mmol). After stirring for 20 minutes, the reaction medium is treated with an ammonium chloride solution and extracted with dichloromethane. The organic phases are combined, dried and concentrated under reduced pressure. The residue obtained is then dissolved in 20 ml of 2-butanone, and 244 mg of dimethyl 4-hydroxyphthalate (1.16 mmol), 160 mg of potassium carbonate (1.16 mmol) and 10 mg of sodium iodide are added. The mixture is heated under reflux for 6 hours and then cooled and filtered. The filtrate is concentrated under reduced pressure and then purified by chromatography on a silica column. A yellow oil is obtained (m=355 mg; Y=79%).

f) {4-[3-((E)-1,5-Diethyl-5-triethylsilanoxyhept-1-enyl) phenoxymethyl]-2-hydroxymethylphenyl}methanol.

1.28 g (2.2 mmol) of dimethyl 4-[3-((E)-1,5-diethyl-5-hydroxyhept-1-enyl)phenylmethoxy]-phthalate are dissolved in 40 ml of anhydrous ethyl ether. 200 mg (5.3 mmol) of lithium aluminium hydride are added and the reaction medium is stirred at room temperature for 30 minutes. 200 l of water, 200 l of 15% NaOH and 600 l of water are then slowly added and the medium is filtered. The filtrate is concentrated under reduced pressure and then the residue is purified by chromatography on a silica column (ethyl acetate 70-heptane 30). A colourless oil is obtained (m=1.03 mg; Y=89%).

g) (E)-7-[3-(3,4-bis-Hydroxymethylphenoxymethyl) phenyl]-3-ethylnon-6-en-3-ol.

1.03 g (1.96 mmol) of {4-[3-((E)-1,5-diethyl-5-triethylsilanoxyhept-1-enyl)phenoxymethyl]-2-hydroxymethylphenyl}methanol are dissolved in 30 ml of THF. 3.9 ml (3.9 mmol) of a tetrabutylammonium fluoride solution (1M in THF) are added and the reaction medium is heated at 60° C. for 3 hours. After treating with an ammonium chloride solution and extracting with ethyl acetate, the organic phases are combined, dried and concentrated under reduced pressure. The residue is purified by chromatography on a silica column. A colourless oil is obtained (m=198 mg; Y=24%).

$^1$H NMR (CDCl$_3$): 0.69 (t, 6H, J=7.6 Hz), 0.91 (t, 3H, 7.5 Hz), 1.40–1.50 (m, 6H), 2.14 (q, 2H, J=7.6 Hz), 2.45 (q, 2H, J=7.5 Hz), 2.8 (bs, 1H), 3.15 (bs, 1H), 4.59 (s, 2H), 4.61 (s, 2H), 4.99 (s, 2H), 5.57 (t, 1H, J=7.3 Hz), 6.79–6.95 (m, 2H), 7.10–7.31 (m, 5H).

EXAMPLE 99

(E)-7-[3-(3,4-bis-Hydroxymethylbenzyl-sulphanyl) phenyl]-3-ethyloct-6-en-3-ol a) (E)-5-(3-Dimethylcarbamoylsulphanylphenyl)hex-4-enoic Acid.

4 g (17.9 mmol) of dimethylthiocarbamic acid S-(3-acetylphenyl) ester are subjected to the same conditions described in Example 98(a) and after chromatography on a silica gel, the acid is obtained in the form of a thick oil (m=3 g; Y=56%).

b) Methyl (E)-5-{3-[3-(4-Methoxycarbonyl-1-methylbut-1-enyl)phenyldisulphanyl]phenyl}hex-4-enoate.

1.5 g of (E)-5-(3-dimethylcarbamoylsulphanylphenyl)hex-4-enoic acid are dissolved in 30 ml of a 1:1 mixture of water and ethanol. 400 mg of NaOH are added and the reaction medium is heated under reflux for 18 hours. The medium is then treated with a 1N solution of hydrogen chloride and then extracted with ethyl acetate. The organic phases are combined, dried and concentrated under reduced pressure. The residue is then dissolved in 30 ml of methanol and 1 ml of sulphuric acid is added. The reaction medium is then stirred under reflux for 15 hours and then cooled and treated with water. After extraction with ethyl acetate, drying and concentrating the organic phases, the residue is purified by chromatography on a silica gel. A yellow oil is obtained (m=360 mg; Y=30%).

c) Methyl (E)-5-[3-(3,4-bis-Hydroxymethylbenzylsulphanyl)phenyl]hex-4-enoate.

200 mg (0.4 mmol) of methyl (E)-5-{3-[3-(4-methoxycarbonyl-1-methylbut-1-enyl)phenyldisulphanyl] phenyl}hex-4-enoate and 370 mg (0.84 mmol) of dimethyl 4-bromomethylphthalate are dissolved in 10 ml of dichloromethane. 140 mg (2.1 mmol) of zinc powder are then added and 100 l of acetic acid are added. The reaction medium is then stirred for 24 hours at room temperature and then treated with water and extracted with dichloromethane. The organic phases are combined, dried and concentrated under reduced pressure. After purification by chromatography on a silica gel, a yellow oil is obtained (m=100 mg; Y=40%).

d) (E)-7-[3-(3,4-bis-Hydroxymethylbenzylsulphanyl) phenyl]-3-ethyloct-6-en-3-ol.

In a manner similar to Example 84(c), 140 mg (0.24 mmol) of methyl (E)-5-[3-(3,4-bis-hydroxymethylbenzylsulphanyl)phenyl]hex-4-enoate are treated with 1 ml (2 mmol) of an ethylmagnesium chloride solution. After purification on a silica column, a colourless oil is obtained (m=70 mg; Y=70%).

$^1$H NMR (DMSO): 0.84 (t, 6H, J=7.3 Hz), 1.37–1.48 (m, 6H), 1.98 (s,. 3H), 2.14–2.19 (m, 2H), 3.94 (s, 1H), 4.28 (s, 2H), 4.53 (t, 4H, J=5.2 Hz), 5.08 (t, 1H, J=5.2 Hz), 5.14 (t, 1H, J=5.2 Hz), 5.83 (t, 1H), 7.20–7.48 (m, 7H).

EXAMPLE 100

(E)-7-{3-[(3,4-bis-Hydroxymethylbenzyl) methylamino]-phenyl)-3-ethyloct-6-en-3-ol a) Dimethyl 4-({Methoxycarbonyl-[3-(2-methyl-[1,3] dioxolan-2-yl)phenyl]amino}methyl)phthalate.

4 g (22.3 mmol) of 3-(2-methyl-[1,3]dioxolan-2-yl) phenylamine are dissolved in 30 ml of anhydrous toluene. 1.85 ml (24 mmol) of methyl chloroformate and 1.57 g (24 mmol) of zinc powder are suspended in 30 ml of toluene and stirred at room temperature.

The solution prepared above is then added dropwise by means of a small tube and then the reaction medium is stirred for 1 hour. The reaction medium is then filtered and the solid residue rinsed with ethyl acetate. The organic phases are washed with a saturated sodium bicarbonate solution and then dried and concentrated under reduced pressure. The residue is dissolved in 50 ml of anhydrous DMF and the mixture is cooled to 0° C. 1.04 g (24 mmol) of sodium hydride are then added and the stirring is continued for 30 minutes. A solution of dimethyl 4-bromomethylphthalate (26 mmol) in 10 ml of DMF is then added, the reaction medium is stirred at room temperature for 2 hours and then treated with a saturated ammonium chloride solution and extracted with ether. The organic phases are combined, dried and concentrated under reduced pressure. The residue is purified by chromatography on a silica column. A yellow oil is obtained (m=6.5 g; Y=67%).

b) 1-{3-[(3,4-bis-Hydroxymethylbenzyl)methylamino]-phenyl}ethanone.

6.5 g of dimethyl 4-((methoxycarbonyl-[3-(2-methyl[1,3] dioxolan-2-yl)phenyl]amino}methyl)phthalate (14.6 mmol) are dissolved in 200 ml of anhydrous THF and the mixture is cooled to 0° C. 2.8 g (74 mmol) of lithium aluminium hydride are added in three portions and the mixture is heated under reflux for 4 hours. After cooling, the reaction medium is successively treated with 2.8 ml of water. 2.8 ml of 15% NaOH and 8.4 ml of water. The medium is diluted with 200 ml of ethyl ether, stirred for 1 hour and then filtered. The filtrate is evaporated under reduced pressure and the residue is dissolved in 100 ml of methanol. 5 g of silica gel are added as well as 100 l of sulphuric acid and the reaction medium is stirred for 24 hours and then filtered and rinsed with a 0.5M solution of NaOH. The organic phase is dried and concentrated under reduced pressure. A colourless oil is obtained (m=3.98 mg; Y=91%).

c) 1-(3-{[3,4-bis(tert-Butyldimethylsilanyloxymethyl) benzyl]methylamino}phenyl)ethanone.

3.89 g (13 mmol) of 1-{3-[(3,4-bis-hydroxymethylbenzyl)methylamino]phenyl}ethanone are dissolved in 20 ml of anhydrous DMF. tert-Butyldimethylsilane chloride (4.7 g; 31 mmol) is added and then 2.48 g (36.4 mmol) of imidazole are added. The medium is stirred at room temperature for 4 hours and then diluted with 100 ml of ethyl ether and filtered. The filtrate is washed with an ammonium chloride solution and then with water and the organic phase is dried and then concentrated under reduced pressure. The residue is purified by chromatography on a silica column in order to obtain a very thick colourless oil (m=5.83 g; Y=85%).

d) (E)-5-{3-[(3,4-bis(tert-Butyldimethylsilanyloxymethyl) benzyl)methylamino]phenyl}hex-4-enoic Acid.

2.85 g (6.6 mmol) of (3-carboxypropyl) triphenylphosphonium bromide are dried under vacuum at 130° C. for 1 hour and then dissolved in 50 ml of anhydrous THF. 1.48 g (13.3 mmol) of potassium tert-butoxide are added and the orange-red mixture is stirred for 15 minutes.

1 g (1.9 mmol) of 1-(3-{[3,4-bis(tert-butyldimethylsilanyloxymethyl)benzyl] methylamino}phenyl)ethanone is dissolved in 10 ml of THF and added dropwise to the above suspension. The medium is then stirred for 5 hours and then treated with a 1N solution of hydrochloric acid and extracted with ethyl ether. The organic phases are dried and concentrated under reduced pressure. The residue is purified by chromatography on a silica column. A colourless oil is obtained (m=570 mg; Y=49%).

e) (E)-7-{3-[(3,4-bis-Hydroxymethylbenzyl)methylamino]phenyl}-3-ethyloct-6-en-3-ol.

550 mg (0.9 mmol) of (E)-5-{3-[(3,4-bis(tert-butyldimethylsilanyloxymethyl)benzyl)methylamino]phenyl}hex-4-enoic acid are dissolved in 20 ml of anhydrous methanol and then 0.5 ml of sulphuric acid are added and the mixture is heated under reflux for 24 hours. The reaction medium is then treated with water and extracted with dichloromethane. The organic phases are dried and then concentrated under reduced pressure. The residue is dissolved in 10 ml of THF and treated with 1.5 ml (4.5 mmol) of an ethylmagnesium bromide solution. The reaction medium is stirred at room temperature for 1 hour and then treated with an ammonium chloride solution and extracted with ethyl acetate. The organic phases are dried and concentrated under reduced pressure and the residue is purified by chromatography on a silica column. A colourless oil is obtained (m=277 mg; Y=71%).

$^1$H NMR (DMSO): 0.66 (t, 6H, J=7.3 Hz), 1.19–1.28 (m, 6H), 1.76 (s, 3H), 1.90–2.00 (m, 2H), 3.21 (s, 3H), 4.09 (d, 2H, J=5.7 Hz), 4.37 (t, 4H, J=5.2 Hz), 4.88 (t, 1H, J=5.2 Hz), 4.94 (t, 1H, J=5.2 Hz), 5.60 (t, 1H), 6.05 (t, 1H), 6.30 (d, 1H), 6.48 (d, 1H), 6.55 (s, 1H), 6.81 (t, 1H), 7.08 (d, 1H), 7.16 (d, 1H), 7.27 (s, 1H).

EXAMPLE 101

(E)-6-[3-(3,4-bis-Hydroxymethylbenzyloxy)phenyl]-3-ethyl-6-methylhept-4-en-3-ol a) Methyl 2-[3-(tert-Butyldimethylsilanyloxy)phenyl]-2-methylpropionate.

10 g of methyl [3-(tert-butyldimethylsilanyloxy)phenyl]acetate (35.6 mmol) are dissolved in 200 ml of anhydrous THF. 35.6 ml of a 2.0M solution of lithium diisopropylamide are then added and then the medium is stirred for 30 minutes. 8.9 ml (142 mmol) of methyl iodide are added and the reaction medium is stirred at room temperature for 40 hours. After treating with an ammonium chloride solution and then extracting with ethyl ether, the organic phases are combined, washed with a saturated sodium chloride solution, dried and concentrated under reduced pressure. A colourless oil is obtained (m=10.8 g; Y=98%).

b) 2-[3-(tert-Butyldimethylsilanyloxy)phenyl]-2-methylpropan-1-ol.

10.8 g of methyl 2-[3-(tert-butyldimethylsilanyloxy)phenyl]-2-methylpropionate (35 mmol) are dissolved in 150 ml of anhydrous THF. 4 portions of 500 mg each of lithium aluminium anhydride (52.5 mmol) are added and the medium is stirred at room temperature for 3 hours. After treating successively with 2 ml of water, 2 ml of 15% NaOH and then 6 ml of water, the reaction medium is diluted by the addition of 200 ml of ethyl ether and then filtered, and the filtrate concentrated under reduced pressure. A colourless oil is obtained (m=9.7 g; Y=99%).

c) Ethyl (E)-4-[3-(tert-Butyldimethylsilanyloxy)phenyl]-4-methylpent-2-enoate.

4.04 ml (43.3 mmol) of oxalyl chloride are dissolved in 150 ml of dichloromethane and then the mixture is cooled to −78° C. A solution of 6.58 ml (92.7 mmol) of DMSO in 20 ml of dichloromethane is then slowly added. When the emission of gas is over (after about 15 minutes), a solution of 6.5 g (23.1 mmol) of 2-[3-(tert-butyldimethylsilanyloxy)phenyl]-2-methylpropan-1-ol and 3.3 ml of triethylamine (23 mmol) in 50 ml of dichloromethane is added dropwise. After 20 minutes, 22.5 ml (162 mmol) of triethylamine are added and then the reaction medium is brought to room temperature and stirred for 1 hour. The medium is then treated with a saturated ammonium chloride solution and then extracted with ethyl ether. The organic phase is washed with water, dried and concentrated under reduced pressure. The residue obtained is then dissolved in 100 ml of anhydrous THF.

In another round-bottomed flask, 9.2 ml (46.3 mmol) of triethylphosphonoacetate are dissolved in 100 ml of anhydrous THF and the the mixture is cooled to 0° C. 22 ml (44 mol) of a 2.0M solution of lithium diisopropylamide is then added and the medium is stirred at 0° C. for 30 minutes. The solution prepared above is then added with the aid of a small tube and the reaction medium is brought to room temperature and then stirred for 15 hours. After treating with a saturated ammonium chloride solution and then extracting with ethyl ether, the organic phases are combined, dried and concentrated under reduced pressure. The residue is purified by chromatography on a silica column. A colourless oil is obtained (m=6.28 g; Y=78%).

d) Ethyl (E)-4-(3-Hydroxyphenyl)-4-methylpent-2-enoate.

400 mg (1.14 mmol) of ethyl (E)-4-[3-(tert-butyldimethylsilanyloxy)phenyl]-4-methylpent-2-enoate are dissolved in 20 ml of anhydrous THF and then 1.5 ml of a tetrabutylammonium fluoride solution (1M in THF) (1.5 mmol) is added. The reaction medium is immediately concentrated under reduced pressure and purified by chromatography. A colourless oil is obtained (m=262 mg; Y=98%).

e) (E)-6-[3-(3,4-bis-Hydroxymethylbenzyloxy)phenyl]-3-ethyl-6-methylhept-4-en-3-ol.

In a manner similar to Examples 84(b, c), starting with 262 mg of ethyl (E)-4-(3-hydroxyphenyl)-4-methylpent-2-enoate (1.12 mmol), (E)-6-[3-(3,4-bis-hydroxymethylbenzyloxy)phenyl]-3-ethyl-6-methylhept-4-en-3-ol is obtained in the form of a colourless oil (m=355 mg; Y=79%).

$^1$H NMR (DMSO): 0.71 (t, 6H, J=7.3 Hz), 1.25 (s, 6H), 1.36 (q, 4H, J=7.3 Hz), 4.03 (s, 1H), 4.47 (t, 4H, J=4.7 Hz), 4.96 (s, 2H), 5.02 (t, 1H, J=4.7 Hz), 5.06 (t, 1H, J=4.7 Hz), 5.23 (d, 1H, J=15.9 Hz), 5.64 (d, 1H, J=15.9 Hz), 6.72–6.87 (m, 3H),. 7.13 (t, 1H, J=7.8 Hz) 7.22 (d, 1H, 7.7 Hz), 7.31 d, 1H, J=7.7 Hz), 7.40 (s, 1H).

EXAMPLE 102

7-[3-(3,4-bis-Hydroxymethylbenzyloxy)phenyl]-3-ethyl-7-methyloctan-3-ol a) 4-[3-(tert-Butyldimethylsilanyloxy)phenyl]-4-methylpentan-1-ol.

6.15 g (17.6 mmol) of ethyl (E)-4-[3-(tert-butyldimethylsilanyloxy)phenyl]-4-methylpent-2-enoate (101 c) are dissolved in 150 ml of anhydrous methanol and the mixture is cooled to 0° C. 1.28 g (52.8 mmol) of magnesium chips are added and the reaction medium is stirred for 4 hours at 0° C. After treating with a saturated ammonium chloride solution and then extracting with ethyl acetate, the organic phases are combined, dried and concentrated under reduced pressure. The residue is then dissolved in 100 ml of anhydrous THF and 1 g (26.4 mmol) of lithium aluminium hydride is added. After stirring for 1 hour at room temperature, the medium is treated successively with 1 ml of water, 1 ml of 15% NaOH, 3 ml of water and diluted by the addition of 150 ml of ethyl ether. After filtration, the filtrate is concentrated under reduced pressure. A colourless oil is obtained (m=3.8 g; Y=70%).

b) tert-Butyl-[3-(4-[1,3]dithian-2-ylidene-1,1-dimethylbutyl)phenoxy]dimethylsilane.

1.94 ml (22.2 mmol) of oxalyl chloride are dissolved in 100 ml of dichloromethane and then the mixture is cooled to −78° C. A solution of 3.15 ml (44.4 mmol) of DMSO in 10 ml of dichloromethane is then slowly added. When the emission of gas is over (after about 15 minutes), a solution of 3.43 g (11.1 mmol) of 4-[3-(tert-butyldimethylsilanyloxy)phenyl]-4-methylpentan-1-ol and 1.6 ml of triethylamine (11.1 mmol) in 50 ml of dichloromethane is added dropwise. After 20 minutes, 10.8 ml (77.7 mmol) of triethylamine are added and then the reaction medium is brought to room temperature and stirred for 1 hour. The medium is then treated with a saturated ammonium chloride solution and then extracted with ethyl ether. The organic phase is washed with two fractions of ammonium chloride and then with water, dried and concentrated under reduced pressure. The residue obtained is then dissolved in 100 ml of anhydrous THF.

In another round-bottomed flask, 2.31 ml (12.2 mmol) of 2-trimethylsilyl-1,3-dithiane are dissolved in 50 ml of anhydrous THF and the mixture is cooled to −78° C. 4.88 ml. of a 2.5M solution of butyllithium (12.2 mmol) are added. The reaction medium is stirred for 30 minutes at −78° C. and then the solution prepared above is added dropwise. The medium is again stirred for 4 hours at −78° C. and then brought to room temperature and treated with an ammonium chloride solution. After extracting with ethyl ether, the organic phases are combined, dried and concentrated under reduced pressure. The residue is purified by chromatography on a silica column. A yellow oil is obtained (m=3.54 g; Y=78%).

c) Methyl 5-(3-Hydroxyphenyl)-5-methylhexanoate.

3.4 g (8.4 mmol) of tert-butyl-[3-(4-[1,3]dithian-2-ylidene-1,1-dimethylbutyl)phenoxy]-dimethylsilane are dissolved in 200 ml of acetonitrile and 50 ml of water. 2.1 g (21 mmol) of calcium carbonate and then 5 g (18.5 mmol) of mercury dichloride are added. After stirring for 48 hours at room temperature, the reaction medium is treated with a saturated ammonium chloride solution and then extracted with ethyl acetate. The organic phases are combined and then washed with a 1N hydrochloric acid solution and with water, and finally dried and concentrated under reduced pressure. The residue is dissolved in 150 ml of methanol, and 2 ml of sulphuric acid are added. The reaction medium is heated under reflux for 15 hours and then treated with water and extracted with ethyl ether. The organic phases are combined, dried and concentrated under reduced pressure. The residue is purified by chromatography on a silica column. A colourless oil is obtained (m=1.1 g; Y=56%).

d) 7-[3-(3,4-bis-Hydroxymethylbenzyloxy)phenyl]-3-ethyl-7-methyloctan-3-ol.

In a manner similar to Example 101(e), 1 g of methyl 5-(3-hydroxyphenyl)-5-methylhexanoate (4.2 mmol) are converted to 7-[3-(3,4-bis-hydroxymethylbenzyloxy)phenyl]-3-ethyl-7-methyloctan-3-ol, in the form of a white crystalline solid (m.p.=88–89° C; m=700 mg; Y=40%).

$^1$H NMR (DMSO): 0.50 (t, 6H, J=7.3 Hz), 0.78–0.84 (m, 2H), 0.96–1.07 (m, 12H), 1.30–1.36 (m, 2H), 3.50 (s, 1H), 4.35 (t, 4H, J=4.9 Hz), 4.86 (s, 2H), 4.90 (t, 1H, J=4.9 Hz), 4.94 (t, 1H, J=4.9 Hz), 6.60–6.73 (m, 3H), 7.01 (t, 1H, J=7.8 Hz) 7.11 (d, 1H, 7.7 Hz), 7.20 (d, 1H, J=7.7 Hz), 7.29 (s, 1H).

EXAMPLE 103

(E)-3-Ethyl-7-[3-(4-hydroxymethyl-3-methylphenoxy-methyl)phenyl]non-6-en-3-ol a) 4-iodo-3-Methylphenol 15 g (122 mol) of 4-hydroxy-2-methylaniline are dissolved in 180 ml of 20% sulphuric acid and then the reaction medium is cooled to 0° C. A solution of sodium nitrite (11.3 g, 163 mmol) in 60 ml of water is then added dropwise and then the medium is stirred for 20 minutes. This solution is then slowly added to a solution at 0° C. of CuI (32.5 g, 170 mmol) and KI (31.9 g, 193 mmol) in 180 ml of 20% sulphuric acid. The reaction medium is heated under reflux for 3 hours, poured into 1 l of water and extracted with ethyl ether. The organic phases are washed with a saturated sodium thiosulphate solution, of water, dried over magnesium sulphate and concentrated under reduced pressure. After purification on a silica column (ethyl acetate 30-heptane 70), a brown oil is obtained (m 4.2 g; Y=15%).

b) Methyl 4-Hydroxy-2-methylbenzoate 4.2 g (18 mmol) of 4-iodo-3-methylphenol are dissolved in 90 ml of anhydrous methanol and then placed in a steel reactor. 5 ml (35 mmol) of triethylamine and 400 mg (1.8 mmol) of palladium diacetate are added, the reaction medium is subjected to a carbon monoxide pressure of 3 bar and heated at 80° C. for 5 hours. The medium is then brought to ambient pressure and temperature and then dissolved in dichloromethane and filtered on celite. After evaporation, the residue is purified by chromatography on a silica column. An orange-coloured powder is obtained (m=1.8 g, Y=61 g).

c) (E)-3-Ethyl-7-[3-(4-hydroxymethyl-3-methylphenoxymethyl)phenyl]non-6-en-3-ol

In a manner identical to Examples 98 e, f, g, by reacting methyl 4-hydroxy-2-methylbenzoate with [3-((E)-5-ethyl-1-methyl-5-triethylsilanyloxyhept-1-enyl)phenyl]methanol (obtained in Example 98 d) and then treating successively with lithium aluminium hydride and then with tetrabutylammonium fluoride, a thick white oil is obtained.

$^1$H NMR (DMSO): 0.64 (t, 6H, J=7.5 Hz), 0.77 (t, 3H, J=7.3 Hz), 1.18–1.29 (m, 6H), 1.94–2.03 (m, 2H), 2.07 (s, 3H), 2.28–2.38 (m, 2H), 3.74 (s, 1H), 4.24 (d, 2H, J=5.2 Hz), 4.73 (t, 1H, J=5.2 Hz), 4.90 (s, 2H), 5.52 (t, 1H, J=7.3 Hz), 6.60–6.65 (m, 2H), 7.03–7.17 (m, 4H), 7.26 (s, 1H).

EXAMPLE 104

(E)-3-Ethyl-7-[3-(3-hydroxymethyl-4-methylphenoxymethyl)phenyl]non-6-en-3-ol a) Methyl 2-Methyl-5-nitrobenzoate 23.2 g (88 mmol) of 2-iodo-4-nitrotoluene are dissolved in 400 ml of anhydrous methanol and then placed in a steel reactor. 25 ml (177 mmol) of triethylamine, 1.97 g (8.8 mmol) of palladium diacetate and 7.3 g of diphenyphosphinopropane are added and the reaction medium is subjected to a carbon monoxide pressure of 4 bar and heated at 110° C. for 18 hours. The medium is then brought to ambient pressure and temperature, dissolved in dichloromethane and filtered on celite. After evaporation, the residue is purified by chromatography on a silica column. An orange-coloured powder is obtained (m=6.3 g, Y=37%).

b) Methyl 3-Amino-6-methylbenzoate 6.3 g (32 mmol) of methyl 2-methyl-5-nitrobenzoate are dissolved in 80 ml of anhydrous methanol and then transferred into a steel reactor. The mixture is degassed with nitrogen and then 630 mg of Pd/C (5%) are added. The reaction medium is then subjected to a hydrogen pressure of 4 bar and to a temperature of 80° C. for 14 hours and then brought to ambient pressure and temperature and filtered. The residue, after evaporation, is purified by chromatography on a silica column. A brown oil is obtained (m=4.6 g, Y=86%).

c) Methyl 3-Hydroxy-6-methylbenzoate 4.6 g (28 mmol) of methyl 3-amino-6-methylbenzoate are dissolved in 50 ml of THF and 50 ml of 1M sulphuric acid and then the reaction medium is cooled to 0° C. A solution of sodium nitrite (2.3 g, 33.6 mmol) in 10 ml of water is then added dropwise and then the medium is stirred for 20 minutes. 15 ml of pure sulphuric acid are then added and the reaction medium is heated under reflux for 2 hours, poured into 500 ml of water and extracted with ethyl ether. The organic phases are dried, concentrated under reduced pressure and the residue obtained is dissolved in 100 ml of methanol. 3 ml of sulphuric acid are added and the reaction medium is heated under reflux for 14 hours, cooled, treated with water and ethyl ether. After extraction with ethyl ether, the organic phases are combined, dried over magnesium sulphate and concentrated under reduced pressure. After purification on a silica column (ethyl acetate 30-heptane 70), a brown oil is obtained (m=1.2 g; Y=25%).

c) ((E)-3-Ethyl-7-[3-(3-hydroxymethyl-4-methylphenoxymethyl)phenyl]non-6-en-3-ol In a manner identical to Examples 98 e, f, g, by reacting methyl 3-hydroxy-6-methylbenzoate with [3-((E)-5-ethyl-1-methyl-5-triethylsilanyloxyhept-1-enyl)phenyl]methanol (obtained in Example 98 d), and then treating successively with lithium aluminium hydride and then with tetrabutylammonium fluoride, a colourless oil is obtained.

$^1$H NMR (DMSO): 0.73 (t, 6H, J=7.5 Hz), 0.85 (5, 3H, J=7.3 Hz), 1.26–1.38 (m, 6H), 2.02–2.12 (m, 5H), 2.38–2.46 (m, 2H), 3.82 (s, 1H), 4.36 (d, 2H, J=5.4 Hz), 4.98–5.03 (m, 3H), 5.61 (t, 1H, J=7.2 Hz), 6.68–6.72 (m, 1H), 6.93–6.96 (m, 2H), 7.22–7.25 (m, 3H), 7.35 (s, 1H).

EXAMPLE 105

(E)-7-[3-(3,4-bis-Hydroxymethylphenoxymethyl)phenyl]-3-ethyloct-6-en-3-ol

In a manner similar to Example 98, (E)-7-[3-(3,4-bishydroxymethyl)phenoxymethyl)phenyl]-3-ethyloct-6-en-3-ol is obtained in the form of a white powder m.p.= 89–91° C.).

$^1$H NMR (DMSO): 0.67 (t, 6H, J=7.4 Hz), 1.21–1.33 (m, 6H), 1.86 (d, 3H, J=2.2 Hz), 1.94–2.06 (m, 2H), 3.78 (s, 1H), 4.30 (d, 2H, J=5.3 Hz), 4.40 (d, 2H, J=5.3 Hz), 4.80 (t, 1H, J=5.3 Hz), 4.95–5.00 (m, 3H), 5.70 (t, 1H, J=7.4 Hz), 6.69–6.73 (m, 1H), 6.94–6.95 (m, 1H), 7.09–7.20 (m, 4H), 7.33 (s, 1H).

EXAMPLE 106

(E)-3-Ethyl-7-[3-(3-hydroxymethylphenoxymethyl)phenyl]non-6-en-3-ol

In a manner identical to Examples 98 e, f, g, by reacting 3-hydroxybenzaldehyde with [3-((E)-5-ethyl-1-methyl-5-triethylsilanyloxyhept-1-enyl)phenyl]methanol (obtained in Example 98 d), and then treating successively with lithium aluminium hydride and then with tetrabutylammonium fluoride, a colourless oil is obtained.

$^1$H NMR (CDCl$_3$): 0.88 (t, 6H, J=7.5 Hz), 0.98 (t, 3H, J=7.3 Hz), 1.26 (s, 1H), 1.48–1.60 (m, 6H), 2.17–2.27 (m, 2H), 2.53 (q, 2H, J=7.3 Hz), 4.62 (s, 2H), 5.06 (s, 2H), 5.65 (t, 1H, J=7.2 Hz), 6.95–7.00 (m, 2H), 7.26–7.31 (m, 5H), 7.39 (s, 1H).

EXAMPLE 107

(E)-3-Ethyl-7-[3-(4-hydroxymethylphenoxymethyl)phenyl]non-6-en-3-ol

In a manner identical to Examples 98 e, f, g, by reacting 4-hydroxybenzaldehyde with [3-((E)-5-ethyl-1-methyl-5-triethylsilanyloxyhept-1-enyl)phenyl]methanol (obtained in Example 98 d), and then treating successively with lithium aluminium hydride and then with tetrabutylammonium fluoride, a white powder (m.p.=67–70° C.) is obtained.

$^1$H NMR (CDCl$_3$): 0.86 (t, 6H, J=7.5 Hz), 0.98 (t, 3H, J=7.3 Hz), 1.26 (s, 1H), 1.47–1.60 (m, 6H), 2.17–2.27 (m, 2H), 2.53 (q, 2H, J=7.3 Hz), 4.66 (s, 2H), 5.06 (s, 2H), 5.65 (t, 1H, J=7.2 Hz), 6.89–7.03 (m, 2H), 7.24–7.30 (m, 5H), 7.40 (s, 1H).

EXAMPLE 108

Examples of Formulation

1) Oral Route (a) The following composition is prepared in the form of a 0.2-g tablet

| | |
|---|---|
| Compound of Example 1 | 0.005 g |
| Pregelatinized starch | 0.065 g |
| Microcrystalline cellulose | 0.075 g |
| Lactose | 0.050 g |
| Magnesium stearate | 0.005 g |

For the treatment of ichthyosis, 1 to 3 tablets are administered to an adult individual per day for 1 to 12 months depending on the seriousness of the case treated.

(b) An oral suspension intended to be packaged in 5-ml vials is prepared

| | |
|---|---|
| Compound of Example 2 | 0.050 mg |
| Glycerin | 0.500 g |
| Sorbitol at 70% | 0.500 g |
| Sodium saccharinate | 0.010 g |
| Methyl para-hydroxybenzoate | 0.040 g |
| Flavouring qs | 5 ml |
| Purified water qs | |

For the treatment of acne, 1 vial is administered to an adult individual per day for 1 to 12 months depending on the seriousness of the case treated.

(c) The following formulation intended to be packaged in gelatin capsules is prepared:

| | |
|---|---|
| Compound of Example 4 | 0.0001 mg |
| Maize starch | 0.060 g |
| Lactose qs | 0.300 g |

In the treatment of psoriasis, 1 gelatin capsule administered to an adult individual per day for 1 to months.

(d) The following formulation intended to be packaged in gelatin capsules is prepared:

| | |
|---|---|
| Compound of Example 5 | 0.02 mg |
| Cyclosporin | 0.050 g |
| Maize starch | 0.060 g |
| Lactose qs | 0.300 g |

The gelatin capsules used consist of gelatin, titanium oxide and a preservative.

In the treatment of psoriasis, 1 gelatin capsule is administered to an adult individual per day for 1 to 12 months.

2) Topical Route (a) The following nonionic Water-in-Oil cream is prepared:

| | |
|---|---|
| Compound of Example 9 | 0.100 g |
| Mixture of emulsive lanolin alcohols, of waxes and of refined oils, sold by the company BDF under the name "Eucérine anhydre" | 39.900 g |
| Methyl para-hydroxybenzoate | 0.075 g |

-continued

| | |
|---|---|
| Propyl para-hydroxybenzoate | 0.075 g |
| Sterile demineralized water qs | 100.000 g |

This cream is applied to a psoriatic skin once or twice per day for 1 to 12 months.

(b) A gel is prepared by producing the following formulation:

| | |
|---|---|
| Compound of Example 18 | 0.001 g |
| Erythromycin base | 4.000 g |
| Butylated hydroxytoluene | 0.050 g |
| Hydroxypropylcellulose sold by the company Hercules under the name "KLUCEL HF" | 2.000 g |
| Ethanol (at 95%) qs | 100.000 g |

This gel is applied to a skin affected by dermatosis or a skin with acne 1 to 3 times per day for 6 to 12 weeks depending on the seriousness of the case treated.

(c) An antiseborrhoeic lotion is prepared by mixing the following ingredients:

| | |
|---|---|
| Compound of Example 12 | 0.030 g |
| Propylene glycol | 5.000 g |
| Butylated hydroxytoluene | 0.100 g |
| Ethanol (at 95%) qs | 100.000 g |

This lotion is applied twice per day to a seborrhoeic scalp and a significant improvement is served within a period of between 2 and 6 weeks.

(d) A cosmetic composition against the harmful effects of the sun is prepared by mixing the following ingredients:

| | |
|---|---|
| Compound of Example 27 | 1.000 g |
| Benzylidene camphor | 4.000 g |
| Fatty acid triglycerides | 31.000 g |
| Glycerol monostearate | 6.000 g |
| Stearic acid | 2.000 g |
| Cetyl alcohol | 1.200 g |
| Lanolin | 4.000 g |
| Preservatives | 0.300 g |
| Propylene glycol | 2.000 g |
| Triethanolamine | 0.500 g |
| Perfume | 0.400 g |
| Demineralized water qs | 100.000 g |

This composition is applied daily; it makes it possible to combat photoinduced ageing.

(e) The following nonionic Oil-in-Water cream is prepared:

| | |
|---|---|
| Compound of Example 38 | 0.500 g |
| Retinoic acid | 0.020 g |
| Cetyl alcohol | 4.000 g |
| Glycerol monostearate | 2.500 g |
| PEG 50 stearate | 2.500 g |
| Shea butter | 9.200 g |
| Propylene glycol | 2.000 g |
| Methyl para-hydroxybenzoate | 0.075 g |
| Propyl para-hydroxybenzoate | 0.075 g |
| Sterile demineralized water qs | 100.000 g |

This cream is applied to a psoriatic skin once or twice per day for 30 days for intensive treatment and indefinitely for maintenance.

(f) A topical gel is prepared by mixing the following ingredients:

| | |
|---|---|
| Compound of Example 49 | 0.050 g |
| Ethanol | 43.000 g |
| α-Tocopherol | 0.050 g |
| Carboxyvinyl polymer sold under the name "Carbopol 941" by the company "Goodrich" | 0.500 g |
| Triethanolamine in aqueous solution at 20% by weight | 3.800 g |
| Water | 9.300 g |
| Propylene glycol qs | 100.000 g |

This gel is applied in the treatment of acne 1 to 3 times per day for 6 to 12 weeks depending on the seriousness of the case treated.

(g) A hair lotion against hair loss and for regrowth is prepared by mixing the following ingredients:

| | |
|---|---|
| Compound of Example 33 | 0.05 g |
| Compound sold under the name "Minoxidil" | 1.00 g |
| Propylene glycol | 20.00 g |
| Ethanol | 34.92 g |
| Polyethylene glycol (molecular mass = 400) | 40.00 g |
| Butylated hydroxyanisole | 0.01 g |
| Butylated hydroxytoluene | 0.02 g |
| Water qs | 100.00 g |

This lotion is applied once or twice per day for 3 months to a scalp having suffered a loss of hair and indefinitely for maintenance treatment.

(h) An antiacne cream is prepared by mixing the following ingredients:

| | |
|---|---|
| Compound of Example 51 | 0.050 g |
| Retinoic acid | 0.010 g |
| Mixture of glycerol stearates and polyethylene glycol (75 mol) sold under the name "Gelot 64" by the company "GATTEFOSSE" | 15.000 g |
| Polyoxyethylenated stone oil containing 6 mol of ethylene oxide sold under the name "Labrafil M2130 CS" by the company "GATTEFOSSE" | 8.000 g |
| Perhydrosqualene | 10.000 g |
| Preservatives | qs |
| Polyethylene glycol (molecular mass = 400) | 8.000 g |
| Disodium salt of ethylenediaminetetraacetic acid | 0.050 g |
| Purified water qs | 100.000 g |

This cream is applied to a skin affected by dermatosis or a skin with acne 1 to 3 times per day for 6 to 12 weeks.

(i) An oil-in-water cream is prepared by producing the following formulation:

| | |
|---|---|
| Compound of Example 44 | 0.020 g |
| Betamethasone 17-valerate | 0.050 g |
| S-carboxymethylcysteine | 3.000 g |
| Polyoxyethylenated stearate (40 mol of ethylene oxide) sold under the name "Myrj 52" by the company "ATLAS" | 4.000 g |

-continued

| | |
|---|---|
| Sorbitan monolaurate, polyoxyethylene containing 20 mol of ethylene oxide sold under the name "Tween 20" by the company "ATLAS" | 1.800 g |
| Mixture of glycerol mono- and distearate sold under the name "Géléol" by the company "GATTEFOSSE" | 4.200 g |
| Propylene glycol | 10.000 g |
| Butylated hydroxyanisole | 0.010 g |
| Butylated hydroxytoluene | 0.020 g |
| Cetylstearyl alcohol | 6.200 g |
| Preservatives | qs |
| Perhydrosqualene | 18.000 g |
| Mixture of caprylic-capric triglycerides sold under the name "Miglyol 812" by the company "DYNAMIT NOBEL" | 4.000 g |
| Triethanolamine (99% by weight) | 2.500 g |
| Water qs | 100.000 g |

This cream is applied twice per day to a skin affected by inflammatory dermatosis for 30 days.

(j) The following cream of oil-in-water type is prepared:

| | |
|---|---|
| Lactic acid | 5.000 g |
| Compound of Example 8 | 0.020 g |
| Polyoxyethylenated stearate (40 mol of ethylene oxide) sold under the name "Myrj 52" by the company "ATLAS" | 4.000 g |
| Sorbitan monolaurate, polyoxyethylene containing 20 mol of ethylene oxide sold under the name "Tween 20" by the company "ATLAS" | 1.800 g |
| Mixture of glycerol mono- and distearate sold under the name "Géléol" by the company "GATTEFOSSE" | 4.200 g |
| Propylene glycol | 10.000 g |
| Butylated hydroxyanisole | 0.010 g |
| Butylated hydroxytoluene | 0.020 g |
| Cetylstearyl alcohol | 6.200 g |
| Preservatives | qs |
| Perhydrosqualene | 18.000 g |
| Mixture of caprylic-capric triglycerides sold under the name "Miglyol 812" by the company "DYNAMIT NOBEL" | 4.000 g |
| Water qs | 100.000 g |

This cream is applied once per day; it helps to combat ageing whether photoinduced or chronologic.

(k) The following anhydrous salve is prepared:

| | |
|---|---|
| Compound of Example 19 | 5.000 g |
| Liquid paraffin | 50.00 g |
| Butylated hydroxytoluene | 0.050 g |
| Petroleum jelly | qs 100 g |

This salve is applied twice per day to a skin affected by squamose dermatosis for 30 days.

3) Intralesion Route (a) The following composition is prepared:

| | |
|---|---|
| Compound of Example 6 | 0.002 g |
| Ethyl oleate | qs 10 g |

In the treatment of malignant melanoma, the composition is injected into an adult individual at a frequency of 1 to 7 times per week for 1 to 12 months.

(b) The following composition is prepared:

| | |
|---|---|
| Compound of Example 11 | 0.050 g |
| Olive Oil | qs 2 g |

In the treatment of basocellular carcinoma, the composition is injected into an adult individual at a frequency of 1 to 7 times per week for 1 to 12 months.

(c) The following composition is prepared:

| | |
|---|---|
| Compound of Example 36 | 0.1 mg |
| Sesame oil | qs 2 g |

In the treatment of spinocellular carcinoma, the composition is injected into an adult individual at a frequency of 1 to 7 times per week for 1 to 12 months.

(d) The following ocmposition is prepared:

| | |
|---|---|
| Compound of Example 24 | 0.001 mg |
| Methyl benzoate | qs 10 g |

In the treatment of colon carcinoma, the composition is injected into an adult individual at a frequency of 1 to 7 times per week for 1 to 12 months.

4) Intravenous Route (a) The following injectable lipid emulsion is prepared:

| | |
|---|---|
| Compound of Example 47 | 0.001 mg |
| Soya bean oil | 10.000 g |
| Egg phospholipid | 1.200 g |
| Glycerin | 2.500 g |
| Water for injection qs | 100.000 g |

In the treatment of psoriasis, the composition is injected into an adult individual at a frequency of 1 to 7 times per week for 1 to 12 months.

(b) The following injectable lipid emulsion is prepared:

| | |
|---|---|
| Compound of Example 13 | 0.010 g |
| Cottonseed oil | 10.000 g |
| Soya bean lecithin | 0.750 g |
| Sorbitol | 5.000 g |
| (DL)-α-Tocopherol | 0.100 g |
| Water for injection qs | 100.000 g |

In the treatment of ichthyosis, the composition is injected into an adult individual at a frequency of 1 to 7 times per week for 1 to 12 months.

(c) The following injectable lipid emulsion is prepared:

| | |
|---|---|
| Compound of Example 29 | 0.001 g |
| Soya bean oil | 15.000 g |
| Acetylated monoglycerides | 10.000 g |
| Pluronic F-108 | 1.000 g |

-continued

| | |
|---|---|
| Glycerol | 2.500 g |
| Water for injection qs | 100.000 g |

In the treatment of leukaemia, the composition is injected into an adult individual at a frequency of 1 to 7 times per week for 1 to 12 months.

(d) The following mixed micell composition is prepared:

| | |
|---|---|
| Compound of Example 22 | 0.001 g |
| Lecithin | 16.930 g |
| Glycocholic acid | 8.850 g |
| Water for injection qs | 100.000 g |

In the treatment of malignant melanoma, the composition is injected into an adult individual at a frequency of 1 to 7 times per week for 1 to 12 months.

(e) The following cyclodextrin composition is prepared:

| | |
|---|---|
| Compound of Example 31 | 0.1 mg |
| β-Cyclodextrin | 0.100 g |
| Water for injection gs | 10.000 g |

In the treatment of graft rejection, the composition is injected into an adult individual at a frequency of 1 to 7 times per week for 1 to 12 months.

(f) The following cyclodextrin composition is prepared:

| | |
|---|---|
| Compound of Example 4 | 0.010 g |
| 2-Hydroxypropyl-β-cyclodextrin | 0.100 g |
| Water for injection qs | 10.000 g |

In the treatment of kidney cancer, the composition is injected into an adult individual at a frequency of 1 to 7 times per week for 1 to 12 months.

EXAMPLE 109

Example of Test for Evaluating the Biological Activity of the Compounds of the Invention The agonist activity for the vitamin D receptors of the compounds of the invention may also be evaluated "in vivo" by the induction of 24-Hydroxylase in SKH mice (Voorhees et al. 1997,108:513–518).

The test protocol used is the following:

SKH mice receive a single topical application of a compound according to the invention in solution in ethanol in increasing concentrations. A volume of 50 µl of the product to be tested or of the vehicle alone is applied to the back of the mice with the aid of a pipette.

Other SKH mice receive a single topical application of 1,25-(OH)$_2$-vitamin D$_3$ in solution in ethanol in increasing concentrations. A volume of 50 µl of the product to be tested or of the vehicle alone is applied to the back of the mice with the aid of a pipette.

8 hours after the topical application, the mice are humanely killed, the skin treated is removed and the epidermis is separated from the dermis. The quantification of the mRNA for 24-Hydroxylase is carried out by semiquantitative PCR. The results are normalized with respect to the expression of the mRNA for GAPDH and the values for the different concentrations of 1,25-(OH)$_2$-vitamin D$_3$ tested and for the different compounds of the invention tested are expressed as induction factor relative to the vehicle.

The results are summarized in the following table:

Expression of the mRNA for 24-Hydroxylase

| Compound tested | Concentration % (weight/volume) | Induction factor versus ethanol |
|---|---|---|
| 1,25-(OH)$_2$-vitamin D$_3$ | 0.0001 | 6.7 |
| 1,25-(OH)$_2$-vitamin D$_3$ | 0.001 | 10.3 |
| 1,25-(OH)$_2$-vitamin D$_3$ | 0.01 | 20.1 |
| 1,25-(OH)$_2$-vitamin D$_3$ | 0.1 | 26 |
| Example 4 | 1 | 11 |
| Example 59 | 0.1 | 20.5 |
| Example 61 | 1 | 10 |
| Example 65 | 1 | 15 |
| Example 68 | 0.1 | 25 |
| Example 72 | 0.1 | 17 |
| Example 82 | 0.1 | 21 |

These results show that the 1,25-(OH)$_2$-vitamin D$_3$ administered as a single topical application induces in the mice, in a dose-dependent manner, the expression of the mRNA for 24-Hydroxylase in the epidermis.

The biological activity of the compounds of the invention is evaluated by comparison between the induction factors obtained for the compounds of the invention and the induction factors obtained for 1,25-(OH)$_2$-vitamin D$_3$.

Thus, the compound 6-[3-(3,4-bis-hydroxymethylbenzyloxy)phenyl]-2-ethylhepta-3,5-dien-2-ol (Example 4) exhibits, at the concentration of 1%, an activity comparable to that of 1,25-(OH)$_2$-vitamin D$_3$ at 0.001%.

What is claimed is:

1. A compound having the formula (I):

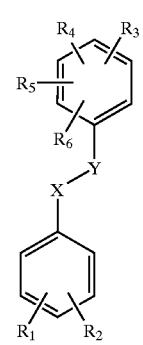

wherein:

R$_1$ represents a methyl radical or a radical —(CH$_2$)$_n$—OR$_7$;

R$_2$ represents a radical —(CH$_2$)$_n$—OR$_8$;

X—Y represents a bond selected from the group consisting of the bonds of the following formulae (a) and (b) which are read from the left to the right or conversely:

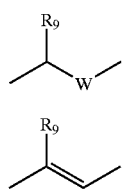

(a)

(b)

$R_3$ represents the chain in vitamin $D_2$ or in vitamin $D_3$,

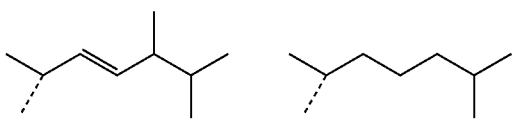

wherein the dotted lines represent the bond linking the $R_3$ chain to the benzene ring represented in formula (I);

or $R_3$ represents a chain having from 4 to 8 carbon atoms which is substituted with one or more hydroxyl groups, the hydroxyl groups being optionally protected in the form of acetoxy, methoxy, ethoxy, trimethylsilyloxy, tert-butyldimethylsilyloxy, or tetrahydropyranyloxy and the chain optionally in addition has at least one feature selected from the following group:
which is substituted with one or more lower alkyl groups or cycloalkyl groups;
which is substituted with one or more halogen atoms;
which is substituted with one or more $CF_3$ groups;
wherein one or more carbon atoms of the chain are replaced by one or more oxygen, sulfur or nitrogen atoms, the nitrogen atoms being optionally substituted with lower alkyl radicals; and
wherein one or more single bonds of the chain are replaced by one or more double and/or triple bonds;

$R_3$ being positioned on the benzene ring at the para or meta position with respect to the X—Y bond;

$R_4$, $R_5$ and $R_6$, which are identical or different, represent a hydrogen atom, a lower alkyl radical, a halogen atom, a radical —$OR_{10}$, or a polyether radical;

n is 0, 1 or 2;

$R_7$ and $R_8$, which are identical or different, represent a hydrogen atom, an acetyl radical, a trimethylsilyl radical, a tert-butyldimethylsilyl radical, or a tetrahydropyranyl radical;

$R_9$ represents a hydrogen atom or a lower alkyl radical;

W represents an oxygen atom, a sulfur atom, a radical —$CH_2$— or a radical —NH— which is optionally substituted with a lower alkyl radical; and $R_{10}$ represents a hydrogen atom or a lower alkyl radical;

or an optical or geometric isomer of the compound of formula (I) or a salt thereof.

2. A compound having the formula (I):

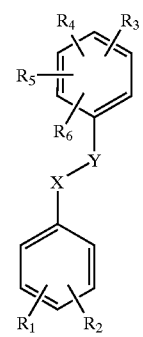

wherein:

$R_1$ represents a radical —$(CH_2)_n$—$OR_7$;
$R_2$ represents a radical —$(CH_2)_n$—$OR_8$;
X—Y represents a bond selected from the group consisting of the bonds of the following formulae (a) and (b) which are read from the left to the right or conversely:

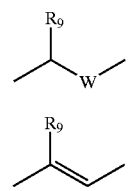

(a)

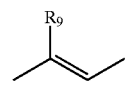

(b)

$R_3$ represents the chain in vitamin $D_2$ or in vitamin $D_3$,

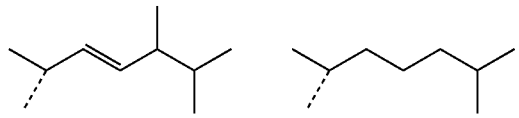

wherein the dotted lines represent the bond linking the $R_3$ chain to the benzene ring represented in formula (I);

or $R_3$ represents a chain having from 4 to 8 carbon atoms which is substituted with one or more hydroxyl groups, the hydroxyl groups being optionally protected in the form of acetoxy, methoxy, ethoxy, trimethylsilyloxy, tert-butyldimethylsilyloxy, or tetrahydropyranyloxy and the chain optionally in addition has at least one feature selected from the following group:
which is substituted with one or more lower alkyl groups or cycloalkyl groups;
which is substituted with one or more halogen atoms;
which is substituted with one or more $CF_3$ groups;
wherein one or more carbon atoms of the chain are replaced by one or more oxygen, sulfur or nitrogen atoms, the nitrogen atoms being optionally substituted with lower alkyl radicals; and
wherein one or more single bonds of the chain are replaced by one or more double and/or triple bonds;

$R_3$ being positioned on the benzene ring at the para or meta position with respect to the X—Y bond;

$R_4$, $R_5$ and $R_6$, which are identical or different, represent a hydrogen atom, a lower alkyl radical, a halogen atom, a radical —$OR_{10}$, or a polyether radical;

n is 0, 1 or 2;

R₇ and R₈, which are identical or different, represent a hydrogen atom, an acetyl radical, a trimethylsilyl radical, a tert-butyldimethylsilyl radical, or a tetrahydropyranyl radical;

R₉ represents a hydrogen atom or a lower alkyl radical;

W represents an oxygen atom, a sulfur atom, a radical —CH₂— or a radical —NH— which is optionally substituted with a lower alkyl radical; and R₁₀ represents a hydrogen atom or a lower alkyl radical;

or an optical or geometric isomer of the compound of formula (I) or a salt thereof.

3. A compound according to claim 2, wherein the lower alkyl radicals are selected from the group consisting of methyl, ethyl, isopropyl, tert-butyl and hexyl radicals.

4. A compound according to claim 2, wherein the cycloalkyl radical is an adamantyl radical or a 1-methylcyclohexyl radical.

5. A compound according to claim 2, wherein the halogen atom is a fluorine, chlorine or bromine atom.

6. A compound according to claim 3, wherein the halogen atom is a fluorine, chlorine or bromine atom.

7. A compound according to claim 4, wherein the halogen atom is a fluorine, chlorine or bromine atom.

8. A compound according to claim 2, wherein the polyether radical is a methoxymethoxy, methoxyethoxy or methoxyethoxymethoxy radical.

9. A compound according to claim 2, having at least one characteristic selected from the group consisting of:
(i) R₁ represents the radical —(CH₂)ₙOH;
(ii) R₂ represents the radical —(CH₂)ₙOH;
(iii) X—Y represents a bond of formula (a); and
(iv) R₃ represents a chain of 4 to 8 carbon atoms which is substituted by at least one member selected from the group consisting of a hydroxyl radical and a lower alkyl radical.

10. A compound according to claim 2, wherein R₁ represents the radical —(CH₂)ₙOH.

11. A compound according to claim 2, wherein R₂ represents the radical —(CH)ₙOH.

12. A compound according to claim 2, wherein X—Y represents a bond of formula (a).

13. A compound according to claim 2, wherein R₃ represents a chain of 4 to 8 carbon atoms which is substituted by at least one member selected from the group consisting of a hydroxyl radical and a lower alkyl radical.

14. A compound according to claim 2, wherein R₁ represents the radical —(CH₂)ₙOH, R₂ represents the radical —(CH₂)ₙOH, X—Y represents a bond of formula (a), and R₃ represents a chain of 4 to 8 carbon atoms which is substituted by at least one member selected from the group consisting of a hydroxyl radical and a lower alkyl radical.

15. The compound according to claim 1, which is:

3-hydroxymethyl-5-{2-[3-(5-hydroxy-5-methylhexyl)phenyl]vinyl}phenol;

3-hydroxymethyl-5-{2-[3-(6-hydroxy-6-methylheptyl)phenyl]vinyl}phenol;

3-[3-(5-hydroxy-1,5-dimethylhexyl)phenoxymethyl]-5-hydroxymethylphenol;

6-[3-(3,4-bis-hydroxymethylbenzyloxy)phenyl]-2-methylhepta-3,5-dien-2-ol;

6-[3-(3,4-bis-hydroxymethylbenzyloxy)phenyl]-2-methylhexan-2-ol;

6-[3-(3,4-bis-hydroxymethylphenoxymethyl)phenyl]-2-methylheptan-2-ol;

7-[3-(3,4-bis-hydroxymethylphenoxymethyl)phenyl]-3-ethyloctan-3-ol;

5-{2-[4-(5-hydroxy-5-methylhexyl)phenyl]vinyl}benzene-1,3-diol;

5-{2-[4-(5-hydroxy-5-methylhexyl)phenyl]ethyl}benzene-1,3-diol;

5-{2-[4-(6-hydroxy-6-methylheptyl)phenyl]vinyl}benene-1,3-diol;

5-{2-[3-(6-hydroxy-6-methylheptyl)phenyl]vinyl}benene-1,3-diol;

5-{2-[4-(6-hydroxy-6-methylheptyl)phenyl]ethyl}benzene-1,3-diol;

5-{2-[3-(6-hydroxy-6-methylheptyl)phenyl]ethyl}benzene-1,3-diol;

2-hydroxymethyl-4-{2-[3-(5-hydroxy-5-methylhexyl)phenyl]vinyl}phenol;

2-hydroxymethyl-4-{2-[4-(5-hydroxy-5-methylhexyl)phenyl]vinyl}phenol;

2-hydroxymethyl-4-{2-[3-(6-hydroxy-6-methylheptyl)phenyl]vinyl}phenol;

2-hydroxymethyl-4-{2-[4-(6-hydroxy-6-methylheptyl)phenyl]vinyl}phenol;

2-hydroxymethyl-4-{2-[3-(5-hydroxy-5-methylheptyl)phenyl]ethyl}phenol;

2-hydroxymethyl-4-{2-[4-(5-hydroxy-5-methylhexyl)phenyl]ethyl}phenol;

2-hydroxymethyl-4-{2-[3-(6-hydroxy-6-methylheptyl)phenyl]ethyl}phenol;

2-hydroxymethyl-4-{2-[4-(6-hydroxy-6-methylheptyl)phenyl]ethyl}phenol;

2-hydroxymethyl-5-{2-[4-(5-hydroxy-5-methylhexyl)phenyl]vinyl}phenol;

6-[3-(3,4-bis-hydroxymethylbenzyloxy)phenyl]-2-methylheptan-2-ol;

4-[3-(5-hydroxy-1,5-dimethylhexyl)phenoxymethyl]-2-hydroxymethylphenol;

6-{3-[2-(3,4-bis-hydroxymethylphenyl)vinyl]phenyl}-2-methylhexan-2-ol;

7-{4-[2-(3,4-bis-hydroxymethylphenyl)vinyl]phenyl}-2-methylheptan-2-ol;

6-{4-[2-(3,4-bis-hydroxymethylphenyl)vinyl]phenyl}-2-methylhexan-2-ol;

5-{2-[3-(6-hydroxy-6-methylheptyl)phenyl]-1-methylvinyl}benzene-1,3-diol;

5-{2-[3-(5-hydroxy-5-methylhexyl)phenyl]vinyl}benzene-1,3-diol;

5-[3-(6-hydroxy-6-methylheptyl)phenoxymethyl]benzene-1,3-diol;

5-{2-[3-(7-hydroxy-7-methyloct-1-enyl)phenyl]vinyl}benzene-1,3-diol;

5-{2-[3-(7-hydroxy-7-methyloctyl)phenyl]vinyl}benzene-1,3-diol;

4-{2-[3-(6-hydroxy-6-methylheptyl)phenyl]vinyl}benzene-1,2-diol;

6-{3-[2-(3,5-bis-hydroxymethylphenyl)vinyl]phenyl}-2-methylhexan-2-ol;

7-{3-[2-(3,5-bis-hydroxymethylphenyl)vinyl]phenyl}-2-methylheptan-2-ol;

7-{3-[2-(3,4-bis-hydroxymethylphenyl)vinyl]phenyl}-2-methylheptan-2-ol;

7-{3-[2-(4-hydroxymethylphenyl)vinyl]phenyl}-2-methylheptan-2-ol;

7-[3-(3,4-bis-hydroxymethylphenylethynyl)phenyl]-2-methylheptan-2-ol;

5-{2-[3-(6-hydroxy-6-methylhept-1-enyl)phenyl]vinyl}benzene-1,3-diol;
5-{2-[3-(7-ethyl-7-hydroxynon-1-enyl)phenyl]vinyl}benzene-1,3-diol;
5-{2-[3-(7-hydroxy-1-methoxy-1,7-dimethyloctyl)phenyl]vinyl}benzene-1,3-diol;
5-{2-[3-(6-hydroxy-1-methoxy-1,6-dimethylheptyl)phenyl]vinyl}benzene-1,3-diol;
5-{2-[3-(5-hydroxypentyl)phenyl]vinyl}benzene-1,3-diol;
5-{2-[3-(5-hydroxy-6-methylheptyl)phenyl]vinyl}benzene-1,3-diol;
5-{2-[3-(6-hydroxy-7-methyloctyl)phenyl]vinyl}benzene-1,3-diol;
5-{2-[3-(5-hydroxy-6-methylhept-1-enyl)phenyl]vinyl}benzene-1,3-diol;
5-{2-[3-(6-hydroxy-7-methyloct-1-enyl)phenyl]vinyl}benzene-1,3-diol;
5-{2-[3-(1,6-dihydroxy-1,6-dimethylheptyl)phenyl]vinyl}benzene-1,3-diol;
5-{2-[3-(6-hydroxy-1,6-dimethylhept-1-enyl)phenyl]vinyl}benzene-1,3-diol;
6-{[3-(3,4-bis-hydroxymethylbenzyloxy)phenyl]methylamino}-2-methylhexan-2-ol;
5-{[3-(3,4-bis-hydroxymethylbenzyloxy)phenyl]methylamino}-2-methylpentan-2-ol;
6-{[3-(3,4-bis-hydroxymethylbenzyloxy)phenyl]methylamino}-3-ethylhexan-3-ol;
7-{[3-(3,4-bis-hydroxymethylbenzyloxy)phenyl]methylamino}-3-ethylheptan-3-ol;
5-{[3-(3,4-bis-hydroxymethylbenzyloxy)phenyl]ethylamino}-2-methylpentan-2-ol;
6-{[3-(3,4-bis-hydroxymethylbenzyloxy)phenyl]benzylamino}-3-ethylhexan-3-ol;
7-{3-[2-(3,4-bis-hydroxymethylphenyl)ethyl]phenyl}-3-ethylocta-4,6-dien-3-ol;
6-{3-[2-(3,4-bis-hydroxymethylphenyl)ethyl]phenyl}-2-methylhepta-3,5-dien-2-ol;
7-{3-[2-(3,4-bis-hydroxymethylphenyl)vinyl]phenyl}-3-ethylocta-4,6-dien-3-ol;
6-{3-[2-(3,4-bis-hydroxymethylphenyl)vinyl]phenyl}-2methylhepta-3,5-dien-2-ol;
7-[3-(3,4-bis-hydroxymethylphenylethynyl)phenyl]-3-ethylocta-4,6-dien-3-ol;
7-[3-(3,4-bis-hydroxymethylbenzyloxy)phenyl]-3-ethyl-3-octanol;
(4E,6E)-7-[3-(3,4-bis-hydroxymethylbenzyloxy)phenyl]-3-ethylocta-4,6-dien-3-ol;
(4E,6Z)-7-[3-(3,4-bis-hydroxymethylbenzyloxy)phenyl]-3-ethylocta-4,6-dien-3-ol;
7-[4-(3,4-bis-hydroxymethylbenzyloxy)phenyl]-3-ethyl-3-octanol;
(4E,6E)-7-[3-(3,4-bis-hydroxymethylbenzyloxy)phenyl]-3-ethylnona-4,6-dien-3-ol;
(4E,6Z)-7-[3-(3,4-bis-hydroxymethylbenzyloxy)phenyl]-3-ethylnona-4,6-dien-3-ol;
(E)-6-[3-(3,4-bis-hydroxymethylbenzyloxy)phenyl]-2-methylhept-3-en-2-ol;
(E)-7-[3-(3,4-bis-hydroxymethylbenzyloxy)phenyl]-3-ethyloct-4-en-3-ol;
(E)-7-[3-(3,4-bis-hydroxymethylbenzyloxy)phenyl]-3-ethyloct-6-en-3-ol;
(Z)-7-[3-(3,4-bis-hydroxymethylbenzyloxy)phenyl]-3-ethyloct-6-en-3-ol;
(E)-8-[3-(3,4-bis-hydroxymethylbenzyloxy)phenyl]-2-methylnon-7-en-2-ol;
(Z)-8-[3-(3,4-bis-hydroxymethylbenzyloxy)phenyl]-2-methylnon-7-en-2-ol;
(E)-9-[3-(3,4-bis-hydroxymethylbenzyloxy)phenyl]-3-ethyldec-8-en-3-ol;
(Z)-9-[3-(3,4-bis-hydroxymethylbenzyloxy)phenyl]-3-ethyldec-8-en-3-ol;
8-[3-(3,4-bis-hydroxymethylbenzyloxy)phenyl]-2-methyl-2-nonanol;
9-[3-(3,4-bis-hydroxymethylbenzyloxy)phenyl]-3-ethyldecan-3-ol;
(E)-7-[3-(3,4-bis-hydroxymethylbenzyloxy)phenyl]-3-ethyloct-6-en-4-yn-3-ol;
(3E,5E)-7-[3-(3,4-bis-hydroxymethylbenzyloxy)phenyl]-2,7-dimethylocta-3,5-dien-2-ol;
(4E,6E)-7-[3-(3,4-bis-hydroxymethylphenoxymethyl)phenyl]-3-ethylocta-4,6-dien-3-ol;
(3E,5E)-6-[3-(3,4-bis-hydroxymethylphenoxymethyl)phenyl]-2-methylhepta-3,5-dien-2-ol;
(Z)-7-[3-(3,4-bis-hydroxymethylbenzyloxy)phenyl]-3-ethylnon-6-en-3-ol;
(Z)-6-[3-(3,4-bis-hydroxymethylbenzyloxy)phenyl]-2-methyloct-5-en-2-ol;
(Z)-7-[3-(3,4-bis-hydroxymethylbenzyloxy)phenyl]-3-ethyldec-6-en-3-ol;
(Z)-6-[3-(3,4-bis-hydroxymethylbenzyloxy)phenyl]-2-methylnon-5-en-2-ol;
(Z)-8-[3-(3,4-bis-hydroxymethylbenzyloxy)phenyl]-3-ethylnon-7-en-3-ol;
(E)-8-[3-(3,4-bis-hydroxymethylbenzyloxy)phenyl]-3-ethylnon-7-en-3-ol;
8-[3-(3,4-bis-hydroxymethylbenzyloxy)phenyl]-3-ethylnonan-3-ol;
7-[5-(3,4-bis-hydroxymethylbenzyloxy)-2-methoxyphenyl]-3-ethylnona-4,6-dien-3-ol;
7-[5-(3,4-bis-hydroxymethylbenzyloxy)-2-methylphenyl]-3-ethylnona-4,6-dien-3-ol;
7-[3-(3,4-bis-hydroxymethylbenzyloxy)-5-methoxyphenyl]-3-ethylnona-4,6-dien-3-ol;
7-[3-(3,4-bis-hydroxymethylbenzyloxy)-2-methoxyphenyl]-3-ethylnona-4,6-dien-3-ol;
7-[3-(3,4-bis-hydroxymethylbenzyloxy)-4-methylphenyl]-3-ethylnona-4,6-dien-3-ol;
1-[3-(3,4)-bis-hydroxymethylbenzyloxy)phenyl]ethanone O-(2-hydroxy-2-methylpropyl)oxime;
1{1-[3-(3,4-bis-hydroxymethylbenzyloxy)phenyl]propoxy}-3-ethylpentan-3-ol;
(E)-7-[3-(3,4-bis-hydroxymethylphenoxymethyl)phenyl]-3-ethylnon-6-en-3-ol;
(E)-7-[3-(3,4-bis-hydroxymethylbenzylsulfanyl)phenyl]-3-ethyloct-6-en-3-ol;
(E)-7-{3-[(3,4-bis-hydroxymethylbenzyl)methylamino]phenyl}-3-ethyloct-6-en-3-ol;
(E)-6-[3-(3,4-bis-hydroxymethylbenzyloxy)phenyl]-3-ethyl-6-methylhept-4-en-3-ol;
7-[3-(3,4-bis-hydroxymethylbenzyloxy)phenyl]-3-ethyl-7-methyloctan-3-ol;
7-[3-(3,4-bis-hydroxymethylbenzyloxy)phenyl]-3,7-diethylnonan-3-ol;

(E)-6-[3-(3,4-bis-hydroxymethylbenzyloxy)phenyl]-1,1,1-trifluoro-2-trifluoromethyloct-5-en-2-ol;

2-{4-[3-(3,4-bis-hydroxymethylbenzyloxy)phenyl]hexyl}-1,1,1,3,3,3-hexafluoropropan-2-ol;

(E)-7-[3-(3,4-bis-hydroxymethylbenzyloxy)phenyl]-3-ethyl-4,4-difluoronon-6-en-3-ol;

7-[3-(3,4-bis-hydroxymethylbenzyloxy)phenyl]-3-ethyl-4,4-difluoro-7-methyloctan-3-ol;

(E)-6-[3-(3,4-bis-hydroxymethylbenzyloxy)phenyl]-2-methyloct-5-en-3-ol;

(E)-4-[3-(3,4-bis-hydroxymethylbenzyloxy)phenyl]-1-cyclopropylhex-3-en-1-ol;

(E)-7-[3-(3,4-bis-hydroxymethylbenzyloxy)phenyl]-3-ethyl-4-methylnon-6-en-3-ol;

(E)-7-[3-(3,4-bis-hydroxymethylbenzyloxy)phenyl]-3-ethyl-4-methyldec-6-en-3-ol;

(4E,6E)-7-[3-(3,4-bis-hydroxymethylphenoxymethyl)phenyl]-3-ethylnona-4,6-dien-3-ol;

(4E,6E)-7-{3-[2-(3,4-bis-hydroxymethylphenyl)ethyl]phenyl}-3-ethylnona-4,6-ol;

(E)-7-{3-[2-(3,4-bis-hydroxymethylphenyl)ethyl]phenyl}-3-ethylnon-6-en-3-ol;

(E)-3-ethyl-7-[3-(3-hydroxymethylphenoxymethyl)phenyl]non-6-en-3-ol;

(E)-3-ethyl-7-[3-(4-hydroxymethylphenoxymethyl)phenyl]-non-6-en-3-ol;

(E)-3-ethyl-7-[(E)-3-(3-hydroxymethyl-4-methylphenoxymethyl)phenyl]non-6-en-3-ol;

(E)-3-ethyl-7-[(E)-3-(4-hydroxymethyl-3-methylphenoxymethyl)phenyl]non-6-en-3-ol;

2-{4-[3-(3,4-bis-hydroxymethylbenzyloxy)phenyl]-4-methylpentyl}-1,1,1,3,3,3-hexafluoropropan-2-ol;

7-[3-(3,4-bis-hydroxymethylbenzyloxy)phenyl]-3-ethyl-4,4-difluoro-7-methyloctan-3-ol;

7-{3-[2-(3,4-bis-hydroxymethylphenyl)ethyl]phenyl}-3,7-diethylnonan-3-ol;

7-[3-(3,4-bis-hydroxymethylbenzyloxy)phenyl]-3-ethyl-7-methyloctane-3,4-diol;

7-{3-[2-(3,4-bis-hydroxymethylphenyl)ethyl]phenyl}-3,7-diethylnonane-3,4-diol;

7-{3-[2-(3,4-bis-hydroxymethylphenyl)ethyl]phenyl}-3-ethyl-7-methyloctane-3,4-diol;

(E)-4-{3-[2-(3,4-bis-hydroxymethylphenyl)ethyl]phenyl}-1-cyclopropylhex-3-en-1-ol;

(4E,6E)-7-{3-[2-(3,4-bis-hydroxymethylphenyl)ethyl]phenyl}-3-ethyl-4-methylnona-4,6-dien-3-ol;

(4E,6E)-7-[3-(3,4-bis-hydroxymethylbenzyloxy)phenyl]-3-ethyl-4-methylnona-4,6-dien-3-ol;

(E)-3-ethyl-7-[3-(4-hydroxymethyl-3-methylphenoxymethyl)phenyl]non-6-en-3-ol;

(E)-3-ethyl-7-[3-(3-hydroxymethyl-4-methylphenoxymethyl)phenyl]non-6-en-3-ol;

(E)-7-[3-(3,4-bis-hydroxymethylphenoxymethyl)phenyl]-3-ethyloct-6-en-3-ol;

(E)-3-ethyl-7-[3-(3-hydroxymethylphenoxymethyl)phenyl]-non-6-en-3-ol; or (E)-3-ethyl-7-[3-(4-hydroxymethylphenoxymethyl)phenyl]-non-6-en-3-ol.

16. A pharmaceutical composition comprising a therapeutically effective vitamin D receptor agonist amount of at least one compound of formula (I) as claimed in claim 2 and a pharmaceutically acceptable carrier therefor.

17. A composition according to claim 16, in oral dosage form.

18. A composition according to claim 16, in topical dosage form.

19. A composition according to claim 16, in injectable dosage form.

20. A composition according to claim 16, wherein the concentration of compound of formula (I) is between 0.001% and 5% by weight relative to the total weight of the composition.

21. A cosmetic composition comprising a cosmetically effective vitamin D receptor agonist amount of at least one compound of formula (I) as claimed in claim 2 and a cosmetically acceptable carrier therefor.

22. A composition according to claim 21, wherein the concentration of compound of formula (I) is between 0.001% and 3% by weight relative to the total weight of the composition.

23. The compound which is:

6-[3-(3,4-bis-hydroxymethylbenzyloxy)phenyl]-2-methylhepta-3,5-dien-2-ol;

(4E,6E)-7-[3-(3,4-bis-hydroxymethylbenzyloxy)phenyl]-3-ethylocta-4,6-dien-3-ol;

(4E,6Z)-7-[3-(3,4-bis-hydroxymethylbenzyloxy)phenyl]-3-ethylocta-4,6-dien-3-ol;

(4E,6E)-7-[3-(3,4-bis-hydroxymethylbenzyloxy)phenyl]-3-ethylnona-4,6-dien-3-ol;

(4E,6Z)-7-[3-(3,4-bis-hydroxymethylbenzyloxy)phenyl]-3-ethylnona-4,6-dien-3-ol;

(3E,5E)-7-[3-(3,4-bis-hydroxymethylbenzyloxy)phenyl]-2,7-dimethylocta-3,5-dien-2-ol;

7-[5-(3,4-bis-hydroxymethylbenzyloxy)-2-methoxyphenyl]-3-ethylnona-4,6-dien-3-ol;

7-[5-(3,4-bis-hydroxymethylbenzyloxy)-2-methylphenyl]-3-ethylnona-4,6-dien-3-ol;

7-[3-(3,4-bis-hydroxymethylbenzyloxy)-5-methoxyphenyl]-3-ethylnona-4,6-dien-3-ol;

7-[3-(3,4-bis-hydroxymethylbenzyloxy)-2-methoxyphenyl]-3-ethylnona-4,6-dien-3-ol;

7-[3-(3,4-bis-hydroxymethylbenzyloxy)-4-methylphenyl]-3-ethylnona-4,6-dien-3-ol; or (4E,6E)-7-[3-(3,4-bis-hydroxymethylbenzyloxy)phenyl]-3-ethyl-4-methylnona-4,6-dien-3-ol.

24. The compound according to claim 22, which is:

(4E,6E)-7-[3-(3,4-bis-hydroxymethylbenzyloxy)phenyl]-3-ethylnona-4,6-dien-3-ol; or (4E,6Z)-7-[3-(3,4-bis-hydroxymethylbenzyloxy)phenyl]-3-ethylnona-4,6-dien-3-ol.

25. The compound according to claim 2, which is:

3-hydroxymethyl-5-{2-[3-(5-hydroxy-5-methylhexyl)phenyl]vinyl}phenol;

3-hydroxymethyl-5-{2-[3-(6-hydroxy-6-methylheptyl)phenyl]vinyl}phenol;

3-[3-(5-hydroxy-1,5-dimethylhexyl)phenoxymethyl]-5-hydroxymethylphenol;

6-[3-(3,4-bis-hydroxymethylbenzyloxy)phenyl]-2-methylhepta-3,5-dien-2-ol;

6-[3-(3,4-bis-hydroxymethylbenzyloxy)phenyl]-2-methylhexan-2-ol;

6-[3-(3,4-bis-hydroxymethylphenoxymethyl)phenyl]-2-methylheptan-2-ol;

7-[3-(3,4-bis-hydroxymethylphenoxymethyl)phenyl]-3-ethyloctan-3-ol;

5-{2-[4-(5-hydroxy-5-methylhexyl)phenyl]vinyl}benzene-1,3-diol;

5-{2-[4-(5-hydroxy-5-methylhexyl)phenyl]ethyl}benzene-1,3-diol;
5-{2-[4-(6-hydroxy-6-methylheptyl)phenyl]vinyl}benene-1,3-diol;
5-{2-[3-(6-hydroxy-6-methylheptyl)phenyl]vinyl}benene-1,3-diol;
5-{2-[4-(6-hydroxy-6-methylheptyl)phenyl]ethyl}benzene-1,3-diol;
5-{2-[3-(6-hydroxy-6-methylheptyl)phenyl]ethyl}benzene-1,3-diol;
2-hydroxymethyl-4-{2-[3-(5-hydroxy-5-methylhexyl)phenyl]vinyl}phenol;
2-hydroxymethyl-4-{2-[4-(5-hydroxy-5-methylhexyl)phenyl]vinyl}phenol;
2-hydroxymethyl-4-{2-[3-(6-hydroxy-6-methylheptyl)phenyl]vinyl}phenol;
2-hydroxymethyl-4-{2-[4-(6-hydroxy-6-methylheptyl)phenyl]vinyl}phenol;
2-hydroxymethyl-4-{2-[3-(5-hydroxy-5-methylheptyl)phenyl]ethyl}phenol;
2-hydroxymethyl-4-{2-[4-(5-hydroxy-5-methylhexyl)phenyl]ethyl}phenol;
2-hydroxymethyl-4-{2-[3-(6-hydroxy-6-methylheptyl)phenyl]ethyl}phenol;
2-hydroxymethyl-4-{2-[4-(6-hydroxy-6-methylheptyl)phenyl]ethyl}phenol;
2-hydroxymethyl-5-{2-[4-(5-hydroxy-5-methylhexyl)phenyl]vinyl}phenol;
6-[3-(3,4-bis-hydroxymethylbenzyloxy)phenyl]-2-methylheptan-2-ol;
4-[3-(5-hydroxy-1,5-dimethylhexyl)phenoxymethyl]-2-hydroxymethylphenol;
6-{3-[2-(3,4-bis-hydroxymethylphenyl)vinyl]phenyl}-2-methylhexan-2-ol;
7-{4-[2-(3,4-bis-hydroxymethylphenyl)vinyl]phenyl}-2-methylheptan-2-ol;
6-{4-[2-(3,4-bis-hydroxymethylphenyl)vinyl]phenyl}-2-methylhexan-2-ol;
5-{2-[3-(6-hydroxy-6-methylheptyl)phenyl]-1-methylvinyl}benzene-1,3-diol;
5-{2-[3-(5-hydroxy-5-methylhexyl)phenyl]vinyl}benzene-1,3-diol;
5-[3-(6-hydroxy-6-methylheptyl)phenoxymethyl]benzene-1,3-diol;
5-{2-[3-(7-hydroxy-7-methyloct-1-enyl)phenyl]vinyl}benzene-1,3-diol;
5-{2-[3-(7-hydroxy-7-methyloctyl)phenyl]vinyl}benzene-1,3-diol;
4-{2-[3-(6-hydroxy-6-methylheptyl)phenyl]vinyl}benzene-1,2-diol;
6-{3-[2-(3,5-bis-hydroxymethylphenyl)vinyl]phenyl}-2-methylhexan-2-ol;
7-{3-[2-(3,5-bis-hydroxymethylphenyl)vinyl]phenyl}-2-methylheptan-2-ol;
7-{3-[2-(3,4-bis-hydroxymethylphenyl)vinyl]phenyl}-2-methylheptan-2-ol;
7-[3-(3,4-bis-hydroxymethylphenylethynyl)phenyl]-2-methylheptan-2-ol;
5-{2-[3-(6-hydroxy-6-methylhept-1-enyl)phenyl]vinyl}benzene-1,3-diol;
5-{2-[3-(7-ethyl-7-hydroxynon-1-enyl)phenyl]vinyl}benzene-1,3-diol;
5-{2-[3-(7-hydroxy-1-methoxy-1,7-dimethyloctyl)phenyl]vinyl}benzene-1,3-diol;
5-{2-[3-(6-hydroxy-1-methoxy-1,6-dimethylheptyl)phenyl]vinyl}benzene-1,3-diol;
5-{2-[3-(5-hydroxypentyl)phenyl]vinyl}benzene-1,3-diol;
5-{2-[3-(5-hydroxy-6-methylheptyl)phenyl]vinyl}benzene-1,3-diol;
5-{2-[3-(6-hydroxy-7-methyloctyl)phenyl]vinyl}benzene-1,3-diol;
5-{2-[3-(5-hydroxy-6-methylhept-1-enyl)phenyl]vinyl}benzene-1,3-diol;
5-{2-[3-(6-hydroxy-7-methyloct-1-enyl)phenyl]vinyl}benzene-1,3-diol;
5-{2-[3-(1,6-dihydroxy-1,6-dimethylheptyl)phenyl]vinyl}benzene-1,3-diol;
5-{2-[3-(6-hydroxy-1,6-dimethylhept-1-enyl)phenyl]vinyl}benzene-1,3-diol;
6-{[3-(3,4-bis-hydroxymethylbenzyloxy)phenyl]methylamino}-2-methylhexan-2-ol;
5-{[3-(3,4-bis-hydroxymethylbenzyloxy)phenyl]methylamino}-2-methylpentan-2-ol;
6-{[3-(3,4-bis-hydroxymethylbenzyloxy)phenyl]methylamino}-3-ethylhexan-3-ol;
7-{[3-(3,4-bis-hydroxymethylbenzyloxy)phenyl]methylamino}-3-ethylheptan-3-ol;
5-{[3-(3,4-bis-hydroxymethylbenzyloxy)phenyl]ethylamino}-2-methylpentan-2-ol;
6-{[3-(3,4-bis-hydroxymethylbenzyloxy)phenyl]benzylamino}-3-ethylhexan-3-ol;
7-{3-[2-(3,4-hydroxymethylphenyl)ethyl]phenyl}-3-ethylocta-4,6-dien-3-ol;
6-{3-[2-(3,4-bis-hydroxymethylphenyl)ethyl]phenyl}-2-methylhepta-3,5-dien-2-ol;
7-{3-[2-(3,4-bis-hydroxymethylphenyl)vinyl]phenyl}-3-ethylocta-4,6-dien-3-ol;
6-{3-[2-(3,4-bis-hydroxymethylphenyl)vinyl]phenyl}-2-methylhepta-3,5-dien-2-ol;
7-[3-(3,4-bis-hydroxymethylphenylethynyl)phenyl]-3-ethylocta-4,6-dien-3-ol;
7-[3-(3,4-bis-hydroxymethylbenzyloxy)phenyl]-3-ethyl-3-octanol;
(4E,6E)-7-[3-(3,4-bis-hydroxymethylbenzyloxy)phenyl]-3-ethylocta-4,6-dien-3-ol;
(4E,6Z)-7-[3-(3,4-bis-hydroxymethylbenzyloxy)phenyl]-3-ethylocta-4,6-dien-3-ol;
7-[4-(3,4-bis-hydroxymethylbenzyloxy)phenyl]-3-ethyl-3-octanol;
(4E,6E)-7-[3-(3,4-bis-hydroxymethylbenzyloxy)phenyl]-3-ethylnona-4,6-dien-3-ol;
(4E,6Z)-7-[3-(3,4-bis-hydroxymethylbenzyloxy)phenyl]-3-ethylnona-4,6-dien-3-ol;
(E)-6-[3-(3,4-bis-hydroxymethylbenzyloxy)phenyl]-2-methylhept-3-en-2-ol;
(E)-7-[3-(3,4-bis-hydroxymethylbenzyloxy)phenyl]-3-ethyloct-4-en-3-ol;
(E)-7-[3-(3,4-bis-hydroxymethylbenzyloxy)phenyl]-3-ethyloct-6-en-3-ol;
(Z)-7-[3-(3,4-bis-hydroxymethylbenzyloxy)phenyl]-3-ethyloct-6-en-3-ol;
(E)-8-[3-(3,4-bis-hydroxymethylbenzyloxy)phenyl]-2-methylnon-7-en-2-ol;

(Z)-8-[3-(3,4-bis-hydroxymethylbenzyloxy)phenyl]-2-methylnon-7-en-2-ol;

(E)-9-[3-(3,4-bis-hydroxymethylbenzyloxy)phenyl]-3-ethyldec-8-en-3-ol;

(Z)-9-[3-(3,4-bis-hydroxymethylbenzyloxy)phenyl]-3-ethyldec-8-en-3-ol;

8-[3-(3,4-bis-hydroxymethylbenzyloxy)phenyl]-2-methyl-2-nonanol;

9-[3-(3,4-bis-hydroxymethylbenzyloxy)phenyl]-3-ethyldecan-3-ol;

(E)-7-[3-(3,4-bis-hydroxymethylbenzyloxy)phenyl]-3-ethyloct-6-en-4-yn-3-ol;

(3E,5E)-7-[3-(3,4-bis-hydroxymethylbenzyloxy)phenyl]-2,7-dimethylocta-3,5-dien-2-ol;

(4E,6E)-7-[3-(3,4-bis-hydroxymethylphenoxymethyl)phenyl]-3-ethylocta-4,6-dien-3-ol;

(3E,5E)-6-[3-(3,4-bis-hydroxymethylphenoxymethyl)phenyl]-2-methylhepta-3,5-dien-2-ol;

(Z)-7-[3-(3,4-bis-hydroxymethylbenzyloxy)phenyl]-3-ethylnon-6-en-3-ol;

(Z)-6-[3-(3,4-bis-hydroxymethylbenzyloxy)phenyl]-2-methyloct-5-en-2-ol;

(Z)-7-[3-(3,4-bis-hydroxymethylbenzyloxy)phenyl]-3-ethyldec-6-en-3-ol;

(Z)-6-[3-(3,4-bis-hydroxymethylbenzyloxy)phenyl]-2-methylnon-5-en-2-ol;

(Z)-8-[3-(3,4-bis-hydroxymethylbenzyloxy)phenyl]-3-ethylnon-7-en-3-ol;

(E)-8-[3-(3,4-bis-hydroxymethylbenzyloxy)phenyl]-3-ethylnon-7-en-3-ol;

8-[3-(3,4-bis-hydroxymethylbenzyloxy)phenyl]-3-ethylnonan-3-ol;

7-[5-(3,4-bis-hydroxymethylbenzyloxy)-2-methoxyphenyl]-3-ethylnona-4,6-dien-3-ol;

7-[5-(3,4-bis-hydroxymethylbenzyloxy)-2-methylphenyl]-3-ethylnona-4,6-dien-3-ol;

7-[3-(3,4-bis-hydroxymethylbenzyloxy)-5-methoxyphenyl]-3-ethylnona-4,6-dien-3-ol;

7-[3-(3,4-bis-hydroxymethylbenzyloxy)-2-methoxyphenyl]-3-ethylnona-4,6-dien-3-ol;

7-[3-(3,4-bis-hydroxymethylbenzyloxy)-4-methylphenyl]-3-ethylnona-4,6-dien-3-ol;

1-[3-(3,4)-bis-hydroxymethylbenzyloxy)phenyl]ethanone O-(2-hydroxy-2-methylpropyl)oxime;

1{1-[3-(3,4-bis-hydroxymethylbenzyloxy)phenyl]propoxy}-3-ethylpentan-3-ol;

(E)-7-[3-(3,4-bis-hydroxymethylphenoxymethyl)phenyl]-3-ethylnon-6-en-3-ol;

(E)-7-[3-(3,4-bis-hydroxymethylbenzylsulfanyl)phenyl]-3-ethyloct-6-en-3-ol;

(E)-7-{3-[(3,4-bis-hydroxymethylbenzyl)methylamino]phenyl}-3-ethyloct-6-en-3-ol;

(E)-6-[3-(3,4-bis-hydroxymethylbenzyloxy)phenyl]-3-ethyl-6-methylhept-4-en-3-ol;

7-[3-(3,4-bis-hydroxymethylbenzyloxy)phenyl]-3-ethyl-7-methyloctan-3-ol;

7-[3-(3,4-bis-hydroxymethylbenzyloxy)phenyl]-3,7-diethylnonan-3-ol;

(E)-6-[3-(3,4-bis-hydroxymethylbenzyloxy)phenyl]-1,1,1-trifluoro-2-trifluoromethyloct-5-en-2-ol;

2-{4-[3-(3,4-bis-hydroxymethylbenzyloxy)phenyl]hexyl}-1,1,1,3,3,3-hexafluoropropan-2-ol;

(E)-7-[3-(3,4-bis-hydroxymethylbenzyloxy)phenyl]-3-ethyl-4,4-difluoronon-6-en-3-ol;

7-[3-(3,4-bis-hydroxymethylbenzyloxy)phenyl]-3-ethyl-4,4-difluoro-7-methyloctan-3-ol;

(E)-6-[3-(3,4-bis-hydroxymethylbenzyloxy)phenyl]-2-methyloct-5-en-3-ol;

(E)-4-[3-(3,4-bis-hydroxymethylbenzyloxy)phenyl]-1-cyclopropylhex-3-en-1-ol;

(E)-7-[3-(3,4-bis-hydroxymethylbenzyloxy)phenyl]-3-ethyl-4-methylnon-6-en-3-ol;

(E)-7-[3-(3,4-bis-hydroxymethylbenzyloxy)phenyl]-3-ethyl-4-methyldec-6-en-3-ol;

(4E,6E)-7-[3-(3,4-bis-hydroxymethylphenoxymethyl)phenyl]-3-ethylnona-4,6-dien-3-ol;

(4E,6E)-7-{3-[2-(3,4-bis-hydroxymethylphenyl)ethyl]phenyl}-3-ethylnona-4,6-dien-3-ol;

(E)-7-{3-[2-(3,4-bis-hydroxymethylphenyl)ethyl]phenyl}-3-ethylnon-6-en-3-ol;

2-{4-[3-(3,4-bis-hydroxymethylbenzyloxy)phenyl]-4-methylpentyl}-1,1,1,3,3,3-hexafluoropropan-2-ol;

7-[3-(3,4-bis-hydroxymethylbenzyloxy)phenyl]-3-ethyl-4,4-difluoro-7-methyloctan-3-ol;

7-{3-[2-(3,4-bis-hydroxymethylphenyl)ethyl]phenyl}-3,7-diethylnonan-3-ol;

7-[3-(3,4-bis-hydroxymethylbenzyloxy)phenyl]-3-ethyl-7-methyloctane-3,4-diol;

7-{3-[2-(3,4-bis-hydroxymethylphenyl)ethyl]phenyl}-3,7-diethylnonane-3,4-diol;

7-{3-[2-(3,4-bis-hydroxymethylphenyl)ethyl]phenyl}-3-ethyl-7-methyloctane-3,4-diol;

(E)-4-{3-[2-(3,4-bis-hydroxymethylphenyl)ethyl]phenyl}-1-cyclopropylhex-3-en-1-ol;

(4E,6E)-7-{3-[2-(3,4-bis-hydroxymethylphenyl)ethyl]phenyl}-3-ethyl-4-methylnona-4,6-dien-3-ol;

(4E,6E)-7-[3-(3,4-bis-hydroxymethylbenzyloxy)phenyl]-3-ethyl-4-methylnona-4,6-dien-3-ol; or (E)-7-[3-(3,4-bis-hydroxymethylphenoxymethyl)phenyl]-3-ethyloct-6-en-3-ol.

26. A compound having the formula:

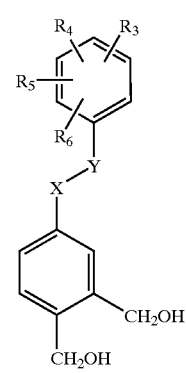

wherein:

X—Y represents a bond selected from the group consisting of the bonds of the following formulae (a) and (b) which are read from the left to the right or conversely:

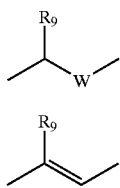

$R_3$ represents the chain in vitamin $D_2$ or in vitamin $D_3$,

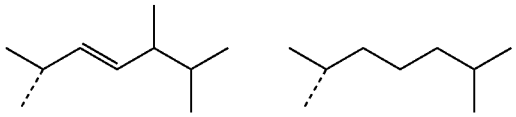

wherein the dotted lines represent the bond linking the $R_3$ chain to the benzene ring represented in formula (I);

or $R_3$ represents a chain having from 4 to 8 carbon atoms which is substituted with one or more hydroxyl groups, the hydroxyl groups being optionally protected in the form of acetoxy, methoxy, ethoxy, trimethylsilyloxy, tert-butyldimethylsilyloxy, or tetrahydropyranyloxy and the chain optionally in addition has at least one feature selected from the following group:
  which is substituted with one or more lower alkyl groups or cycloalkyl groups;
  which is substituted with one or more halogen atoms;
  which is substituted with one or more $CF_3$ groups;
  wherein one or more carbon atoms of the chain are replaced by one or more oxygen, sulfur or nitrogen atoms, the nitrogen atoms being optionally substituted with lower alkyl radicals; and
  wherein one or more single bonds of the chain are replaced by one or more double and/or triple bonds;

$R_3$ being positioned on the benzene ring at the para or meta position with respect to the X—Y bond;

$R_4$, $R_5$ and $R_6$, which are identical or different, represent a hydrogen atom, a lower alkyl radical, a halogen atom, a radical —$OR_{10}$, or a polyether radical;

$R_9$ represents a hydrogen atom or a lower alkyl radical;

W represents an oxygen atom, a sulfur atom, a radical —$CH_2$— or a radical —NH— which is optionally substituted with a lower alkyl radical; and $R_{10}$ represents a hydrogen atom or a lower alkyl radical;

or an optical or geometric isomer of the compound of formula (I) or a salt thereof.

27. A compound according to claim 26, wherein the lower alkyl radicals are selected from the group consisting of methyl, ethyl, isopropyl, tert-butyl and hexyl radicals.

28. A compound according to claim 26, wherein the cycloalkyl radical is an adamantyl radical or a 1-methylcyclohexyl radical.

29. A compound according to claim 26, wherein the halogen atom is a fluorine, chlorine or bromine atom.

30. A compound according to claim 26, wherein X—Y represents a bond of formula (a).

31. A compound according to claim 26, wherein $R_3$ represents a chain of 4 to 8 carbon atoms which is substituted by at least one member selected from the group consisting of a hydroxyl radical and a lower alkyl radical.

32. A compound according to claim 26, wherein X—Y represents a bond of formula (a), and $R_3$ represents a chain of 4 to 8 carbon atoms which is substituted by at least one member selected from the group consisting of a hydroxyl radical and a lower alkyl radical.

33. The compound according to claim 26, which is:
  6-[3-(3,4-bis-hydroxymethylbenzyloxy)phenyl]-2-methylhepta-3,5-dien-2-ol;
  6-[3-(3,4-bis-hydroxymethylbenzyloxy)phenyl]-2-methylhexan-2-ol;
  6-[3-(3,4-bis-hydroxymethylphenoxymethyl)phenyl]-2-methylheptan-2-ol;
  7-[3-(3,4-bis-hydroxymethylphenoxymethyl)phenyl]-3-ethyloctan-3-ol;
  6-[3-(3,4-bis-hydroxymethylbenzyloxy)phenyl]-2-methylheptan-2-ol;
  6-{3-[2-(3,4-bis-hydroxymethylphenyl)vinyl]phenyl}-2-methylhexan-2-ol;
  7-{4-[2-(3,4-bis-hydroxymethylphenyl)vinyl]phenyl}-2-methylheptan-2-ol;
  6-{4-[2-(3,4-bis-hydroxymethylphenyl)vinyl]phenyl}-2-methylhexan-2-ol;
  6-{3-[2-(3,5-bis-hydroxymethylphenyl)vinyl]phenyl}-2-methylhexan-2-ol;
  7-{3-[2-(3,5-bis-hydroxymethylphenyl)vinyl]phenyl}-2-methylheptan-2-ol;
  7-{3-[2-(3,4-bis-hydroxymethylphenyl)vinyl]phenyl}-2-methylheptan-2-ol;
  7-[3-(3,4-bis-hydroxymethylphenylethynyl)phenyl]-2-methylheptan-2-ol;
  6-{[3-(3,4-bis-hydroxymethylbenzyloxy)phenyl]methylamino}-2-methylhexan-2-ol;
  5-{[3-(3,4-bis-hydroxymethylbenzyloxy)phenyl]methylamino}-2-methylpentan-2-ol;
  6-{[3-(3,4-bis-hydroxymethylbenzyloxy)phenyl]methylamino}-3-ethylhexan-3-ol;
  7-{[3-(3,4-bis-hydroxymethylbenzyloxy)phenyl]methylamino}-3-ethylheptan-3-ol;
  5-{[3-(3,4-bis-hydroxymethylbenzyloxy)phenyl]ethylamino}-2-methylpentan-2-ol;
  6-{[3-(3,4-bis-hydroxymethylbenzyloxy)phenyl]benzylamino}-3-ethylhexan-3-ol;
  7-{3-[2-(3,4-bis-hydroxymethylphenyl)ethyl]phenyl}-3-ethylocta-4,6-dien-3-ol;
  6-{3-[2-(3,4-bis-hydroxymethylphenyl)ethyl]phenyl}-2-methylhepta-3,5-dien-2-ol;
  7-{3-[2-(3,4-bis-hydroxymethylphenyl)vinyl]phenyl}-3-ethylocta-4,6-dien-3-ol;
  6-{3-[2-(3,4-bis-hydroxymethylphenyl)vinyl]phenyl}-2-methylhepta-3,5-dien-2-ol;
  7-[3-(3,4-bis-hydroxymethylphenylethynyl)phenyl]-3-ethylocta-4,6-dien-3-ol;
  7-[3-(3,4-bis-hydroxymethylbenzyloxy)phenyl]-3-ethyl-3-octanol;
  (4E,6E)-7-[3-(3,4-bis-hydroxymethylbenzyloxy)phenyl]-3-ethylocta-4,6-dien-3-ol;
  (4E,6Z)-7-[3-(3,4-bis-hydroxymethylbenzyloxy)phenyl]-3-ethylocta-4,6-dien-3-ol;
  7-[4-(3,4-bis-hydroxymethylbenzyloxy)phenyl]-3-ethyl-3-octanol;
  (4E,6E)-7-[3-(3,4-bis-hydroxymethylbenzyloxy)phenyl]-3-ethylnona-4,6-dien-3-ol;
  (4E,6Z)-7-[3-(3,4-bis-hydroxymethylbenzyloxy)phenyl]-3-ethylnona-4,6-dien-3-ol;
  (E)-6-[3-(3,4-bis-hydroxymethylbenzyloxy)phenyl]-2-methylhept-3-en-2-ol;

(E)-7-[3-(3,4-bis-hydroxymethylbenzyloxy)phenyl]-3-ethyloct-4-en-3-ol;
(E)-7-[3-(3,4-bis-hydroxymethylbenzyloxy)phenyl]-3-ethyloct-6-en-3-ol;
(Z)-7-[3-(3,4-bis-hydroxymethylbenzyloxy)phenyl]-3-ethyloct-6-en-3-ol;
(E)-8-[3-(3,4-bis-hydroxymethylbenzyloxy)phenyl]-2-methylnon-7-en-2-ol;
(Z)-8-[3-(3,4-bis-hydroxymethylbenzyloxy)phenyl]-2-methylnon-7-en-2-ol;
(E)-9-[3-(3,4-bis-hydroxymethylbenzyloxy)phenyl]-3-ethyldec-8-en-3-ol;
(Z)-9-[3-(3,4-bis-hydroxymethylbenzyloxy)phenyl]-3-ethyldec-8-en-3-ol;
8-[3-(3,4-bis-hydroxymethylbenzyloxy)phenyl]-2-methyl-2-nonanol;
9-[3-(3,4-bis-hydroxymethylbenzyloxy)phenyl]-3-ethyldecan-3-ol;
(E)-7-[3-(3,4-bis-hydroxymethylbenzyloxy)phenyl]-3-ethyloct-6-en-4-yn-3-ol;
(3E,5E)-7-[3-(3,4-bis-hydroxymethylbenzyloxy)phenyl]-2,7-dimethylocta-3,5-dien-2-ol;
(4E,6E)-7-[3-(3,4-bis-hydroxymethylphenoxymethyl)phenyl]-3-ethylocta-4,6-dien-3-ol;
(3E,5E)-6-[3-(3,4-bis-hydroxymethylphenoxymethyl)phenyl]-2-methylhepta-3,5-dien-2-ol;
(Z)-7-[3-(3,4-bis-hydroxymethylbenzyloxy)phenyl]-3-ethylnon-6-en-3-ol;
(Z)-6-[3-(3,4-bis-hydroxymethylbenzyloxy)phenyl]-2-methyloct-5-en-2-ol;
(Z)-7-[3-(3,4-bis-hydroxymethylbenzyloxy)phenyl]-3-ethyldec-6-en-3-ol;
(Z)-6-[3-(3,4-bis-hydroxymethylbenzyloxy)phenyl]-2-methylnon-5-en-2-ol;
(Z)-8-[3-(3,4-bis-hydroxymethylbenzyloxy)phenyl]-3-ethylnon-7-en-3-ol;
(E)-8-[3-(3,4-bis-hydroxymethylbenzyloxy)phenyl]-3-ethylnon-7-en-3-ol;
8-[3-(3,4-bis-hydroxymethylbenzyloxy)phenyl]-3-ethylnonan-3-ol;
7-[5-(3,4-bis-hydroxymethylbenzyloxy)-2-methoxyphenyl]-3-ethylnona-4,6-dien-3-ol;
7-[5-(3,4-bis-hydroxymethylbenzyloxy)-2-methylphenyl]-3-ethylnona-4,6-dien-3-ol;
7-[3-(3,4-bis-hydroxymethylbenzyloxy)-5-methoxyphenyl]-3-ethylnona-4,6-dien-3-ol;
7-[3-(3,4-bis-hydroxymethylbenzyloxy)-2-methoxyphenyl]-3-ethylnona-4,6-dien-3-ol;
7-[3-(3,4-bis-hydroxymethylbenzyloxy)-4-methylphenyl]-3-ethylnona-4,6-dien-3-ol;
1-[3-(3,4)-bis-hydroxymethylbenzyloxy)phenyl]ethanone O-(2-hydroxy-2-methylpropyl)oxime;
1{1-[3-(3,4-bis-hydroxymethylbenzyloxy)phenyl]propoxy}-3-ethylpentan-3-ol;
(E)-7-[3-(3,4-bis-hydroxymethylphenoxymethyl)phenyl]-3-ethylnon-6-en-3-ol;
(E)-7-[3-(3,4-bis-hydroxymethylbenzylsulfanyl)phenyl]-3-ethyloct-6-en-3-ol;
(E)-7-{3-[(3,4-bis-hydroxymethylbenzyl)methylamino]phenyl}-3-ethyloct-6-en-3-ol;
(E)-6-[3-(3,4-bis-hydroxymethylbenzyloxy)phenyl]-3-ethyl-6-methylhept-4-en-3-ol;
7-[3-(3,4-bis-hydroxymethylbenzyloxy)phenyl]-3-ethyl-7-methyloctan-3-ol;
7-[3-(3,4-bis-hydroxymethylbenzyloxy)phenyl]-3,7-diethylnonan-3-ol;
(E)-6-[3-(3,4-bis-hydroxymethylbenzyloxy)phenyl]-1,1,1-trifluoro-2-trifluoromethyloct-5-en-2-ol;
2-{4-[3-(3,4-bis-hydroxymethylbenzyloxy)phenyl]hexyl}-1,1,1,3,3,3-hexafluoropropan-2-ol;
(E)-7-[3-(3,4-bis-hydroxymethylbenzyloxy)phenyl]-3-ethyl-4,4-difluoronon-6-en-3-ol;
7-[3-(3,4-bis-hydroxymethylbenzyloxy)phenyl]-3-ethyl-4,4-difluoro-7-methyloctan-3-ol;
(E)-6-[3-(3,4-bis-hydroxymethylbenzyloxy)phenyl]-2-methyloct-5-en-3-ol;
(E)-4-[3-(3,4-bis-hydroxymethylbenzyloxy)phenyl]-1-cyclopropylhex-3-en-1-ol;
(E)-7-[3-(3,4-bis-hydroxymethylbenzyloxy)phenyl]-3-ethyl-4-methylnon-6-en-3-ol;
(E)-7-[3-(3,4-bis-hydroxymethylbenzyloxy)phenyl]-3-ethyl-4-methyldec-6-en-3-ol;
(4E,6E)-7-[3-(3,4-bis-hydroxymethylphenokymethyl)phenyl]-3-ethylnona-4,6-dien-3-ol;
(4E,6E)-7-{3-[2-(3,4-bis-hydroxymethylphenyl)ethyl]phenyl}-3-ethylnona-4,6-dien-3-ol;
(E)-7-{3-[2-(3,4-bis-hydroxymethylphenyl)ethyl]phenyl}-3-ethylnon-6-en-3-ol;
2-{4-[3-(3,4-bis-hydroxymethylbenzyloxy)phenyl]-4-methylpentyl}-1,1,1,3,3,3-hexafluoropropan-2-ol;
7-[3-(3,4-bis-hydroxymethylbenzyloxy)phenyl]-3-ethyl-4,4-difluoro-7-methyloctan-3-ol;
7-{3-[2-(3,4-bis-hydroxymethylphenyl)ethyl]phenyl}-3,7-diethylnonan-3-ol;
7-[3-(3,4-bis-hydroxymethylbenzyloxy)phenyl]-3-ethyl-7-methyloctane-3,4-diol;
7-{3-[2-(3,4-bis-hydroxymethylphenyl)ethyl]phenyl}-3,7-diethylnonane-3,4-diol;
7-{3-[2-(3,4-bis-hydroxymethylphenyl)ethyl]phenyl}-3-ethyl-7-methyloctane-3,4-diol;
(E)-4-{3-[2-(3,4-bis-hydroxymethylphenyl)ethyl]phenyl}-1-cyclopropylhex-3-en-1-ol;
(4E,6E)-7-{3-[2-(3,4-bis-hydroxymethylphenyl)ethyl]phenyl}-3-ethyl-4-methylnona-4,6-dien-3-ol;
(4E,6E)-7-[3-(3,4-bis-hydroxymethylbenzyloxy)phenyl]-3-ethyl-4-methylnona-4,6-dien-3-ol; or
(E)-7-[3-(3,4-bis-hydroxymethylphenoxymethyl)phenyl]-3-ethyloct-6-en-3-ol.

34. A pharmaceutical composition comprising a therapeutically effective vitamin D receptor agonist amount of at least one compound as claimed in claim 26, and a pharmaceutically acceptable carrier therefor.

35. A composition according to claim 34, in oral dosage form.

36. A composition according to claim 34, in topical dosage form.

37. A composition according to claim 34, in injectable dosage form.

38. A composition according to claim 34, wherein the concentration of compound is between 0.001% and 5% by weight relative to the total weight of the composition.

39. A cosmetic composition comprising a cosmetically effective vitamin D receptor agonist amount of at least one compound as claimed in claim 26, and a cosmetically acceptable carrier therefor.

40. A composition according to claim 39, wherein the concentration of compound is between 0.001% and 3% by weight relative to the total weight of the composition.

41. A compound having the formula:

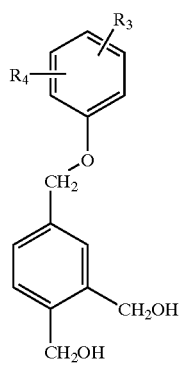

wherein:
- $R_3$ represents a chain having from 4 to 8 carbon atoms which is substituted with one hydroxyl group and optionally in addition is substituted with one or more lower alkyl groups; wherein two single bonds of the chain are replaced by two double bonds; and wherein $R_3$ is positioned on the benzene ring at the para or meta position with respect to the —$CH_2$—O— group; and
- $R_4$ is hydrogen, a lower alkyl radical, or a radical of the formula —O—(lower alkyl);

or an optical or geometric isomer or salt thereof.

42. A compound according to claim 41, wherein the lower alkyl radicals are selected from the group consisting of methyl, ethyl, isopropyl, tert-butyl and hexyl radicals.

43. A method for treating a dermatological condition linked to a keratinocyte or sebocyte differentiation or proliferation disorder in a human or other animal in need of such treatment, said method comprising administering to said human or other animal a therapeutically effective vitamin D receptor agonist amount of at least one compound of formula (I) as claimed in claim 2.

44. A method according to claim 43, wherein the condition is acne vulgaris, comedo-type acne, polymorphic acne, acne rosacea, nodulocystic acne, acne conglobata, senile acne, secondary acne, acne medicamentosa or occupational acne.

45. A method for treating a keratinization disorder selected from the group consisting of ichthyosis, ichthyosiform states, Darier's disease, keratosis palmeris and plantaris, leukoplasia, leukoplasiform states, cutaneous lichen and buccal mucosal lichen in a human or other animal in need of such treatment, said method comprising administering to said human or other animal a therapeutically effective vitamin D receptor agonist amount of at least one compound of formula (I) as claimed in claim 2.

46. A method for treating a dematological condition linked to a keratinization disorder with an inflammatory component, with an immunoallergic component, or with inflammatory and immunoallergic components, in a human or other animal in need of such treatment, said method comprising administering to said human or other animal a therapeutically effective vitamin D receptor agonist amount of at least one compound of formula (I) as claimed in claim 2.

47. A method according to claim 46, wherein the condition is psoriasis.

48. A method according to claim 46, wherein the condition is cutaneous psoriasis, mucosal psoriasis, ungual psoriasis, psoriatic rheumatism or cutaneous atopy.

49. A method according to claim 46, wherein the condition is eczema, respiratory atopy or gingival hypertropy.

50. A method for treating an inflammatory condition which does not exhibit a keratinization disorder, in a human or other animal in need of such treatment, said method comprising administering to said human or other animal a therapeutically effective vitamin D receptor agonist amount of at least one compound of formula (I) as claimed in claim 2.

51. A method for treating a dermal or epidermal proliferation which is benign or malignant in a human or other animal in need of such treatment, said method comprising administering to said human on other animal a therapeutically effective vitamin D receptor agonist amount of at least one compound of formula (I) as claimed in claim 2.

52. A method according to claim 51, wherein the proliferation is of viral origin.

53. The method according to claim 51, wherein the proliferation is verruca vulgaris, verruca plana or epidermodysplasia verruciformis.

54. A method according to claim 51, wherein the proliferation comprises oral or florid papillomatoses.

55. A method according to claim 51, wherein the proliferation is induced by ultraviolet radiation.

56. A method according to claim 51, wherein the proliferation comprises baso- and spinocellular epithelioma.

57. A method for treating a bullous dermatosis or collagen disease in a human or other animal in need of such treatment, said method comprising administering to said human or other animal a therapeutically effective vitamin D receptor agonist amount of at least one compound of formula (I) as claimed in claim 2.

58. A method for treating photoinduced or chronologic skin ageing, pigmentation, actinic keratosis or other pathology associated with chronologic or actinic ageing in a human or other animal in need of such treatment, said method comprising administering to said human or other animal a therapeutically effective vitamin D receptor agonist amount of at least one compound of formula (I) as claimed in claim 2.

59. A method for treating a cicatrization disorder or vibicis in a human or other animal in need of such treatment, said method comprising administering to said human or other animal a therapeutically effective vitamin D receptor agonist amount of at least one compound of formula (I) as claimed in claim 2.

60. A method for treating a disorder of the sebaceous function in a human or other animal in need of such treatment, said method comprising administering to said human or other animal a therapeutically effective vitamin D receptor agonist amount of at least one compound of formula (I) as claimed in claim 2.

61. A method according to claim 60, wherein the disorder is hyperseborrhoea of acne, simple seborrhoea or seborrhoeic eczema.

62. A method for treating an opthalmological disorder susceptible to treatment with a vitamin D receptor agonist in a human or other animal in need of such treatment, said method comprising administering to said human or other animal a therapeutically effective vitamin D receptor agonist amount of at least one compound of formula (I) as claimed in claim 2.

63. A method according to claim 62, wherein the disorder is a corneopathy.

64. A method for treating a cancerous or precancerous state of a cancer exhibiting or capable of being induced by vitamin D receptors in a human or other animal in need of such treatment, said method comprising administering to said human or other animal a therapeutically effective vitamin D receptor agonist amount of at least one compound of formula (I) as claimed in claim 2.

65. A method according to claim 64, wherein said cancerous or precancerous state is breast cancer, leukemia, myelodysplasic syndrome or lymphoma, carcinoma of the cells of the malpighian epithelium, gastrointestinal cancer, melanoma or osteosarcoma.

66. A method for treating an inflammatory condition susceptible to treatment with a vitamin D receptor agonist in a human or other animal in need of such treatment, said method comprising administering to said human or other animal a therapeutically effective vitamin D receptor agonist amount of at least one compound of formula (I) as claimed in claim 2.

67. A method according to claim 66, wherein the inflammatory condition is arthritis.

68. A method according to claim 66, wherein the inflammatory condition is rheumatoid arthritis.

69. A method for treating a condition of viral origin which is susceptible to treatment with a vitamin D receptor agonist in a human or other animal in need of such treatment, said method comprising administering to said human or other animal a therapeutically effective vitamin D agonist amount of at least one compound of formula (I) as claimed in claim 2.

70. A method for treating alopecia in a human or other animal in need of such treatment, said method comprising administering to said human or other animal a therapeutically effective vitamin D agonist amount of at least one compound of formula (I) as claimed in claim 2.

71. A method according to claim 70, wherein the alopecia is due to chemotherapy or radiation.

72. A method for treating a dermatological or general condition with an immunological component which is susceptible to treatment with a vitamin D receptor agonist in a human or other animal in need of such treatment, said method comprising administering to said human or other animal a therapeutically effective vitamin D agonist amount of at least one compound of formula (I) as claimed in claim 2.

73. A method for treating an immunological condition which is susceptible to treatment with a vitamin D receptor agonist in a human or other animal in need of such treatment, said method comprising administering to said human or other animal a therapeutically effective vitamin D agonist amount of at least one compound of formula (I) as claimed in claim 2.

74. A method according to claim 73, wherein the immunological condition is an autoimmune disease.

75. A method according to claim 73, wherein the immunological condition is type 1 diabetes mellitus, multiple sclerosis, lupus, a lupus-type condition, asthma or glomerulonephritis.

76. A method according to claim 73, wherein the condition is a selective dysfunction of the immune system.

77. A method for treating a hormonal condition which is susceptible to treatment with a vitamin D receptor agonist in a human or other animal in need of such treatment, said method comprising administering to said human or other animal a therapeutically effective vitamin D agonist amount of at least one compound of formula (I) as claimed in claim 2.

78. A method for treating a condition characterized by abnormal management of intracellular calcium in a human or other animal in need of such treatment, said method comprising administering to said human or other animal a therapeutically effective vitamin D agonist amount of at least one compound of formula (I) as claimed in claim 2.

79. A method for treating a vitamin D deficiency or other condition of the homeostasis of the minerals in the plasma and bones in a human or other animal in need of such treatment, said method comprising administering to said human or other animal a therapeutically effective vitamin D agonist amount of at least one compound of formula (I) as claimed in claim 2.

80. A method according to claim 79, wherein said vitamin D deficiency or other condition comprises rickets, osteoporosis, renal osteodystrophy or parathyroid function disorder.

81. A method according to claim 80, wherein the condition is osteoporosis in a menopausal woman.

82. A method for cosmetically treating the body or hair of a human or other animal in need of such treatment, said method comprising topically applying to the body or hair of said human or other animal a cosmetically effective amount of a composition as claimed in claim 21.

* * * * *